US007862821B2

(12) United States Patent
Audonnet et al.

(10) Patent No.: US 7,862,821 B2
(45) Date of Patent: Jan. 4, 2011

(54) RECOMBINANT VACCINE AGAINST BLUETONGUE VIRUS

(75) Inventors: Jean Christophe Francis Audonnet, Lyons (FR); Kemal Karaca, Athens, GA (US); Jiansheng Yao, North York (CA); Nigel James MacLachlan, Davis, CA (US)

(73) Assignees: Merial Limited, Duluth, GA (US); The Regents of the University of California, Oakland, CA (US)

( * ) Notice: Subject to any disclaimer, the term of this patent is extended or adjusted under 35 U.S.C. 154(b) by 622 days.

(21) Appl. No.: 11/444,698

(22) Filed: Jun. 1, 2006

(65) Prior Publication Data

US 2007/0280960 A1 Dec. 6, 2007

(51) Int. Cl.
A61K 39/15 (2006.01)
A61K 39/275 (2006.01)
C12N 7/01 (2006.01)
C12Q 1/70 (2006.01)
G01N 33/569 (2006.01)

(52) U.S. Cl. .............. 424/185.1; 424/186.1; 424/215.1; 424/232.1; 435/5; 435/7.1; 435/235.1

(58) Field of Classification Search ........................ None
See application file for complete search history.

(56) References Cited

U.S. PATENT DOCUMENTS

| 5,830,463 A * | 11/1998 | Duke et al. .............. 424/93.51 |
| 6,130,066 A * | 10/2000 | Tartaglia et al. ............ 435/69.1 |
| 2005/0255127 A1 | 11/2005 | Loosmore et al. ........ 424/199.1 |
| 2007/0141557 A1 | 6/2007 | Raab et al. ..................... 435/5 |

FOREIGN PATENT DOCUMENTS

WO    WO 2004/059556 A    7/2004

OTHER PUBLICATIONS

Lobato et al. Veterinary Immunology and Immunopathology, 1997, vol. 59, pp. 293-309.*
Taylor et al. Vaccine, 1995, vol. 13, No. 6, pp. 539-549.*
Minke et al. Veterinary Research, 2004, vol. 35, pp. 425-443.*
Harpin et al. Journal of General Virology, 1999, vol. 80, pp. 3137-3144.*
Abaza et al. Journal of Protein Chemistry, 1992, vol. 11, No. 5, pp. 433-444.*
Riffkin et al. Gene, 1995, vol. 167, pp. 279-283.*
Martyn et al., "Expression of the outer capsid proteins VP2 and VP5 of bluetongue virus in *Saccharomyces cereuisiae*," Virus Research, vol. 33 No. 1, pp. 11-25 (Jul. 1994).*
GenBank AAB70533., "outer capsid protein VP2 [Bluetongue virus]," Sep. 1997.*
GenBank AAA42823, "capsid protein VP5 [Bluetongue virus]," Apr. 1993.*
Roy P et al., Vaccine, Butterworth Scientific. Guildford, GB, vol. 12, No. 9, Jan. 1, 1994, pp. 805-811.
Roy P et al., Vaccine, Butterworth Scientific. Guildford, GB, vol. 10, No. 1, Jan. 1, 1992, pp. 28-32.
Anderson J et al., Journal of Virological Methods, Elsevier BV, NL, vol. 43, No. 2, Jul. 1, 1993, pp. 167-175.
Karaca K et al., Vaccine, Butterworth Scientific. Guildford, GB, vol. 23, No. 29, May 31, 2005, pp. 3808-3813.
Bradel-Tretheway B G et al., Journal of Virological Methods, Elsevier BV, NL, vol. 111, No. 2, Aug. 1, 2003, pp. 145-156.
Disbrow G L et al., Virology, Academic Press, Orlando, US, vol. 311, No. 1, Jun. 20, 2003, pp. 105-114.
Murray P K et al., Australian Veterinary Journal, Australian Veterinary Association, Brunswick, AU, vol. 73, No. 6, Jan. 1, 1996, pp. 207-210.
Aucouturier et al. Vaccine 19 (2001) 2666-2672 "Adjuvants designed for veterinary and human vaccines".
Edelman R. et al. AIDS Rfsearch and Human Retroviruses vol. 8, No. 8, 1992 "An Update on Vaccine Adjuvants in Clinical Trial".
McElrath, MJ. Seminars in Cancer Biology, vol. 6, 1995: pp. 375-385 Selection of potent immunological adjuvants for vaccine construction.
Willson, PJ et al. Tissue Reaction and Immunity in Swine Immunized with *Actinobacillus pleuropneumoniae* Vaccines. Can J Vet Res 1995; 59: 299-305.
Boone JD et al., "Recombinant canarypox virus vaccine co-expressing genes encoding the VP2 and VP5 . . . ", Vaccine. Jan. 8, 2007;25(4):672-8.
Verwwoerd DW et al., "Structure of the bluetongue virus capsid", J Virol. Oct. 1972;10(4):783-94.
Roy P et al., "Recombinant virus vaccine for bluetongue disease in sheep", J Virol. May 1990;64(5):1998-2003.
Hassan SS, et al., "Expression and functional characterization of bluetongue virus VP2 protein: role in cell entry", J Virol. Dec. 1999;73(12):9832-42.

(Continued)

*Primary Examiner*—Zachariah Lucas
(74) *Attorney, Agent, or Firm*—Judy Jarecki-Black; Ruoying Chen; Merial Limited

(57) ABSTRACT

The present invention relates to an immunogenic or vaccine composition to induce an immune response or protective immune response against *Orbiviruses*, more specifically bluetongue virus (BTV) in an animal susceptible to BTV infection. The composition may include a pharmaceutically or veterinarily acceptable vehicle or excipient, and a vector. The vector may contain heterologous nucleic acid molecule(s), expresses in vivo in the animal BTV antigen, immunogen or epitope thereof, e.g., BTV VP2; BTV VP2 and VP5; BTV VP2 and VP5 and VP3 and/or VP7. The composition can contain an adjuvant, such as carbomer. Methods for making and using such a composition, including prime-boost regimes and including as to differential diagnosis, are also contemplated.

AGACAGTGGTCAATTCCAATGGTACTGTTTGACGATAC

22 Claims, 41 Drawing Sheets

OTHER PUBLICATIONS

Perrin A et al., "Recombinant capripoxviruses expressing proteins of bluetongue virus: Evaluation of immune . . . ",Vaccine 25 Jul. 2007 6774-6783.

Andrew M et al., "Antigen specificity of the ovine cytotoxic T lymphocyte response to bluetongue virus", Vet Immunol Immunopathol Aug. 1995 47(3-4) 311-22.

Lobato Z et al., "Antibody responses and protective immunity to recombinant vaccinia virus-expressed bluetongue", Vet Immunol Immunopathol Nov. 1997 59(3-4) 293-309.

Huismans H et al., "Isolation of a Capsid Protein of Bluetongue Virus That Induces a Protective Immune Response in Sheep", Virology Mar. 1987 157(1) 172-9.

Roy P, "Orbivirus Structure and Assembly", Virology Feb. 1996 216(1) 1-11.

De Mattos C et al.,"Heterogeneity of the L2 gene of field isolates of bluetongue virus serotype 17 from the San Joaquin", Virus Res Jan. 1994 31(1) 67-87.

Demaula C et al., "Changes in the outer capsid proteins of bluetongue virus serotype ten that abrogate neutralization . . . ", Virus Research 67 Jan. 2000 59-66.

Jones L et al., "The non-structural proteins of bluetongue virus are a dominant source of cytotoxic T cell peptide determinants . . . ", J. General Virology (1996), 77, 99. UK.

Hyatt A et al., "Localization of the non-structural protein NS3 in bluetongue virus-infected cells", J. General Virology (1991), 72, 2263-2267. Printed in UK.

Roy P et al., "Evidence for genetic relationship between RNA and DNA viruses from the sequence homology of a putative polymerase gene of Bluetongue virus . . . ", NAR 1988, 16(28).

Janardhana V et al., "The ovine cytotoxic T lymphocyte responses to bluetongue virus", Res Vet Sci. Dec. 1999;67(3):213-21.

Wilson et al., "Molecular Evolution of Orbiviruses", The British Library—"The World's Knowledge", pp. 169-180.

Andrew M et al., "Antigen specificity of the ovine cytotoxic T lymphocyte response to bluetongue virus", Vet Immunol Immunopathol. Aug. 1995;47(3-4):311-22.

Cloete M et al., "Vaccinia virus expression of the VP7 protein of South African bluetongue virus serotype 4 . . . ", Arch Virol. 1994;135(3-4):405-18.

Eaton BT et al., "A bluetongue serogroup-reactive epitope in the amino terminal half of the major core protein VP7 is accessible . . . ", Virology. Feb. 1991;180(2):687-96.

Takamatsu H et al., "Identification of a bluetongue virus serotype 1-specific ovine helper T-cell determinant . . . ", Virology. Jul. 1990;177(1):396-400.

Wade-Evans AM et al., "Expression of the outer capsid protein, VP2, from a full length cDNA clone of genome segment 2 . . . ", Virus Res. Mar. 1990;15(3):213-29.

Roy et al., "Orbiviruses and their Replication", Fields Virology, 3rd Edition, 1996, Chapter 56, pp. 1709-1734.

Identification of the Serotype-specific and Group-Specific antigens of Bluetongue Virus, Onderstepoort J. Vet Research, 1981, 48, 51-58.

* cited by examiner

|                      |       | 1                                                  50 |
|----------------------|-------|---------------------------------------------------------|
| BTV17 VP2 native     | (1)   | ATGGAGGAGTTCGTCATTCCAGTCTATTCAGAAGATGAAATTCCATACGC |
| Synthetic BTV17 VP2  | (1)   | ATGGAGGAGTTCGTGATCCCCGTGTACAGCGAGGACGAGATCCCCTACGC |

SEQ ID NO: 1

|                      |       | 51                                                100 |
|----------------------|-------|---------------------------------------------------------|
| BTV17 VP2 native     | (51)  | TTTACTGAGCAGATACCCTTTGGCGATACAGACAAATGTTAAAATAGAGG |
| Synthetic BTV17 VP2  | (51)  | CCTGCTGAGCAGATACCCTCTGGCCATCCAGACCAACGTGAAGATCGAGG |
|                      |       | 101                                               150 |
| BTV17 VP2 native     | (101) | ATGTTGAAGGAAAACATAATGTTGTAAAAATTCCTGAATCCGATATGATA |
| Synthetic BTV17 VP2  | (101) | ACGTGGAGGGCAAGCACAACGTGGTGAAGATCCCCGAGAGCGACATGATC |
|                      |       | 151                                               200 |
| BTV17 VP2 native     | (151) | GATATACCAAGATTAACAATTGTAGAGGCGATGAATTATAAACCAGCGAG |
| Synthetic BTV17 VP2  | (151) | GACATCCCCCGGCTGACCATCGTGGAGGCCATGAACTACAAGCCCGCCAG |
|                      |       | 201                                               250 |
| BTV17 VP2 native     | (201) | AAACGATGGAATCGTTGTACCTAGATTACTTGATATAACATTACGTGCTT |
| Synthetic BTV17 VP2  | (201) | GAACGACGGCATCGTGGTGCCTAGACTGCTGGACATCACCCTGAGAGCCT |
|                      |       | 251                                               300 |
| BTV17 VP2 native     | (251) | ATGATGATAGGAAATCGACAAAAAGTGCTCGAGGGATAGAGTTCATGACG |
| Synthetic BTV17 VP2  | (251) | ACGACGACCGGAAGAGCACCAAGAGCGCCAGAGGCATCGAGTTCATGACC |
|                      |       | 301                                               350 |
| BTV17 VP2 native     | (301) | AACGCTAGATGGATGAAATGGGCCATAGATGATAGAATGGATATCCAACC |
| Synthetic BTV17 VP2  | (301) | AACGCCCGGTGGATGAAGTGGGCCATCGACGACAGGATGGACATCCAGCC |
|                      |       | 351                                               400 |
| BTV17 VP2 native     | (351) | GCTTAAAGTCACTTTTGGATCATTACTGTTCCGTCAACCATCAGCTCTTTA |
| Synthetic BTV17 VP2  | (351) | CCTGAAGGTGACCCTGGACCACTACTGCAGCGTGAATCACCAGCTGTTCA |
|                      |       | 401                                               450 |
| BTV17 VP2 native     | (401) | ACTGCGTCGTCAAAGCGAATGCTGCCAACGCTGATACGATCTATTATGAT |
| Synthetic BTV17 VP2  | (401) | ACTGCGTGGTGAAGGCCAACGCCGCCAATGCCGACACCATCTACTACGAC |
|                      |       | 451                                               500 |
| BTV17 VP2 native     | (451) | TATTTCCCACTTGAAGACCATAAAAAAAGATGTAACCACACAAATCTTGA |
| Synthetic BTV17 VP2  | (451) | TACTTCCCCCTGGAGGACCACAAGAAGCGGTGCAACCACACCAACCTGGA |
|                      |       | 501                                               550 |
| BTV17 VP2 native     | (501) | TTTATTGAGAAGTTTGACCAATATGGAGTTGTTCCACGCGTTGCAAGGTG |
| Synthetic BTV17 VP2  | (501) | CCTGCTGAGGAGCCTGACCAACATGGAGCTGTTCCACGCCCTGCAGGGAG |
|                      |       | 551                                               600 |
| BTV17 VP2 native     | (551) | CTGCATACAGTATCAAATCGAGCTACGAATTAGTGGCAAACTCCGAAAGA |
| Synthetic BTV17 VP2  | (551) | CCGCCTACAGCATCAAGAGCAGCTACGAACTGGTGGCCAACAGCGAGAGA |
|                      |       | 601                                               650 |
| BTV17 VP2 native     | (601) | GAAAGCTTGGAGGAGACTTATGCGATAGGACAGCCAAAGTGGATACATTT |
| Synthetic BTV17 VP2  | (601) | GAGAGCCTGGAGGAGACCTACGCCATCGGCCAGCCTAAGTGGATCCACCT |
|                      |       | 651                                               700 |
| BTV17 VP2 native     | (651) | GACTAGAGGAACGCGAATAGGCAATAGTGGATTACCTTATGAACGGTTTA |
| Synthetic BTV17 VP2  | (651) | GACCAGGGGCACCAGAATCGGCAACAGCGGCCTGCCTTACGAGAGATTCA |
|                      |       | 701                                               750 |
| BTV17 VP2 native     | (701) | TCTCAAGCATGGTCCAGGTGATCGTAAATGGCAAGATTCCAAGCGAGATA |
| Synthetic BTV17 VP2  | (701) | TCAGCAGCATGGTGCAGGTGATCGTGAACGGCAAGATCCCTAGCGAGATC |
|                      |       | 751                                               800 |
| BTV17 VP2 native     | (751) | GCGAACGAGGTCGCGCAACTGAATAGAATAAGGGCAGAGTGGATAGCGGC |
| Synthetic BTV17 VP2  | (751) | GCCAACGAGGTGGCCCAGCTGAACAGAATCCGGGCCGAGTGGATCGCCGC |
|                      |       | 801                                               850 |
| BTV17 VP2 native     | (801) | TACATACGATAGAGGCAGGATTAGAGCGCTAGAGCTATGCAAGATCCTTT |
| Synthetic BTV17 VP2  | (801) | CACCTACGACAGAGGCAGGATCAGAGCCCTGGAGCTGTGCAAGATCCTGA |
|                      |       | 851                                               900 |
| BTV17 VP2 native     | (851) | CCACGATTGGGCGTAAGATACTGAACACGCATGAAGAGCCGAAAGATGAA |
| Synthetic BTV17 VP2  | (851) | GCACCATCGGCCGGAAGATCCTGAATACCCACGAGGAGCCCAAGGACGAG |
|                      |       | 901                                               950 |
| BTV17 VP2 native     | (901) | ATGGATCTATCAACAAGATTTCAGTTCAAACTTGACGAAAAATTTAACAG |
| Synthetic BTV17 VP2  | (901) | ATGGACCTGTCCACCCGGTTCCAGTTCAAGCTGGACGAGAAGTTCAACAG |
|                      |       | 951                                              1000 |
| BTV17 VP2 native     | (951) | AACAGATCCAGAACATGTTAATATTTTTGGTGTAAGAGCCCCAGCGACAG |
| Synthetic BTV17 VP2  | (951) | GACCGACCCCGAGCACGTGAATATCTTCGGAGTGAGGGCCCCTGCCACCG |

Fig.1

```
                            1001                                              1050
BTV17 VP2 native    (1001)  ATGAAGGAAGATTTTACGCTCTGATTGCAATCGCAGCGACGGATACACAA
Synthetic BTV17 VP2 (1001)  ACGAGGGCAGATTCTACGCCCTGATCGCCATTGCCGCCACCGACACCCAG
                            1051                                              1100
BTV17 VP2 native    (1051)  AAGGGTAGAGTGTGGAGAACAAATCCGTATCCATGCTTGCGAGGTGCTTT
Synthetic BTV17 VP2 (1051)  AAGGGCAGAGTGTGGAGGACCAACCCCTACCCTTGCCTGAGAGGCGCCCT
                            1101                                              1150
BTV17 VP2 native    (1101)  AGTTGCAGCTGAGTGTGAATTAGGTGACGTTTACAGTACGCTCCGACGTG
Synthetic BTV17 VP2 (1101)  GGTGGCCGCCGAGTGCGAGCTGGGCGACGTGTACAGCACCCTGCGGAGGG
                            1151                                              1200
BTV17 VP2 native    (1151)  TGTATAGATGGAGTCTAAGGCCGGAGTATGGACAGCACGAGCGACAATTA
Synthetic BTV17 VP2 (1151)  TGTACAGATGGAGCCTGAGACCTGAGTACGGCCAGCACGAGAGACAGCTG
                            1201                                              1250
BTV17 VP2 native    (1201)  GAGAACAATAAATACGTCTTTAATCGTATAAATTTATTCGATTCAAACTT
Synthetic BTV17 VP2 (1201)  GAGAACAACAAGTACGTGTTCAACCGGATCAACCTGTTCGACAGCAATCT
                            1251                                              1300
BTV17 VP2 native    (1251)  AGCGGTCGGCGATCAGATAATTCATTGGCGTTATGAGGTTAAAGCATCGG
Synthetic BTV17 VP2 (1251)  GGCCGTGGGCGACCAGATCATCCACTGGCGCTACGAGGTGAAGGCCTCCG
                            1301                                              1350
BTV17 VP2 native    (1301)  CGGAGACGACTTATGACAGTGGATACATGTGTCGGCATGAGGTTGAGGAG
Synthetic BTV17 VP2 (1301)  CCGAGACCACCTACGATAGCGGCTACATGTGCAGGCACGAGGTGGAGGAG
                            1351                                              1400
BTV17 VP2 native    (1351)  GATGAACTATTATGTAAAATCAATGAGGACAAATATAAAGACATGCTGGA
Synthetic BTV17 VP2 (1351)  GACGAGCTGCTGTGTAAGATCAACGAGGACAAGTACAAGGACATGCTGGA
                            1401                                              1450
BTV17 VP2 native    (1401)  CAGAATGATTCAGGGTGGGTGGGATCAGGAAAGATTTAAACTTCATAACA
Synthetic BTV17 VP2 (1401)  CCGGATGATCCAGGGCGGCTGGGATCAGGAGAGGTTCAAGCTGCACAACA
                            1451                                              1500
BTV17 VP2 native    (1451)  TACTGACGGACCCTAACTTATTGACGATTGACTTTGAAAAAGATGCGTAT
Synthetic BTV17 VP2 (1451)  TCCTGACCGACCCCAACCTGCTGACAATCGACTTCGAGAAGGACGCCTAC
                            1501                                              1550
BTV17 VP2 native    (1501)  CTGAACTCACGGTCCGAGTTAGTTTTTCCGGATTATTTCGACAAATGGAT
Synthetic BTV17 VP2 (1501)  CTGAACAGCAGAAGCGAGCTGGTGTTCCCCGACTACTTCGACAAGTGGAT
                            1551                                              1600
BTV17 VP2 native    (1551)  CAGTTCACCAATGTTTAACGCGCGCTTAAGAATTACTAAAGGGGAGATCG
Synthetic BTV17 VP2 (1551)  CAGCAGCCCCATGTTCAACGCCCGGCTGAGAATCACCAAGGGCGAGATCG
                            1601                                              1650
BTV17 VP2 native    (1601)  GAACATCGAAAAGGATGATCCATGGAACAACCGCGCAGTACGTGGATAC
Synthetic BTV17 VP2 (1601)  GCACCAGCAAGAAGGACGACCCCTGGAACAACAGAGCCGTGCGGGGCTAC
                            1651                                              1700
BTV17 VP2 native    (1651)  ATCAAGTCCCCTGCGGAGTCGTTGGATTTTGTTCTCGGGCCTTACTACGA
Synthetic BTV17 VP2 (1651)  ATCAAGAGCCCTGCCGAGTCCCTGGACTTCGTGCTGGGCCCCTACTACGA
                            1701                                              1750
BTV17 VP2 native    (1701)  TCTGCGGCTACTATTTTTTGGCGAGGCGTTGAGCTTAAAACAGGAACAAT
Synthetic BTV17 VP2 (1701)  TCTGCGGCTGCTGTTCTTCGGCGAGGCCCTGAGCCTGAAGCAGGAGCAGA
                            1751                                              1800
BTV17 VP2 native    (1751)  CCGCGGTTTTTCAATATTTGAGTCAGCTCGATGATTTTCCCGCGCTTACG
Synthetic BTV17 VP2 (1751)  GCGCCGTGTTCCAGTACCTGAGCCAGCTGGACGACTTCCCCGCCCTGACC
                            1801                                              1850
BTV17 VP2 native    (1801)  CAGCTAACAGGAGATGCCGTATGCCCACATTCAGGCGGAGCGCTATATAC
Synthetic BTV17 VP2 (1801)  CAGCTGACCGGCGACGCCGTGTGTCCTCACAGCGGCGGAGCCCTGTACAC
                            1851                                              1900
BTV17 VP2 native    (1851)  GTTTAGGAAAGTCGCGCTATTTTTAATCGGGAATTATGAAAAGTTAAGTC
Synthetic BTV17 VP2 (1851)  CTTCAGGAAGGTGGCCCTGTTCCTGATCGGCAACTACGAGAAGCTGAGCC
                            1901                                              1950
BTV17 VP2 native    (1901)  CGGATCTACATGAAGGTATGGAACATCAAACATATGTGCATCCGTCGACT
Synthetic BTV17 VP2 (1901)  CCGACCTGCACGAGGGCATGGAGCACCAGACCTACGTGCACCCCAGCACC
                            1951                                              2000
BTV17 VP2 native    (1951)  GGTGGGACGTATCAGAAATGCGTGCTAGAGATGAAGGACCCTTGTCAACT
Synthetic BTV17 VP2 (1951)  GGCGGCACCTACCAGAAATGCGTGCTGGAGATGAAGGACCCCTGCCAGCT
```

Fig.1 (Continued)

```
                              2001                            2050
BTV17 VP2 native     (2001) AATGTGCTTTGTGATTGATTACATCTTTGAAAAACGTGAGCAGCTACGTG
Synthetic BTV17 VP2  (2001) GATGTGCTTCGTGATCGACTACATCTTCGAGAAGCGGGAGCAGCTGAGAG
                              2051                            2100
BTV17 VP2 native     (2051) ATACCAAAGAGGCGAGGTACATCGTGTATCTAATTCAAAGTCTCACTGGG
Synthetic BTV17 VP2  (2051) ACACCAAGGAGGCCCGGTACATCGTGTACCTGATCCAGAGCCTGACCGGC
                              2101                            2150
BTV17 VP2 native     (2101) ATACAACGGCTGGATGTTCTGAAATCGACGTTCCCGAATTTTTTCCAACG
Synthetic BTV17 VP2  (2101) ATCCAGAGACTGGACGTGCTGAAGAGCACCTTCCCCAACTTCTTCCAGCG
                              2151                            2200
BTV17 VP2 native     (2151) ATTATTAATGCTGAAAGAGATCAAATTTGTGCGTGATTTAAATGTGATCA
Synthetic BTV17 VP2  (2151) GCTGCTGATGCTGAAGGAGATCAAGTTTGTGCGGGACCTGAACGTGATCA
                              2201                            2250
BTV17 VP2 native     (2201) ACTTCCTCCCTCTGATGTTCCTTGTTCATGATAACATCTCGTATTCGCAT
Synthetic BTV17 VP2  (2201) ACTTCCTGCCCCTGATGTTCCTGGTGCACGACAACATCAGCTACAGCCAC
                              2251                            2300
BTV17 VP2 native     (2251) AGACAGTGGTCAATTCCAATGGTACTGTTTGACGATACGATTAAGTTAAT
Synthetic BTV17 VP2  (2251) CGGCAGTGGAGCATCCCTATGGTGCTGTTCGACGACACCATCAAGCTGAT
                              2301                            2350
BTV17 VP2 native     (2301) ACCCGTAGAGGTTGGCGCGTATGCAAATAGATTTGGATTCAAAAGTTTTA
Synthetic BTV17 VP2  (2301) CCCTGTGGAAGTGGGCGCCTACGCCAACAGATTCGGCTTCAAGAGCTTCA
                              2351                            2400
BTV17 VP2 native     (2351) TGAACTTTACACGGTTTCACCCTGGTGAGTCAAAGAAAAAACAGATTGCC
Synthetic BTV17 VP2  (2351) TGAACTTCACCAGGTTCCACCCTGGCGAGAGCAAGAAGAAGCAGATCGCC
                              2401                            2450
BTV17 VP2 native     (2401) GAGGATGTGCATAAGGAGTTTGGAGTGGTCGCTTTCGAATATTACACCAA
Synthetic BTV17 VP2  (2401) GAGGACGTGCACAAGGAGTTCGGCGTGGTGGCCTTCGAGTACTACACCAA
                              2451                            2500
BTV17 VP2 native     (2451) TACAAAAATTTCCCAGGGGAGTGTCCATACACCAGTAATGACTACGAAAA
Synthetic BTV17 VP2  (2451) CACCAAGATCAGCCAGGGCAGCGTGCACACCCCCGTGATGACCACCAAGA
                              2501                            2550
BTV17 VP2 native     (2501) TGGATGTATTGAAGATACATTTGTCTTCTTTATGTGCAGGTCTGGCGGAT
Synthetic BTV17 VP2  (2501) TGGATGTGCTGAAAATCCACCTGAGCAGCCTGTGTGCCGGCCTGGCCGAC
                              2551                            2600
BTV17 VP2 native     (2551) TCTATCGTATATACATTACCGGTTGCGCATCCTAAGAAATGCATCGTTCT
Synthetic BTV17 VP2  (2551) AGCATCGTGTACACCCTGCCCGTGGCCCACCCCAAGAAGTGCATCGTGCT
                              2601                            2650
BTV17 VP2 native     (2601) AATAATTGTGGGAGATGACAAATTGGAACCGCATACGCGTTCAGAACAAA
Synthetic BTV17 VP2  (2601) GATCATTGTGGGCGACGACAAGCTGGAGCCTCACACCAGATCCGAGCAGA
                              2651                            2700
BTV17 VP2 native     (2651) TAGTTAGTCGGTATAATTACTCACGTAAGCACATTTGTGGAGTTGTATCC
Synthetic BTV17 VP2  (2651) TCGTGTCCCGGTACAACTACAGCCGGAAGCACATCTGCGGCGTGGTGTCC
                              2701                            2750
BTV17 VP2 native     (2701) GTCACCGTCGGGCAGAATAGTCAGTTGAGAGTTTATACCTCTGGAATTGT
Synthetic BTV17 VP2  (2701) GTGACAGTGGGCCAGAACAGCCAGCTGAGAGTGTACACCAGCGGCATCGT
                              2751                            2800
BTV17 VP2 native     (2751) TAAACACCGTGTATGCGACAAGTTCATTCTAAAACACAAGTGCAAGGTGA
Synthetic BTV17 VP2  (2751) GAAGCACAGAGTGTGCGACAAGTTCATCCTGAAGCACAAATGCAAGGTGA
                              2801                            2850
BTV17 VP2 native     (2801) TATTAGTGAGGATGCCGGGGTACGTTTTCGGAAATGATGAATTAATGACG
Synthetic BTV17 VP2  (2801) TCCTGGTGAGGATGCCCGGCTACGTGTTCGGCAACGACGAGCTGATGACC
                              2851      2868
BTV17 VP2 native     (2851) AAACTATTGAATGTCTAG
Synthetic BTV17 VP2  (2851) AAGCTGCTGAATGTGTGA
```

Fig.1 (Continued)

```
                              951                                              50
BTV17 VP5 native         (1)  ATGGGGAAGATAATTAAATCGCTAAGTAGATTTGGAAAGAAGGTTGGGAA
synthetic BTV17 VP5      (1)  ATGGGCAAGATCATCAAGAGCCTGAGCCGCTTCGGCAAGAAAGTGGGCAA
SEQ ID NO: 2
                              951                                             100
BTV17 VP5 native        (51)  TGCATTGACGTCGAACACAGCGAAGAAGATTTATTCAACCATCGGGAAAG
synthetic BTV17 VP5     (51)  TGCCCTGACCAGCAACACCGCCAAGAAGATCTACAGCACCATCGGCAAGG
                              951                                             150
BTV17 VP5 native       (101)  CAGCGGAGCGATTTGCTGAAAGTGAAATCGGTGCGGCAACGATAGACGGT
synthetic BTV17 VP5    (101)  CCGCCGAGAGATTCGCCGAGAGCGAGATCGGAGCCGCCACCATCGACGGC
                              951                                             200
BTV17 VP5 native       (151)  TTGGTGCAGGGCAGTGTTCATTCCATAATTACAGGTGAATCGTATGGAGA
synthetic BTV17 VP5    (151)  CTGGTGCAGGGCAGCGTGCACAGCATCATCACCGGCGAGAGCTACGGCGA
                              951                                             250
BTV17 VP5 native       (201)  GTCAGTTAAACAAGCGGTTCTTCTCAACGTGTTAGGTACAGGTGAAGAAT
synthetic BTV17 VP5    (201)  GAGCGTGAAGCAGGCCGTGCTGCTGAACGTGCTGGGCACAGGCGAGGAGC
                              951                                             300
BTV17 VP5 native       (251)  TACCAGATCCTCTGAGCCCCGGCGAACGTGGTATCCAAACGAAAATAAAG
synthetic BTV17 VP5    (251)  TGCCCGACCCCCTGAGCCCTGGCGAGAGAGGCATCCAGACCAAGATCAAG
                              951                                             350
BTV17 VP5 native       (301)  GAATTAGAAGATGAGCAGCGAAATGAACTTGTTCGATTGAAGTATAACAA
synthetic BTV17 VP5    (301)  GAGCTGGAGGACGAGCAGAGAAACGAGCTGGTGCGGCTGAAGTACAACAA
                              951                                             400
BTV17 VP5 native       (351)  AGAGATAACAAAGGAGTTTGGGAAGGAGTTAGAGGAAGTCTACGACTTCA
synthetic BTV17 VP5    (351)  GGAGATCACCAAGGAGTTCGGCAAGGAACTGGAAGAGGTGTACGACTTCA
                              951                                             450
BTV17 VP5 native       (401)  TGAATGGCGAGGCGAAGGAGGAGGAAGTGGTTCAGGAACAATACTCAATG
synthetic BTV17 VP5    (401)  TGAACGGCGAGGCCAAGGAGGAGGAGGTGGTGCAAGAACAGTACAGCATG
                              951                                             500
BTV17 VP5 native       (451)  TTATGTAAAGCAGTGGATTCTTACGAGAAAATATTAAAGGCGGAAGACTC
synthetic BTV17 VP5    (451)  CTGTGCAAGGCCGTGGACAGCTACGAGAAGATCCTGAAGGCCGAGGACTC
                              951                                             550
BTV17 VP5 native       (501)  GAAAATGGCAATGTTGGCGCGCGCACTGCAACGGGAGGCTTCAGAGAGAA
synthetic BTV17 VP5    (501)  CAAGATGGCCATGCTGGCCAGAGCCCTGCAGAGGGAGGCCAGCGAGAGAA
                              951                                             600
BTV17 VP5 native       (551)  GTCAGGACGAGATCAAAATGGTAAAGGAGTACAGACAGAAAATTGATGCG
synthetic BTV17 VP5    (551)  GCCAGGACGAGATCAAGATGGTGAAGGAGTACCGGCAGAAGATCGACGCC
                              951                                             650
BTV17 VP5 native       (601)  CTTAAGAATGCGATCGAGATTGAACGAGACGGAATGCAGGAGGAGGCGAT
synthetic BTV17 VP5    (601)  CTGAAGAACGCCATCGAGATCGAGAGGGACGGCATGCAGGAGGAGGCCAT
                              951                                             700
BTV17 VP5 native       (651)  CCAGGAGATTGCTGGAATGACCGCTGACGTCTTAGAAGCGGCTTCAGAGG
synthetic BTV17 VP5    (651)  CCAAGAAATCGCCGGCATGACCGCCGACGTGCTGGAGGCCGCCAGCGAGG
                              951                                             750
BTV17 VP5 native       (701)  AAGTGCCCTTAATCGGTGCAGGTATGGCCACTGCTGTAGCAACCGGCAGA
synthetic BTV17 VP5    (701)  AGGTGCCCCTGATTGGCGCCGGAATGGCCACCGCCGTGGCCACCGGCAGA
                              951                                             800
BTV17 VP5 native       (751)  GCAATAGAGGGCGCATATAAATTGAAGAAAGTTATAAATGCGTTAAGTGG
synthetic BTV17 VP5    (751)  GCCATCGAGGGCGCCTACAAGCTGAAGAAGGTGATCAACGCCCTGAGCGG
                              951                                             850
BTV17 VP5 native       (801)  AATCGATTTGTCGCATATGAGGAGTCCAAAGATCGAACCAACTATTATCG
synthetic BTV17 VP5    (801)  CATCGACCTGAGCCACATGAGGAGCCCCAAGATCGAGCCTACCATCATCG
                              951                                             900
BTV17 VP5 native       (851)  CTACAACACTGGAGCACCGATTTAAAGAGATACCAGATGAGCAGCTAGCA
synthetic BTV17 VP5    (851)  CCACCACCCTGGAGCACCGGTTCAAGGAGATCCCTGACGAGCAGCTGGCC
                              951                                             950
BTV17 VP5 native       (901)  GTAAGTGTGTTGAATAAGAAGACAGCCGTAACTGATAACTGCAATGAAAT
synthetic BTV17 VP5    (901)  GTGTCCGTGCTGAACAAGAAAACCGCCGTGACCGACAACTGCAACGAGAT
                              951                                            1000
BTV17 VP5 native       (951)  CGCGCATATTAAACAAGAAATATTACCAAAGTTTAAGCAGATTATGGATG
synthetic BTV17 VP5    (951)  CGCCCACATCAAGCAGGAGATCCTGCCCAAGTTCAAGCAGATCATGGACG
```

Fig.2

```
                              1001                                      1050
BTV17 VP5 native      (1001) AGGAGAAGGAGATTGAAGGAATAGAGGACAAAGTGATTCACCCGCGGGTG
synthetic BTV17 VP5   (1001) AGGAGAAGGAGATCGAGGGCATCGAGGACAAGGTGATCCACCCCCGGGTG
                              1051                                      1100
BTV17 VP5 native      (1051) ATGATGAGGTTCAAGATTCCTAGAACGCAGCAACCGCAAATCCACATTTA
synthetic BTV17 VP5   (1051) ATGATGAGGTTCAAGATCCCCAGAACCCAGCAGCCTCAGATCCACATCTA
                              1101                                      1150
BTV17 VP5 native      (1101) TGCGGCTCCGTGGGATTCTGATGACGTATTTTTCTTTCATTGCGTTTCAC
synthetic BTV17 VP5   (1101) TGCCGCCCCTTGGGACAGCGACGACGTGTTCTTCTTCCACTGCGTGTCCC
                              1151                                      1200
BTV17 VP5 native      (1151) ACCATCATCGGAATGAATCTTTCTTTTTGGGATTTGATTTAGGAATCGAT
synthetic BTV17 VP5   (1151) ACCACCACAGGAACGAGAGCTTCTTCCTGGGCTTCGACCTGGGCATCGAC
                              1201                                      1250
BTV17 VP5 native      (1201) GTCGTTCACTTCGAAGACTTAACCAGCCATTGGCACGCATTAGGGCTAGC
synthetic BTV17 VP5   (1201) GTGGTGCACTTCGAGGATCTGACCAGCCACTGGCACGCCCTGGGCCTGGC
                              1251                                      1300
BTV17 VP5 native      (1251) GCAAGAGGCGAGCGGGCGTACGTTAACGGAGGCGTATCGTGAATTTCTCA
synthetic BTV17 VP5   (1251) CCAGGAGGCCTCCGGCAGAACCCTGACCGAGGCCTACAGGGAGTTCCTGA
                              1301                                      1350
BTV17 VP5 native      (1301) ATCTATCAATTTCAAGCACGTATAGTAGCGCGATACATGCGAGACGCATG
synthetic BTV17 VP5   (1301) ACCTGAGCATCAGCAGCACCTACAGCAGCGCCATCCACGCCCGGAGAATG
                              1351                                      1400
BTV17 VP5 native      (1351) ATCAGGTCACGAGCAGTACATCCGATCTTTTTAGGATCAACGCACTACGA
synthetic BTV17 VP5   (1351) ATCAGATCCAGGGCCGTGCACCCTATCTTTCTGGGCAGCACCCACTACGA
                              1401                                      1450
BTV17 VP5 native      (1401) TATTACATATGAGGCTTTAAAAAATAATGCGCAGAGAATAGTCTATGATG
synthetic BTV17 VP5   (1401) CATCACCTACGAGGCCCTGAAAAACAACGCCCAGCGGATCGTGTACGATG
                              1451                                      1500
BTV17 VP5 native      (1451) AGGAACTGCAAATGCATATTCTAAGGGGACCTTTGCATTTTCAACGCCGA
synthetic BTV17 VP5   (1451) AGGAGCTGCAGATGCACATCCTGAGAGGCCCTCTGCACTTCCAGAGGAGA
                              1501                                      1550
BTV17 VP5 native      (1501) GCCATTCTGGGAGCGCTGAAATTTGGAATCAAAATATTAGGCGATAAAAT
synthetic BTV17 VP5   (1501) GCCATCCTGGGCGCCCTGAAGTTCGGCATCAAGATCCTGGGCGACAAGAT
                              1551           1581
BTV17 VP5 native      (1551) TGATGTTCCCCTCTTCTTACGAAATGCATGA
synthetic BTV17 VP5   (1551) CGACGTGCCCCTGTTCCTGAGGAACGCCTGA
```

SEQ ID NO:13
ttaccagtggctgctgccagtggcgataagtcgtgtcttaccggggttggactcaagacgatagtt
accggataaggcgcagcggtcgggctgaacggggggttcgtgcacacagcccagcttggagcgaa
cgacctacaccgaactgagatacctacagcgtgagctatgagaaagcgccacgcttcccgaaggg
agaaaggcggacaggtatccggtaagcggcagggtcggaacaggagagcgcacgagggagcttcc
agggggaaacgcctggtatctttatagtcctgtcgggtttcgccacctctgacttgagcgtcgat
ttttgtgatgctcgtcagggggcggagcctatggaaaaacgccagcaacgcggccttttttacgg
ttcctggccttttgctggccttttgctcacatgttctttcctgcgttatcccctgattctgtgga
taaccgtattaccgcctttgagtgagctgataccgctcgccgcagccgaacgaccgagcgcagcg
agtcagtgagcgaggaagcggaagagcgcccaatacgcaaaccgcctctcccgcgcgttggccg
attcattaatgcagctggcacgacaggtttcccgactggaaagcgggcagtgagcgcaacgcaat
taatgtgagttagctcactcattaggcaccccaggctttacactttatgcttccggctcgtatgt
tgtgtggaattgtgagcggataacaatttcacacaggaaacagctatgaccatgattacgaattg
cggccgcaattctgaatgtttaaatgttatactttggatgaagctataaatatgcattggaaaaat
aatccatttaaagaaaggattcaaatactacaaaacctaagcgataatatgttaactaagcttat
tcttaacgacgctttaaatatacacaaataaacataatttttgtataacctaacaaataactaaa
acataaaaataataaaaggaaatgtaatatcgtaattatttttactcaggaatgggggttaaatatt
tatatcacgtgtatatctatactgttatcgtatactctttacaattactattacgaatatgcaag
agataataagattacgtatttaagagaatcttgtcatgataattgggtacgacatagtgataaat
gctatttcgcatcgttacataaagtcagttggaaagatggatttgacagatgtaacttaataggt
gcaaaaatgttaaataacagcattctatcggaagataggataccagttatattatacaaaaatca
ctggttggataaaacagattctgcaatattcgtaaaagatgaagattactgcgaatttgtaaact
atgacaataaaaagccatttatctcaacgacatcgtgtaattcttccatgttttatgtatgtgtt
tcagatattatgagattactataaacttttgtatacttatattccgtaaactatattaatcatg
aagaaatgaaaagtatagaagctgttcacgagcggttgttgaaaacaacaaaattatacattc
aagatggcttacatatacgtctgtgaggctatcatggataatgacaatgcatctctaaataggtt
tttggacaatggattcgaccctaacacggaatatggtactctacaatctcctcttgaaatggctg
taatgttcaagaataccgaggctataaaaatcttgatgaggtatggagctaaacctgtagttact
gaatgcacaacttcttgtctgcatgatgcggtgttgagagacgactacaaaatagtgaaagatct
gttgaagaataactatgtaaacaatgttctttacagcggaggctttactcctttgtgtttggcag
cttaccttaacaaagttaatttggttaaacttctattggctcattcggcggatgtagatatttca
aacacggatcggttaactcctctacatatagccgtatcaaataaaaatttaacaatggttaaact
tctattgaacaaaggtgctgatactgacttgctggataacatgggacgtactcctttaatgatcg
ctgtacaatctggaaatattgaatatgtagcacactacttaaaaaaaataaaatgtccagaact
gggaaaaattgatcttgccagctgtaattcatggtagaaaagaagtgctcaggctacttttcaac
aaaggagcagatgtaaactacatctttgaaagaaatggaaaatcatatactgttttggaattgat
taaagaaagttactctgagacacaaaagaggtagctgaagtggtactctcaaaggtacgtgacta
attagctataaaaaggatccgggttaattaattagtcatcaggcagggcgagaacgagactatct
gctcgttaattaattagagcttctttattctatacttaaaaagtgaaaataaatacaaaggttct
tgagggttgtgttaaattgaaagcgagaaataatcataaattatttcattatcgcgatatccgtt
aagtttgtatcgtaggtaccctcgagtctagaatcgatcccgggttttatgactagttaatcac
ggccgcttataaagatctaaatgcataatttctaaataatgaaaaaaagtacatcatgagcaac
gcgttagtatattttacaatggagattaacgctctataccgttctatgttattgattcagatga
tgttttagaaaagaaagttattgaatatgaaaactttaatgaagatgaagatgacgacgatgatt
attgttgtaaatctgttttagatgaagaagatgacgcgctaaagtatactatggttacaaagtat
aagtctatactactaatggcgacttgtgcaagaaggtatagtatagtgaaatgttgttagatta
tgattatgaaaaaccaaataaatcagatccatatctaaaggtatctcctttgcacataatttcat
ctattcctagtttagaatacctgcagccaagcttggcactggccgtcgttttacaacgtcgtgac
tgggaaaaccctggcgttacccaacttaatcgccttgcagcacatccccctttcgccagctggcg
taatagcgaagaggcccgcaccgatcgcccttcccaacagttgcgcagcctgaatggcgaatggc

Fig. 6

```
gcctgatgcggtattttctccttacgcatctgtgcggtatttcacaccgcatatggtgcactctc
agtacaatctgctctgatgccgcatagttaagccagccccgacacccgccaacacccgctgacgc
gccctgacgggcttgtctgctcccggcatccgcttacagacaagctgtgaccgtctccgggagct
gcatgtgtcagaggttttcaccgtcatcaccgaaacgcgcgagacgaaagggcctcgtgatacgc
ctattttataggttaatgtcatgataataatggtttcttagacgtcaggtggcacttttcgggg
aaatgtgcgcggaacccctatttgtttattttctaaatacattcaaatatgtatccgctcatga
gacaataaccctgataaatgcttcaataatattgaaaaaggaagagtatgagtattcaacatttc
cgtgtcgcccttattccctttttgcggcattttgccttcctgttttttgctcacccagaaacgct
ggtgaaagtaaaagatgctgaagatcagttgggtgcacgagtgggttacatcgaactggatctca
acagcggtaagatccttgagagttttcgccccgaagaacgttttccaatgatgagcacttttaaa
gttctgctatgtggcgcggtattatcccgtattgacgccgggcaagagcaactcggtcgccgcat
acactattctcagaatgacttggttgagtactcaccagtcacagaaaagcatcttacggatggca
tgacagtaagagaattatgcagtgctgccataaccatgagtgataacactgcggccaacttactt
ctgacaacgatcggaggaccgaaggagctaaccgcttttttgcacaacatgggggatcatgtaac
tcgccttgatcgttgggaaccggagctgaatgaagccataccaaacgacgagcgtgacaccacga
tgcctgtagcaatggcaacaacgttgcgcaaactattaactggcgaactacttactctagcttcc
cggcaacaattaatagactggatggaggcggataaagttgcaggaccacttctgcgctcggccct
tccggctggctggtttattgctgataaatctggagccggtgagcgtgggtctcgcggtatcattg
cagcactggggccagatggtaagccctcccgtatcgtagttatctacacgacggggagtcaggca
actatggatgaacgaaatagacagatcgctgagataggtgcctcactgattaagcattggtaact
gtcagaccaagtttactcatatactttagattgatttaaaacttcatttttaatttaaaagga
tctaggtgaagatcctttttgataatctcatgaccaaaatcccttaacgtgagttttcgttccac
tgagcgtcagaccccgtagaaaagatcaaaggatcttcttgagatccttttttctgcgcgtaat
ctgctgcttgcaaacaaaaaaaccaccgctaccagcggtggtttgtttgccggatcaagagctac
caactctttttccgaaggtaactggcttcagcagagcgcagataccaaatactgtccttctagtg
tagccgtagttaggccaccacttcaagaactctgtagcaccgcctacatacctcgctctgctaat
cctg
```

Feature Map
CDS (3 total)
```
    Synthetic BTV-VP2           Start: 2005    End: 4875
    Synthetic BTV-VP5           Start: 4921    End: 6498
    AmpR                        Start: 7579    End: 8436
Misc. Feature (2 total)
    C5L                         Start: 6562    End: 6966
    C5R                         Start: 248     End: 1783
Promoter Eukaryotic (2 total)
    H6                          Start: 1881    End: 2004
    42K                         Start: 4889    End: 4920
```

Predicted amino acid sequence of product(s)
Synthetic BTV-VP2
```
    1   MEEFVIPVYS EDEIPYALLS RYPLAIQTNV KIEDVEGKHN VVKIPESDMI
   51   DIPRLTIVEA MNYKPARNDG IVVPRLLDIT LRAYDDRKST KSARGIEFMT
  101   NARWMKWAID DRMDIQPLKV TLDHYCSVNH QLFNCVVKAN AANADTIYYD
  151   YFPLEDHKKR CNHTNLDLLR SLTNMELFHA LQGAAYSIKS SYELVANSER
  201   ESLEETYAIG QPKWIHLTRG TRIGNSGLPY ERFISSMVQV IVNGKIPSEI
  251   ANEVAQLNRI RAEWIAATYD RGRIRALELC KILSTIGRKI LNTHEEPKDE
  301   MDLSTRFQFK LDEKFNRTDP EHVNIFGVRA PATDEGRFYA LIAIAATDTQ
  351   KGRVWRTNPY PCLRGALVAA ECELGDVYST LRRVYRWSLR PEYGQHERQL
  401   ENNKYVFNRI NLFDSNLAVG DQIIHWRYEV KASAETTYDS GYMCRHEVEE
  451   DELLCKINED KYKDMLDRMI QGGWDQERFK LHNILTDPNL LTIDFEKDAY
  501   LNSRSELVFP DYFDKWISSP MFNARLRITK GEIGTSKKDD PWNNRAVRGY
  551   IKSPAESLDF VLGPYYDLRL LFFGEALSLK QEQSAVFQYL SQLDDFPALT
  601   QLTGDAVCPH SGGALYTFRK VALFLIGNYE KLSPDLHEGM EHQTYVHPST
  651   GGTYQKCVLE MKDPCQLMCF VIDYIFEKRE QLRDTKEARY IVYLIQSLTG
  701   IQRLDVLKST FPNFFQRLLM LKEIKFVRDL NVINFLPLMF LVHDNISYSH
  751   RQWSIPMVLF DDTIKLIPVE VGAYANRFGF KSFMNFTRFH PGESKKKQIA
  801   EDVHKEFGVV AFEYYTNTKI SQGSVHTPVM TTKMDVLKIH LSSLCAGLAD
  851   SIVYTLPVAH PKKCIVLIIV GDDKLEPHTR SEQIVSRYNY SRKHICGVVS
  901   VTVGQNSQLR VYTSGIVKHR VCDKFILKHK CKVILVRMPG YVFGNDELMT
  951   KLLNV**
```

Synthetic BTV-VP5
```
    1   MGKIIKSLSR FGKKVGNALT SNTAKKIYST IGKAAERFAE SEIGAATIDG
   51   LVQGSVHSII TGESYGESVK QAVLLNVLGT GEELPDPLSP GERGIQTKIK
  101   ELEDEQRNEL VRLKYNKEIT KEFGKELEEV YDFMNGEAKE EEVVQEQYSM
  151   LCKAVDSYEK ILKAEDSKMA MLARALQREA SERSQDEIKM VKEYRQKIDA
  201   LKNAIEIERD GMQEEAIQEI AGMTADVLEA ASEEVPLIGA GMATAVATGR
  251   AIEGAYKLKK VINALSGIDL SHMRSPKIEP TIIATTLEHR FKEIPDEQLA
  301   VSVLNKKTAV TDNCNEIAHI KQEILPKFKQ IMDEEKEIEG IEDKVIHPRV
  351   MMRFKIPRTQ QPQIHIYAAP WDSDDVFFFH CVSHHHRNES FFLGFDLGID
  401   VVHFEDLTSH WHALGLAQEA SGRTLTEAYR EFLNLSISST YSSAIHARRM
  451   IRSRAVHPIF LGSTHYDITY EALKNNAQRI VYDEELQMHI LRGPLHFQRR
  501   AILGALKFGI KILGDKIDVP LFLRNA
```

Fig.11

Nucleotide sequence of arms and insert with translation
Bold: C5 right arm
Italic: BTV-VP2
................: H6 promoter
Double underline: 42K promoter
_____: C5 left arm

```
              M13R                                           C5R→
201        GGAAA CAGCTATGAC CATGATTACG AATTGCGGCC GCAATTCTGA
           CCTTT GTCGATACTG GTACTAATGC TTAACGCCGG CGTTAAGACT
251  ATGTTAAATG TTATACTTTG GATGAAGCTA TAAATATGCA TTGGAAAAAT
     TACAATTTAC AATATGAAAC CTACTTCGAT ATTTATACGT AACCTTTTTA
301  AATCCATTTA AAGAAAGGAT TCAAATACTA CAAAACCTAA GCGATAATAT
     TTAGGTAAAT TTCTTTCCTA AGTTTATGAT GTTTTGGATT CGCTATTATA
351  GTTAACTAAG CTTATTCTTA ACGACGCTTT AAATATACAC AAATAAACAT
     CAATTGATTC GAATAAGAAT TGCTGCGAAA TTTATATGTG TTTATTTGTA
401  AATTTTTGTA TAACCTAACA ATAACTAAA ACATAAAAAT AATAAAGGA
     TTAAAAACAT ATTGGATTGT TTATTGATTT TGTATTTTA TTATTTTCCT
451  AATGTAATAT CGTAATTATT TTACTCAGGA ATGGGGTTAA ATATTTATAT
     TTACATTATA GCATTAATAA AATGAGTCCT TACCCCAATT TATAAATATA
501  CACGTGTATA TCTATACTGT TATCGTATAC TCTTTACAAT TACTATTACG
     GTGCACATAT AGATATGACA ATAGCATATG AGAAATGTTA ATGATAATGC
                                                  7927.DC
551  AATATGCAAG AGATAATAAG ATTACGTATT TAAGAGAATC TTGTCATGAT
     TTATACGTTC TCTATTATTC TAATGCATAA ATTCTCTTAG AACAGTACTA
     7927.DC
601  AATTGGGTAC GACATAGTGA TAAATGCTAT TTCGCATCGT TACATAAAGT
     TTAACCCATG CTGTATCACT ATTTACGATA AAGCGTAGCA ATGTATTTCA
651  CAGTTGGAAA GATGGATTTG ACAGATGTAA CTTAATAGGT GCAAAAATGT
     GTCAACCTTT CTACCTAAAC TGTCTACATT GAATTATCCA CGTTTTTACA
                          7696.CXL
701  TAAATAACAG CATTCTATCG GAAGATAGGA TACCAGTTAT ATTATACAAA
     ATTTATTGTC GTAAGATAGC CTTCTATCCT ATGGTCAATA TAATATGTTT
751  AATCACTGGT TGGATAAAAC AGATTCTGCA ATATTCGTAA AAGATGAAGA
     TTAGTGACCA ACCTATTTTG TCTAAGACGT TATAAGCATT TTCTACTTCT
801  TTACTGCGAA TTTGTAAACT ATGACAATAA AAAGCCATTT ATCTAACGA
     AATGACGCTT AAACATTTGA TACTGTTATT TTTCGGTAAA TAGAGTTGCT
851  CATCGTGTAA TTCTTCCATG TTTTATGTAT GTGTTTCAGA TATTATGAGA
     GTAGCACATT AAGAAGGTAC AAAATACATA CACAAAGTCT ATAATACTCT
901  TTACTATAAA CTTTTTGTAT ACTTATATTC CGTAAACTAT ATTAATCATG
     AATGATATTT GAAAACATA TGAATATAAG GCATTTGATA TAATTAGTAC
951  AAGAAAATGA AAAGTATAG AAGCTGTTCA CGAGCGGTTG TTGAAAACAA
     TTCTTTTACT TTTTCATATC TTCGACAAGT GCTCGCCAAC AACTTTTGTT
                                   7926.DC
1001 CAAAATTATA CATTCAAGAT GGCTTACATA TACGTCTGTG AGGCTATCAT
     GTTTTAATAT GTAAGTTCTA CCGAATGTAT ATGCAGACAC TCCGATAGTA
1051 GGATAATGAC AATGCATCTC TAAATAGGTT TTTGGACAAT GGATTCGACC
     CCTATTACTG TTACGTAGAG ATTTATCCAA AAACCTGTTA CCTAAGCTGG
1101 CTAACACGGA ATATGGTACT CTACAATCTC CTCTTGAAAT GGCTGTAATG
     GATTGTGCCT TATACCATGA GATGTTAGAG GAGAACTTTA CCGACATTAC
1151 TTCAAGAATA CCGAGGCTAT AAAAATCTTG ATGAGGTATG GAGCTAAACC
```

Fig.11 (Continued)

```
              AAGTTCTTAT GGCTCCGATA TTTTTAGAAC TACTCCATAC CTCGATTTGG
                                    7697.CXL
      1201    TGTAGTTACT GAATGCACAA CTTCTTGTCT GCATGATGCG GTGTTGAGAG
              ACATCAATGA CTTACGTGTT GAAGAACAGA CGTACTACGC CACAACTCTC
      1251    ACGACTACAA AATAGTGAAA GATCTGTTGA AGAATAACTA TGTAAACAAT
              TGCTGATGTT TTATCACTTT CTAGACAACT TCTTATTGAT ACATTTGTTA
      1301    GTTCTTTACA GCGGAGGCTT TACTCCTTTG TGTTTGGCAG CTTACCTTAA
              CAAGAAATGT CGCCTCCGAA ATGAGGAAAC ACAAACCGTC GAATGGAATT
      1351    CAAAGTTAAT TTGGTTAAAC TTCTATTGGC TCATTCGGCG GATGTAGATA
              GTTTCAATTA AACCAATTTG AAGATAACCG AGTAAGCCGC CTACATCTAT
      1401    TTTCAAACAC GGATCGGTTA ACTCCTCTAC ATATAGCCGT ATCAAATAAA
              AAAGTTTGTG CCTAGCCAAT TGAGGAGATG TATATCGGCA TAGTTTATTT
                                              7925.DC
      1451    AATTTAACAA TGGTTAAACT TCTATTGAAC AAAGGTGCTG ATACTGACTT
              TTAAATTGTT ACCAATTTGA AGATAACTTG TTTCCACGAC TATGACTGAA
      1501    GCTGGATAAC ATGGGACGTA CTCCTTTAAT GATCGCTGTA CAATCTGGAA
              CGACCTATTG TACCCTGCAT GAGGAAATTA CTAGCGACAT GTTAGACCTT
      1551    ATATTGAAAT ATGTAGCACA CTACTTAAAA AAAATAAAAT GTCCAGAACT
              TATAACTTTA TACATCGTGT GATGAATTTT TTTTATTTTA CAGGTCTTGA
      1601    GGGAAAAATT GATCTTGCCA GCTGTAATTC ATGGTAGAAA AGAAGTGCTC
              CCCTTTTTAA CTAGAACGGT CGACATTAAG TACCATCTTT TCTTCACGAG
                                                              7792.SL
      1651    AGGCTACTTT TCAACAAAGG AGCAGATGTA AACTACATCT TTGAAAGAAA
              TCCGATGAAA AGTTGTTTCC TCGTCTACAT TTGATGTAGA AACTTTCTTT
              7792.SL
      1701    TGGAAAATCA TATACTGTTT TGGAATTGAT TAAAGAAAGT TACTCTGAGA
              ACCTTTTAGT ATATGACAAA ACCTTAACTA ATTTCTTTCA ATGAGACTCT
      1751    CACAAAAGAG GTAGCTGAAG TGGTACTCTC AAAGGTACGT GACTAATTAG
              GTGTTTTCTC CATCGACTTC ACCATGAGAG TTTCCATGCA CTGATTAATC
      1801    CTATAAAAAG GATCCGGGTT AATTAATTAG TCATCAGGCA GGGCGAGAAC
              GATATTTTTC CTAGGCCCAA TTAATTAATC AGTAGTCCGT CCCGCTCTTG
                                                    H6p→
      1851    GAGACTATCT GCTCGTTAAT TAATTAGAGC TTCTTTATTC TATACTTAAA
              CTCTGATAGA CGAGCAATTA ATTAATCTCG AAGAAATAAG ATATGAATTT
      1901    AAGTGAAAAT AAATACAAAG GTTCTTGAGG GTTGTGTTAA ATTGAAAGCG
              TTCACTTTTA TTTATGTTTC CAAGAACTCC CAACACAATT TAACTTTCGC
      1951    AGAAATAATC ATAAATTATT TCATTATCGC GATATCCGTT AAGTTTGTAT
              TCTTTATTAG TATTTAATAA AGTAATAGCG CTATAGGCAA TTCAAACATA
              BTV-VP2→
                13249JY
                 M  E    E  F  V  I    P  V  Y    S  E  D    E  I  P  Y ·
      2001    CGTAATGGAG GAGTTCGTGA TCCCCGTGTA CAGCGAGGAC GAGATCCCCT
              GCATTACCTC CTCAAGCACT AGGGGCACAT GTCGCTCCTG CTCTAGGGGA
                            13250JY
              .. A  L  L    S  R  Y    P  L  A  I    Q  T  N    V  K  I
      2051    ACGCCCTGCT GAGCAGATAC CCTCTGGCCA TCCAGACCAA CGTGAAGATC
              TGCGGGACGA CTCGTCTATG GGAGACCGGT AGGTCTGGTT GCACTTCTAG
                 E  D  V  E    G  K  H    N  V  V    K  I  P  E    S  D  M ·
      2101    GAGGACGTGG AGGGCAAGCA CAACGTGGTG AAGATCCCCG AGAGCGACAT
              CTCCTGCACC TCCCGTTCGT GTTGCACCAC TTCTAGGGGC TCTCGCTGTA
```

Fig. 11 (Continued)

```
            . I D I   P R L T   I V E   A M N   Y K P A ·
2151    GATCGACATC CCCCGGCTGA CCATCGTGGA GGCCATGAAC TACAAGCCCG
        CTAGCTGTAG GGGGCCGACT GGTAGCACCT CCGGTACTTG ATGTTCGGGC
        .. R N D   G I V   V P R L   L D I   T L R
2201    CCAGGAACGA CGGCATCGTG GTGCCTAGAC TGCTGGACAT CACCCTGAGA
        GGTCCTTGCT GCCGTAGCAC CACGGATCTG ACGACCTGTA GTGGGACTCT
          A Y D D   R K S   T K S   A R G I   E F M ·
2251    GCCTACGACG ACCGGAAGAG CACCAAGAGC GCCAGAGGCA TCGAGTTCAT
        CGGATGCTGC TGGCCTTCTC GTGGTTCTCG CGGTCTCCGT AGCTCAAGTA
        . T N A   R W M K   W A I   D D R   M D I Q ·
2301    GACCAACGCC CGGTGGATGA AGTGGGCCAT CGACGACAGG ATGGACATCC
        CTGGTTGCGG GCCACCTACT TCACCCGGTA GCTGCTGTCC TACCTGTAGG
                                                13251JY
        . P L K   V T L   D H Y C   S V N   H Q L
2351    AGCCCCTGAA GGTGACCCTG GACCACTACT GCAGCGTGAA TCACCAGCTG
        TCGGGGACTT CCACTGGGAC CTGGTGATGA CGTCGCACTT AGTGGTCGAC
                                                    13252JY
          F N C   V V K A   N A A   N A D T   I Y Y ·
2401    TTCAACTGCG TGGTGAAGGC CAACGCCGCC AATGCCGACA CCATCTACTA
        AAGTTGACGC ACCACTTCCG GTTGCGGCGG TTACGGCTGT GGTAGATGAT
        . D Y F   P L E D   H K K   R C N   H T N L ·
2451    CGACTACTTC CCCCTGGAGG ACCACAAGAA GCGGTGCAAC CACACCAACC
        GCTGATGAAG GGGGACCTCC TGGTGTTCTT CGCCACGTTG GTGTGGTTGG
        .. D L L   R S L   T N M E   L F H   A L Q
2501    TGGACCTGCT GAGGAGCCTG ACCAACATGG AGCTGTTCCA CGCCCTGCAG
        ACCTGGACGA CTCCTCGGAC TGGTTGTACC TCGACAAGGT GCGGGACGTC
          G A A Y   S I K   S S Y   E L V A   N S E ·
2551    GGAGCCGCCT ACAGCATCAA GAGCAGCTAC GAACTGGTGG CCAACAGCGA
        CCTCGGCGGA TGTCGTAGTT CTCGTCGATG CTTGACCACC GGTTGTCGCT
        . R E S   L E E T   Y A I   G Q P   K W I H ·
2601    GAGAGAGAGC CTGGAGGAGA CCTACGCCAT CGGCCAGCCT AAGTGGATCC
        CTCTCTCTCG GACCTCCTCT GGATGCGGTA GCCGGTCGGA TTCACCTAGG
        .. L T R   G T R   I G N S   G L P   Y E R
2651    ACCTGACCAG GGGCACCAGA ATCGGCAACA GCGGCCTGCC TTACGAGAGA
        TGGACTGGTC CCCGTGGTCT TAGCCGTTGT CGCCGGACGG AATGCTCTCT
          F I S S   M V Q   V I V   N G K I   P S E ·
2701    TTCATCAGCA GCATGGTGCA GGTGATCGTG AACGGCAAGA TCCCTAGCGA
        AAGTAGTCGT CGTACCACGT CCACTAGCAC TTGCCGTTCT AGGGATCGCT
        . I A N   E V A Q   L N R   I R A   E W I A ·
2751    GATCGCCAAC GAGGTGGCCC AGCTGAACAG AATCCGGGCC GAGTGGATCG
        CTAGCGGTTG CTCCACCGGG TCGACTTGTC TTAGGCCCGG CTCACCTAGC
                13253JY
        .. A T Y   D R G   R I R A   L E L   C K I
2801    CCGCCACCTA CGACAGAGGC AGGATCAGAG CCCTGGAGCT GTGCAAGATC
        GGCGGTGGAT GCTGTCTCCG TCCTAGTCTC GGGACCTCGA CACGTTCTAG
                13254JY
          L S T I   G R K   I L N   T H E E   P K D ·
2851    CTGAGCACCA TCGGCCGGAA GATCCTGAAT ACCCACGAGG AGCCCAAGGA
        GACTCGTGGT AGCCGGCCTT CTAGGACTTA TGGGTGCTCC TCGGGTTCCT
        . E M D   L S T R   F Q F   K L D   E K F N ·
```

Fig. 11 (Continued)

```
2901  CGAGATGGAC CTGTCCACCC GGTTCCAGTT CAAGCTGGAC GAGAAGTTCA
      GCTCTACCTG GACAGGTGGG CCAAGGTCAA GTTCGACCTG CTCTTCAAGT
       .. R   T   D    P  E   H   V   N    I  F   G   V   R    A  P   A
2951  ACAGGACCGA CCCCGAGCAC GTGAATATCT TCGGAGTGAG GGCCCCTGCC
      TGTCCTGGCT GGGGCTCGTG CACTTATAGA AGCCTCACTC CCGGGGACGG
          T   D   E   G    R  F   Y   A    L  I   A   I   A    A  T   D   T  ·
3001  ACCGACGAGG GCAGATTCTA CGCCCTGATC GCCATTGCCG CCACCGACAC
      TGGCTGCTCC CGTCTAAGAT GCGGGACTAG CGGTAACGGC GGTGGCTGTG
       .  Q  K   G   R    V  W   R   T    N  P   Y   P   C    L  R   G   A  ·
3051  CCAGAAGGGC AGAGTGTGGA GGACCAACCC CTACCCTTGC CTGAGAGGCG
      GGTCTTCCCG TCTCACACCT CCTGGTTGGG GATGGGAACG GACTCTCCGC
       .. L   V   A   A    E  C   E   L    G  D   V   Y   S    T  L   R
3101  CCCTGGTGGC CGCCGAGTGC GAGCTGGGCG ACGTGTACAG CACCCTGCGG
      GGGACCACCG GCGGCTCACG CTCGACCCGC TGCACATGTC GTGGGACGCC
          R   V   Y   R    W  S   L   R    P  E   Y   G   Q    H  E   R   Q  ·
3151  AGGGTGTACA GATGGAGCCT GAGACCTGAG TACGGCCAGC ACGAGAGACA
      TCCCACATGT CTACCTCGGA CTCTGGACTC ATGCCGGTCG TGCTCTCTGT
                                                       13255JY
       L   E   N   N    K  Y   V    F  N   R    I  N   L   F    D  S   N  ·
3201  GCTGGAGAAC AACAAGTACG TGTTCAACCG GATCAACCTG TTCGACAGCA
      CGACCTCTTG TTGTTCATGC ACAAGTTGGC CTAGTTGGAC AAGCTGTCGT
                                                 13256JY
       .. L   A   V    G  D   Q    I  I   H    W  R   Y   E    V  K   A
3251  ATCTGGCCGT GGGCGACCAG ATCATCCACT GGCGCTACGA GGTGAAGGCC
      TAGACCGGCA CCCGCTGGTC TAGTAGGTGA CCGCGATGCT CCACTTCCGG
          S   A   E   T    T  Y   D    S  G   Y    M  C   R   H    E  V   E  ·
3301  TCCGCCGAGA CCACCTACGA TAGCGGCTAC ATGTGCAGGC ACGAGGTGGA
      AGGCGGCTCT GGTGGATGCT ATCGCCGATG TACACGTCCG TGCTCCACCT
       .  E  D   E    L  L   C   K    I  N   E    D  K   Y    K  D   M   L  ·
3351  GGAGGACGAG CTGCTGTGTA AGATCAACGA GGACAAGTAC AAGGACATGC
      CCTCCTGCTC GACGACACAT TCTAGTTGCT CCTGTTCATG TTCCTGTACG
       .. D   R   M    I  Q   G    G  W   D    Q  E   R   F    K  L   H
3401  TGGACCGGAT GATCCAGGGC GGCTGGGATC AGGAGAGGTT CAAGCTGCAC
      ACCTGGCCTA CTAGGTCCCG CCGACCCTAG TCCTCTCCAA GTTCGACGTG
          N   I   L   T    D  P   N    L  L   T    I  D   F   E    K  D   A  ·
3451  AACATCCTGA CCGACCCCAA CCTGCTGACA ATCGACTTCG AGAAGGACGC
      TTGTAGGACT GGCTGGGGTT GGACGACTGT TAGCTGAAGC TCTTCCTGCG
       .  Y  L   N    S  R   S   E    L  V   F    P  D   Y    F  D   K   W  ·
3501  CTACCTGAAC AGCAGAAGCG AGCTGGTGTT CCCCGACTAC TTCGACAAGT
      GATGGACTTG TCGTCTTCGC TCGACCACAA GGGGCTGATG AAGCTGTTCA
       .. I   S   S    P  M   F    N  A   R    L  R   I   T    K  G   E
3551  GGATCAGCAG CCCCATGTTC AACGCCCGGC TGAGAATCAC CAAGGGCGAG
      CCTAGTCGTC GGGGTACAAG TTGCGGGCCG ACTCTTAGTG GTTCCCGCTC
                                                       13257JY
       I   G   T   S    K  K   D    D  P   W    N  N   R   A    V  R   G  ·
3601  ATCGGCACCA GCAAGAAGGA CGACCCCTGG AACAACAGAG CCGTGCGGGG
      TAGCCGTGGT CGTTCTTCCT GCTGGGGACC TTGTTGTCTC GGCACGCCCC
             13257JY                                   13258JY
       Y   I   K   S    P  A   E    S  L   D    F  V   L    G  P   Y   Y  ·
3651  CTACATCAAG AGCCCTGCCG AGTCCCTGGA CTTCGTGCTG GGCCCCTACT
      GATGTAGTTC TCGGGACGGC TCAGGGACCT GAAGCACGAC CCGGGGATGA
```

Fig.11 (Continued)

```
                13258JY
          ..  D   L   R      L   L   F      F   G   E      A   L   S      L   K   Q   E
3701      ACGATCTGCG  GCTGCTGTTC  TTCGGCGAGG  CCCTGAGCCT  GAAGCAGGAG
          TGCTAGACGC  CGACGACAAG  AAGCCGCTCC  GGGACTCGGA  CTTCGTCCTC
            Q   S   A   V      F   Q   Y      L   S   Q      L   D   D   F      P   A   L   .
3751      CAGAGCGCCG  TGTTCCAGTA  CCTGAGCCAG  CTGGACGACT  TCCCCGCCCT
          GTCTCGCGGC  ACAAGGTCAT  GGACTCGGTC  GACCTGCTGA  AGGGGCGGGA
          .  T   Q   L      T   G   D      A   V   C      P   H   S   G      G   A   L   Y   .
3801      GACCCAGCTG  ACCGGCGACG  CCGTGTGTCC  TCACAGCGGC  GGAGCCCTGT
          CTGGGTCGAC  TGGCCGCTGC  GGCACACAGG  AGTGTCGCCG  CCTCGGGACA
          ..  T   F   R      K   V   A      L   F   L   I      G   N   Y      E   K   L
3851      ACACCTTCAG  GAAGGTGGCC  CTGTTCCTGA  TCGGCAACTA  CGAGAAGCTG
          TGTGGAAGTC  CTTCCACCGG  GACAAGGACT  AGCCGTTGAT  GCTCTTCGAC
            S   P   D      L   H   E   G      M   E   H      Q   T   Y      V   H   P   S   .
3901      AGCCCCGACC  TGCACGAGGG  CATGGAGCAC  CAGACCTACG  TGCACCCCAG
          TCGGGGCTGG  ACGTGCTCCC  GTACCTCGTG  GTCTGGATGC  ACGTGGGGTC
          .  T   G   G      T   Y   Q   K      C   V   L      E   M   K      D   P   C   Q   .
3951      CACCGGCGGC  ACCTACCAGA  AATGCGTGCT  GGAGATGAAG  GACCCCTGCC
          GTGGCCGCCG  TGGATGGTCT  TTACGCACGA  CCTCTACTTC  CTGGGGACGG
          ..  L   M   C      F   V   I      D   Y   I   F      E   K   R      E   Q   L
4001      AGCTGATGTG  CTTCGTGATC  GACTACATCT  TCGAGAAGCG  GGAGCAGCTG
          TCGACTACAC  GAAGCACTAG  CTGATGTAGA  AGCTCTTCGC  CCTCGTCGAC
                               13259JY
            R   D   T   K      E   A   R      Y   I   V      Y   L   I   Q      S   L   T   .
4051      AGAGACACCA  AGGAGGCCCG  GTACATCGTG  TACCTGATCC  AGAGCCTGAC
          TCTCTGTGGT  TCCTCCGGGC  CATGTAGCAC  ATGGACTAGG  TCTCGGACTG
                               13260JY
          .  G   I   Q      R   L   D   V      L   K   S      T   F   P      N   F   F   Q   .
4101      CGGCATCCAG  AGACTGGACG  TGCTGAAGAG  CACCTTCCCC  AACTTCTTCC
          GCCGTAGGTC  TCTGACCTGC  ACGACTTCTC  GTGGAAGGGG  TTGAAGAAGG
          ..  R   L   L      M   L   K      E   I   K   F      V   R   D      L   N   V
4151      AGCGGCTGCT  GATGCTGAAG  GAGATCAAGT  TTGTGCGGGA  CCTGAACGTG
          TCGCCGACGA  CTACGACTTC  CTCTAGTTCA  AACACGCCCT  GGACTTGCAC
            I   N   F   L      P   L   M      F   L   V      H   D   N   I      S   Y   S   .
4201      ATCAACTTCC  TGCCCCTGAT  GTTCCTGGTG  CACGACAACA  TCAGCTACAG
          TAGTTGAAGG  ACGGGGACTA  CAAGGACCAC  GTGCTGTTGT  AGTCGATGTC
          .  H   R   Q      W   S   I   P      M   V   L      F   D   D      T   I   K   L   .
4251      CCACCGGCAG  TGGAGCATCC  CTATGGTGCT  GTTCGACGAC  ACCATCAAGC
          GGTGGCCGTC  ACCTCGTAGG  GATACCACGA  CAAGCTGCTG  TGGTAGTTCG
          ..  I   P   V      E   V   G      A   Y   A   N      R   F   G      F   K   S
4301      TGATCCCTGT  GGAAGTGGGC  GCCTACGCCA  ACAGATTCGG  CTTCAAGAGC
          ACTAGGGACA  CCTTCACCCG  CGGATGCGGT  TGTCTAAGCC  GAAGTTCTCG
            F   M   N   F      T   R   F      H   P   G      E   S   K   K      K   Q   I   .
4351      TTCATGAACT  TCACCAGGTT  CCACCCTGGC  GAGAGCAAGA  AGAAGCAGAT
          AAGTACTTGA  AGTGGTCCAA  GGTGGGACCG  CTCTCGTTCT  TCTTCGTCTA
          .  A   E   D      V   H   K   E      F   G   V      A   F   E      Y   Y   T   .
4401      CGCCGAGGAC  GTGCACAAGG  AGTTCGGCGT  GGTGGCCTTC  GAGTACTACA
          GCGGCTCCTG  CACGTGTTCC  TCAAGCCGCA  CCACCGGAAG  CTCATGATGT
                               13261JY
          ..  N   T   K      I   S   Q      G   S   V   H      T   P   V      M   T   T
4451      CCAACACCAA  GATCAGCCAG  GGCAGCGTGC  ACACCCCCGT  GATGACCACC
          GGTTGTGGTT  CTAGTCGGTC  CCGTCGCACG  TGTGGGGGCA  CTACTGGTGG
```

Fig.11 (Continued)

```
                                                              13262JY
               K  M  D  V  L  K  I  H  L  S  S  L  C  A  G  L  A ·
       4501    AAGATGGATG TGCTGAAAAT CCACCTGAGC AGCCTGTGTG CCGGCCTGGC
               TTCTACCTAC ACGACTTTTA GGTGGACTCG TCGGACACAC GGCCGGACCG
                . D  S  I  V  Y  T  L  P  V  A  H  P  K  K  C  I  V ·
       4551    CGACAGCATC GTGTACACCC TGCCCGTGGC CCACCCCAAG AAGTGCATCG
               GCTGTCGTAG CACATGTGGG ACGGGCACCG GGTGGGGTTC TTCACGTAGC
                .. L  I  I  V  G  D  D  K  L  E  P  H  T  R  S  E
       4601    TGCTGATCAT TGTGGGCGAC GACAAGCTGG AGCCTCACAC CAGATCCGAG
               ACGACTAGTA ACACCCGCTG CTGTTCGACC TCGGAGTGTG GTCTAGGCTC
                   Q  I  V  S  R  Y  N  Y  S  R  K  H  I  C  G  V  V ·
       4651    CAGATCGTGT CCCGGTACAA CTACAGCCGG AAGCACATCT GCGGCGTGGT
               GTCTAGCACA GGGCCATGTT GATGTCGGCC TTCGTGTAGA CGCCGCACCA
                . S  V  T  V  G  Q  N  S  Q  L  R  V  Y  T  S  G  I ·
       4701    GTCCGTGACA GTGGGCCAGA ACAGCCAGCT GAGAGTGTAC ACCAGCGGCA
               CAGGCACTGT CACCCGGTCT TGTCGGTCGA CTCTCACATG TGGTCGCCGT
                .. V  K  H  R  V  C  D  K  F  I  L  K  H  K  C  K
       4751    TCGTGAAGCA CAGAGTGTGC GACAAGTTCA TCCTGAAGCA CAAATGCAAG
               AGCACTTCGT GTCTCACACG CTGTTCAAGT AGGACTTCGT GTTTACGTTC
                                                              13263JY
               V  I  L  V  R  M  P  G  Y  V  F  G  N  D  E  L  M ·
       4801    GTGATCCTGG TGAGGATGCC CGGCTACGTG TTCGGCAACG ACGAGCTGAT
               CACTAGGACC ACTCCTACGG GCCGATGCAC AAGCCGTTGC TGCTCGACTA
                                                                    13264JY
                    13263JY
                . T  K  L  L  N  V  *  *           42Kp→
       4851    GACCAAGCTG CTGAATGTGT GATGACTCGA GTTTTTATTC AAAATTGAAA
               CTGGTTCGAC GACTTACACA CTACTGAGCT CAAAAATAAG TTTTTAACTTT
               13264JY              BTV-VP5→
                                        13265.JY
                                M  G  K  I  I  K  S  L  S  R
       4901    ATATATAATT ACAATATAAA ATGGGCAAGA TCATCAAGAG CCTGAGCCGC
               TATATATTAA TGTTATATTT TACCCGTTCT AGTAGTTCTC GGACTCGGCG
                                        13266.JY
                F  G  K  K  V  G  N  A  L  T  S  N  T  A  K  K  I ·
       4951    TTCGGCAAGA AAGTGGGCAA TGCCCTGACC AGCAACACCG CCAAGAAGAT
               AAGCCGTTCT TTCACCCGTT ACGGGACTGG TCGTTGTGGC GGTTCTTCTA
                . Y  S  T  I  G  K  A  A  E  R  F  A  E  S  E  I  G ·
       5001    CTACAGCACC ATCGGCAAGG CCGCCGAGAG ATTCGCCGAG AGCGAGATCG
               GATGTCGTGG TAGCCGTTCC GGCGGCTCTC TAAGCGGCTC TCGCTCTAGC
                .. A  A  T  I  D  G  L  V  Q  G  S  V  H  S  I  I
       5051    GAGCCGCCAC CATCGACGGC CTGGTGCAGG GCAGCGTGCA CAGCATCATC
               CTCGGCGGTG GTAGCTGCCG GACCACGTCC CGTCGCACGT GTCGTAGTAG
                   T  G  E  S  Y  G  E  S  V  K  Q  A  V  L  L  N  V ·
       5101    ACCGGCGAGA GCTACGGCGA GAGCGTGAAG CAGGCCGTGC TGCTGAACGT
               TGGCCGCTCT CGATGCCGCT CTCGCACTTC GTCCGGCACG ACGACTTGCA
                . L  G  T  G  E  E  L  P  D  P  L  S  P  G  E  R  G ·
       5151    GCTGGGCACA GGCGAGGAGC TGCCCGACCC CCTGAGCCCT GGCGAGAGAG
               CGACCCGTGT CCGCTCCTCG ACGGGCTGGG GGACTCGGGA CCGCTCTCTC
                .. I  Q  T  K  I  K  E  L  E  D  E  Q  R  N  E  L
       5201    GCATCCAGAC CAAGATCAAG GAGCTGGAGG ACGAGCAGAG AAACGAGCTG
```

Fig.11 (Continued)

```
         CGTAGGTCTG GTTCTAGTTC CTCGACCTCC TGCTCGTCTC TTTGCTCGAC
           V  R  L  K  Y  N  K  E  I  T  K  E  F  G  K  E  L  ·
   5251  GTGCGGCTGA AGTACAACAA GGAGATCACC AAGGAGTTCG GCAAGGAACT
         CACGCCGACT TCATGTTGTT CCTCTAGTGG TTCCTCAAGC CGTTCCTTGA
                                  13267.JY
         .  E  E  V  Y  D  F  M  N  G  E  A  K  E  E  V  V  ·
   5301  GGAAGAGGTG TACGACTTCA TGAACGGCGA GGCCAAGGAG GAGGAGGTGG
         CCTTCTCCAC ATGCTGAAGT ACTTGCCGCT CCGGTTCCTC CTCCTCCACC
                                  13268.JY
         ..  Q  E  Q  Y  S  M  L  C  K  A  V  D  S  Y  E  K
   5351  TGCAAGAACA GTACAGCATG CTGTGCAAGG CCGTGGACAG CTACGAGAAG
         ACGTTCTTGT CATGTCGTAC GACACGTTCC GGCACCTGTC GATGCTCTTC
           I  L  K  A  E  D  S  K  M  A  M  L  A  R  A  L  Q  ·
   5401  ATCCTGAAGG CCGAGGACTC CAAGATGGCC ATGCTGGCCA GAGCCCTGCA
         TAGGACTTCC GGCTCCTGAG GTTCTACCGG TACGACCGGT CTCGGGACGT
         .  R  E  A  S  E  R  S  Q  D  E  I  K  M  V  K  E  Y  ·
   5451  GAGGGAGGCC AGCGAGAGAA GCCAGGACGA GATCAAGATG GTGAAGGAGT
         CTCCCTCCGG TCGCTCTCTT CGGTCCTGCT CTAGTTCTAC CACTTCCTCA
         ..  R  Q  K  I  D  A  L  K  N  A  I  E  I  E  R  D
   5501  ACCGGCAGAA GATCGACGCC CTGAAGAACG CCATCGAGAT CGAGAGGGAC
         TGGCCGTCTT CTAGCTGCGG GACTTCTTGC GGTAGCTCTA GCTCTCCCTG
           G  M  Q  E  E  A  I  Q  E  I  A  G  M  T  A  D  V  ·
   5551  GGCATGCAGG AGGAGGCCAT CCAAGAAATC GCCGGCATGA CCGCCGACGT
         CCGTACGTCC TCCTCCGGTA GGTTCTTTAG CGGCCGTACT GGCGGCTGCA
         .  L  E  A  A  S  E  E  V  P  L  I  G  A  G  M  A  T  ·
   5601  GCTGGAGGCC GCCAGCGAGG AGGTGCCCCT GATTGGCGCC GGAATGGCCA
         CGACCTCCGG CGGTCGCTCC TCCACGGGGA CTAACCGCGG CCTTACCGGT
         ..  A  V  A  T  G  R  A  I  E  G  A  Y  K  L  K  K
   5651  CCGCCGTGGC CACCGGCAGA GCCATCGAGG GCGCCTACAA GCTGAAGAAG
         GGCGGCACCG GTGGCCGTCT CGGTAGCTCC CGCGGATGTT CGACTTCTTC
                                  13269.JY
           V  I  N  A  L  S  G  I  D  L  S  H  M  R  S  P  K  ·
   5701  GTGATCAACG CCCTGAGCGG CATCGACCTG AGCCACATGA GGAGCCCCAA
         CACTAGTTGC GGGACTCGCC GTAGCTGGAC TCGGTGTACT CCTCGGGGTT
                                  13270.JY
         .  I  E  P  T  I  I  A  T  T  L  E  H  R  F  K  E  I  ·
   5751  GATCGAGCCT ACCATCATCG CCACCACCCT GGAGCACCGG TTCAAGGAGA
         CTAGCTCGGA TGGTAGTAGC GGTGGTGGGA CCTCGTGGCC AAGTTCCTCT
         ..  P  D  E  Q  L  A  V  S  V  L  N  K  K  T  A  V
   5801  TCCCTGACGA GCAGCTGGCC GTGTCCGTGC TGAACAAGAA AACCGCCGTG
         AGGGACTGCT CGTCGACCGG CACAGGCACG ACTTGTTCTT TTGGCGGCAC
           T  D  N  C  N  E  I  A  H  I  K  Q  E  I  L  P  K  ·
   5851  ACCGACAACT GCAACGAGAT CGCCCACATC AAGCAGGAGA TCCTGCCCAA
         TGGCTGTTGA CGTTGCTCTA GCGGGTGTAG TTCGTCCTCT AGGACGGGTT
         .  F  K  Q  I  M  D  E  E  K  E  I  E  G  I  E  D  K  ·
   5901  GTTCAAGCAG ATCATGGACG AGGAGAAGGA GATCGAGGGC ATCGAGGACA
         CAAGTTCGTC TAGTACCTGC TCCTCTTCCT CTAGCTCCCG TAGCTCCTGT
         ..  V  I  H  P  R  V  M  M  R  F  K  I  P  R  T  Q
   5951  AGGTGATCCA CCCCCGGGTG ATGATGAGGT TCAAGATCCC CAGAACCCAG
         TCCACTAGGT GGGGGCCCAC TACTACTCCA AGTTCTAGGG GTCTTGGGTC
           Q  P  Q  I  H  I  Y  A  A  P  W  D  S  D  D  V  F
   6001  CAGCCTCAGA TCCACATCTA TGCCGCCCCT TGGGACAGCG ACGACGTGTT
```

Fig.11 (Continued)

```
             GTCGGAGTCT AGGTGTAGAT ACGGCGGGGA ACCCTGTCGC TGCTGCACAA
             . F   F   H   C   V   S   H   H   H   R   N   E   S   F   F   L   G  ·
      6051   CTTCTTCCAC TGCGTGTCCC ACCACCACAG GAACGAGAGC TTCTTCCTGG
             GAAGAAGGTG ACGCACAGGG TGGTGGTGTC CTTGCTCTCG AAGAAGGACC
             ..  F   D   L   G   I   D   V   V   H   F   E   D   L   T   S   H
      6101   GCTTCGACCT GGGCATCGAC GTGGTGCACT TCGAGGATCT GACCAGCCAC
             CGAAGCTGGA CCCGTAGCTG CACCACGTGA AGCTCCTAGA CTGGTCGGTG
                        13271.JY
              W   H   A   L   G   L   A   Q   E   A   S   G   R   T   L   T   E  ·
      6151   TGGCACGCCC TGGGCCTGGC CCAGGAGGCC TCCGGCAGAA CCCTGACCGA
             ACCGTGCGGG ACCCGGACCG GGTCCTCCGG AGGCCGTCTT GGGACTGGCT
                        13272.JY
             .  A   Y   R   E   F   L   N   L   S   I   S   S   T   Y   S   S   A  ·
      6201   GGCCTACAGG GAGTTCCTGA ACCTGAGCAT CAGCAGCACC TACAGCAGCG
             CCGGATGTCC CTCAAGGACT TGGACTCGTA GTCGTCGTGG ATGTCGTCGC
             ..  I   H   A   R   R   M   I   R   S   R   A   V   H   P   I   F
      6251   CCATCCACGC CCGGAGAATG ATCAGATCCA GGGCCGTGCA CCCTATCTTT
             GGTAGGTGCG GGCCTCTTAC TAGTCTAGGT CCCGGCACGT GGGATAGAAA
              L   G   S   T   H   Y   D   I   T   Y   E   A   L   K   N   N   A  ·
      6301   CTGGGCAGCA CCCACTACGA CATCACCTAC GAGGCCCTGA AAAACAACGC
             GACCCGTCGT GGGTGATGCT GTAGTGGATG CTCCGGGACT TTTTGTTGCG
             .  Q   R   I   V   Y   D   E   L   Q   M   H   I   L   R   G   P  ·
      6351   CCAGCGGATC GTGTACGATG AGGAGCTGCA GATGCACATC CTGAGAGGCC
             GGTCGCCTAG CACATGCTAC TCCTCGACGT CTACGTGTAG GACTCTCCGG
             ..  L   H   F   Q   R   R   A   I   L   G   A   L   K   F   G   I
      6401   CTCTGCACTT CCAGAGGAGA GCCATCCTGG GCGCCCTGAA GTTCGGCATC
             GAGACGTGAA GGTCTCCTCT CGGTAGGACC CGCGGGACTT CAAGCCGTAG
                                                      13273.JY
              K   I   L   G   D   K   I   D   V   P   L   F   L   R   N   A
      6451   AAGATCCTGG GCGACAAGAT CGACGTGCCC CTGTTCCTGA GGAACGCCTG
             TTCTAGGACC CGCTGTTCTA GCTGCACGGG GACAAGGACT CCTTGCGGAC
                                                       13274.JY
      6501   ATGATTTTTA TCTCGAGTCT AGAATCGATC CCGGGTTTTT ATGACTAGTT
             TACTAAAAAT AGAGCTCAGA TCTTAGCTAG GGCCCAAAAA TACTGATCAA
                           C5L→
      6551   AATCACGGCC GCTTATAAAG ATCTAAAATG CATAATTTCT AAATAATGAA
             TTAGTGCCGG CGAATATTTC TAGATTTTAC GTATTAAAGA TTTATTACTT
                                        7928.DC
      6601   AAAAAGTACA TCATGAGCAA CGCGTTAGTA TATTTTACAA TGGAGATTAA
             TTTTTCATGT AGTACTCGTT GCGCAATCAT ATAAAATGTT ACCTCTAATT
                                                                    7793.SL
      6651   CGCTCTATAC CGTTCTATGT TTATTGATTC AGATGATGTT TTAGAAAAGA
             GCGAGATATG GCAAGATACA AATAACTAAG TCTACTACAA AATCTTTTCT
                        7793.SL
      6701   AAGTTATTGA ATATGAAAAC TTTAATGAAG ATGAAGATGA CGACGATGAT
             TTCAATAACT TATACTTTTG AAATTACTTC TACTTCTACT GCTGCTACTA
      6751   TATTGTTGTA AATCTGTTTT AGATGAAGAA GATGACGCGC TAAAGTATAC
             ATAACAACAT TTAGACAAAA TCTACTTCTT CTACTGCGCG ATTTCATATG
      6801   TATGGTTACA AAGTATAAGT CTATACTACT AATGGCGACT TGTGCAAGAA
             ATACCAATGT TCATATTCA GATATGATGA TTACCGCTGA ACACGTTCTT
      6851   GGTATAGTAT AGTGAAAATG TTGTTAGATT ATGATTATGA AAACCAAAT
```

Fig.11 (Continued)

```
               CCATATCATA TCACTTTTAC AACAATCTAA TACTAATACT TTTTGGTTTA
     6901      AAATCAGATC CATATCTAAA GGTATCTCCT TTGCACATAA TTTCATCTAT
               TTTAGTCTAG GTATAGATTT CCATAGAGGA AACGTGTATT AAAGTAGATA
                                    7929.DC
     6951      TCCTAGTTTA GAATACCTGC AGCCAAGCTT GGCACTGGCC GTCGTTTTAC
               AGGATCAAAT CTTATGGACG TCGGTTCGAA CCGTGACCGG CAGCAAAATG
                                                                 M13F
```

Nucleotide sequence and translation of insert

```
            BTV_VP2
             M   E   E   F   V   I   P   V   Y   S   E   D   E   I   P   Y ·
     2001    ATGGAG GAGTTCGTGA TCCCCGTGTA CAGCGAGGAC GAGATCCCCT
             TACCTC CTCAAGCACT AGGGGCACAT GTCGCTCCTG CTCTAGGGGA
             .. A   L   L   S   R   Y   P   L   A   I   Q   T   N   V   K   I
     2051    ACGCCCTGCT GAGCAGATAC CCTCTGGCCA TCCAGACCAA CGTGAAGATC
             TGCGGGACGA CTCGTCTATG GGAGACCGGT AGGTCTGGTT GCACTTCTAG
             E   D   V   E   G   K   H   N   V   V   K   I   P   E   S   D   M ·
     2101    GAGGACGTGG AGGGCAAGCA CAACGTGGTG AAGATCCCCG AGAGCGACAT
             CTCCTGCACC TCCCGTTCGT GTTGCACCAC TTCTAGGGGC TCTCGCTGTA
             .  I   D   I   P   R   L   T   I   V   E   A   M   N   Y   K   P   A ·
     2151    GATCGACATC CCCCGGCTGA CCATCGTGGA GGCCATGAAC TACAAGCCCG
             CTAGCTGTAG GGGGCCGACT GGTAGCACCT CCGGTACTTG ATGTTCGGGC
             .. R   N   D   G   I   V   V   P   R   L   L   D   I   T   L   R
     2201    CCAGGAACGA CGGCATCGTG GTGCCTAGAC TGCTGGACAT CACCCTGAGA
             GGTCCTTGCT GCCGTAGCAC CACGGATCTG ACGACCTGTA GTGGGACTCT
             A   Y   D   D   R   K   S   T   K   S   A   R   G   I   E   F   M ·
     2251    GCCTACGACG ACCGGAAGAG CACCAAGAGC GCCAGAGGCA TCGAGTTCAT
             CGGATGCTGC TGGCCTTCTC GTGGTTCTCG CGGTCTCCGT AGCTCAAGTA
             .  T   N   A   R   W   M   K   W   A   I   D   D   R   M   D   I   Q ·
     2301    GACCAACGCC CGGTGGATGA AGTGGGCCAT CGACGACAGG ATGGACATCC
             CTGGTTGCGG GCCACCTACT TCACCCGGTA GCTGCTGTCC TACCTGTAGG
             .. P   L   K   V   T   L   D   H   Y   C   S   V   N   H   Q   L
     2351    AGCCCCTGAA GGTGACCCTG GACCACTACT GCAGCGTGAA TCACCAGCTG
             TCGGGGACTT CCACTGGGAC CTGGTGATGA CGTCGCACTT AGTGGTCGAC
             F   N   C   V   V   K   A   N   A   A   N   A   D   T   I   Y   Y ·
     2401    TTCAACTGCG TGGTGAAGGC CAACGCCGCC AATGCCGACA CCATCTACTA
             AAGTTGACGC ACCACTTCCG GTTGCGGCGG TTACGGCTGT GGTAGATGAT
             .  D   Y   F   P   L   E   D   H   K   K   R   C   N   H   T   N   L ·
     2451    CGACTACTTC CCCCTGGAGG ACCACAAGAA GCGGTGCAAC CACACCAACC
             GCTGATGAAG GGGGACCTCC TGGTGTTCTT CGCCACGTTG GTGTGGTTGG
             .. D   L   L   R   S   L   T   N   M   E   L   F   H   A   L   Q
     2501    TGGACCTGCT GAGGAGCCTG ACCAACATGG AGCTGTTCCA CGCCCTGCAG
             ACCTGGACGA CTCCTCGGAC TGGTTGTACC TCGACAAGGT GCGGGACGTC
             G   A   A   Y   S   I   K   S   S   Y   E   L   V   A   N   S   E ·
     2551    GGAGCCGCCT ACAGCATCAA GAGCAGCTAC GAACTGGTGG CCAACAGCGA
             CCTCGGCGGA TGTCGTAGTT CTCGTCGATG CTTGACCACC GGTTGTCGCT
             .  R   E   S   L   E   E   T   Y   A   I   G   Q   P   K   W   I   H ·
     2601    GAGAGAGAGC CTGGAGGAGA CCTACGCCAT CGGCCAGCCT AAGTGGATCC
             CTCTCTCTCG GACCTCCTCT GGATGCGGTA GCCGGTCGGA TTCACCTAGG
             .. L   T   R   G   T   R   I   G   N   S   G   L   P   Y   E   R
     2651    ACCTGACCAG GGGCACCAGA ATCGGCAACA GCGGCCTGCC TTACGAGAGA
```

Fig. 11 (Continued)

```
          TGGACTGGTC CCCGTGGTCT TAGCCGTTGT CGCCGGACGG AATGCTCTCT
           F  I  S  S  M  V  Q  V  I  V  N  G  K  I  P  S  E  ·
     2701 TTCATCAGCA GCATGGTGCA GGTGATCGTG AACGGCAAGA TCCCTAGCGA
          AAGTAGTCGT CGTACCACGT CCACTAGCAC TTGCCGTTCT AGGGATCGCT
          .  I  A  N  E  V  A  Q  L  N  R  I  R  A  E  W  I  A  ·
     2751 GATCGCCAAC GAGGTGGCCC AGCTGAACAG AATCCGGGCC GAGTGGATCG
          CTAGCGGTTG CTCCACCGGG TCGACTTGTC TTAGGCCCGG CTCACCTAGC
          .. A  T  Y  D  R  G  R  I  R  A  L  E  L  C  K  I
     2801 CCGCCACCTA CGACAGAGGC AGGATCAGAG CCCTGGAGCT GTGCAAGATC
          GGCGGTGGAT GCTGTCTCCG TCCTAGTCTC GGGACCTCGA CACGTTCTAG
           L  S  T  I  G  R  K  I  L  N  T  H  E  E  P  K  D  ·
     2851 CTGAGCACCA TCGGCCGGAA GATCCTGAAT ACCCACGAGG AGCCCAAGGA
          GACTCGTGGT AGCCGGCCTT CTAGGACTTA TGGGTGCTCC TCGGGTTCCT
          .  E  M  D  L  S  T  R  F  Q  F  K  L  D  E  K  F  N  ·
     2901 CGAGATGGAC CTGTCCACCC GGTTCCAGTT CAAGCTGGAC GAGAAGTTCA
          GCTCTACCTG GACAGGTGGG CCAAGGTCAA GTTCGACCTG CTCTTCAAGT
          .. R  T  D  P  E  H  V  N  I  F  G  V  R  A  P  A
     2951 ACAGGACCGA CCCCGAGCAC GTGAATATCT TCGGAGTGAG GGCCCCTGCC
          TGTCCTGGCT GGGGCTCGTG CACTTATAGA AGCCTCACTC CCGGGGACGG
           T  D  E  G  R  F  Y  A  L  I  A  I  A  A  T  D  T  ·
     3001 ACCGACGAGG GCAGATTCTA CGCCCTGATC GCCATTGCCG CCACCGACAC
          TGGCTGCTCC CGTCTAAGAT GCGGGACTAG CGGTAACGGC GGTGGCTGTG
          .  Q  K  G  R  V  W  R  T  N  P  Y  P  C  L  R  G  A  ·
     3051 CCAGAAGGGC AGAGTGTGGA GGACCAACCC CTACCCTTGC CTGAGAGGCG
          GGTCTTCCCG TCTCACACCT CCTGGTTGGG GATGGGAACG GACTCTCCGC
          .. L  V  A  A  E  C  E  L  G  D  V  Y  S  T  L  R
     3101 CCCTGGTGGC CGCCGAGTGC GAGCTGGGCG ACGTGTACAG CACCCTGCGG
          GGGACCACCG GCGGCTCACG CTCGACCCGC TGCACATGTC GTGGGACGCC
           R  V  Y  R  W  S  L  R  P  E  Y  G  Q  H  E  R  Q  ·
     3151 AGGGTGTACA GATGGAGCCT GAGACCTGAG TACGGCCAGC ACGAGAGACA
          TCCCACATGT CTACCTCGGA CTCTGGACTC ATGCCGGTCG TGCTCTCTGT
          .  L  E  N  N  K  Y  V  F  N  R  I  N  L  F  D  S  N  ·
     3201 GCTGGAGAAC AACAAGTACG TGTTCAACCG GATCAACCTG TTCGACAGCA
          CGACCTCTTG TTGTTCATGC ACAAGTTGGC CTAGTTGGAC AAGCTGTCGT
          .. L  A  V  G  D  Q  I  I  H  W  R  Y  E  V  K  A
     3251 ATCTGGCCGT GGGCGACCAG ATCATCCACT GGCGCTACGA GGTGAAGGCC
          TAGACCGGCA CCCGCTGGTC TAGTAGGTGA CCGCGATGCT CCACTTCCGG
           S  A  E  T  T  Y  D  S  G  Y  M  C  R  H  E  V  E  ·
     3301 TCCGCCGAGA CCACCTACGA TAGCGGCTAC ATGTGCAGGC ACGAGGTGGA
          AGGCGGCTCT GGTGGATGCT ATCGCCGATG TACACGTCCG TGCTCCACCT
          .  E  D  E  L  L  C  K  I  N  D  K  Y  K  D  M  L  ·
     3351 GGAGGACGAG CTGCTGTGTA AGATCAACGA GGACAAGTAC AAGGACATGC
          CCTCCTGCTC GACGACACAT TCTAGTTGCT CCTGTTCATG TTCCTGTACG
          .. D  R  M  I  Q  G  W  D  Q  E  R  F  K  L  H
     3401 TGGACCGGAT GATCCAGGGC GGCTGGGATC AGGAGAGGTT CAAGCTGCAC
          ACCTGGCCTA CTAGGTCCCG CCGACCCTAG TCCTCTCCAA GTTCGACGTG
           N  I  L  T  D  P  N  L  L  T  I  D  F  E  K  D  A  ·
     3451 AACATCCTGA CCGACCCCAA CCTGCTGACA ATCGACTTCG AGAAGGACGC
          TTGTAGGACT GGCTGGGGTT GGACGACTGT TAGCTGAAGC TCTTCCTGCG
          .  Y  L  N  S  R  S  E  L  V  F  P  D  Y  F  D  K  W  ·
     3501 CTACCTGAAC AGCAGAAGCG AGCTGGTGTT CCCCGACTAC TTCGACAAGT
          GATGGACTTG TCGTCTTCGC TCGACCACAA GGGGCTGATG AAGCTGTTCA
```

Fig.11 (Continued)

```
           ..I  S  S     P  M  F     N  A  R  L     R  I  T     K  G  E
     3551  GGATCAGCAG CCCCATGTTC AACGCCCGGC TGAGAATCAC CAAGGGCGAG
           CCTAGTCGTC GGGGTACAAG TTGCGGGCCG ACTCTTAGTG GTTCCCGCTC
             I  G  T  S     K  K  D     D  P  W     N  N  R     A  V  R  G·
     3601  ATCGGCACCA GCAAGAAGGA CGACCCCTGG AACAACAGAG CCGTGCGGGG
           TAGCCGTGGT CGTTCTTCCT GCTGGGGACC TTGTTGTCTC GGCACGCCCC
           .Y  I  K     S  P  A  E     S  L  D     F  V  L     G  P  Y  Y·
     3651  CTACATCAAG AGCCCTGCCG AGTCCCTGGA CTTCGTGCTG GGCCCCTACT
           GATGTAGTTC TCGGGACGGC TCAGGGACCT GAAGCACGAC CCGGGGATGA
           ..D  L  R     L  L  F     F  G  E  A     L  S  L     K  Q  E
     3701  ACGATCTGCG GCTGCTGTTC TTCGGCGAGG CCCTGAGCCT GAAGCAGGAG
           TGCTAGACGC CGACGACAAG AAGCCGCTCC GGGACTCGGA CTTCGTCCTC
             Q  S  A  V     F  Q  Y     L  S  Q     L  D  D  F     P  A  L·
     3751  CAGAGCGCCG TGTTCCAGTA CCTGAGCCAG CTGGACGACT TCCCCGCCCT
           GTCTCGCGGC ACAAGGTCAT GGACTCGGTC GACCTGCTGA AGGGGCGGGA
           .T  Q  L     T  G  D  A     V  C  P     H  S  G     G  A  L  Y·
     3801  GACCCAGCTG ACCGGCGACG CCGTGTGTCC TCACAGCGGC GGAGCCCTGT
           CTGGGTCGAC TGGCCGCTGC GGCACACAGG AGTGTCGCCG CCTCGGGACA
           ..T  F  R     K  V  A     L  F  L  I     G  N  Y     E  K  L
     3851  ACACCTTCAG GAAGGTGGCC CTGTTCCTGA TCGGCAACTA CGAGAAGCTG
           TGTGGAAGTC CTTCCACCGG GACAAGGACT AGCCGTTGAT GCTCTTCGAC
             S  P  D  L     H  E  G     M  E  H     Q  T  Y  V     H  P  S·
     3901  AGCCCCGACC TGCACGAGGG CATGGAGCAC CAGACCTACG TGCACCCCAG
           TCGGGGCTGG ACGTGCTCCC GTACCTCGTG GTCTGGATGC ACGTGGGGTC
           .T  G  G     T  Y  Q  K     C  V  L     E  M  K     D  P  C  Q·
     3951  CACCGGCGGC ACCTACCAGA AATGCGTGCT GGAGATGAAG GACCCCTGCC
           GTGGCCGCCG TGGATGGTCT TTACGCACGA CCTCTACTTC CTGGGGACGG
           ..L  M  C     F  V  I     D  Y  I  F     E  K  R     E  Q  L
     4001  AGCTGATGTG CTTCGTGATC GACTACATCT TCGAGAAGCG GGAGCAGCTG
           TCGACTACAC GAAGCACTAG CTGATGTAGA AGCTCTTCGC CCTCGTCGAC
             R  D  T  K     E  A  R     Y  I  V     Y  L  I  Q     S  L  T·
     4051  AGAGACACCA AGGAGGCCCG GTACATCGTG TACCTGATCC AGAGCCTGAC
           TCTCTGTGGT TCCTCCGGGC CATGTAGCAC ATGGACTAGG TCTCGGACTG
           .G  I  Q     R  L  D  V     L  K  S     T  F  P     N  F  F  Q·
     4101  CGGCATCCAG AGACTGGACG TGCTGAAGAG CACCTTCCCC AACTTCTTCC
           GCCGTAGGTC TCTGACCTGC ACGACTTCTC GTGGAAGGGG TTGAAGAAGG
           ..R  L  L     M  L  K     E  I  K  F     V  R  D     L  N  V
     4151  AGCGGCTGCT GATGCTGAAG GAGATCAAGT TTGTGCGGGA CCTGAACGTG
           TCGCCGACGA CTACGACTTC CTCTAGTTCA AACACGCCCT GGACTTGCAC
             I  N  F  L     P  L  M     F  L  V     H  D  N  I     S  Y  S·
     4201  ATCAACTTCC TGCCCCTGAT GTTCCTGGTG CACGACAACA TCAGCTACAG
           TAGTTGAAGG ACGGGGACTA CAAGGACCAC GTGCTGTTGT AGTCGATGTC
           .H  R  Q     W  S  I  P     M  V  L     F  D  D     T  I  K  L·
     4251  CCACCGGCAG TGGAGCATCC CTATGGTGCT GTTCGACGAC ACCATCAAGC
           GGTGGCCGTC ACCTCGTAGG GATACCACGA CAAGCTGCTG TGGTAGTTCG
           ..I  P  V     E  V  G     A  Y  A  N     R  F  G     F  K  S
     4301  TGATCCCTGT GGAAGTGGGC GCCTACGCCA ACAGATTCGG CTTCAAGAGC
           ACTAGGGACA CCTTCACCCG CGGATGCGGT TGTCTAAGCC GAAGTTCTCG
             F  M  N  F     T  R  F     H  P  G     E  S  K  K     K  Q  I·
     4351  TTCATGAACT TCACCAGGTT CCACCCTGGC GAGAGCAAGA AGAAGCAGAT
           AAGTACTTGA AGTGGTCCAA GGTGGGACCG CTCTCGTTCT TCTTCGTCTA
           .A  E  D     V  H  K  E     F  G  V     V  A  F     E  Y  Y  T·
```

Fig.11 (Continued)

```
4401   CGCCGAGGAC GTGCACAAGG AGTTCGGCGT GGTGGCCTTC GAGTACTACA
       GCGGCTCCTG CACGTGTTCC TCAAGCCGCA CCACCGGAAG CTCATGATGT
       .. N  T  K   I  S  Q   G  S  V  H   T  P  V   M  T  T
4451   CCAACACCAA GATCAGCCAG GGCAGCGTGC ACACCCCCGT GATGACCACC
       GGTTGTGGTT CTAGTCGGTC CCGTCGCACG TGTGGGGGCA CTACTGGTGG
        K  M  D  V   L  K  I   H  L  S   S  L  C  A   G  L  A ·
4501   AAGATGGATG TGCTGAAAAT CCACCTGAGC AGCCTGTGTG CCGGCCTGGC
       TTCTACCTAC ACGACTTTTA GGTGGACTCG TCGGACACAC GGCCGGACCG
       . D  S  I   V  Y  T  L   P  V  A   H  P  K   K  C  I V ·
4551   CGACAGCATC GTGTACACCC TGCCCGTGGC CCACCCCAAG AAGTGCATCG
       GCTGTCGTAG CACATGTGGG ACGGGCACCG GGTGGGGTTC TTCACGTAGC
       .. L  I  I   V  G  D   D  K  L  E   P  H  T   R  S  E
4601   TGCTGATCAT TGTGGGCGAC GACAAGCTGG AGCCTCACAC CAGATCCGAG
       ACGACTAGTA ACACCCGCTG CTGTTCGACC TCGGAGTGTG GTCTAGGCTC
        Q  I  V  S   R  Y  N   Y  S  R   K  H  I  C   G  V  V ·
4651   CAGATCGTGT CCCGGTACAA CTACAGCCGG AAGCACATCT GCGGCGTGGT
       GTCTAGCACA GGGCCATGTT GATGTCGGCC TTCGTGTAGA CGCCGCACCA
       . S  V  T   V  G  Q  N   S  Q  L   R  V  Y   T  S  G I ·
4701   GTCCGTGACA GTGGGCCAGA ACAGCCAGCT GAGAGTGTAC ACCAGCGGCA
       CAGGCACTGT CACCCGGTCT TGTCGGTCGA CTCTCACATG TGGTCGCCGT
       .. V  K  H   R  V  C   D  K  F  I   L  K  H   K  C  K
4751   TCGTGAAGCA CAGAGTGTGC GACAAGTTCA TCCTGAAGCA CAAATGCAAG
       AGCACTTCGT GTCTCACACG CTGTTCAAGT AGGACTTCGT GTTTACGTTC
        V  I  L  V   R  M  P   G  Y  V   F  G  N  D   E  L  M ·
4801   GTGATCCTGG TGAGGATGCC CGGCTACGTG TTCGGCAACG ACGAGCTGAT
       CACTAGGACC ACTCCTACGG GCCGATGCAC AAGCCGTTGC TGCTCGACTA
       . T  K  L   L  N  V  *   *
4851   GACCAAGCTG CTGAATGTGT GATGACTCGA GTTTTTATTC AAAATTGAAA
       CTGGTTCGAC GACTTACACA CTACTGAGCT CAAAAATAAG TTTTAACTTT
                  BTV-VP5   M  G  K  I   I  K  S   L  S  R
4901   ATATATAATT ACAATATAAA ATGGGCAAGA TCATCAAGAG CCTGAGCCGC
       TATATATTAA TGTTATATTT TACCCGTTCT AGTAGTTCTC GGACTCGGCG
        F  G  K  K   V  G  N   A  L  T   S  N  T  A   K  K  I ·
4951   TTCGGCAAGA AAGTGGGCAA TGCCCTGACC AGCAACACCG CCAAGAAGAT
       AAGCCGTTCT TTCACCCGTT ACGGGACTGG TCGTTGTGGC GGTTCTTCTA
       . Y  S  T   I  G  K  A   A  E  R   F  A  E   S  E  I G ·
5001   CTACAGCACC ATCGGCAAGG CCGCCGAGAG ATTCGCCGAG AGCGAGATCG
       GATGTCGTGG TAGCCGTTCC GGCGGCTCTC TAAGCGGCTC TCGCTCTAGC
       .. A  A  T   I  D  G   L  V  Q  G   S  V  H   S  I  I
5051   GAGCCGCCAC CATCGACGGC CTGGTGCAGG GCAGCGTGCA CAGCATCATC
       CTCGGCGGTG GTAGCTGCCG GACCACGTCC CGTCGCACGT GTCGTAGTAG
        T  G  E  S   Y  G  E   S  V  K   Q  A  V  L   L  N  V ·
5101   ACCGGCGAGA GCTACGGCGA GAGCGTGAAG CAGGCCGTGC TGCTGAACGT
       TGGCCGCTCT CGATGCCGCT CTCGCACTTC GTCCGGCACG ACGACTTGCA
       . L  G  T   G  E  E  L   P  D  P   L  S  P   G  E  R G ·
5151   GCTGGGCACA GGCGAGGAGC TGCCCGACCC CCTGAGCCCT GGCGAGAGAG
       CGACCCGTGT CCGCTCCTCG ACGGGCTGGG GGACTCGGGA CCGCTCTCTC
       .. I  Q  T   K  I  K   E  L  E  D   E  Q  R   N  E  L
5201   GCATCCAGAC CAAGATCAAG GAGCTGGAGG ACGAGCAGAG AAACGAGCTG
       CGTAGGTCTG GTTCTAGTTC CTCGACCTCC TGCTCGTCTC TTTGCTCGAC
        V  R  L  K   Y  N  K   E  I  T   K  E  F  G   K  E  L ·
5251   GTGCGGCTGA AGTACAACAA GGAGATCACC AAGGAGTTCG GCAAGGAACT
```

Fig.11 (Continued)

```
          CACGCCGACT TCATGTTGTT CCTCTAGTGG TTCCTCAAGC CGTTCCTTGA
           . E  E  V    Y  D  F  M    N  G  E  A    K  E    E  E  V  .
     5301 GGAAGAGGTG TACGACTTCA TGAACGGCGA GGCCAAGGAG GAGGAGGTGG
          CCTTCTCCAC ATGCTGAAGT ACTTGCCGCT CCGGTTCCTC CTCCTCCACC
           .. Q  E  Q    Y  S  M    L  C  K  A    V  D  S    Y  E  K
     5351 TGCAAGAACA GTACAGCATG CTGTGCAAGG CCGTGGACAG CTACGAGAAG
          ACGTTCTTGT CATGTCGTAC GACACGTTCC GGCACCTGTC GATGCTCTTC
            I  L  K  A    E  D  S    K  M  A  M    L  A  R    A  L  Q  .
     5401 ATCCTGAAGG CCGAGGACTC CAAGATGGCC ATGCTGGCCA GAGCCCTGCA
          TAGGACTTCC GGCTCCTGAG GTTCTACCGG TACGACCGGT CTCGGGACGT
           . R  E  A    S  E  R  S    Q  D  E    I  K  M    V  K  E  Y  .
     5451 GAGGGAGGCC AGCGAGAGAA GCCAGGACGA GATCAAGATG GTGAAGGAGT
          CTCCCTCCGG TCGCTCTCTT CGGTCCTGCT CTAGTTCTAC CACTTCCTCA
           .. R  Q  K    I  D  A    L  K  N  A    I  E  I    E  R  D
     5501 ACCGGCAGAA GATCGACGCC CTGAAGAACG CCATCGAGAT CGAGAGGGAC
          TGGCCGTCTT CTAGCTGCGG GACTTCTTGC GGTAGCTCTA GCTCTCCCTG
            G  M  Q  E    E  A  I    Q  E  I  A    G  M  T    A  D  V  .
     5551 GGCATGCAGG AGGAGGCCAT CCAAGAAATC GCCGGCATGA CCGCCGACGT
          CCGTACGTCC TCCTCCGGTA GGTTCTTTAG CGGCCGTACT GGCGGCTGCA
           . L  E  A    A  S  E  E    V  P  L    I  G  A    G  M  A  T  .
     5601 GCTGGAGGCC GCCAGCGAGG AGGTGCCCCT GATTGGCGCC GGAATGGCCA
          CGACCTCCGG CGGTCGCTCC TCCACGGGGA CTAACCGCGG CCTTACCGGT
           .. A  V  A    T  G  R    A  I  E  G    A  Y  K    L  K  K
     5651 CCGCCGTGGC CACCGGCAGA GCCATCGAGG GCGCCTACAA GCTGAAGAAG
          GGCGGCACCG GTGGCCGTCT CGGTAGCTCC CGCGGATGTT CGACTTCTTC
            V  I  N  A    L  S  G    I  D  L  S    H  M  R    S  P  K  .
     5701 GTGATCAACG CCCTGAGCGG CATCGACCTG AGCCACATGA GGAGCCCCAA
          CACTAGTTGC GGGACTCGCC GTAGCTGGAC TCGGTGTACT CCTCGGGGTT
           . I  E  P    T  I  I  A    T  T  L    E  H  R    F  K  E  I  .
     5751 GATCGAGCCT ACCATCATCG CCACCACCCT GGAGCACCGG TTCAAGGAGA
          CTAGCTCGGA TGGTAGTAGC GGTGGTGGGA CCTCGTGGCC AAGTTCCTCT
           .. P  D  E    Q  L  A    V  S  V  L    N  K  K    T  A  V
     5801 TCCCTGACGA GCAGCTGGCC GTGTCCGTGC TGAACAAGAA AACCGCCGTG
          AGGGACTGCT CGTCGACCGG CACAGGCACG ACTTGTTCTT TTGGCGGCAC
            T  D  N  C    N  E  I    A  H  I  K    Q  E  I    L  P  K  .
     5851 ACCGACAACT GCAACGAGAT CGCCCACATC AAGCAGGAGA TCCTGCCCAA
          TGGCTGTTGA CGTTGCTCTA GCGGGTGTAG TTCGTCCTCT AGGACGGGTT
           . F  K  Q    I  M  D  E    E  K  E    I  E  G    I  E  D  K  .
     5901 GTTCAAGCAG ATCATGGACG AGGAGAAGGA GATCGAGGGC ATCGAGGACA
          CAAGTTCGTC TAGTACCTGC TCCTCTTCCT CTAGCTCCCG TAGCTCCTGT
           .. V  I  H    P  R  V    M  M  R  F    K  I  P    R  T  Q
     5951 AGGTGATCCA CCCCCGGGTG ATGATGAGGT TCAAGATCCC CAGAACCCAG
          TCCACTAGGT GGGGGCCCAC TACTACTCCA AGTTCTAGGG GTCTTGGGTC
            Q  P  Q  I    H  I  Y    A  A  P  W    D  S  D    D  V  F  .
     6001 CAGCCTCAGA TCCACATCTA TGCCGCCCCT TGGGACAGCG ACGACGTGTT
          GTCGGAGTCT AGGTGTAGAT ACGGCGGGGA ACCCTGTCGC TGCTGCACAA
           . F  F  H    C  V  S  H    H  H  R    N  E  S    F  F  L  G  .
     6051 CTTCTTCCAC TGCGTGTCCC ACCACCACAG GAACGAGAGC TTCTTCCTGG
          GAAGAAGGTG ACGCACAGGG TGGTGGTGTC CTTGCTCTCG AAGAAGGACC
           .. F  D  L    G  I  D    V  V  H  F    E  D  L    T  S  H
     6101 GCTTCGACCT GGGCATCGAC GTGGTGCACT TCGAGGATCT GACCAGCCAC
          CGAAGCTGGA CCCGTAGCTG CACCACGTGA AGCTCCTAGA CTGGTCGGTG
```

Fig.11 (Continued)

```
        W   H   A   L    G   L   A    Q   E   A    S   G   R   T    L   T   E   ·
6151    TGGCACGCCC  TGGGCCTGGC  CCAGGAGGCC  TCCGGCAGAA  CCCTGACCGA
        ACCGTGCGGG  ACCCGGACCG  GGTCCTCCGG  AGGCCGTCTT  GGGACTGGCT
        .   A   Y   R    E   F   L   N    L   S   I    S   S   T    Y   S   S   A   ·
6201    GGCCTACAGG  GAGTTCCTGA  ACCTGAGCAT  CAGCAGCACC  TACAGCAGCG
        CCGGATGTCC  CTCAAGGACT  TGGACTCGTA  GTCGTCGTGG  ATGTCGTCGC
        ..  I   H   A    R   R   M    I   R   S   R    A   V   H    P   I   F
6251    CCATCCACGC  CCGGAGAATG  ATCAGATCCA  GGGCCGTGCA  CCCTATCTTT
        GGTAGGTGCG  GGCCTCTTAC  TAGTCTAGGT  CCCGGCACGT  GGGATAGAAA
            L   G   S   T    H   Y   D    I   T   Y    E   A   L   K    N   N   A   ·
6301    CTGGGCAGCA  CCCACTACGA  CATCACCTAC  GAGGCCCTGA  AAAACAACGC
        GACCCGTCGT  GGGTGATGCT  GTAGTGGATG  CTCCGGGACT  TTTTGTTGCG
        .   Q   R   I    V   Y   D    E   L   Q    M   H   I    L   R   G   P   ·
6351    CCAGCGGATC  GTGTACGATG  AGGAGCTGCA  GATGCACATC  CTGAGAGGCC
        GGTCGCCTAG  CACATGCTAC  TCCTCGACGT  CTACGTGTAG  GACTCTCCGG
        ..  L   H   F    Q   R   R    A   I   L    G   A   L   K    F   G   I
6401    CTCTGCACTT  CCAGAGGAGA  GCCATCCTGG  GCGCCCTGAA  GTTCGGCATC
        GAGACGTGAA  GGTCTCCTCT  CGGTAGGACC  CGCGGGACTT  CAAGCCGTAG
            K   I   L   G    D   K   I    D   V   P    L   F   L   R    N   A
6451    AAGATCCTGG  GCGACAAGAT  CGACGTGCCC  CTGTTCCTGA  GGAACGCC
        TTCTAGGACC  CGCTGTTCTA  GCTGCACGGG  GACAAGGACT  CCTTGCGG
```

Theoretical sequence of entire vector: (unannotated for use in DNA programs)

gcgcccaatacgcaaaccgcctctccccgcgcgttggccgattcattaatgcagctggcacgaca
ggtttcccgactggaaagcgggcagtgagcgcaacgcaattaatgtgagttagctcactcattag
gcaccccaggctttacactttatgcttccggctcgtatgttgtgtggaattgtgagcggataaca
atttcacacaggaaacagctatgaccatgattacgaattgcggccgcaattctgaatgttaaatg
ttatactttggatgaagctataaatatgcattggaaaaataatccatttaaagaaggattcaaa
tactacaaaacctaagcgataatatgttaactaagcttattcttaacgacgctttaaatatacac
aaataaacataattttttgtataacctaacaaataactaaaacataaaaataataaaaggaaatgt
aatatcgtaattattttactcaggaatggggttaaatatttatatcacgtgtatatctatactgt
tatcgtatactctttacaattactattacgaatatgcaagagataataagattacgtatttaaga
gaatcttgtcatgataattgggtacgacatagtgataaatgctatttcgcatcgttacataaagt
cagttggaaagatggatttgacagatgtaacttaataggtgcaaaaatgttaaataacagcattc
tatcggaagataggataccagttatattatacaaaaatcactggttggataaaacagattctgca
atattcgtaaaagatgaagattactgcgaatttgtaaactatgacaataaaaagccatttatctc
aacgacatcgtgtaattcttccatgttttatgtatgtgtttcagatattatgagattactataaa
ctttttgtatacttatattccgtaaactatattaatcatgaagaaaatgaaaagtatagaagct
gttcacgagcggttgttgaaaacaacaaaattatacattcaagatggcttacatatacgtctgtg
aggctatcatggataatgacaatgcatctctaaataggttttttggacaatggattcgaccctaac
acggaatatggtactctacaatctcctcttgaaatggctgtaatgttcaagaataccgaggctat
aaaaatcttgatgaggtatggagctaaacctgtagttactgaatgcacaacttcttgtctgcatg
atgcggtgttgagagacgactacaaaatagtgaaagatctgttgaagaataactatgtaaacaat
gttctttacagcggaggctttactcctttgtgtttggcagcttaccttaacaaagttaatttggt
taaacttctattggctcattcggcggatgtagatatttcaaacacggatcggttaactcctctac
atatagccgtatcaaataaaaatttaacaatggttaaacttctattgaacaaggtgctgatact
gacttgctggataacatgggacgtactcctttaatgatcgctgtacaatctggaaatattgaaat
atgtagcacactacttaaaaaaaataaaatgtccagaactgggaaaaattgatcttgccagctgt
aattcatggtagaaaagaagtgctcaggctacttttcaacaaggagcagatgtaaactacatct
ttgaaagaaatggaaaatcatatactgttttggaattgattaaagaaagttactctgagacacaa Fig.11 (Continued)

```
aagaggtagctgaagtggtactctcaaaggtacgtgactaattagctataaaaaggatccgggtt
aattaattagtcatcaggcagggcgagaacgagactatctgctcgttaattaattagagcttctt
tattctatacttaaaaagtgaaaataaatacaaaggttcttgagggttgtgttaaattgaaagcg
agaaataatcataaattatttcattatcgcgatatccgttaagtttgtatcgtaatggaggagtt
cgtgatcccgtgtacagcgaggacgagatcccctacgccctgctgagcagatacctctggcca
tccagaccaacgtgaagatcgaggacgtggagggcaagcacaacgtggtgaagatccccgagagc
gacatgatcgacatccccggctgaccatcgtggaggccatgaactacaagcccgccaggaacga
cggcatcgtggtgcctagactgctggacatcaccctgagagcctacgacgaccggaagagcacca
agagcgccagaggcatcgagttcatgaccaacgcccggtggatgaagtgggccatcgacgacagg
atggacatccagcccctgaaggtgaccctggaccactactgcagcgtgaatcaccagctgttcaa
ctgcgtggtgaaggccaacgccgccaatgccgacaccatctactacgactacttcccccctggagg
accacaagaagcggtgcaaccacaccaacctggacctgctgaggagcctgaccaacatggagctg
ttccacgccctgcagggagccgcctacagcatcaagagcagctacgaactggtggccaacagcga
gagagagagcctggaggagacctacgccatcggccagcctaagtggatccacctgaccaggggca
ccagaatcggcaacagcggcctgccttacgagagattcatcagcagcatggtgcaggtgatcgtg
aacggcaagatccctagcgagatcgccaacgaggtggcccagctgaacagaatccgggccgagtg
gatcgccgccacctacgacagaggcaggatcagagccctggagctgtgcaagatcctgagcacca
tcggccggaagatcctgaatacccacgaggagcccaaggacgagatggacctgtccacccggttc
cagttcaagctggacgagaagttcaacaggaccgaccccgagcacgtgaatatcttcggagtgag
ggcccctgccaccgacgagggcagattctacgccctgatcgccattgccgccaccgacacccaga
agggcagagtgtggaggaccaacccctacccttgcctgagaggcgccctggtggccgccgagtgc
gagctgggcgacgtgtacagcaccctgcggagggtgtacagatggagcctgagacctgagtacgg
ccagcacgagagacagctggagaacaacaagtacgtgttcaaccggatcaacctgttcgacagca
atctggccgtgggcgaccagatcatccactggcgctacgaggtgaaggcctccgccgagaccacc
tacgatagcggctacatgtgcaggcacgaggtggaggaggacgagctgctgtgtaagatcaacga
ggacaagtacaaggacatgctggaccggatgatccagggcggctgggatcaggagaggttcaagc
tgcacaacatcctgaccgaccccaacctgctgacaatcgacttcgagaaggacgcctacctgaac
agcagaagcgagctggtgttccccgactacttcgacaagtggatcagcagccccatgttcaacgc
ccggctgagaatcaccaagggcgagatcggcaccagcaagaaggacgacccctggaacaacagag
ccgtgcggggctacatcaagagccctgccgagtccctggacttcgtgctgggcccctactacgat
ctgcggctgctgttcttcggcgaggccctgagcctgaagcaggagcagagcgccgtgttccagta
cctgagccagctggacgacttccccgccctgacccagctgaccggcgacgccgtgtgtcctcaca
gcggcggagccctgtacaccttcaggaaggtggccctgttcctgatcggcaactacgagaagctg
agccccgacctgcacgagggcatggagcaccagacctacgtgcaccccagcaccggcggcaccta
ccagaaatgcgtgctggagatgaaggaccctgccagctgatgtgcttcgtgatcgactacatct
tcgagaagcgggagcagctgagagacaccaaggaggcccggtacatcgtgtacctgatccagagc
ctgaccggcatccagagactggacgtgctgaagagcaccttccccaacttcttccagcggctgct
gatgctgaaggagatcaagtttgtgcgggacctgaacgtgatcaacttcctgcccctgatgttcc
tggtgcacgacaacatcagctacagccaccggcagtggagcatccctatggtgctgttcgacgac
accatcaagctgatccctgtggaagtgggcgcctacgccaacagattcggcttcaagagcttcat
gaacttcaccaggttccaccctggcgagagcaagaagaagcagatcgccgaggacgtgcacaagg
agttcggcgtggtggccttcgagtactacaccaacaccaagatcagccagggcagcgtgcacacc
cccgtgatgaccaccaagatggatgtgctgaaaatccacctgagcagcctgtgtgccggcctggc
cgacagcatcgtgtacacctgcccgtggcccaccccaagaagtgcatcgtgctgatcattgtgg
gcgacgacaagctggagcctcacaccagatccgagcagatcgtgtcccggtacaactacagccgg
aagcacatctgcggcgtggtgtccgtgacagtgggccagaacagccagctgagagtgtacaccag
cggcatcgtgaagcacagagtgtgcgacaagttcatcctgaagcacaaatgcaaggtgatcctgg
tgaggatgcccggctacgtgttcggcaacgacgagctgatgaccaagctgctgaatgtgtgatga
ctcgagttttttattcaaaattgaaaatatataattacaatataaaatgggcaagatcatcaagag
cctgagccgcttcggcaagaaagtgggcaatgccctgaccagcaacaccgccaagaagatctaca
```

Fig.11 (Continued)

```
gcaccatcggcaaggccgccgagagattcgccgagagcgagatcggagccgccaccatcgacggc
ctggtgcagggcagcgtgcacagcatcatcaccggcgagagctacggcgagagcgtgaagcaggc
cgtgctgctgaacgtgctgggcacaggcgaggagctgcccgaccccctgagccctggcgagagag
gcatccagaccaagatcaaggagctggaggacgagcagagaaacgagctggtgcggctgaagtac
aacaaggagatcaccaaggagttcggcaaggaactggaagaggtgtacgacttcatgaacggcga
ggccaaggaggaggaggtggtgcaagaacagtacagcatgctgtgcaaggccgtggacagctacg
agaagatcctgaaggccgaggactccaagatggccatgctggccagagccctgcagagggaggcc
agcgagagaagccaggacgagatcaagatggtgaaggagtaccggcagaagatcgacgccctgaa
gaacgccatcgagatcgagagggacggcatgcaggaggaggccatccaagaaatcgccggcatga
ccgccgacgtgctggaggccgccagcgaggaggtgcccctgattggcgccggaatggccaccgcc
gtggccaccggcagagccatcgagggcgcctacaagctgaagaaggtgatcaacgccctgagcgg
catcgacctgagccacatgaggagccccaagatcgagcctaccatcatcgccaccaccctggagc
accggttcaaggagatccctgacgagcagctggccgtgtccgtgctgaacaagaaaaccgccgtg
accgacaactgcaacgagatcgcccacatcaagcaggagatcctgcccaagttcaagcagatcat
ggacgaggagaaggagatcgagggcatcgaggacaaggtgatccaccccgggtgatgatgaggt
tcaagatccccagaacccagcagcctcagatccacatctatgccgcccttgggacagcgacgac
gtgttcttcttccactgcgtgtcccaccaccacaggaacgagagcttcttcctgggcttcgacct
gggcatcgacgtggtgcacttcgaggatctgaccagccactggcacgccctgggcctggcccagg
aggcctccggcagaaccctgaccgaggcctacagggagttcctgaacctgagcatcagcagcacc
tacagcagcgccatccacgcccggagaatgatcagatccagggccgtgcaccctatctttctggg
cagcacccactacgacatcacctacgaggccctgaaaaacaacgcccagcggatcgtgtacgatg
aggagctgcagatgcacatcctgagaggccctctgcacttccagaggagagccatcctgggcgcc
ctgaagttcggcatcaagatcctgggcgacaagatcgacgtgcccctgttcctgaggaacgcctg
atgattttatctcgagtctagaatcgatcccgggttttttatgactagttaatcacggccgctta
taaagatctaaaatgcataatttctaaataatgaaaaaaagtacatcatgagcaacgcgttagta
tattttacaatggagattaacgctctataccgttctatgtttattgattcagatgatgttttaga
aaagaaagttattgaatatgaaaactttaatgaagatgaagatgacgacgatgattattgttgta
aatctgttttagatgaagaagatgacgcgctaaagtatactatggttacaaagtataagtctata
ctactaatggcgacttgtgcaagaaggtatagtatagtgaaaatgttgttagattatgattatga
aaaaccaaataaatcagatccatatctaaaggtatctcctttgcacataatttcatctattccta
gtttagaatacctgcagccaagcttggcactggccgtcgttttacaacgtcgtgactgggaaaac
cctggcgttacccaacttaatcgccttgcagcacatccccctttcgccagctggcgtaatagcga
agaggcccgcaccgatcgcccttcccaacagttgcgcagcctgaatggcgaatggcgcctgatgc
ggtattttctccttacgcatctgtgcggtatttcacaccgcatatggtgcactctcagtacaatc
tgctctgatgccgcatagttaagccagccccgacacccgccaacacccgctgacgcgccctgacg
ggcttgtctgctcccggcatccgcttacagacaagctgtgaccgtctccgggagctgcatgtgtc
agaggttttcaccgtcatcaccgaaacgcgcgagacgaaagggcctcgtgatacgcctatttta
taggttaatgtcatgataataatggtttcttagacgtcaggtggcacttttcggggaaatgtgcg
cggaacccctatttgtttatttttctaaatacattcaaatatgtatccgctcatgagacaataac
cctgataaatgcttcaataatattgaaaaaggaagagtatgagtattcaacatttccgtgtcgcc
cttattcccttttttgcggcattttgccttcctgtttttgctcacccagaaacgctggtgaaagt
aaaagatgctgaagatcagttgggtgcacgagtgggttacatcgaactggatctcaacagcggta
agatccttgagagttttcgccccgaagaacgttttccaatgatgagcacttttaaagttctgcta
tgtggcgcggtattatcccgtattgacgccgggcaagagcaactcggtcgccgcatacactattc
tcagaatgacttggttgagtactcaccagtcacagaaaagcatcttacggatggcatgacagtaa
gagaattatgcagtgctgccataaccatgagtgataacactgcggccaacttacttctgacaacg
atcggaggaccgaaggagctaaccgcttttttgcacaacatgggggatcatgtaactcgccttga
tcgttgggaaccggagctgaatgaagccataccaaacgacgagcgtgacaccacgatgcctgtag
caatggcaacaacgttgcgcaaactattaactggcgaactacttactctagcttcccggcaacaa
ttaatagactggatggaggcggataaagttgcaggaccacttctgcgctcggcccttccggctgg
```

Fig.11 (Continued)

```
ctggtttattgctgataaatctggagccggtgagcgtgggtctcgcggtatcattgcagcactgg
ggccagatggtaagccctcccgtatcgtagttatctacacgacggggagtcaggcaactatggat
gaacgaaatagacagatcgctgagataggtgcctcactgattaagcattggtaactgtcagacca
agtttactcatatactttagattgatttaaaacttcatttttaatttaaaaggatctaggtga
agatccttttgataatctcatgaccaaaatcccttaacgtgagttttcgttccactgagcgtca
gacccgtagaaaagatcaaaggatcttcttgagatccttttttctgcgcgtaatctgctgctt
gcaaacaaaaaaaccaccgctaccagcggtggtttgtttgccggatcaagagctaccaactctt
ttccgaaggtaactggcttcagcagagcgcagataccaaatactgtccttctagtgtagccgtag
ttaggccaccacttcaagaactctgtagcaccgcctacatacctcgctctgctaatcctgttacc
agtggctgctgccagtggcgataagtcgtgtcttaccgggttggactcaagacgatagttaccgg
ataaggcgcagcggtcgggctgaacggggggttcgtgcacacagcccagcttggagcgaacgacc
tacaccgaactgagatacctacagcgtgagctatgagaaagcgccacgcttcccgaagggagaaa
ggcggacaggtatccggtaagcggcagggtcggaacaggagagcgcacgagggagcttccagggg
gaaacgcctggtatctttatagtcctgtcgggtttcgccacctctgacttgagcgtcgattttg
tgatgctcgtcaggggggcggagcctatggaaaaacgccagcaacgcggccttttacggttcct
ggccttttgctggccttttgctcacatgttctttcctgcgttatcccctgattctgtggataacc
gtattaccgcctttgagtgagctgataccgctcgccgcagccgaacgaccgagcgcagcgagtca
                gtgagcgaggaagcggaaga
```

— 14974bp Hind III
— 12Kb

— 9508bp BamH I
— 8.0Kb

— 6.0Kb

— 5.0Kb

— 4.0Kb

— 2901bp Pst I
— 3.0Kb

Probe: BTV-specific probe
Lane 1: ALVAC-1 digested with *BamH I*
Lane 2: vCP2289.1.2.1.1 digested with *BamH I*
Lane 3: vCP2289.2.1.1.1 digested with *BamH I*
Lane 4: ALVAC-1 digested with *Hind III*
Lane 5: vCP2289.1.2.1.1 digested with *Hind III*
Lane 6: vCP2289.2.1.1.1 digested with *Hind III*
Lane 7: ALVAC-1 digested with *Pst I*
Lane 8: vCP2289.1.2.1.1 digested with *Pst I*
Lane 9: vCP2289.2.1.1.1 digested with *Pst I*

*Fig. 15*

Lane 1: ALVAC cell pellet
Lane 2: vCP2289.1.2.1.1 cell pellet
Lane 3: vCP2289.2.1.1.1 cell pellet
Lane 4: ALVAC supernatant
Lane 5: vCP2289.1.2.1.1 supernatant
Lane 6: vFP2289.2.1.1.1 supernatant 13247.JY (forward)

```
     XhoI              42Kp                     M  G  K  I  I  K  S  L
                 5'
GCGCTCGAGTTTTTATTCAAAATTGAAAATATATAATTACAATATAAAATGGGCAAGATCATCAAGAGCCTG
```

13248.JY (reverse)

```
            XhoI   T5NT           A  N  R  L  F  L  P  V  D
       5'  ATCTCGAGATAAAAATCATCAGGCGTTCCTCAGGAACAGGGGCACGTC
```

//!PAGE_START

SEQUENCE LISTING

```
<160> NUMBER OF SEQ ID NOS: 26

<210> SEQ ID NO 1
<211> LENGTH: 2868
<212> TYPE: DNA
<213> ORGANISM: Artificial Sequence
<220> FEATURE:
<223> OTHER INFORMATION: Description of Artificial Sequence: Synthetic
      BTV17 codon optimized VP2

<400> SEQUENCE: 1
atggaggagt tcgtgatccc cgtgtacagc gaggacgaga tcccctacgc cctgctgagc        60
agataccctc tggccatcca gaccaacgtg aagatcgagg acgtggaggg caagcacaac       120
gtggtgaaga tccccgagag cgacatgatc gacatccccc ggctgaccat cgtggaggcc       180
atgaactaca gcccgccag gaacgacggc atcgtggtgc ctagactgct ggacatcacc       240
ctgagagcct acgacgaccg gaagagcacc aagagcgcca gaggcatcga gttcatgacc       300
aacgcccggt ggatgaagtg ggccatcgac gacaggatgg acatccagcc cctgaaggtg       360
accctggacc actactgcag cgtgaatcac cagctgttca actgcgtggt gaaggccaac       420
gccgccaatg ccgacaccat ctactacgac tacttccccc tggaggacca caagaagcgg       480
tgcaaccaca ccaacctgga cctgctgagg agcctgacca acatggagct gttccacgcc       540
ctgcagggag ccgcctacag catcaagagc agctacgaac tggtggccaa cagcgagaga       600
gagagcctgg aggagaccta cgccatcggc cagcctaagt ggatccacct gaccaggggc       660
accagaatcg gcaacagcgg cctgccttac gagagattca tcagcagcat ggtgcaggtg       720
atcgtgaacg gcaagatccc tagcgagatc gccaacgagg tggcccagct gaacagaatc       780
cgggccgagt ggatcgccgc cacctacgac agaggcagga tcagagccct ggagctgtgc       840
```

-continued

```
aagatcctga gcaccatcgg ccggaagatc ctgaataccc acgaggagcc caaggacgag    900
atggacctgt ccacccggtt ccagttcaag ctggacgaga agttcaacag gaccgacccc    960
gagcacgtga atatcttcgg agtgagggcc cctgccaccg acgagggcag attctacgcc   1020
ctgatcgcca ttgccgccac cgacacccag aagggcagag tgtggaggac caaccccta c  1080
ccttgcctga gaggcgccct ggtggccgcc gagtgcgagc tgggcgacgt gtacagcacc   1140
ctgcggaggg tgtacagatg gagcctgaga cctgagtacg ccagcacga gagacagctg    1200
gagaacaaca gtacgtgtt caaccggatc aacctgttcg acagcaatct ggccgtgggc    1260
gaccagatca tccactggcg ctacgaggtg aaggcctccg ccgagaccac ctacgatagc   1320
ggctacatgt gcaggcacga ggtggaggag gacgagctgc tgtgtaagat caacgaggac   1380
aagtacaagg acatgctgga ccggatgatc cagggcggct gggatcagga gggttcaag    1440
ctgcacaaca tcctgaccga ccccaacctg ctgacaatcg acttcgagaa ggacgcctac   1500
ctgaacagca gaagcgagct ggtgttcccc gactacttcg acaagtggat cagcagcccc   1560
atgttcaacg cccggctgag aatcaccaag ggcgagatcg caccagcaa aaggacgac    1620
ccctggaaca acagagccgt gcggggctac atcaagagcc tgccgagtc cctggacttc    1680
gtgctgggcc cctactacga tctgcggctg ctgttcttcg gcgaggccct gagcctgaag   1740
caggagcaga gcgccgtgtt ccagtacctg agccagctgg acgacttccc cgccctgacc   1800
cagctgaccg gcgacgccgt gtgtcctcac agcggcggag ccctgtacac cttcaggaag   1860
gtggccctgt tcctgatcgg caactacgag aagctgagcc ccgacctgca cgagggcatg   1920
gagcaccaga cctacgtgca ccccagcacc ggcggcacct accagaaatg cgtgctggag   1980
atgaaggacc cctgccagct gatgtgcttc gtgatcgact acatcttcga aagcgggag    2040
cagctgagag acaccaagga ggcccggtac atcgtgtacc tgatccagag cctgaccggc   2100
atccagagac tggacgtgct gaagagcacc ttccccaact tcttccagcg gctgctgatg   2160
ctgaaggaga tcaagtttgt gcgggacctg aacgtgatca cttcctgcc cctgatgttc    2220
ctggtgcacg acaacatcag ctacagccac cggcagtgga gcatccctat ggtgctgttc   2280
gacgacacca tcaagctgat ccctgtggaa gtgggcgcct acgccaacag attcggcttc   2340
aagagcttca tgaacttcac caggttccac cctggcgaga gcaagaagaa gcagatcgcc   2400
gaggacgtgc acaaggagtt cggcgtggtg gccttcgagt actacaccaa caccaagatc   2460
agccagggca gcgtgcacac ccccgtgatg accaccaaga tggatgtgct gaaaatccac   2520
ctgagcagcc tgtgtgccgg cctggccgac agcatcgtgt acaccctgcc cgtgccca c   2580
cccaagaagt gcatcgtgct gatcattgtg ggcgacgaca agctggagcc tcacaccaga   2640
tccgagcaga tcgtgtcccg gtacaactac agccggaagc acatctgcgg cgtggtgtcc   2700
gtgacagtgg ccagaacag ccagctgaga gtgtacacca gcggcatcgt gaagcacaga   2760
gtgtgcgaca agttcatcct gaagcacaaa tgcaaggtga tcctggtgag gatgcccggc   2820
tacgtgttcg gcaacgacga gctgatgacc aagctgctga atgtgtga                2868
```

<210> SEQ ID NO 2
<211> LENGTH: 1581
<212> TYPE: DNA
<213> ORGANISM: Artificial Sequence
<220> FEATURE:
<223> OTHER INFORMATION: Description of Artificial Sequence: Synthetic BTV17 codon optimized VP5

-continued

<400> SEQUENCE: 2

```
atgggcaaga tcatcaagag cctgagccgc ttcggcaaga aagtgggcaa tgccctgacc     60
agcaacaccg ccaagaagat ctacagcacc atcggcaagg ccgccgagag attcgccgag    120
agcgagatcg gagccgccac catcgacggc ctggtgcagg gcagcgtgca cagcatcatc    180
accggcgaga gctacggcga gagcgtgaag caggccgtgc tgctgaacgt gctgggcaca    240
ggcgaggagc tgcccgaccc cctgagccct ggcgagagag gcatccagac caagatcaag    300
gagctggagg acgagcagag aaacgagctg gtgcggctga agtacaacaa ggagatcacc    360
aaggagttcg gcaaggaact ggaagaggtg tacgacttca tgaacggcga ggccaaggag    420
gaggaggtgg tgcaagaaca gtacagcatg ctgtgcaagg ccgtggacag ctacgagaag    480
atcctgaagg ccgaggactc caagatggcc atgctggcca gagccctgca gagggaggcc    540
agcgagagaa gccaggacga gatcaagatg gtgaaggagt accggcagaa gatcgacgcc    600
ctgaagaacg ccatcgagat cgagagggac ggcatgcagg aggaggccat ccaagaaatc    660
gccggcatga ccgccgacgt gctggaggcc gccagcgagg aggtgcccct gattggcgcc    720
ggaatggcca ccgccgtggc caccggcaga gccatcgagg gcgcctacaa gctgaagaag    780
gtgatcaacg ccctgagcgg catcgacctg agccacatga ggagccccaa gatcgagcct    840
accatcatcg ccaccaccct ggagcaccgg ttcaaggaga tccctgacga gcagctggcc    900
gtgtccgtgc tgaacaagaa aaccgccgtg accgacaact gcaacgagat cgcccacatc    960
aagcaggaga tcctgcccaa gttcaagcag atcatggacg aggagaagga gatcgagggc   1020
atcgaggaca aggtgatcca cccccgggtg atgatgaggt tcaagatccc cagaacccag   1080
cagcctcaga tccacatcta tgccgcccct tgggacagcg acgacgtgtt cttcttccac   1140
tgcgtgtccc accaccacag gaacgagagc ttcttcctgg gcttcgacct gggcatcgac   1200
gtggtgcact tcgaggatct gaccagccac tggcacgccc tgggcctggc ccaggaggcc   1260
tccggcagaa ccctgaccga ggcctacagg gagttcctga acctgagcat cagcagcacc   1320
tacagcagcg ccatccacgc ccggagaatg atcagatcca gggccgtgca ccctatcttt   1380
ctgggcagca cccactacga catcacctac gaggccctga aaaacaacgc ccagcggatc   1440
gtgtacgatg aggagctgca gatgcacatc ctgagaggcc ctctgcactt ccagaggaga   1500
gccatcctgg gcgccctgaa gttcggcatc aagatcctgg gcgacaagat cgacgtgccc   1560
ctgttcctga ggaacgcctg a                                              1581
```

<210> SEQ ID NO 3
<211> LENGTH: 2868
<212> TYPE: DNA
<213> ORGANISM: Bluetongue virus 17

<400> SEQUENCE: 3

```
atggaggagt tcgtcattcc agtctattca gaagatgaaa ttccatacgc tttactgagc     60
agataccctt tggcgataca gacaaatgtt aaaatagagg atgttgaagg aaaacataat    120
gttgtaaaaa ttcctgaatc cgatatgata gatataccaa gattaacaat tgtagaggcg    180
atgaattata aaccagcgag aaacgatgga atcgttgtac ctagattact tgatataaca    240
ttacgtgctt atgatgatag gaaatcgaca aaaagtgctc gagggataga gttcatgacg    300
aacgctagat ggatgaaatg ggccatagat gatagaatgg atatccaacc gcttaaagtc    360
actttggatc attactgttc cgtcaaccat cagctcttta actgcgtcgt caaagcgaat    420
gctgccaacg ctgatacgat ctattatgat tatttcccac ttgaagacca taaaaaaaga    480
```

```
tgtaaccaca caaatcttga tttattgaga agtttgacca atatggagtt gttccacgcg    540
ttgcaaggtg ctgcatacag tatcaaatcg agctacgaat tagtggcaaa ctccgaaaga    600
gaaagcttgg aggagactta tgcgatagga cagccaaagt ggatacattt gactagagga    660
acgcgaatag gcaatagtgg attaccttat gaacggttta tctcaagcat ggtccaggtg    720
atcgtaaatg gcaagattcc aagcgagata gcgaacgagg tcgcgcaact gaatagaata    780
agggcagagt ggatagcggc tacatacgat agaggcagga ttagagcgct agagctatgc    840
aagatccttt ccacgattgg gcgtaagata ctgaacacgc atgaagagcc gaaagatgaa    900
atggatctat caacaagatt tcagttcaaa cttgacgaaa aatttaacag aacagatcca    960
gaacatgtta atattttggg tgtaagagcc ccagcgacag atgaaggaag attttacgct   1020
ctgattgcaa tcgcagcgac ggatacacaa aagggtagag tgtggagaac aaatccgtat   1080
ccatgcttgc gaggtgcttt agttgcagct gagtgtgaat taggtgacgt ttacagtacg   1140
ctccgacgtg tgtatagatg gagtctaagg ccggagtatg gacagcacga gcgacaatta   1200
gagaacaata aatacgtctt taatcgtata aatttattcg attcaaactt agcggtcggc   1260
gatcagataa ttcattggcg ttatgaggtt aaagcatcgg cggagacgac ttatgacagt   1320
ggatacatgt gtcggcatga ggttgaggag gatgaactat tatgtaaaat caatgaggac   1380
aaatataaag acatgctgga cagaatgatt cagggtgggt gggatcagga aagatttaaa   1440
cttcataaca tactgacgga ccctaactta ttgacgattg actttgaaaa agatgcgtat   1500
ctgaactcac ggtccgagtt agttttccg gattatttcg acaaatggat cagttcacca   1560
atgtttaacg cgcgcttaag aattactaaa ggggagatcg gaacatcgaa aaaggatgat   1620
ccatggaaca accgcgcagt acgtggatac atcaagtccc ctgcggagtc gttggatttt   1680
gttctcgggc cttactacga tctgcggcta ctattttttg gcgaggcgtt gagcttaaaa   1740
caggaacaat ccgcggtttt tcaatatttg agtcagctcg atgattttcc cgcgcttacg   1800
cagctaacag gagatgccgt atgcccacat tcaggcggag cgctatatac gtttaggaaa   1860
gtcgcgctat ttttaatcgg gaattatgaa aagttaagtc cggatctaca tgaaggtatg   1920
gaacatcaaa catatgtgca tccgtcgact ggtgggacgt atcagaaatg cgtgctagag   1980
atgaaggacc cttgtcaact aatgtgcttt gtgattgatt acatctttga aaaacgtgag   2040
cagctacgtg ataccaaaga ggcgaggtac atcgtgtatc taattcaaag tctcactggg   2100
atacaacggc tggatgttct gaaatcgacg ttcccgaatt ttttccaacg attattaatg   2160
ctgaaagaga tcaaatttgt gcgtgattta aatgtgatca acttcctccc tctgatgttc   2220
cttgttcatg ataacatctc gtattcgcat agacagtggt caattccaat ggtactgttt   2280
gacgatacga ttaagttaat acccgtagag gttggcgcgt atgcaaatag atttggattc   2340
aaaagtttta tgaactttac acggtttcac cctggtgagt caaagaaaaa acagattgcc   2400
gaggatgtgc ataaggagtt tggagtggtc gctttcgaat attacaccaa tacaaaaatt   2460
tcccagggga gtgtccatac accagtaatg actacgaaaa tggatgtatt gaagatacat   2520
ttgtcttctt tatgtgcagg tctggcggat tctatcgtat atacattacc ggttgcgcat   2580
cctaagaaat gcatcgttct aataattgtg ggagatgaca aattggaacc gcatacgcgt   2640
tcagaacaaa tagttagtcg gtataattac tcacgtaagc acatttgtgg agttgtatcc   2700
gtcaccgtcg ggcagaatag tcagttgaga gtttatacct ctggaattgt taaacaccgt   2760
gtatgcgaca agttcattct aaaacacaag tgcaaggtga tattagtgag gatgccgggg   2820
tacgttttcg gaaatgatga attaatgacg aaactattga atgtctag                2868
```

<210> SEQ ID NO 4
<211> LENGTH: 1581
<212> TYPE: DNA
<213> ORGANISM: Bluetongue virus 17

<400> SEQUENCE: 4

| | |

-continued

```
<220> FEATURE:
<223> OTHER INFORMATION: Description of Artificial Sequence: Synthetic
      primer

<400> SEQUENCE: 6
cccgggatcg atggatcctt tttatagcta attagtcacg tacctttgag agtaccactt    60
cagcta                                                               66

<210> SEQ ID NO 7
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggatccatcg atcccgggtt tttatgacta gttaatcacg gccgcttata aagatctaaa    60
atgcat                                                               66

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctgcaggt attctaaact aggaatagat                                     30

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcgttaatta attagagctt ctttattcta tacttaaaaa g                        41

<210> SEQ ID NO 10
<211> LENGTH: 56
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aaaacccggg atcgattcta gactcgaggg tacctacgat acaaacttaa cggata        56

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ttatttagaa attatgcatt ttaga                                          25
```

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttctcgtag gagagaacta ttgac                                           25

<210> SEQ ID NO 13
<211> LENGTH: 4879
<212> TYPE: DNA
<213> ORGANISM: Artificial Sequence
<220> FEATURE:
<223> OTHER INFORMATION: Description of Artificial Sequence: Synthetic
      pCXL148.2 donor plasmid sequence

<400> SEQUENCE: 13

| | | | | | |
|---|---|---|---|---|---|
| ttaccagtgg | ctgctgccag | tggcgataag | tcgtgtctta | ccgggttgga | ctcaagacga | 60 |
| tagttaccgg | ataaggcgca | gcggtcgggc | tgaacggggg | gttcgtgcac | acagcccagc | 120 |
| ttggagcgaa | cgacctacac | cgaactgaga | tacctacagc | gtgagctatg | agaaagcgcc | 180 |
| acgcttcccg | aagggagaaa | ggcggacagg | tatccggtaa | gcggcagggt | cggaacagga | 240 |
| gagcgcacga | gggagcttcc | aggggggaaac | gcctggtatc | tttatagtcc | tgtcgggttt | 300 |
| cgccacctct | gacttgagcg | tcgatttttg | tgatgctcgt | caggggggcg | gagcctatgg | 360 |
| aaaaacgcca | gcaacgcggc | cttttttacgg | ttcctggcct | tttgctggcc | ttttgctcac | 420 |
| atgttctttc | ctgcgttatc | ccctgattct | gtggataacc | gtattaccgc | ctttgagtga | 480 |
| gctgataccg | ctcgccgcag | ccgaacgacc | gagcgcagcg | agtcagtgag | cgaggaagcg | 540 |
| gaagagcgcc | caatacgcaa | accgcctctc | cccgcgcgtt | ggccgattca | ttaatgcagc | 600 |
| tggcacgaca | ggtttcccga | ctggaaagcg | ggcagtgagc | gcaacgcaat | taatgtgagt | 660 |
| tagctcactc | attaggcacc | ccaggcttta | cactttatgc | ttccggctcg | tatgttgtgt | 720 |
| ggaattgtga | gcggataaca | atttcacaca | ggaaacagct | atgaccatga | ttacgaattg | 780 |
| cggccgcaat | tctgaatgtt | aaatgttata | ctttggatga | agctataaat | atgcattgga | 840 |
| aaataatcc | atttaaagaa | aggattcaaa | tactacaaaa | cctaagcgat | aatatgttaa | 900 |
| ctaagcttat | tcttaacgac | gctttaaata | tacacaaata | aacataattt | ttgtataacc | 960 |
| taacaaataa | ctaaaacata | aaaataataa | aaggaaatgt | aatatcgtaa | ttatttact | 1020 |
| caggaatggg | gttaaatatt | tatatcacgt | gtatatctat | actgttatcg | tatactcttt | 1080 |
| acaattacta | ttacgaatat | gcaagagata | ataagattac | gtatttaaga | gaatcttgtc | 1140 |
| atgataattg | ggtacgacat | agtgataaat | gctatttcgc | atcgttacat | aaagtcagtt | 1200 |
| ggaaagatgg | atttgacaga | tgtaacttaa | taggtgcaaa | aatgttaaat | aacagcattc | 1260 |
| tatcggaaga | taggatacca | gttatattat | acaaaaatca | ctggttggat | aaaacagatt | 1320 |
| ctgcaatatt | cgtaaaagat | gaagattact | gcgaatttgt | aaactatgac | aataaaaagc | 1380 |
| catttatctc | aacgacatcg | tgtaattctt | ccatgtttta | tgtatgtgtt | tcagatatta | 1440 |
| tgagattact | ataaactttt | tgtatactta | tattccgtaa | actatattaa | tcatgaagaa | 1500 |
| aatgaaaaag | tatagaagct | gttcacgagc | ggttgttgaa | aacaacaaaa | ttatacattc | 1560 |
| aagatggctt | acatatacgt | ctgtgaggct | atcatggata | atgacaatgc | atctctaaat | 1620 |
| aggttttttgg | acaatggatt | cgaccctaac | acggaatatg | gtactctaca | atctcctctt | 1680 |

```
gaaatggctg taatgttcaa gaataccgag gctataaaaa tcttgatgag gtatggagct    1740
aaacctgtag ttactgaatg cacaacttct tgtctgcatg atgcggtgtt gagagacgac    1800
tacaaaatag tgaaagatct gttgaagaat aactatgtaa acaatgttct ttacagcgga    1860
ggctttactc ctttgtgttt ggcagcttac cttaacaaag ttaatttggt taaacttcta    1920
ttggctcatt cggcggatgt agatatttca aacacggatc ggttaactcc tctacatata    1980
gccgtatcaa ataaaaattt aacaatggtt aaacttctat tgaacaaagg tgctgatact    2040
gacttgctgg ataacatggg acgtactcct ttaatgatcg ctgtacaatc tggaaatatt    2100
gaaatatgta gcacactact taaaaaaaat aaaatgtcca gaactgggaa aaattgatct    2160
tgccagctgt aattcatggt agaaaagaag tgctcaggct acttttcaac aaaggagcag    2220
atgtaaacta catctttgaa agaaatggaa atcatatac tgttttggaa ttgattaaag     2280
aaagttactc tgagacacaa agaggtagc tgaagtggta ctctcaaagg tacgtgacta     2340
attagctata aaaaggatcc gggttaatta attagtcatc aggcagggcg agaacgagac    2400
tatctgctcg ttaattaatt agagcttctt tattctatac ttaaaaagtg aaaataaata    2460
caaaggttct tgagggttgt gttaaattga agcgagaaa taatcataaa ttatttcatt     2520
atcgcgatat ccgttaagtt tgtatcgtag gtaccctcga gtctagaatc gatcccgggt    2580
ttttatgact agttaatcac ggccgcttat aaagatctaa aatgcataat ttctaaataa    2640
tgaaaaaaag tacatcatga gcaacgcgtt agtatatttt acaatggaga ttaacgctct    2700
ataccgttct atgtttattg attcagatga tgttttagaa aagaaagtta ttgaatatga    2760
aaactttaat gaagatgaag atgacgacga tgattattgt tgtaaatctg ttttagatga    2820
agaagatgac gcgctaaagt atactatggt tacaaagtat aagtctatac tactaatggc    2880
gacttgtgca agaaggtata gtatagtgaa atgttgtta gattatgatt atgaaaaacc     2940
aaataaatca gatccatatc taaaggtatc tcctttgcac ataatttcat ctattcctag    3000
tttagaatac ctgcagccaa gcttggcact ggccgtcgtt ttacaacgtc gtgactggga    3060
aaaccctggc gttacccaac ttaatcgcct tgcagcacat ccccctttcg ccagctggcg    3120
taatagcgaa gaggcccgca ccgatcgccc ttcccaacag ttgcgcagcc tgaatggcga    3180
atggcgcctg atgcggtatt ttctccttac gcatctgtgc ggtatttcac accgcatatg    3240
gtgcactctc agtacaatct gctctgatgc cgcatagtta agccagcccc gacacccgcc    3300
aacacccgct gacgcgccct gacgggcttg tctgctcccg gcatccgctt acagacaagc    3360
tgtgaccgtc tccgggagct gcatgtgtca gaggttttca ccgtcatcac cgaaacgcgc    3420
gagacgaaag gcctcgtga tacgcctatt tttataggtt aatgtcatga taataatggt     3480
ttcttagacg tcaggtggca cttttcgggg aaatgtgcgc ggaaccccta tttgtttatt    3540
tttctaaata cattcaaata tgtatccgct catgagacaa taaccctgat aaatgcttca    3600
ataatattga aaaggaaga gtatgagtat tcaacatttc cgtgtcgccc ttattccctt     3660
ttttgcggca ttttgccttc ctgttttgc tcacccagaa acgctggtga agtaaaaga     3720 tgctgaagat cagttgggtg cacgagtggg ttacatcgaa ctggatctca acagcggtaa    3780
gatccttgag agttttcgcc ccgaagaacg ttttccaatg atgagcactt ttaaagttct    3840
gctatgtggc gcggtattat cccgtattga cgccgggcaa gagcaactcg gtcgccgcat    3900
acactattct cagaatgact tggttgagta ctcaccagtc acagaaaagc atcttacgga    3960
tggcatgaca gtaagagaat tatgcagtgc tgccataacc atgagtgata acactgcggc    4020
caacttactt ctgacaacga tcggaggacc gaaggagcta accgcttttt tgcacaacat    4080
```

-continued

```
ggggatcat gtaactcgcc ttgatcgttg ggaaccggag ctgaatgaag ccataccaaa    4140
cgacgagcgt gacaccacga tgcctgtagc aatggcaaca acgttgcgca aactattaac    4200
tggcgaacta cttactctag cttcccggca acaattaata gactggatgg aggcggataa    4260
agttgcagga ccacttctgc gctcggccct tccggctggc tggtttattg ctgataaatc    4320
tggagccggt gagcgtgggt ctcgcggtat cattgcagca ctggggccag atggtaagcc    4380
ctcccgtatc gtagttatct acacgacggg gagtcaggca actatggatg aacgaaatag    4440
acagatcgct gagataggtg cctcactgat taagcattgg taactgtcag accaagttta    4500
ctcatatata ctttagattg atttaaaact tcatttttaa tttaaaagga tctaggtgaa    4560 gatcctttt gataatctca tgaccaaaat cccttaacgt gagttttcgt tccactgagc     4620
gtcagacccc gtagaaaaga tcaaaggatc ttcttgagat ccttttttc tgcgcgtaat    4680 ctgctgcttg caaacaaaaa aaccaccgct accagcggtg gtttgtttgc cggatcaaga    4740
gctaccaact cttttccga aggtaactgg cttcagcaga gcgcagatac caaatactgt     4800
ccttctagtg tagccgtagt taggccacca cttcaagaac tctgtagcac cgcctacata    4860
cctcgctctg ctaatcctg                                                 4879
```

```
<210> SEQ ID NO 14
<211> LENGTH: 72
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcgctcgagt ttttattcaa aattgaaaat atataattac aatataaaat gggcaagatc    60
atcaagagcc tg                                                        72

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atctcgagat aaaaatcatc aggcgttcct caggaacagg ggcacgtc                 48

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gaatctgtta gttagttact tggat                                          25

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 17
tgattatagc tattatcaca gactc                                        25

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aattgcggcc gc                                                      12

<210> SEQ ID NO 19
<211> LENGTH: 6795
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (1800)..(4664)
<220> FEATURE:
<221> NAME/KEY: CDS
<222> LOCATION: (4716)..(6293)

<400> SEQUENCE: 19
ggaaacagct atgaccatga ttacgaattg cggccgcaat tctgaatgtt aaatgttata     60
ctttggatga agctataaat atgcattgga aaataatcc atttaaagaa aggattcaaa    120
tactacaaaa cctaagcgat aatatgttaa ctaagcttat tcttaacgac gctttaaata   180
tacacaaata aacataattt ttgtataacc taacaaataa ctaaacata aaaataataa    240 aaggaaatgt aatatcgtaa ttattttact caggaatggg gttaaatatt tatatcacgt   300
gtatatctat actgttatcg tatactcttt acaattacta ttacgaatat gcaagagata   360
ataagattac gtatttaaga gaatcttgtc atgataattg ggtacgacat agtgataaat   420
gctatttcgc atcgttacat aaagtcagtt ggaaagatgg atttgacaga tgtaacttaa   480
taggtgcaaa aatgttaaat aacagcattc tatcggaaga taggatacca gttatattat   540
acaaaaatca ctggttggat aaaacagatt ctgcaatatt cgtaaaagat gaagattact   600
gcgaatttgt aaactatgac aataaaaagc catttatctc aacgacatcg tgtaattctt   660
ccatgtttta tgtatgtgtt tcagatatta tgagattact ataaactttt tgtatactta   720
tattccgtaa actatattaa tcatgaagaa aatgaaaaag tatagaagct gttcacgagc   780
ggttgttgaa acaacaaaa ttatacattc aagatggctt acatatacgt ctgtgaggct    840
atcatggata atgacaatgc atctctaaat aggtttttgg acaatggatt cgaccctaac   900
acggaatatg gtactctaca atctcctctt gaaatggctg taatgttcaa gaataccgag   960
gctataaaaa tcttgatgag gtatggagct aaacctgtag ttactgaatg cacaacttct  1020
tgtctgcatg atgcggtgtt gagagacgac tacaaaatag tgaaagatct gttgaagaat  1080
aactatgtaa acaatgttct ttacagcgga ggctttactc ctttgtgttt ggcagcttac  1140
cttaacaaag ttaatttggt taaacttcta ttggctcatt cggcggatgt agatatttca  1200
aacacggatc ggttaactcc tctacatata gccgtatcaa ataaaaattt aacaatggtt  1260
aaacttctat tgaacaaagg tgctgatact gacttgctgg ataacatggg acgtactcct  1320
ttaatgatcg ctgtacaatc tggaaatatt gaaatatgta gcacactact taaaaaaat   1380
```

```
aaaatgtcca gaactgggaa aaattgatct tgccagctgt aattcatggt agaaaagaag    1440
tgctcaggct acttttcaac aaaggagcag atgtaaacta catctttgaa agaaatggaa    1500
aatcatatac tgttttggaa ttgattaaag aaagttactc tgagacacaa aagaggtagc    1560
tgaagtggta ctctcaaagg tacgtgacta attagctata aaaaggatcc gggttaatta    1620
attagtcatc aggcagggcg agaacgagac tatctgctcg ttaattaatt agagcttctt    1680
tattctatac ttaaaaagtg aaaataaata caaaggttct tgagggttgt gttaaattga    1740
aagcgagaaa taatcataaa ttatttcatt atcgcgatat ccgttaagtt tgtatcgta     1799
```

| atg gag gag ttc gtg atc ccc gtg tac agc gag gac gag atc ccc tac | 1847 |
|---|---|
| Met Glu Glu Phe Val Ile Pro Val Tyr Ser Glu Asp Glu Ile Pro Tyr | |
| 1               5                  10                 15 | |

| gcc ctg ctg agc aga tac cct ctg gcc atc cag acc aac gtg aag atc | 1895 |
|---|---|
| Ala Leu Leu Ser Arg Tyr Pro Leu Ala Ile Gln Thr Asn Val Lys Ile | |
|             20              25                 30 | |

| gag gac gtg gag ggc aag cac aac gtg gtg aag atc ccc gag agc gac | 1943 |
|---|---|
| Glu Asp Val Glu Gly Lys His Asn Val Val Lys Ile Pro Glu Ser Asp | |
|         35                 40                 45 | |

| atg atc gac atc ccc cgg ctg acc atc gtg gag gcc atg aac tac aag | 1991 |
|---|---|
| Met Ile Asp Ile Pro Arg Leu Thr Ile Val Glu Ala Met Asn Tyr Lys | |
| 50                 55                 60 | |

| ccc gcc agg aac gac ggc atc gtg gtg cct aga ctg ctg gac atc acc | 2039 |
|---|---|
| Pro Ala Arg Asn Asp Gly Ile Val Val Pro Arg Leu Leu Asp Ile Thr | |
| 65              70                 75              80 | |

| ctg aga gcc tac gac gac cgg aag agc acc aag agc gcc aga ggc atc | 2087 |
|---|---|
| Leu Arg Ala Tyr Asp Asp Arg Lys Ser Thr Lys Ser Ala Arg Gly Ile | |
|             85                 90                 95 | |

| gag ttc atg acc aac gcc cgg tgg atg aag tgg gcc atc gac gac agg | 2135 |
|---|---|
| Glu Phe Met Thr Asn Ala Arg Trp Met Lys Trp Ala Ile Asp Asp Arg | |
|         100                105                110 | |

| atg gac atc cag ccc ctg aag gtg acc ctg gac cac tac tgc agc gtg | 2183 |
|---|---|
| Met Asp Ile Gln Pro Leu Lys Val Thr Leu Asp His Tyr Cys Ser Val | |
|     115                120                125 | |

| aat cac cag ctg ttc aac tgc gtg gtg aag gcc aac gcc gcc aat gcc | 2231 |
|---|---|
| Asn His Gln Leu Phe Asn Cys Val Val Lys Ala Asn Ala Ala Asn Ala | |
| 130                135                140 | |

| gac acc atc tac tac gac tac ttc ccc ctg gag gac cac aag aag cgg | 2279 |
|---|---|
| Asp Thr Ile Tyr Tyr Asp Tyr Phe Pro Leu Glu Asp His Lys Lys Arg | |
| 145             150                155                160 | |

| tgc aac cac acc aac ctg gac ctg ctg agg agc ctg acc aac atg gag | 2327 |
|---|---|
| Cys Asn His Thr Asn Leu Asp Leu Leu Arg Ser Leu Thr Asn Met Glu | |
|             165                170                175 | |

| ctg ttc cac gcc ctg cag gga gcc gcc tac agc atc aag agc agc tac | 2375 |
|---|---|
| Leu Phe His Ala Leu Gln Gly Ala Ala Tyr Ser Ile Lys Ser Ser Tyr | |
|         180                185                190 | |

| gaa ctg gtg gcc aac agc gag aga gag agc ctg gag gag acc tac gcc | 2423 |
|---|---|
| Glu Leu Val Ala Asn Ser Glu Arg Glu Ser Leu Glu Glu Thr Tyr Ala | |
|     195                200                205 | |

| atc ggc cag cct aag tgg atc cac ctg acc agg ggc acc aga atc ggc | 2471 |
|---|---|
| Ile Gly Gln Pro Lys Trp Ile His Leu Thr Arg Gly Thr Arg Ile Gly | |
| 210                215                220 | |

| aac agc ggc ctg cct tac gag aga ttc atc agc agc atg gtg cag gtg | 2519 |
|---|---|
| Asn Ser Gly Leu Pro Tyr Glu Arg Phe Ile Ser Ser Met Val Gln Val | |
| 225             230                235                240 | |

| atc gtg aac ggc aag atc cct agc gag atc gcc aac gag gtg gcc cag | 2567 |
|---|---|
| Ile Val Asn Gly Lys Ile Pro Ser Glu Ile Ala Asn Glu Val Ala Gln | |
|             245                250                255 | |

```
ctg aac aga atc cgg gcc gag tgg atc gcc gcc acc tac gac aga ggc      2615
Leu Asn Arg Ile Arg Ala Glu Trp Ile Ala Ala Thr Tyr Asp Arg Gly
        260                 265                 270 agg atc aga gcc ctg gag ctg tgc aag atc ctg agc acc atc ggc cgg      2663
Arg Ile Arg Ala Leu Glu Leu Cys Lys Ile Leu Ser Thr Ile Gly Arg
    275                 280                 285 aag atc ctg aat acc cac gag gag ccc aag gac gag atg gac ctg tcc      2711
Lys Ile Leu Asn Thr His Glu Glu Pro Lys Asp Glu Met Asp Leu Ser
290                 295                 300 acc cgg ttc cag ttc aag ctg gac gag aag ttc aac agg acc gac ccc      2759
Thr Arg Phe Gln Phe Lys Leu Asp Glu Lys Phe Asn Arg Thr Asp Pro
305                 310                 315                 320 gag cac gtg aat atc ttc gga gtg agg gcc cct gcc acc gac gag ggc      2807
Glu His Val Asn Ile Phe Gly Val Arg Ala Pro Ala Thr Asp Glu Gly
                325                 330                 335 aga ttc tac gcc ctg atc gcc att gcc gcc acc gac acc cag aag ggc      2855
Arg Phe Tyr Ala Leu Ile Ala Ile Ala Ala Thr Asp Thr Gln Lys Gly
            340                 345                 350 aga gtg tgg agg acc aac ccc tac cct tgc ctg aga ggc gcc ctg gtg      2903
Arg Val Trp Arg Thr Asn Pro Tyr Pro Cys Leu Arg Gly Ala Leu Val
        355                 360                 365 gcc gcc gag tgc gag ctg ggc gac gtg tac agc acc ctg cgg agg gtg      2951
Ala Ala Glu Cys Glu Leu Gly Asp Val Tyr Ser Thr Leu Arg Arg Val
    370                 375                 380 tac aga tgg agc ctg aga cct gag tac ggc cag cac gag aga cag ctg      2999
Tyr Arg Trp Ser Leu Arg Pro Glu Tyr Gly Gln His Glu Arg Gln Leu
385                 390                 395                 400 gag aac aac aag tac gtg ttc aac cgg atc aac ctg ttc gac agc aat      3047
Glu Asn Asn Lys Tyr Val Phe Asn Arg Ile Asn Leu Phe Asp Ser Asn
                405                 410                 415 ctg gcc gtg ggc gac cag atc atc cac tgg cgc tac gag gtg aag gcc      3095
Leu Ala Val Gly Asp Gln Ile Ile His Trp Arg Tyr Glu Val Lys Ala
            420                 425                 430 tcc gcc gag acc acc tac gat agc ggc tac atg tgc agg cac gag gtg      3143
Ser Ala Glu Thr Thr Tyr Asp Ser Gly Tyr Met Cys Arg His Glu Val
        435                 440                 445 gag gag gac gag ctg ctg tgt aag atc aac gag gac aag tac aag gac      3191
Glu Glu Asp Glu Leu Leu Cys Lys Ile Asn Glu Asp Lys Tyr Lys Asp
    450                 455                 460 atg ctg gac cgg atg atc cag ggc ggc tgg gat cag gag agg ttc aag      3239
Met Leu Asp Arg Met Ile Gln Gly Gly Trp Asp Gln Glu Arg Phe Lys
465                 470                 475                 480 ctg cac aac atc ctg acc gac ccc aac ctg ctg aca atc gac ttc gag      3287
Leu His Asn Ile Leu Thr Asp Pro Asn Leu Leu Thr Ile Asp Phe Glu
                485                 490                 495 aag gac gcc tac ctg aac agc aga agc gag ctg gtg ttc ccc gac tac      3335
Lys Asp Ala Tyr Leu Asn Ser Arg Ser Glu Leu Val Phe Pro Asp Tyr
            500                 505                 510 ttc gac aag tgg atc agc agc ccc atg ttc aac gcc cgg ctg aga atc      3383
Phe Asp Lys Trp Ile Ser Ser Pro Met Phe Asn Ala Arg Leu Arg Ile
        515                 520                 525 acc aag ggc gag atc ggc acc agc aag aag gac gac ccc tgg aac aac      3431
Thr Lys Gly Glu Ile Gly Thr Ser Lys Lys Asp Asp Pro Trp Asn Asn
    530                 535                 540 aga gcc gtg cgg ggc tac atc aag agc cct gcc gag tcc ctg gac ttc      3479
Arg Ala Val Arg Gly Tyr Ile Lys Ser Pro Ala Glu Ser Leu Asp Phe
545                 550                 555                 560 gtg ctg ggc ccc tac tac gat ctg cgg ctg ctg ttc ttc ggc gag gcc      3527
Val Leu Gly Pro Tyr Tyr Asp Leu Arg Leu Leu Phe Phe Gly Glu Ala
                565                 570                 575
```

-continued

| | |
|---|---|
| ctg agc ctg aag cag gag cag agc gcc gtg ttc cag tac ctg agc cag<br>Leu Ser Leu Lys Gln Glu Gln Ser Ala Val Phe Gln Tyr Leu Ser Gln<br>580                           585                         590 | 3575 |
| ctg gac gac ttc ccc gcc ctg acc cag ctg acc ggc gac gcc gtg tgt<br>Leu Asp Asp Phe Pro Ala Leu Thr Gln Leu Thr Gly Asp Ala Val Cys<br>          595                         600                         605 | 3623 |
| cct cac agc ggc gga gcc ctg tac acc ttc agg aag gtg gcc ctg ttc<br>Pro His Ser Gly Gly Ala Leu Tyr Thr Phe Arg Lys Val Ala Leu Phe<br>610                           615                         620 | 3671 |
| ctg atc ggc aac tac gag aag ctg agc ccc gac ctg cac gag ggc atg<br>Leu Ile Gly Asn Tyr Glu Lys Leu Ser Pro Asp Leu His Glu Gly Met<br>625                           630                         635                         640 | 3719 |
| gag cac cag acc tac gtg cac ccc agc acc ggc ggc acc tac cag aaa<br>Glu His Gln Thr Tyr Val His Pro Ser Thr Gly Gly Thr Tyr Gln Lys<br>                        645                         650                         655 | 3767 |
| tgc gtg ctg gag atg aag gac ccc tgc cag ctg atg tgc ttc gtg atc<br>Cys Val Leu Glu Met Lys Asp Pro Cys Gln Leu Met Cys Phe Val Ile<br>660                           665                         670 | 3815 |
| gac tac atc ttc gag aag cgg gag cag ctg aga gac acc aag gag gcc<br>Asp Tyr Ile Phe Glu Lys Arg Glu Gln Leu Arg Asp Thr Lys Glu Ala<br>                        675                         680                         685 | 3863 |
| cgg tac atc gtg tac ctg atc cag agc ctg acc ggc atc cag aga ctg<br>Arg Tyr Ile Val Tyr Leu Ile Gln Ser Leu Thr Gly Ile Gln Arg Leu<br>690                           695                         700 | 3911 |
| gac gtg ctg aag agc acc ttc ccc aac ttc ttc cag cgg ctg ctg atg<br>Asp Val Leu Lys Ser Thr Phe Pro Asn Phe Phe Gln Arg Leu Leu Met<br>705                           710                         715                         720 | 3959 |
| ctg aag gag atc aag ttt gtg cgg gac ctg aac gtg atc aac ttc ctg<br>Leu Lys Glu Ile Lys Phe Val Arg Asp Leu Asn Val Ile Asn Phe Leu<br>                        725                         730                         735 | 4007 |
| ccc ctg atg ttc ctg gtg cac gac aac atc agc tac agc cac cgg cag<br>Pro Leu Met Phe Leu Val His Asp Asn Ile Ser Tyr Ser His Arg Gln<br>                        740                         745                         750 | 4055 |
| tgg agc atc cct atg gtg ctg ttc gac gac acc atc aag ctg atc cct<br>Trp Ser Ile Pro Met Val Leu Phe Asp Asp Thr Ile Lys Leu Ile Pro<br>755                           760                         765 | 4103 |
| gtg gaa gtg ggc gcc tac gcc aac aga ttc ggc ttc aag agc ttc atg<br>Val Glu Val Gly Ala Tyr Ala Asn Arg Phe Gly Phe Lys Ser Phe Met<br>          770                         775                         780 | 4151 |
| aac ttc acc agg ttc cac cct ggc gag agc aag aag aag cag atc gcc<br>Asn Phe Thr Arg Phe His Pro Gly Glu Ser Lys Lys Lys Gln Ile Ala<br>785                           790                         795                         800 | 4199 |
| gag gac gtg cac aag gag ttc ggc gtg gtg gcc ttc gag tac tac acc<br>Glu Asp Val His Lys Glu Phe Gly Val Val Ala Phe Glu Tyr Tyr Thr<br>                        805                         810                         815 | 4247 |
| aac acc aag atc agc cag ggc agc gtg cac acc ccc gtg atg acc acc<br>Asn Thr Lys Ile Ser Gln Gly Ser Val His Thr Pro Val Met Thr Thr<br>                        820                         825                         830 | 4295 |
| aag atg gat gtg ctg aaa atc cac ctg agc agc ctg tgt gcc ggc ctg<br>Lys Met Asp Val Leu Lys Ile His Leu Ser Ser Leu Cys Ala Gly Leu<br>          835                         840                         845 | 4343 |
| gcc gac agc atc gtg tac acc ctg ccc gtg gcc cac ccc aag aag tgc<br>Ala Asp Ser Ile Val Tyr Thr Leu Pro Val Ala His Pro Lys Lys Cys<br>850                           855                         860 | 4391 |
| atc gtg ctg atc att gtg ggc gac gac aag ctg gag cct cac acc aga<br>Ile Val Leu Ile Ile Val Gly Asp Asp Lys Leu Glu Pro His Thr Arg<br>865                           870                         875                         880 | 4439 |
| tcc gag cag atc gtg tcc cgg tac aac tac agc cgg aag cac atc tgc<br>Ser Glu Gln Ile Val Ser Arg Tyr Asn Tyr Ser Arg Lys His Ile Cys<br>                        885                         890                         895 | 4487 |

```
                                                        -continued
ggc gtg gtg tcc gtg aca gtg ggc cag aac agc cag ctg aga gtg tac    4535
Gly Val Val Ser Val Thr Val Gly Gln Asn Ser Gln Leu Arg Val Tyr
        900                 905                 910 acc agc ggc atc gtg aag cac aga gtg tgc gac aag ttc atc ctg aag    4583
Thr Ser Gly Ile Val Lys His Arg Val Cys Asp Lys Phe Ile Leu Lys
        915                 920                 925 cac aaa tgc aag gtg atc ctg gtg agg atg ccc ggc tac gtg ttc ggc    4631
His Lys Cys Lys Val Ile Leu Val Arg Met Pro Gly Tyr Val Phe Gly
        930                 935                 940 aac gac gag ctg atg acc aag ctg ctg aat gtg tgatgactcg agttttatt   4684
Asn Asp Glu Leu Met Thr Lys Leu Leu Asn Val
945                 950                 955 caaaattgaa aatatataat tacaatataa a atg ggc aag atc atc aag agc     4736
                                 Met Gly Lys Ile Ile Lys Ser
                                                     960 ctg agc cgc ttc ggc aag aaa gtg ggc aat gcc ctg acc agc aac acc    4784
Leu Ser Arg Phe Gly Lys Lys Val Gly Asn Ala Leu Thr Ser Asn Thr
        965                 970                 975 gcc aag aag atc tac agc acc atc ggc aag gcc gcc gag aga ttc gcc    4832
Ala Lys Lys Ile Tyr Ser Thr Ile Gly Lys Ala Ala Glu Arg Phe Ala
980                 985                 990 gag agc gag atc gga gcc gcc acc atc gac ggc ctg gtg cag ggc agc    4880
Glu Ser Glu Ile Gly Ala Ala Thr Ile Asp Gly Leu Val Gln Gly Ser
995                 1000                1005                1010 gtg cac agc atc atc acc ggc gag agc tac ggc gag agc gtg aag cag    4928
Val His Ser Ile Ile Thr Gly Glu Ser Tyr Gly Glu Ser Val Lys Gln
            1015                1020                1025 gcc gtg ctg ctg aac gtg ctg ggc aca ggc gag gag ctg ccc gac ccc    4976
Ala Val Leu Leu Asn Val Leu Gly Thr Gly Glu Glu Leu Pro Asp Pro
            1030                1035                1040 ctg agc cct ggc gag aga ggc atc cag acc aag atc aag gag ctg gag    5024
Leu Ser Pro Gly Glu Arg Gly Ile Gln Thr Lys Ile Lys Glu Leu Glu
            1045                1050                1055 gac gag cag aga aac gag ctg gtg cgg ctg aag tac aac aag gag atc    5072
Asp Glu Gln Arg Asn Glu Leu Val Arg Leu Lys Tyr Asn Lys Glu Ile
            1060                1065                1070 acc aag gag ttc ggc aag gaa ctg gaa gag gtg tac gac ttc atg aac    5120
Thr Lys Glu Phe Gly Lys Glu Leu Glu Glu Val Tyr Asp Phe Met Asn
1075                1080                1085                1090 ggc gag gcc aag gag gag gag gtg gtg caa gaa cag tac agc atg ctg    5168
Gly Glu Ala Lys Glu Glu Glu Val Val Gln Glu Gln Tyr Ser Met Leu
            1095                1100                1105 tgc aag gcc gtg gac agc tac gag aag atc ctg aag gcc gag gac tcc    5216
Cys Lys Ala Val Asp Ser Tyr Glu Lys Ile Leu Lys Ala Glu Asp Ser
            1110                1115                1120 aag atg gcc atg ctg gcc aga gcc ctg cag agg gag gcc agc gag aga    5264
Lys Met Ala Met Leu Ala Arg Ala Leu Gln Arg Glu Ala Ser Glu Arg
            1125                1130                1135 agc cag gac gag atc aag atg gtg aag gag tac cgg cag aag atc gac    5312
Ser Gln Asp Glu Ile Lys Met Val Lys Glu Tyr Arg Gln Lys Ile Asp
            1140                1145                1150 gcc ctg aag aac gcc atc gag atc gag agg gac ggc atg cag gag gag    5360
Ala Leu Lys Asn Ala Ile Glu Ile Glu Arg Asp Gly Met Gln Glu Glu
1155                1160                1165                1170 gcc atc caa gaa atc gcc ggc atg acc gcc gac gtg ctg gag gcc gcc    5408
Ala Ile Gln Glu Ile Ala Gly Met Thr Ala Asp Val Leu Glu Ala Ala
                1175                1180                1185 agc gag gag gtg ccc ctg att ggc gcc gga atg gcc acc gcc gtg gcc    5456
Ser Glu Glu Val Pro Leu Ile Gly Ala Gly Met Ala Thr Ala Val Ala
                1190                1195                1200
```

| | |
|---|---|
| acc ggc aga gcc atc gag ggc gcc tac aag ctg aag aag gtg atc aac<br>Thr Gly Arg Ala Ile Glu Gly Ala Tyr Lys Leu Lys Lys Val Ile Asn<br>   1205                    1210                  1215 | 5504 |
| gcc ctg agc ggc atc gac ctg agc cac atg agg agc ccc aag atc gag<br>Ala Leu Ser Gly Ile Asp Leu Ser His Met Arg Ser Pro Lys Ile Glu<br>   1220                    1225                  1230 | 5552 |
| cct acc atc atc gcc acc acc ctg gag cac cgg ttc aag gag atc cct<br>Pro Thr Ile Ile Ala Thr Thr Leu Glu His Arg Phe Lys Glu Ile Pro<br>1235                  1240                  1245                  1250 | 5600 |
| gac gag cag ctg gcc gtg tcc gtg ctg aac aag aaa acc gcc gtg acc<br>Asp Glu Gln Leu Ala Val Ser Val Leu Asn Lys Lys Thr Ala Val Thr<br>   1255                    1260                  1265 | 5648 |
| gac aac tgc aac gag atc gcc cac atc aag cag gag atc ctg ccc aag<br>Asp Asn Cys Asn Glu Ile Ala His Ile Lys Gln Glu Ile Leu Pro Lys<br>   1270                    1275                  1280 | 5696 |
| ttc aag cag atc atg gac gag gag aag gag atc gag ggc atc gag gac<br>Phe Lys Gln Ile Met Asp Glu Glu Lys Glu Ile Glu Gly Ile Glu Asp<br>   1285                    1290                  1295 | 5744 |
| aag gtg atc cac ccc cgg gtg atg atg agg ttc aag atc ccc aga acc<br>Lys Val Ile His Pro Arg Val Met Met Arg Phe Lys Ile Pro Arg Thr<br>   1300                    1305                  1310 | 5792 |
| cag cag cct cag atc cac atc tat gcc gcc cct tgg gac agc gac gac<br>Gln Gln Pro Gln Ile His Ile Tyr Ala Ala Pro Trp Asp Ser Asp Asp<br>1315                  1320                  1325                  1330 | 5840 |
| gtg ttc ttc ttc cac tgc gtg tcc cac cac cac agg aac gag agc ttc<br>Val Phe Phe Phe His Cys Val Ser His His His Arg Asn Glu Ser Phe<br>   1335                    1340                  1345 | 5888 |
| ttc ctg ggc ttc gac ctg ggc atc gac gtg gtg cac ttc gag gat ctg<br>Phe Leu Gly Phe Asp Leu Gly Ile Asp Val Val His Phe Glu Asp Leu<br>   1350                    1355                  1360 | 5936 |
| acc agc cac tgg cac gcc ctg ggc ctg gcc cag gag gcc tcc ggc aga<br>Thr Ser His Trp His Ala Leu Gly Leu Ala Gln Glu Ala Ser Gly Arg<br>   1365                    1370                  1375 | 5984 |
| acc ctg acc gag gcc tac agg gag ttc ctg aac ctg agc atc agc agc<br>Thr Leu Thr Glu Ala Tyr Arg Glu Phe Leu Asn Leu Ser Ile Ser Ser<br>   1380                    1385                  1390 | 6032 |
| acc tac agc agc gcc atc cac gcc cgg aga atg atc aga tcc agg gcc<br>Thr Tyr Ser Ser Ala Ile His Ala Arg Arg Met Ile Arg Ser Arg Ala<br>1395                  1400                  1405                  1410 | 6080 |
| gtg cac cct atc ttt ctg ggc agc acc cac tac gac atc acc tac gag<br>Val His Pro Ile Phe Leu Gly Ser Thr His Tyr Asp Ile Thr Tyr Glu<br>   1415                    1420                  1425 | 6128 |
| gcc ctg aaa aac aac gcc cag cgg atc gtg tac gat gag gag ctg cag<br>Ala Leu Lys Asn Asn Ala Gln Arg Ile Val Tyr Asp Glu Glu Leu Gln<br>   1430                    1435                  1440 | 6176 |
| atg cac atc ctg aga ggc cct ctg cac ttc cag agg aga gcc atc ctg<br>Met His Ile Leu Arg Gly Pro Leu His Phe Gln Arg Arg Ala Ile Leu<br>   1445                    1450                  1455 | 6224 |
| ggc gcc ctg aag ttc ggc atc aag atc ctg ggc gac aag atc gac gtg<br>Gly Ala Leu Lys Phe Gly Ile Lys Ile Leu Gly Asp Lys Ile Asp Val<br>   1460                    1465                  1470 | 6272 |
| ccc ctg ttc ctg agg aac gcc tgatgatttt tatctcgagt ctagaatcga<br>Pro Leu Phe Leu Arg Asn Ala<br>1475                  1480 | 6323 |
| tcccgggttt ttatgactag ttaatcacgg ccgcttataa agatctaaaa tgcataattt | 6383 |
| ctaaataatg aaaaaaagta catcatgagc aacgcgttag tatattttac aatggagatt | 6443 |
| aacgctctat accgttctat gtttattgat tcagatgatg ttttagaaaa gaaagttatt | 6503 |
| gaatatgaaa actttaatga agatgaagat gacgacgatg attattgttg taaatctgtt | 6563 |

-continued

```
ttagatgaag aagatgacgc gctaaagtat actatggtta caaagtataa gtctatacta    6623
ctaatggcga cttgtgcaag aaggtatagt atagtgaaaa tgttgttaga ttatgattat    6683
gaaaaaccaa ataaatcaga tccatatcta aaggtatctc ctttgcacat aatttcatct    6743
attcctagtt tagaataccs gcagccaagc ttggcactgg ccgtcgtttt ac            6795
```

<210> SEQ ID NO 20
<211> LENGTH: 955
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 20

```
Met Glu Glu Phe Val Ile Pro Val Tyr Ser Glu Asp Glu Ile Pro Tyr
  1               5                  10                  15

Ala Leu Leu Ser Arg Tyr Pro Leu Ala Ile Gln Thr Asn Val Lys Ile
             20                  25                  30

Glu Asp Val Glu Gly Lys His Asn Val Val Lys Ile Pro Glu Ser Asp
         35                  40                  45

Met Ile Asp Ile Pro Arg Leu Thr Ile Val Glu Ala Met Asn Tyr Lys
     50                  55                  60

Pro Ala Arg Asn Asp Gly Ile Val Val Pro Arg Leu Leu Asp Ile Thr
 65                  70                  75                  80

Leu Arg Ala Tyr Asp Asp Arg Lys Ser Thr Lys Ser Ala Arg Gly Ile
                 85                  90                  95

Glu Phe Met Thr Asn Ala Arg Trp Met Lys Trp Ala Ile Asp Asp Arg
            100                 105                 110

Met Asp Ile Gln Pro Leu Lys Val Thr Leu Asp His Tyr Cys Ser Val
        115                 120                 125

Asn His Gln Leu Phe Asn Cys Val Val Lys Ala Asn Ala Ala Asn Ala
    130                 135                 140

Asp Thr Ile Tyr Tyr Asp Tyr Phe Pro Leu Glu Asp His Lys Lys Arg
145                 150                 155                 160

Cys Asn His Thr Asn Leu Asp Leu Leu Arg Ser Leu Thr Asn Met Glu
                165                 170                 175

Leu Phe His Ala Leu Gln Gly Ala Ala Tyr Ser Ile Lys Ser Ser Tyr
            180                 185                 190

Glu Leu Val Ala Asn Ser Glu Arg Glu Ser Leu Glu Glu Thr Tyr Ala
        195                 200                 205

Ile Gly Gln Pro Lys Trp Ile His Leu Thr Arg Gly Thr Arg Ile Gly
    210                 215                 220

Asn Ser Gly Leu Pro Tyr Glu Arg Phe Ile Ser Ser Met Val Gln Val
225                 230                 235                 240

Ile Val Asn Gly Lys Ile Pro Ser Glu Ile Ala Asn Glu Val Ala Gln
                245                 250                 255

Leu Asn Arg Ile Arg Ala Glu Trp Ile Ala Ala Thr Tyr Asp Arg Gly
            260                 265                 270

Arg Ile Arg Ala Leu Glu Leu Cys Lys Ile Leu Ser Thr Ile Gly Arg
        275                 280                 285

Lys Ile Leu Asn Thr His Glu Glu Pro Lys Asp Glu Met Asp Leu Ser
    290                 295                 300

Thr Arg Phe Gln Phe Lys Leu Asp Glu Lys Phe Asn Arg Thr Asp Pro
305                 310                 315                 320
```

-continued

```
Glu His Val Asn Ile Phe Gly Val Arg Ala Pro Ala Thr Asp Glu Gly
                325                 330                 335

Arg Phe Tyr Ala Leu Ile Ala Ile Ala Ala Thr Asp Thr Gln Lys Gly
                340                 345                 350

Arg Val Trp Arg Thr Asn Pro Tyr Pro Cys Leu Arg Gly Ala Leu Val
                355                 360                 365

Ala Ala Glu Cys Glu Leu Gly Asp Val Tyr Ser Thr Leu Arg Arg Val
                370                 375                 380

Tyr Arg Trp Ser Leu Arg Pro Glu Tyr Gly Gln His Glu Arg Gln Leu
385                 390                 395                 400

Glu Asn Asn Lys Tyr Val Phe Asn Arg Ile Asn Leu Phe Asp Ser Asn
                405                 410                 415

Leu Ala Val Gly Asp Gln Ile Ile His Trp Arg Tyr Glu Val Lys Ala
                420                 425                 430

Ser Ala Glu Thr Thr Tyr Asp Ser Gly Tyr Met Cys Arg His Glu Val
                435                 440                 445

Glu Glu Asp Glu Leu Leu Cys Lys Ile Asn Glu Asp Lys Tyr Lys Asp
                450                 455                 460

Met Leu Asp Arg Met Ile Gln Gly Gly Trp Asp Gln Glu Arg Phe Lys
465                 470                 475                 480

Leu His Asn Ile Leu Thr Asp Pro Asn Leu Leu Thr Ile Asp Phe Glu
                485                 490                 495

Lys Asp Ala Tyr Leu Asn Ser Arg Ser Glu Leu Val Phe Pro Asp Tyr
                500                 505                 510

Phe Asp Lys Trp Ile Ser Ser Pro Met Phe Asn Ala Arg Leu Arg Ile
                515                 520                 525

Thr Lys Gly Glu Ile Gly Thr Ser Lys Lys Asp Asp Pro Trp Asn Asn
                530                 535                 540

Arg Ala Val Arg Gly Tyr Ile Lys Ser Pro Ala Glu Ser Leu Asp Phe
545                 550                 555                 560

Val Leu Gly Pro Tyr Tyr Asp Leu Arg Leu Leu Phe Phe Gly Glu Ala
                565                 570                 575

Leu Ser Leu Lys Gln Glu Gln Ser Ala Val Phe Gln Tyr Leu Ser Gln
                580                 585                 590

Leu Asp Asp Phe Pro Ala Leu Thr Gln Leu Thr Gly Asp Ala Val Cys
                595                 600                 605

Pro His Ser Gly Gly Ala Leu Tyr Thr Phe Arg Lys Val Ala Leu Phe
                610                 615                 620

Leu Ile Gly Asn Tyr Glu Lys Leu Ser Pro Asp Leu His Glu Gly Met
625                 630                 635                 640

Glu His Gln Thr Tyr Val His Pro Ser Thr Gly Thr Tyr Gln Lys
                645                 650                 655

Cys Val Leu Glu Met Lys Asp Pro Cys Gln Leu Met Cys Phe Val Ile
                660                 665                 670

Asp Tyr Ile Phe Glu Lys Arg Glu Gln Leu Arg Asp Thr Lys Glu Ala
                675                 680                 685

Arg Tyr Ile Val Tyr Leu Ile Gln Ser Leu Thr Gly Ile Gln Arg Leu
                690                 695                 700

Asp Val Leu Lys Ser Thr Phe Pro Asn Phe Gln Arg Leu Leu Met
705                 710                 715                 720

Leu Lys Glu Ile Lys Phe Val Arg Asp Leu Asn Val Ile Asn Phe Leu
                725                 730                 735
```

```
Pro Leu Met Phe Leu Val His Asp Asn Ile Ser Tyr Ser His Arg Gln
            740                 745                 750

Trp Ser Ile Pro Met Val Leu Phe Asp Asp Thr Ile Lys Leu Ile Pro
        755                 760                 765

Val Glu Val Gly Ala Tyr Ala Asn Arg Phe Gly Phe Lys Ser Phe Met
770                 775                 780

Asn Phe Thr Arg Phe His Pro Gly Glu Ser Lys Lys Gln Ile Ala
785                 790                 795                 800

Glu Asp Val His Lys Glu Phe Gly Val Val Ala Phe Glu Tyr Tyr Thr
                805                 810                 815

Asn Thr Lys Ile Ser Gln Gly Ser Val His Thr Pro Val Met Thr Thr
            820                 825                 830

Lys Met Asp Val Leu Lys Ile His Leu Ser Ser Leu Cys Ala Gly Leu
        835                 840                 845

Ala Asp Ser Ile Val Tyr Thr Leu Pro Val Ala His Pro Lys Lys Cys
850                 855                 860

Ile Val Leu Ile Ile Val Gly Asp Asp Lys Leu Glu Pro His Thr Arg
865                 870                 875                 880

Ser Glu Gln Ile Val Ser Arg Tyr Asn Tyr Ser Arg Lys His Ile Cys
                885                 890                 895

Gly Val Val Ser Val Thr Val Gly Gln Asn Ser Gln Leu Arg Val Tyr
            900                 905                 910

Thr Ser Gly Ile Val Lys His Arg Val Cys Asp Lys Phe Ile Leu Lys
        915                 920                 925

His Lys Cys Lys Val Ile Leu Val Arg Met Pro Gly Tyr Val Phe Gly
        930                 935                 940

Asn Asp Glu Leu Met Thr Lys Leu Leu Asn Val
945                 950                 955

<210> SEQ ID NO 21
<211> LENGTH: 526
<212> TYPE: PRT
<213> ORGANISM: Artificial Sequence
<220> FEATURE:
<223> OTHER INFORMATION: Description of Artificial Sequence: Synthetic
      protein sequence

<400> SEQUENCE: 21

Met Gly Lys Ile Ile Lys Ser Leu Ser Arg Phe Gly Lys Lys Val Gly
1               5                   10                  15

Asn Ala Leu Thr Ser Asn Thr Ala Lys Lys Ile Tyr Ser Thr Ile Gly
            20                  25                  30

Lys Ala Ala Glu Arg Phe Ala Glu Ser Glu Ile Gly Ala Ala Thr Ile
        35                  40                  45

Asp Gly Leu Val Gln Gly Ser Val His Ser Ile Ile Thr Gly Glu Ser
    50                  55                  60

Tyr Gly Glu Ser Val Lys Gln Ala Val Leu Leu Asn Val Leu Gly Thr
65                  70                  75                  80

Gly Glu Glu Leu Pro Asp Pro Leu Ser Pro Gly Glu Arg Gly Ile Gln
                85                  90                  95

Thr Lys Ile Lys Glu Leu Glu Asp Glu Gln Arg Asn Glu Leu Val Arg
            100                 105                 110

Leu Lys Tyr Asn Lys Glu Ile Thr Lys Glu Phe Gly Lys Glu Leu Glu
        115                 120                 125

Glu Val Tyr Asp Phe Met Asn Gly Glu Ala Lys Glu Glu Val Val
    130                 135                 140
```

```
Gln Glu Gln Tyr Ser Met Leu Cys Lys Ala Val Asp Ser Tyr Glu Lys
145                 150                 155                 160

Ile Leu Lys Ala Glu Asp Ser Lys Met Ala Met Leu Ala Arg Ala Leu
                165                 170                 175

Gln Arg Glu Ala Ser Glu Arg Ser Gln Asp Glu Ile Lys Met Val Lys
            180                 185                 190

Glu Tyr Arg Gln Lys Ile Asp Ala Leu Lys Asn Ala Ile Glu Ile Glu
        195                 200                 205

Arg Asp Gly Met Gln Glu Glu Ala Ile Gln Glu Ile Ala Gly Met Thr
    210                 215                 220

Ala Asp Val Leu Glu Ala Ser Glu Glu Val Pro Leu Ile Gly Ala
225                 230                 235                 240

Gly Met Ala Thr Ala Val Ala Thr Gly Arg Ala Ile Glu Gly Ala Tyr
                245                 250                 255

Lys Leu Lys Lys Val Ile Asn Ala Leu Ser Gly Ile Asp Leu Ser His
            260                 265                 270

Met Arg Ser Pro Lys Ile Glu Pro Thr Ile Ile Ala Thr Thr Leu Glu
        275                 280                 285

His Arg Phe Lys Glu Ile Pro Asp Glu Gln Leu Ala Val Ser Val Leu
    290                 295                 300

Asn Lys Lys Thr Ala Val Thr Asp Asn Cys Asn Glu Ile Ala His Ile
305                 310                 315                 320

Lys Gln Glu Ile Leu Pro Lys Phe Lys Gln Ile Met Asp Glu Glu Lys
                325                 330                 335

Glu Ile Glu Gly Ile Glu Asp Lys Val Ile His Pro Arg Val Met Met
            340                 345                 350

Arg Phe Lys Ile Pro Arg Thr Gln Gln Pro Gln Ile His Ile Tyr Ala
        355                 360                 365

Ala Pro Trp Asp Ser Asp Asp Val Phe Phe His Cys Val Ser His
    370                 375                 380

His His Arg Asn Glu Ser Phe Phe Leu Gly Phe Asp Leu Gly Ile Asp
385                 390                 395                 400

Val Val His Phe Glu Asp Leu Thr Ser His Trp His Ala Leu Gly Leu
                405                 410                 415

Ala Gln Glu Ala Ser Gly Arg Thr Leu Thr Glu Ala Tyr Arg Glu Phe
            420                 425                 430

Leu Asn Leu Ser Ile Ser Ser Thr Tyr Ser Ser Ala Ile His Ala Arg
        435                 440                 445

Arg Met Ile Arg Ser Arg Ala Val His Pro Ile Phe Leu Gly Ser Thr
    450                 455                 460

His Tyr Asp Ile Thr Tyr Glu Ala Leu Lys Asn Asn Ala Gln Arg Ile
465                 470                 475                 480

Val Tyr Asp Glu Glu Leu Gln Met His Ile Leu Arg Gly Pro Leu His
                485                 490                 495

Phe Gln Arg Arg Ala Ile Leu Gly Ala Leu Lys Phe Gly Ile Lys Ile
            500                 505                 510

Leu Gly Asp Lys Ile Asp Val Pro Leu Phe Leu Arg Asn Ala
        515                 520                 525

<210> SEQ ID NO 22
<211> LENGTH: 9380
<212> TYPE: DNA
<213> ORGANISM: Artificial Sequence
```

<220> FEATURE:
<223> OTHER INFORMATION: Description of Artificial Sequence: Synthetic
      nucleotide sequence

<400> SEQUENCE: 22

| | |
|---|---|
| gcgcccaata cgcaaaccgc ctctccccgc gcgttggccg attcattaat gcagctggca | 60 |
| cgacaggttt cccgactgga aagcgggcag tgagcgcaac gcaattaatg tgagttagct | 120 |
| cactcattag gcaccccagg ctttacactt tatgcttccg gctcgtatgt tgtgtggaat | 180 |
| tgtgagcgga taacaatttc acacaggaaa cagctatgac catgattacg aattgcggcc | 240 |
| gcaattctga atgttaaatg ttatactttg gatgaagcta taaatatgca ttggaaaaat | 300 |
| aatccattta agaaaggat tcaaatacta caaaacctaa gcgataatat gttaactaag | 360 |
| cttattctta acgacgcttt aaatatacac aaataaacat aattttgta aacctaaca | 420 |
| aataactaaa acataaaaat aataaaagga aatgtaatat cgtaattatt ttactcagga | 480 |
| atggggttaa atatttatat cacgtgtata tctatactgt tatcgtatac tctttacaat | 540 |
| tactattacg aatatgcaag agataataag attacgtatt taagagaatc ttgtcatgat | 600 |
| aattgggtac gacatagtga taaatgctat ttcgcatcgt tacataaagt cagttggaaa | 660 |
| gatggatttg acagatgtaa cttaataggt gcaaaaatgt taaataacag cattctatcg | 720 |
| gaagatagga taccagttat attatacaaa atcactggt tggataaaac agattctgca | 780 |
| atattcgtaa aagatgaaga ttactgcgaa tttgtaaact atgacaataa aaagccattt | 840 |
| atctcaacga catcgtgtaa ttcttccatg ttttatgtat gtgtttcaga tattatgaga | 900 |
| ttactataaa cttttgtat acttatattc cgtaaactat attaatcatg aagaaaatga | 960 |
| aaaagtatag aagctgttca cgagcggttg ttgaaaacaa caaaattata cattcaagat | 1020 |
| ggcttacata tacgtctgtg aggctatcat ggataatgac aatgcatctc taaataggtt | 1080 |
| tttggacaat ggattcgacc ctaacacgga atatggtact ctacaatctc ctcttgaaat | 1140 |
| ggctgtaatg ttcaagaata ccgaggctat aaaaatcttg atgaggtatg gagctaaacc | 1200 |
| tgtagttact gaatgcacaa cttccttgtct gcatgatgcg gtgttgagag acgactacaa | 1260 |
| aatagtgaaa gatctgttga agaataacta tgtaaacaat gttctttaca gcggaggctt | 1320 |
| tactcctttg tgtttggcag cttaccttaa caaagttaat ttggttaaac ttctattggc | 1380 |
| tcattcggcg gatgtagata tttcaaacac ggatcggtta actcctctac atatagccgt | 1440 |
| atcaaataaa aatttaacaa tggttaaact tctattgaac aaaggtgctg atactgactt | 1500 |
| gctggataac atgggacgta ctcctttaat gatcgctgta caatctggaa atattgaaat | 1560 |
| atgtagcaca ctacttaaaa aaaataaaat gtccagaact gggaaaaatt gatcttgcca | 1620 |
| gctgtaattc atggtagaaa agaagtgctc aggctacttt tcaacaaagg agcagatgta | 1680 |
| aactacatct ttgaaagaaa tggaaaatca tatactgttt tggaattgat taagaaaagt | 1740 |
| tactctgaga cacaaaagag gtagctgaag tggtactctc aaaggtacgt gactaattag | 1800 |
| ctataaaaag gatccgggtt aattaattag tcatcaggca gggcgagaac gagactatct | 1860 |
| gctcgttaat taattagagc ttctttattc tatacttaaa aagtgaaaat aaatacaaag | 1920 |
| gttcttgagg gttgtgttaa attgaaagcg agaaataatc ataaattatt tcattatcgc | 1980 |
| gatatccgtt aagtttgtat cgtaatggag gagttcgtga tccccgtgta cagcgaggac | 2040 |
| gagatcccct acgccctgct gagcagatac cctctggcca tccagaccaa cgtgaagatc | 2100 |
| gaggacgtgg agggcaagca caacgtggtg aagatccccg agagcgacat gatcgacatc | 2160 |
| ccccggctga ccatcgtgga ggccatgaac tacaagcccg ccaggaacga cggcatcgtg | 2220 |

-continued

```
gtgcctagac tgctggacat caccctgaga gcctacgacg accggaagag caccaagagc    2280
gccagaggca tcgagttcat gaccaacgcc cggtggatga agtgggccat cgacgacagg    2340
atggacatcc agcccctgaa ggtgaccctg accactact  gcagcgtgaa tcaccagctg    2400
ttcaactgcg tggtgaaggc caacgccgcc aatgccgaca ccatctacta cgactacttc    2460
cccctggagg accacaagaa gcggtgcaac cacaccaacc tggacctgct gaggagcctg    2520
accaacatgg agctgttcca cgccctgcag ggagccgcct acagcatcaa gagcagctac    2580
gaactggtgg ccaacagcga gagagagagc ctggaggaga cctacgccat cggccagcct    2640
aagtggatcc acctgaccag ggcaccagag atcggcaaca gcggcctgcc ttacgagaga    2700
ttcatcagca gcatggtgca ggtgatcgtg aacggcaaga tccctagcga gatcgccaac    2760
gaggtggccc agctgaacag aatccgggcc gagtggatcg ccgccaccta cgacagaggc    2820
aggatcagag ccctggagct gtgcaagatc ctgagcacca tcggccggaa gatcctgaat    2880
acccacgagg agcccaagga cgagatggac ctgtccaccc ggttccagtt caagctggac    2940
gagaagttca acaggaccga ccccgagcac gtgaatatct tcggagtgag ggcccctgcc    3000
accgacgagg gcagattcta cgccctgatc gccattgccg ccaccgacac ccagaagggc    3060
agagtgtgga ggaccaaccc ctaccccttgc ctgagaggcg ccctggtggc cgccgagtgc    3120
gagctgggcg acgtgtacag caccctgcgg agggtgtaca gatggagcct gagacctgag    3180
tacggccagc acgagagaca gctggagaac aacaagtacg tgttcaaccg gatcaacctg    3240
ttcgacagca atctggccgt gggcgaccag atcatccact ggcgctacga ggtgaaggcc    3300
tccgccgaga ccacctacga tagcggctac atgtgcaggc acgaggtgga ggaggacgag    3360
ctgctgtgta agatcaacga ggacaagtac aaggacatgc tggaccggat gatccagggc    3420
ggctgggatc aggagaggtt caagctgcac aacatcctga ccgaccccaa cctgctgaca    3480
atcgacttcg agaaggacgc ctacctgaac agcagaagcg agctggtgtt ccccgactac    3540
ttcgacaagt ggatcagcag ccccatgttc aacgcccggc tgagaatcac caagggcgag    3600
atcggcacca gcaagaagga cgaccctctgg aacaacagag ccgtgcgggg ctacatcaag    3660
agccctgccg agtccctgga cttcgtgctg ggcccctact acgatctgcg gctgctgttc    3720
ttcggcgagg ccctgagcct gaagcaggag cagagcgccg tgttccagta cctgagccag    3780
ctggacgact ccccgccct gacccagctg accggcgacg ccgtgtgtcc tcacagcggc    3840
ggagccctgt acaccttcag gaaggtggcc ctgttcctga tcggcaacta cgagaagctg    3900
agccccgacc tgcacgaggg catggagcac cagacctacg tgcaccccag caccggcggc    3960
acctaccaga aatgcgtgct ggagatgaag gaccccctgcc agctgatgtg cttcgtgatc    4020
gactacatct tcgagaagcg ggagcagctg agagacacca aggaggcccg gtacatcgtg    4080
tacctgatcc agagcctgac cggcatccag agactggacg tgctgaagag caccttcccc    4140
aacttcttcc agcggctgct gatgctgaag gagatcaagt tgtgcgggga cctgaacgtg    4200
atcaacttcc tgcccctgat gttcctggtg cacgacaaca tcagctacag ccaccggcag    4260
tggagcatcc ctatggtgct gttcgacgac accatcaagc tgatccctgt ggaagtgggc    4320
gcctacgcca acagattcgg cttcaagagc ttcatgaact tcaccaggtt ccaccctggc    4380
gagagcaaga agaagcagat cgccgaggac gtgcacaagg agttcggcgt ggtggccttc    4440
gagtactaca ccaacaccaa gatcagccag ggcagcgtgc acaccccgt gatgaccacc    4500
aagatggatg tgctgaaaat ccacctgagc agcctgtgtg ccggcctggc cgacagcatc    4560
gtgtacaccc tgcccgtggc ccaccccaag aagtgcatcg tgctgatcat tgtgggcgac    4620
```

```
gacaagctgg agcctcacac cagatccgag cagatcgtgt cccggtacaa ctacagccgg    4680
aagcacatct gcggcgtggt gtccgtgaca gtgggccaga acagccagct gagagtgtac    4740
accagcggca tcgtgaagca cagagtgtgc gacaagttca tcctgaagca caatgcaag     4800 gtgatcctgg tgaggatgcc cggctacgtg ttcggcaacg acgagctgat gaccaagctg    4860
ctgaatgtgt gatgactcga gttttattc aaaattgaaa atatataatt acaatataaa     4920
atgggcaaga tcatcaagag cctgagccgc ttcggcaaga agtgggcaa tgccctgacc     4980 agcaacaccg ccaagaagat ctacagcacc atcggcaagg ccgccgagag attcgccgag    5040
agcgagatcg gagccgccac catcgacggc ctggtgcagg gcagcgtgca cagcatcatc    5100
accggcgaga gctacggcga gagcgtgaag caggccgtgc tgctgaacgt gctgggcaca    5160
ggcgaggagc tgcccgaccc cctgagccct ggcgagagag gcatccagac caagatcaag    5220
gagctggagg acgagcagag aaacgagctg gtgcggctga agtacaacaa ggagatcacc    5280
aaggagttcg gcaaggaact ggaagagtg tacgacttca tgaacggcga ggccaaggag     5340
gaggaggtgg tgcaagaaca gtacagcatg ctgtgcaagg ccgtggacag ctacgagaag    5400
atcctgaagg ccgaggactc caagatggcc atgctggcca gagccctgca gagggaggcc    5460
agcgagagaa gccaggacga gatcaagatg gtgaaggagt accggcagaa gatcgacgcc    5520
ctgaagaacg ccatcgagat cgagagggac ggcatgcagg aggaggccat ccaagaaatc    5580
gccggcatga ccgccgacgt gctggaggcc gccagcgagg aggtgcccct gattggcgcc    5640
ggaatggcca ccgccgtggc caccggcaga gccatcgagg gcgcctacaa gctgaagaag    5700
gtgatcaacg ccctgagcgg catcgacctg agccacatga ggagccccaa gatcgagcct    5760
accatcatcg ccaccaccct ggagcaccgg ttcaaggaga tccctgacga gcagctggcc    5820
gtgtccgtgc tgaacaagaa aaccgccgtg accgacaact gcaacgagat cgcccacatc    5880
aagcaggaga tcctgcccaa gttcaagcag atcatggacg aggagaagga gatcgagggc    5940
atcgaggaca aggtgatcca ccccggggtg atgatgaggt tcaagatccc cagaacccag    6000
cagcctcaga tccacatcta tgccgccct tgggacagcg acgacgtgtt cttcttccac     6060
tgcgtgtccc accaccacag gaacgagagc ttcttcctgg gcttcgacct gggcatcgac    6120
gtggtgcact tcgaggatct gaccagccac tggcacgccc tgggcctggc ccaggaggcc    6180
tccggcagaa ccctgaccga ggcctacagg gagttcctga acctgagcat cagcagcacc    6240
tacagcagcg ccatccacgc ccggagaatg atcagatcca gggccgtgca ccctatcttt    6300
ctgggcagca cccactacga catcacctac gaggccctga aaaacaacgc ccagcggatc    6360
gtgtacgatg aggagctgca gatgcacatc ctgagaggcc ctctgcactt ccagaggaga    6420
gccatcctgg gcgccctgaa gttcggcatc aagatcctgg cgacaagat cgacgtgccc     6480 ctgttcctga ggaacgcctg atgatttta tctcgagtct agaatcgatc ccgggttttt      6540
atgactagtt aatcacggcc gcttataaag atctaaaatg cataattct aaataatgaa     6600 aaaaagtaca tcatgagcaa cgcgttagta tatttacaa tggagattaa cgctctatac     6660
cgttctatgt ttattgattc agatgatgtt ttagaaaaga agttattga atatgaaaac      6720 tttaatgaag atgaagatga cgacgatgat tattgttgta atctgttttt agatgaagaa    6780
gatgacgcgc taaagtatac tatggttaca agtataagt ctatactact aatggcgact     6840
tgtgcaagaa ggtatagtat agtgaaaatg ttgttagatt atgattatga aaaccaaat     6900 aaatcagatc catatctaaa ggtatctcct ttgcacataa tttcatctat tcctagttta    6960
gaatacctgc agccaagctt ggcactggcc gtcgttttac aacgtcgtga ctgggaaaac    7020
```

```
cctggcgtta cccaacttaa tcgccttgca gcacatcccc ctttcgccag ctggcgtaat      7080
agcgaagagg cccgcaccga tcgcccttcc aacagttgc gcagcctgaa tggcgaatgg       7140
cgcctgatgc ggtattttct ccttacgcat ctgtgcggta tttcacaccg catatggtgc      7200
actctcagta caatctgctc tgatgccgca tagttaagcc agccccgaca cccgccaaca      7260
cccgctgacg cgccctgacg ggcttgtctg ctcccggcat ccgcttacag acaagctgtg      7320
accgtctccg ggagctgcat gtgtcagagg ttttcaccgt catcaccgaa acgcgcgaga      7380
cgaaagggcc tcgtgatacg cctatttttta taggttaatg tcatgataat aatggtttct     7440
tagacgtcag gtggcacttt tcggggaaat gtgcgcggaa cccctatttg tttatttttc      7500
taaatacatt caaatatgta tccgctcatg agacaataac cctgataaat gcttcaataa      7560
tattgaaaaa ggaagagtat gagtattcaa catttccgtg tcgcccttat ccctttttt       7620 gcggcatttt gccttcctgt ttttgctcac ccagaaacgc tggtgaaagt aaaagatgct      7680
gaagatcagt tgggtgcacg agtgggttac atcgaactgg atctcaacag cggtaagatc      7740
cttgagagtt ttcgccccga agaacgtttt ccaatgatga gcacttttaa agttctgcta      7800
tgtggcgcgg tattatcccg tattgacgcc gggcaagagc aactcggtcg ccgcatacac      7860
tattctcaga atgacttggt tgagtactca ccagtcacag aaaagcatct tacggatggc      7920
atgacagtaa gagaattatg cagtgctgcc ataaccatga gtgataacac tgcggccaac      7980
ttacttctga caacgatcgg aggaccgaag gagctaaccg ctttttttgca caacatgggg     8040 gatcatgtaa ctcgccttga tcgttgggaa ccggagctga atgaagccat accaaacgac      8100
gagcgtgaca ccacgatgcc tgtagcaatg gcaacaacgt tgcgcaaact attaactggc      8160
gaactactta ctctagcttc ccggcaacaa ttaatagact ggatggaggc ggataaagtt      8220
gcaggaccac ttctgcgctc ggcccttccg gctggctggt ttattgctga taaatctgga      8280
gccggtgagc gtgggtctcg cggtatcatt gcagcactgg ggccagatgg taagccctcc      8340
cgtatcgtag ttatctacac gacggggagt caggcaacta tggatgaacg aaatagacag      8400
atcgctgaga taggtgcctc actgattaag cattggtaac tgtcagacca agtttactca      8460
tatatacttt agattgattt aaaacttcat ttttaattta aaaggatcta ggtgaagatc      8520 cttttttgata atctcatgac caaaatccct taacgtgagt tttcgttcca ctgagcgtca     8580
gaccccgtag aaaagatcaa aggatcttct tgagatcctt ttttttctgcg cgtaatctgc     8640 tgcttgcaaa caaaaaaacc accgctacca gcggtggttt gtttgccgga tcaagagcta      8700
ccaactcttt ttccgaaggt aactggcttc agcagagcgc agataccaaa tactgtcctt      8760
ctagtgtagc cgtagttagg ccaccacttc aagaactctg tagcaccgcc tacatacctc      8820
gctctgctaa tcctgttacc agtggctgct gccagtggcg ataagtcgtg tcttaccggg      8880
ttggactcaa gacgatagtt accggataag gcgcagcggt cgggctgaac ggggggttcg      8940
tgcacacagc ccagcttgga gcgaacgacc tacaccgaac tgagatacct acagcgtgag      9000
ctatgagaaa gcgccacgct tcccgaaggg agaaaggcgg acaggtatcc ggtaagcggc      9060
agggtcggaa caggagagcg cacgagggag cttccagggg gaaacgcctg gtatctttat      9120
agtcctgtcg ggtttcgcca cctctgactt gagcgtcgat ttttgtgatg ctcgtcaggg      9180
gggcggagcc tatggaaaaa cgccagcaac gcggcctttt tacggttcct ggccttttgc      9240
tggccttttg ctcacatgtt ctttcctgcg ttatcccctg attctgtgga taaccgtatt      9300
accgcctttg agtgagctga taccgctcgc cgcagccgaa cgaccgagcg cagcgagtca      9360
gtgagcgagg aagcggaaga                                                 9380
```

```
<210> SEQ ID NO 23
<211> LENGTH: 72
<212> TYPE: DNA
<213> ORGANISM: Artificial Sequence
<220> FEATURE:
<223> OTHER INFORMATION: Description of Artificial Sequence: Synthetic
      nucleotide sequence
<220> FEATURE:
<221> NAME/KEY: CDS
<222> LOCATION: (49)..(72)

<400> SEQUENCE: 23
gcgctcgagt ttttattcaa aattgaaaat atataattac aatataaa atg ggc aag      57
                                                     Met Gly Lys
                                                      1 atc atc aag agc ctg                                                   72
Ile Ile Lys Ser Leu
      5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gly Lys Ile Ile Lys Ser Leu
 1               5

<210> SEQ ID NO 25
<211> LENGTH: 48
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 25
atctcgagat aaaaatcatc aggcgttcct caggaacagg ggcacgtc                  48

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Asn Arg Leu Phe Leu Pro Val Asp
 1               5
```

RECOMBINANT VACCINE AGAINST BLUETONGUE VIRUS

RELATED APPLICATIONS/INCORPORATION BY REFERENCE

Each of the above applications, together with each document cited therein, and each of the documents referenced or cited in documents cited therein, are hereby incorporated herein by reference.

Each document cited in this text ("application cited documents") and each document cited or referenced in each of the application cited documents, and any manufacturer's specifications or instructions for any products mentioned in this text and in any document incorporated into this text, are hereby incorporated herein by reference; and, technology in each of the documents incorporated herein by reference can be used in the practice of this invention.

FIELD OF THE INVENTION

The present invention relates to vectors containing at least one polynucleotide of the *Orbivirus* genus of the Reoviridae family, more specifically, bluetongue virus (or BTV) or at least one nucleic acid molecule encoding at least one BTV antigen, immunogen or epitope, e.g., in vivo and in vitro expression vectors which may comprise and express at least one polynucleotide of the BTV or in vivo and in vitro expression vectors which may comprise and express at least one BTV antigen, immunogen or epitope, as well as immunogenic compositions and vaccines against bluetongue disease; for instance, such compositions or vaccines that may contain one or more of the vectors and/or one or more of the expression products of the vectors. The invention also relates to methods for using the vectors, compositions and vaccines, including immunizing and vaccinating against this virus, expressing expression products of the polynucleotide(s), using the expression products in assays or to generate antibodies useful in assays, as well as to methods for making the, polynucleotide(s), vectors, compositions vaccines, assays, inter alia.

BACKGROUND OF THE INVENTION

Bluetongue (BT) is an arthropod-borne infectious viral disease of ruminants. Cattle and goats may be readily infected with the causative BTV but without extensive vascular injury and therefore these species generally fail to show pronounced clinical signs. In contrast, the disease in sheep is characterized by catarrhal inflammation of the mucous membranes of the mouth, nose and forestomachs, and by inflammation of the coronary bands and laminae of the hoofs. There is an excoriation of the epithelium, and ultimately necrosis of the buccal mucosa; the swollen and inflamed tongue and mouth can take on a blue color from which the disease is named (Spreull 1905). The mortality rate in sheep is estimated at 1-30%.

BTV is the prototype virus of the *Orbivirus* genus (Reoviridae family) and is made up of at least 24 different serotypes (Wilson and Mecham 2000). Different strains of BTV have been identified world-wide throughout tropical and temperate zones. BTV infection has occurred as far as 45° N in Europe, as far as 50° N in Asia and North America, and as far South as 35°. BTV is not contagious between ruminants thus the distribution of BTV is dependent on the presence of arthropod vector species of *coides* sp. (biting midges), with different vector species occurring in different regions of the world. Recent data suggests that genetic drift and founder effect contribute to diversification of individual gene segments of field strains of BTV (Bonneau, Mullens et al. 2001). It has been shown that BTV seropositive animals are resistant to reinfection with the homologous BTV serotype.

BTV infection of ruminants is transient, while infection of the *Culicoides* insect vector is persistent. The duration of viremia depends on the animal species and the strain of BTV. It has been reported that viremia can be very transient in sheep and may last for up to 41 days in BTV-infected individuals, up to 42 days in goats, and up to 100 days in cattle. Since BTV infection of cattle often results in prolonged but not persistent viremia, cattle serve as a reservoir from which virus may be ingested by the *Culicoides* vector and then transmitted to other ruminants (Anderson, Stott et al. 1985; MacLachlan 1994; MacLachlan and Pearson 2004). The ecology of many species of *Culicoides* vectors is poorly understood and their breeding sites are largely uncharacterized, and their rates of dispersal unknown. *Culicoides sonorensis* is the principal vector of BTV in North America. Female *Culicoides* insects become persistently infected with BTV and can transmit the virus after an extrinsic incubation period of up to 14 days (Mullens, Tabachnick et al. 1995). BTV overwintering in temperate zones may occur through vertically infected insect vectors, although recent data indicates that there is reduced expression of the outer capsid genes during persistent BTV infection in larval stages of the insect vectors (White, Wilson et al. 2005).

The virions of BTV have a diameter of ~69 nm with a double-shelled coat (capsid) that sometimes is surrounded by a lipoprotein "pseudo-envelope" derived from the cell membranes of infected cells. The BTV genome includes 10 distinct segments of double-stranded RNA that collectively encode seven structural (VP1 through VP7) and four non-structural (NS1, NS2, NS3 and NS3a) proteins (Roy 1996); 9 of the genome segments are monocistronic whereas segment 10 encodes both NS3 and NS3A using a second, inframe initiation codon. Genomic RNA is encapsidated in the icosahedral virion particle by a double layered protein capsid (Verwoerd, Els et al. 1972). The icosahedral core consists of two major (VP3 and VP7) and three minor proteins (VP1, VP4, VP6) and is surrounded by the outer capsid which consists of VP2 and VP5 that respectively are encoded by genomic segments 2 and 5 (Roy 1996). VP2 is responsible for binding and entry of BTV into cells, neutralization, serotype-specificity and hemagglutination. Multimeric forms of VP2 (dimers and trimers) decorate much of the surface of a VP5 scaffold on the outer surface of viral particles (Hassan and Roy 1999). VP2 varies most amongst the 24 BTV serotypes, and levels of anti-VP2 antibody correlate with virus neutralization in vitro and in vivo (Huismans and Erasmus 1981). VP5 also varies markedly between different serotypes and strains of BTV (de Mattos, de Mattos et al. 1994; DeMaula, Bonneau et al. 2000) and although no VP5-specific neutralizing MAb's have been identified to date, data suggests that this protein has a role in neutralization and serotype determination through its conformational influence on VP2 (Huismans and Erasmus 1981; Roy, Urakawa et al. 1990; DeMaula et al., 2000). Purified VP2, immunoadsorbed with BTV anti-core serum to remove trace amounts of VP7, was injected into sheep. An initial dose of 50 micrograms of VP2 was sufficient to induce VP2-precipitating antibodies as well as neutralizing and hemagglutination-inhibiting antibodies. These sheep were fully protected against challenge with a virulent strain of the same BTV serotype. Lower doses of VP2 still provided a significant level of protection even though no neutralizing antibodies were not detected prior to challenge (Huismans, van der Walt et al. 1987). Recent results show that VP2 and NS1 express epitopes recognized by cytotoxic T-lymphocytes (CTL) (Andrew, Whiteley et al. 1995) while it is unlikely that VP7 and VP5 have CTL epitopes. So far, VP3, VP4, VP6, NS2 and NS3 have not stimulated a CTL response in sheep (Lobato, Coupar et al. 1997) Table 1 (modified from, (Wilson and Mecham 2000)), below summarizes the genes of BTV and their protein function:

TABLE 1

Bluetongue virus genes and encoded proteins with location, properties, and function of proteins.

| Genome Segment | Protein | Location | Properties & Function |
|---|---|---|---|
| L1 (3954 bp) (150 kDa) | VP1 | Within the sub-core at the 5-fold axis | RNA dependent RNA polymerase |
| L2 (2926 bp) (111 kDa) | VP2 | Outer capsid (trimer) | Outer capsid, serotype specific antigen, mammalian cell attachment protein, neutralizing epitopes |
| L3 (2770 bp) (103 kDa) | VP3 | Sub-core capsid layer (T = 2 symmetry) | Innermost protein capsid shell, sub-core capsid layer, self assembles, retains icosahedral symmetry, RNA binding, interacts with internal minor proteins |
| M4 (2011 bp) (76 kDa) | VP4 | Within the sub-core at the 5-fold axis (dimer) | Capping enzyme. guanylyltransferase |
| M5 (1638 bp) (59 kDa) | VP5 | Outer capsid (trimer) | Inner outer capsid protein, can affect virus serotype characteristics |
| M6 (1769 bp) (64 kDa) | NS1 | Cytoplasm | Forms tubules in the cell cytoplasm |
| S7 (1156 bp) (38 kDa) | VP7 | Outer core (T = 13 symmetry, trimer) | Outer core surface protein, immuno-dominant major serogroup specific antigen, attachment protein for vector insect cells, reacts with 'core neutralizing' antibodies |
| S8 (1124 bp) (41 kDa) | NS2 | Cytoplasm, viral inclusion bodies (VIB) | Important viral inclusion body matrix protein, ssRNA binding, phosphorylated, can be associated with outer capsid |
| S9 (1046 bp) (36 kDa) | VP6 | Within the sub-core at the 5-fold axis | ssRNA and dsRNA binding, helicase, NTPase |
| S10 (822 bp) (24 kDa) | NS3, NS3a | Cell membranes | Glycoproteins, membrane proteins, involved in cell exit |

Lobato and Coupar (Lobato, Coupar et al. 1997) developed vaccinia virus-based expression vectors containing various inserts corresponding to nucleotide sequences encoding for structural proteins VP2, VP5 and VP7 of BTV for both in vivo and in vitro studies. These expression vectors were administered to rabbits and sheep to evaluate the immune response with respect to ELISA and neutralizing antibody titer, and the protective efficacy of the VP2 and VP5 constructs was tested in sheep. Vaccinia virus-expressed VP2, VP5 and VP2+VP5 were protective, with the most reproducible protection occurring in animals immunized with both VP2 and VP5 however protection even with this construct was variable.

It would be advantageous to provide improved immunogenic and vaccine compositions against BTV, and methods for making and using such compositions, including such compositions that provide for differential diagnostic methods, assays and kits.

Citation or identification of any document in this application is not admission that such document is available as prior art to the present invention.

OBJECTS AND/OR SUMMARY OF THE INVENTION

The invention provides an immunogenic or vaccine composition to induce an immune response or protective immune response against Orbiviruses, especially bluetongue virus (BTV) in an animal susceptible to BTV or related virus comprising or consisting essentially of a pharmaceutically or veterinarily acceptable vehicle or excipient and a vector that contains or consists essentially of heterologous nucleic acid molecule(s), and that expresses in vivo in the animal an Orbivirus-BTV protein, antigen, immunogen or epitope thereof, such as but is not limited to, BTV VP2 (L2) and BTV VP5 (M5) polypeptides.

The vector may be a recombinant DNA plasmid or a recombinant virus, such as a recombinant adenovirus, herpesvirus or poxvirus, e.g., an avipox virus, such as a canarypox virus or a fowlpox virus. The animal may be selected from the ungulate group consisting of an ovine, a bovine, a porcine, a goat, an antelope, an equine, a llama and others.

Advantageously, the nucleic acid molecule comprises or consists essentially of nucleotides 20-2887 (SEQ ID NO:3 and 1) encoding BTV VP2 (L2) and respectively, nucleotides 30-1610 (SEQ ID NO:4 and 2) encoding BTV protein VP5 (M5). A preferred embodiment comprises or consists of mammalian codon optimized nucleic acid molecules.

The immunogenic or vaccine composition may further comprise an adjuvant, such as a carbomer.

The immunogenic or vaccine composition may further comprise an antigen or immunogen or epitope thereof of a pathogen other than BTV of the animal, or a vector that contains a nucleic acid molecule encoding the antigen, immunogen or epitope thereof and expresses it in vivo in the animal, or an inactivated or attenuated pathogen other than BTV.

The invention additionally involves a kit comprising or consisting essentially of (a) the immunogenic or vaccine composition, and (b) the antigen or immunogen or epitope thereof of a pathogen other than BTV of the animal, or the vector that contains a nucleic acid molecule encoding the antigen, immunogen or epitope thereof and expresses it in vivo in the animal, or the inactivated or attenuated pathogen other than BTV of the animal, wherein (a) and (b) are in separate containers, and the kit optionally contains instructions for admixture and/or administration of (a) and (b).

The invention also comprehends a method for inducing an immunological or protective immune response against BTV in an animal that may comprise administering to the animal the immunogenic or vaccine composition that contains a nucleic acid molecule encoding the antigen, immunogen or epitope thereof.

The invention further comprehends a method for inducing an immunological or protective immune response against BTV in an animal which may comprise administering to the animal (a) the immunogenic or vaccine composition, and (b) a BTV isolated antigen, immunogen or epitope thereof, wherein (a) is administered prior to (b) in a prime-boost regimen, or (b) is administered prior to (a) in a prime-boost regimen, or (a) and (b) are administered together, either sequentially or in admixture. The invention also involves a kit for performing this which may comprise (a) and (b) in separate containers, optionally with instructions for admixture and/or administration.

The invention even further comprehends a prime-boost immunization or vaccination against BTV, wherein the priming with (a) DNA vaccine(s) or immunological or immunogenic composition(s) that contains or consists essentially of (a) nucleic acid molecule(s) encoding and express(es) in vivo a BTV immunogen, antigen or epitope and the boost is done with (a) vaccine(s) or immunological or immunogenic composition(s) that is a BTV inactivated or attenuated or subunit (antigen, immunogen and/or epitope) preparation(s) and/or (a) recombinant or modified virus vaccine or immunological or immunogenic composition(s) that contains or consists essentially of (a) nucleic acid molecule encoding and express(es) in vivo (a) BTV immunogen(s), antigen(s) or epitope(s). Thus, the invention provides a prime-boost immunization or vaccination method against BTV, such as a prime-boost immunization or vaccination which may comprise administering to a target species animal (a) DNA vaccine(s) or immunological or immunogenic composition(s) of the invention (that contains or consists essentially of nucleic acid molecule(s) encoding and express(es) in vivo BTV antigen(s), immunogen(s) or epitope(s) (as the prime) and thereafter administering (as the boost) administering inactivated BTV and/or attenuated BTV or a BTV subunit (antigen, immunogen and/or epitope) preparation(s)) and/or a recombinant or modified virus vaccine or immunological or immunogenic composition that may comprise nucleic acid molecule(s) encoding and express(es) in vivo BTV immunogen(s), antigen(s) or epitope(s), advantageously (a) recombinant vaccine or immunological or immunogenic composition(s) that expresses the BTV immunogen. antigen or epitope in vivo. The boost may be advantageously matched to the prime, e.g., the boost contains or consists essentially of or expresses at least one antigen, epitope or immunogen that is expressed by the prime.

The prime-boost regimen according to the invention may be used in animals of any age, advantageously young animals (e.g., animals that have detectable maternal antibodies and/or are suckling or nursing or breast-feeding), pre-adult animals (animals that are older than being a young animal but have not yet reached maturity or adulthood or an age to mate or reproduce), adult animals (e.g., animals that are of an age to mate or reproduce or are beyond such a period in life), and it is advantageous to employ the prime-boost regimen in pregnant females or females prior to giving birth, laying, or insemination.

The invention also relates to such immunogenic and vaccine compositions and kits thereof suitable for use in such prime-boost regimens and prime-boost regimens. The host or target species upon which the prime-boost regimen can be practiced includes any animal (target or host) species susceptible to disease caused by Orbivirus infection, including mammals, reptiles, birds, especially humans, companion mammals or animals such as but not limited to canines, felines, equines, zoo mammals or animals, such as aquatic mammals e.g. seals, felines, equines, zoo reptiles such as snakes, crocodiles, alligators, and avian species.

The prime-boost regimen is especially advantageous to practice in a young animal, as it allows vaccination or immunization at an early age, for instance, the first administration in the prime-boost regimen when practiced on a young animal can be at an age at which the young animal has maternal antibodies. Another advantage of this regimen is that it can provide a degree of safety for pregnant females present in the same location or in close proximity to the young or to each other. Thus, the invention provides a prime-boost immunization or vaccination method against BTV, and the method may be practiced upon a young animal, such as a lamb, puppy or kitten, for instance, wherein the priming is done at a time that the young animal has maternal antibodies against BTV, with the boost advantageously at a time when maternal antibodies may be waning or decreasing or normally not present, such as a period of time post-nursing. breastfeeding.

Accordingly, the invention also involves kits for performing a prime-boost regimen comprising or consisting essentially of a priming vaccine or immunological or immunogenic composition and a boost vaccine or immunological or immunogenic compositions, in separate containers, optionally with instructions for admixture and/or administration.

Further still, the invention provides a differential diagnosis method comprising administering to animals an immunogenic or vaccine composition and/or a BTV antigen, immunogen or epitope, and testing the animals for presence or absence of a BTV protein or antibody thereto not expressed by the immunogenic or vaccine composition and/or not present in the BTV antigen, immunogen or epitope. The invention additionally involves a kit for performing this method comprising the immunogenic or vaccine composition and/or the BTV antigen, immunogen or epitope, and an assay for testing for the presence or absence of the BTV protein, in separate containers, optionally with instructions for administration of the immunogenic or vaccine composition and/or the BTV antigen, immunogen or epitope and/or for performing the assay.

It is noted that in this disclosure and particularly in the claims and/or paragraphs, terms such as "comprises", "comprised", "comprising" and the like, and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIG. 1 depicts the nucleic acid sequence of BTV-17 native VP2 (SEQ ID NO: 3) versus synthetic BTV17 codon optimized VP2 (SEQ ID NO: 1).

FIG. 2 depicts the nucleic acid sequence of BTV-17 native VP5 (SEQ ID NO: 4) versus synthetic BTV17 codon optimized VP5 (SEQ ID NO: 2).

FIG. 3 is a schematic showing construction of plasmid 043004pPCR-Script encoding the optimized synthetic BTV VP2 protein.

FIG. 6 provides the nucleic sequence of pCXL148.2 donor plasmid (SEQ ID NO: 13).

FIG. 7 is a schematic showing construction of pALVAC C5H6p-synthetic BTV VP2 (pLH2030.2), donor plasmid.

FIG. 8 is a schematic showing construction of plasmid 043005pPCR-Script encoding the optimized synthetic BTV VP5 protein for addition of the 42Kpsynthetic promoter sequence of Entomopoxvirus Amsacta moorei to the BTV-VP5 fragment.

FIG. 9 is a schematic showing the cloning scheme for the 42Kp promoter-driven optimized synthetic BTV VP5 in the pCR2.1 TOPO cloning/shuttle vector (creating pCR2-42KpVP5) for amplification of the 42KpVP5 cassette.

FIG. 10 is a schematic showing construction of the final donor homology vector pC5H6pVP2 42KpVP5 (pLH2078.15) containing optimized VP2 driven by H6 promoter and optimized BTV VP5 driven by the 42K promoter with vector homology to the C5R region of ALVAC.

FIG. 11 provides nucleic acid and protein sequence data for pLH2078.15 (pC5 H6p synthetic BTV-VP2 42Kp synthetic BTV-VP5), the final homology vector for creation of recombinant ALVAC+BTV. A discloses SEQ ID NOS: 20-21, respectively, in order of appearance. B discloses SEQ ID NO: 19 coding SEQ ID NOS: 20-21. C discloses nucleotides 1800-6293 of SEQ ID NO: 19 coding SEQ ID NOS: 20-21. D discloses SEQ ID NO: 22.

FIG. 12 depicts a flow diagram illustrating construction of recombinant ALVAC viral vector encoding the BTV optimized synthetic VP2 and VP5 (vCP2289).

FIG. 15 shows a southern blot analysis of restriction endonuclease digested vCP2289 genomic DNA probed with a BTV-specific DNA probe.

DETAILED DESCRIPTION

Figure 4:
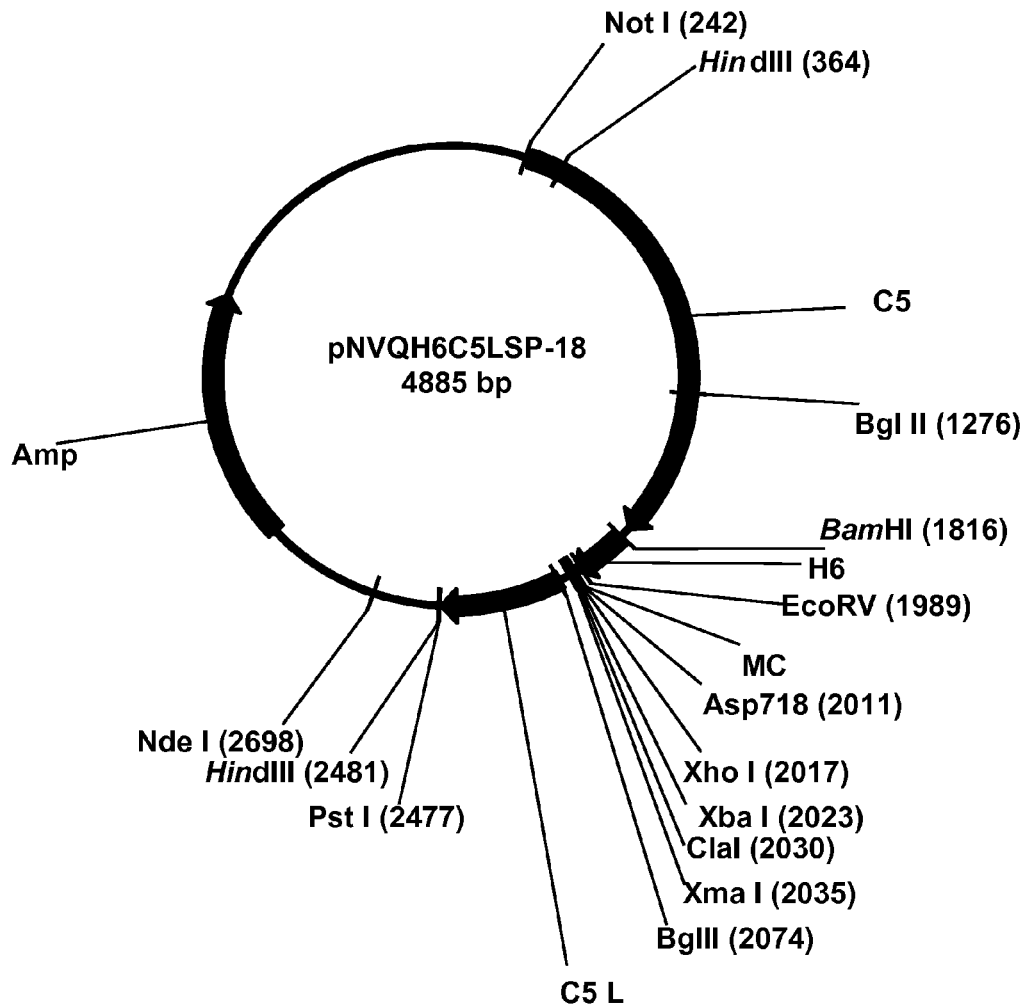
FIG. 4 is a schematic showing a restriction endonuclease map of the pNVH6C5LSP-18 donor plasmid

As discussed herein, the present invention relates to vectors containing at least one polynucleotide of BTV or at least one nucleic acid molecule encoding at least one BTV antigen, immunogen or epitope, e.g., in vivo and in vitro expression vectors comprising at least one polynucleotide of BTV or in vivo and in vitro expression vectors comprising and expressing at least one BTV antigen, immunogen or epitope, as well as immunogenic compositions and vaccines against bluetongue disease; for instance, such compositions or vaccines that contain one or more of the vectors and/or one or more of the expression products of the vectors.

Advantageously, the immunogens, antigens comprise the outer capsid protein VP2 (L2), or the outer capsid protein VP5 (M5), or epitopes or combinations thereof, e.g., VP2 and VP5; VP2; and VP5 or a fragment thereof. The combinations can be separate proteins or polyproteins. The compositions or vaccines can thus contain one or more vectors expressing more than one of the proteins, e.g., different proteins. The compositions or vaccines can comprise, or vectors thereof express, proteins from different strains or isolates of BTV. Thus, the compositions or vaccines can comprise, or the vectors thereof express, VP2, VP5 or combinations thereof, wherein the VP2 and VP5 are from different strains or isolates.

In this regard, it is noted that there is the serotype 17 BTV isolate or strain, e.g., field isolates (deposited as segments in GenBank: (de Mattos, de Mattos et al. 1994)[VP2] isolate 17B81, SEQ ID No. S72158; (Mecham and Johnson 2005) [VP5] isolate FL99, SEQ ID No: AY855281); and/or American Type Culture Collection VR-875™ (deposited as BTV serotype 17; blood from sheep with typical bluetongue disease, Wyoming, 1962). Due to the segmented nature of the BTV genome, genomic nucleotide sequences for each segment are determined individually for each serotype segment. Table 2 lists the sequences available for BTV serotype 17.

TABLE 2

BTV-17 - Number of available RNA sequences for BTV serotype 17.

| Genome Segment Number | | | | | | | | | |
|---|---|---|---|---|---|---|---|---|---|
| 1 (VP1(Pol)) | 2 (VP2) | 3 (VP3(T2)) | 4 (VP4(CaP)) | 5 (NS1(ATuP)) | 6 (VP5) | 7 (VP7(T13)) | 8 (NS2(ViP)) | 9 (VP6(Hel)) | 10 (NS3) |
| 1 | 5 | 2 | 1 | 2 | 2 | 6 | 1 | 7 | 8 |

Also, it is noted that comparative phylogenetic analysis of VP2 sequences within serotypes indicates a degree of homology but enough inherent variability exists to allow distinction of virus lineages within a single serotype. BTV serotype is controlled primarily by the viral outer capsid protein VP2, encoded by genome segment 2. It is envisaged that sequence analysis of segment 2 could be used not only to identify virus serotype but also, by comparison to sequences of reference strains, to identify the origins of individual virus strains.

Advantageously in embodiments involving at least one epitope present in, or expressed by vector or vectors in, compositions or vaccines of the invention, the epitope or epitopes are from VP2, VP5 or combinations thereof, and the epitope or epitopes can be from different strains or isolates. In this regard, it is noted that one can locate or map epitopes in BTV antigens or immunogens, such as the VP5 protein; see, e.g., (Martinez-Torrecuadrada, Langeveld et al. 1999) and (Wang, Du Plessis et al. 1995), VP2 protein (Heidner, Rossitto et al. 1990; Rossitto and MacLachlan 1992; DeMaula, Bonneau et al. 2000) and VP1 protein (Huang, Hwang et al. 1995).

Also as discussed herein, the invention relates to methods for using the vectors, immunological compositions and vaccines, including for immunizing and vaccinating against this virus, for expressing polypeptides encoded by the polynucleotide(s), and methods for using the expression products in assays or to generate antibodies useful in assays, as well as to methods for making the polynucleotide(s), vectors, compositions vaccines, assays, inter alia.

The present invention thus relates to means for preventing and/or combating diseases caused by the BTV, so as to decrease or to abolish clinical signs and/or viremia, and/or lesions.

The invention relates to such immunogenic and vaccine compositions suitable for use in different animal (target or host) species susceptible to disease caused by BTV, including, but not limited to, mammals, reptiles, birds, especially humans, companion mammals or animals such as canines, felines, equines, zoo mammals or animals, such as aquatic mammals, felines, equines, zoo reptiles, and avian species.

The invention further relates to immunization and vaccination methods involving the immunogenic and vaccine compositions, for the target or host species. And on this aspect of the invention, mention is made that as to wild or non-domesticated animals, such as, but not limited to, wild or non-domesticated birds or mammals compositions comprising one or more vectors that express one or more BTV epitopes or antigens or immunogens can be delivered via food, e.g., a bait drop, or mammal or bird food, left for consumption by wild or non-domesticated birds or mammals, that includes or contains the one or more vectors, so there may be administration thereof orally by the mammal or bird consuming the food. This route of administration may be advantageous when the one or more vectors is one or more poxviruses, e.g., an avipox virus such as an attenuated canarypox virus, for instance ALVAC, or an attenuated fowlpox virus, for instance TROVAC, or a vaccinia virus, such as an attenuated vaccinia virus, for instance NYVAC. Accordingly, the invention envisions oral or mucosal administration, as well as edible compositions that contain one or more of the inventive vectors, akin to the MERIAL rabies product RABORAL™. From this disclosure and the knowledge in the art, the skilled artisan can formulate edible animal feed for a bird or mammal that contains a suitable dose of one or more inventive vectors. Furthermore, the invention comprehends topical administration of compositions containing vectors, see, e.g., U.S. Pat. No. 6,348,450 regarding topical administration of vector compositions, and devices for topical administration of compositions to wild or non-domesticated animals, see, e.g., WO01/95715, U.S. application Ser. No. 10/374,627, filed Feb. 26, 2003, for such devices for rodents and birds; each of which, together with each document cited or referenced therein, as with each document cited herein and each document referenced or cited in each document cited herein, is hereby incorporated herein by reference.

The invention further relates to means and methods that make differential diagnosis possible, e.g., methods that make it possible to make, or allow for, a distinction between an animal infected by pathogenic BTV and an animal administered a vaccine or immunogenic composition according to the invention.

In addition to the polynucleotide encoding VP2 and VP5, the expression vectors according to the invention can comprise one or more other polynucleotides encoding other proteins of BTV, preferably structural proteins of BTV and said sequences are preferably chosen from among those encoding the structural viral proteins.

The vector preferably comprises a polynucleotide encoding regions corresponding e.g. to VP2, VP5, or advantageously VP2 and VP5, or epitopes thereof; that is, expression of multiple proteins or epitopes thereof are considered advantageous. A vector comprising several separate polynucleotides encoding the different proteins (e.g. VP2 and/or VP5 or epitopes thereof) also falls within the scope of the present invention. The vector, especially for in vivo expression, can also comprise polynucleotides corresponding to more than one BTV serotype, strain or isolate, for instance, two or more polynucleotides encoding VP2 or VP5, or epitope(s) thereof, of different strains. From all different serotypes such as, but not limited to, serotypes 1, 2, 4, 9, 10, 11, 13, 16, and 17.

Likewise, an immunogenic or vaccine composition can comprise one or more vectors for expression of polynucleotides corresponding to more than one BTV serotype, strain or isolate, for instance, two or more polynucleotides encoding VP2 or VP5, or epitope(s) thereof, of different strains. The vector, especially for in vivo expression, can additionally comprise one or more nucleotide sequences encoding immunogens of other pathogenic agents and/or cytokines.

The term polynucleotide encoding a protein of BTV primarily means a DNA fragment or isolated DNA molecule encoding said protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

The term protein includes peptides and polypeptides. A protein fragment is immunologically active in the sense that once administered to the host; it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

Accordingly, a minimum structure of the polynucleotide is that it comprises or consists essentially of or consists of nucleotides that encode an epitope or antigenic determinant of the BTV protein. A polynucleotide encoding a fragment of the total protein, more advantageously, comprises or consists essentially of or consists of a minimum of 21 nucleotides, advantageously at least 42 nucleotides, and preferably at least 57, 87 or 150 consecutive or contiguous nucleotides of the sequence encoding the total protein or polyprotein. As mentioned earlier, epitope determination procedures, such as, generating overlapping peptide libraries (Hemmer, Pinilla et al. 1998), Pepscan (Geysen, Meloen et al. 1984); (Geysen, Barteling et al. 1985); (Van der Zee, Van Eden et al. 1989); (Geysen 1990); Multipin® Peptide Synthesis Kits de Chiron) and algorithms (De Groot and Rothman 1999), can be used in the practice of the invention, without undue experimentation. Other documents cited and incorporated herein may also be consulted for methods for determining epitopes of an immunogen or antigen and thus nucleic acid molecules that encode such epitopes.

Elements for the expression of the polynucleotide or polynucleotides are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a protein fragment, e.g., advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 6,130,066, 5,494,807, 5,514,375, 5,744,140, 5,744, 141, 5,756,103, 5,762,938, 5,766,599, 5,990,091, 6,004,777, 6,130,066, 6,497,883, 6,464,984, 6,451,770, 6,391,314, 6,387,376, 6,376,473, 6,368,603, 6,348,196, 6,306,400, 6,228,846, 6,221,362, 6,217,883, 6,207,166, 6,207,165, 6,159,477, 6,153,199, 6,090,393, 6,074,649, 6,045,803, 6,033,670, 6,485,729, 6,103,526, 6,224,882, 6,312,682, 6, 312,683, 6,348,450, 4,603,112; 4,769,330; 5,174,993; 5,505, 941; 5,338,683; 5,494,807; 4,394,448; 4,722,848; 4,745,051; 4,769,331; 5,591,639; 5,589,466; 4,945,050; 5,677,178; 5,591,439; 5,552,143; and 5,580,859; U.S. patent application Ser. No. 920,197, filed Oct. 16, 1986; WO 94/16716; WO 96/39491; WO91/11525; WO 98/33510; WO 90/01543; EP 0 370 573; EP 265785; (Paoletti 1996); (Moss 1996); Richardson (Ed) (1995) Methods in Molecular Biology 39, "Baculovirus Expression Protocols," Humana Press Inc.; (Smith, Summers et al. 1983); (Pennock, Shoemaker et al. 1984); (Roizman 1996); (Andreansky, He et al. 1996); (Robertson, Ooka et al. 1996); (Frolov, Hoffman et al. 1996); (Kitson, Burke et al. 1991); (Ballay, Levrero et al. 1985); (Graham 1990); (Prevec, Schneider et al. 1989); (Felgner, Kumar et al. 1994); (Ulmer, Donnelly et al. 1993); (McClements, Armstrong et al. 1996);(Ju, Edelstein et al. 1998); and (Robinson and Torres 1997). Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-BTV proteins or epitopes thereof, e.g., non-BTV immunogens or epitopes thereof, cytokines, etc. to be expressed by vector or vectors in, or included in, multivalent or cocktail immunogenic compositions or vaccines of the invention.

The present invention also relates to preparations comprising vectors, such as expression vectors, e.g., vaccines or immunogenic compositions. The preparations can comprise, consist essentially of, or consist of one or more vectors, e.g., expression vectors, such as in vivo expression vectors, comprising, consisting essentially or consisting of (and advantageously expressing) one or more of the BTV polynucleotides encoding VP2, VP5, or combinations or polyproteins thereof, especially as above-mentioned (e.g., VP2, VP5, VP2 and VP5 or at least an epitope thereof); and, advantageously, the vector contains and expresses a polynucleotide that includes, consists essentially of, or consists of a coding region encoding BTV VP2 and/or VP5, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of BTV, e.g. VP2, VP5, or an epitope thereof.

According to another embodiment, the vector or vectors in the preparation comprise, or consist essentially of, or consist of polynucleotide(s) encoding one or more proteins or epitope(s) thereof of BTV, e.g., of one or more BTV serotypes, strains or isolates; and, advantageously, in a suitable host cell or under appropriate conditions, the vector or vectors express polypeptides encoded by the polynucleotide(s). The inventive preparation advantageously comprises, consists essentially of, or consists of, at least two vectors comprising, consisting essentially of, or consisting of, and advantageously also expressing, preferably in vivo under appropriate conditions or suitable conditions or in a suitable host cell, polypeptides encoded by polynucleotides from different BTV serotypes, strains or isolates encoding the same proteins and/or for different proteins, but preferably for the same proteins. As to preparations containing one or more vectors containing, consisting essentially of or consisting of polynucleotides encoding, and preferably expressing, advantageously in vivo, BTV VP2, or VP5, or an epitope thereof, it is preferred that the expression products be from two, three or more different BTV serotypes, strains or isolates, advantageously strains. The invention is also directed at mixtures of vectors that contain, consist essentially of, or consist of coding for, and express, VP2, or VP5 of different strains. It is preferred that in such mixtures, at least one vector contain, consist essentially of, or consist of, coding for, and express, VP2.

According to yet another embodiment and as will be shown in greater detail hereinafter, the other vector or vectors in the preparation comprise and express one or more cytokines and/or one or more immunogens of one or more other pathogenic agents. Sources for cytokines, immunogens for other pathogenic agents or epitope(s) thereof, and nucleic acid molecules encoding the same, may be found in herein cited documents, as well as in, WO02096349, WO0208162, WO0020025, WO00152888, WO0145735, WO00127097, WO0116330, WO0077210, WO0077188, WO0077043, WO9842743, WO9833928, WO9749826, WO9749825, U.S. Pat. Nos. 6,387,376, 6,306,400, 6,159,477, 6,156,567, 6,153,199, 6,090,393, 6,074,649, 6,033,670.

The invention also relates to various combinations of different embodiments herein disclosed, e.g., compositions or vaccines containing various vectors, compositions or vaccines containing a vector and a protein (BTV and/or non-BTV) and/or cytokine, etc.

The preparations comprising an in vitro or in vivo expression vector comprising and expressing a polynucleotide encoding VP2, VP5 constitute a preferred embodiment of the invention.

According to a further advantageous embodiment, one or more of the additional structural proteins VP7, and/or VP3 are expressed jointly with the VP2 and VP5 structural proteins according to the invention, either via the same expression vector, or via their own expression vector. They are preferably expressed together on the basis of a single polynucleotide, e.g., as a polyprotein. That is, in certain embodiments, the vector further contains, consists essentially of or consists of, one or more nucleotides encoding VP7, and/or VP3, or a composition or vaccine further contains, consists essentially of or consists of one or more additional vectors that contains, consists essentially of or consists of, one or more nucleotides encoding VP7, and/or VP3; this vector or these vectors advantageously express(es) the structural protein(s); and, VP7 and VP3 are advantageously expressed jointly, and more advantageously, as a polyprotein.

According to a further advantageous embodiment, one or more of the non-structural proteins NS1, NS2 and NS3 and/or VP1, VP4 are expressed jointly with the VP2 and VP5 structural proteins according to the invention, either via the same expression vector, or via their own expression vector. That is, in certain embodiments, the vector further contains, consists essentially of or consists of, one or more nucleotides encoding VP1, VP4, NS1, NS2, and/or NS3, or a composition or vaccine further contains, consists essentially of or consists of one or more additional vectors that contains, consists essentially of or consists of, one or more nucleotides encoding VP1, VP4, NS1, NS2 and/or NS3; this vector or these vectors advantageously express(es) the structural protein(s); and, VP1, VP4, NS1, NS2 and/or NS3 are advantageously expressed. Thus, the invention also relates to vector such as an in vivo or in vitro expression vector comprising, consisting essentially of or consisting of the polynucleotide(s) encoding VP1, VP4, NS1, NS2 and NS3, combinations thereof, including polyproteins thereof. The vector can be one of the above-described vectors comprising, consisting essentially of or consisting of a polynucleotide encoding one or more structural proteins, e.g., VP2, VP5, VP7 and/or VP3 combinations and polyproteins thereof e.g., such a vector that contains or consists essentially of polynucleotides encoding structural protein or proteins or epitopes thereof can also contain or consist essentially thereof polynucleotides encoding one or more non-structural proteins, combination thereof, polyproteins thereof, or epitopes thereof. As an alternative, the invention relates to a preparation as described hereinbefore, also incorporating at least one of the vectors that contain polynucleotide(s) encoding and advantageously expressing a non-structural protein and optionally a pharmaceutically or veterinarily acceptable carrier, vehicle or excipient.

For preparing vectors, e.g., expression vectors, according to the invention, the skilled artisan has available various serotypes, strains and isolates of BTV and the description of the nucleotide sequence of their genome, see, e.g., discussion herein, also referring to 24 BTV serotypes where nucleic acid sequence information is available(Wilson and Mecham 2000).

Reference is, for example, made to strain BTV-17. For each protein the corresponding nucleotide sequence is provided (de Mattos, de Mattos et al. 1994; Huang, Hwang et al. 1995; Bernard, Israel et al. 1997). By comparison and alignment of the sequences, the determination of a polynucleotide encoding such a protein in another BTV serotype or strain is readily determined.

As discussed herein, the term polynucleotide is understood to mean a nucleic acid sequence encoding a protein or a fragment thereof or an epitope thereof specific to a particular BTV strain; and, by equivalence, the term polynucleotide is understood to include the corresponding nucleotide sequences of different strains of BTV and nucleotide sequences differing due to codon degeneracy. Thus, a polynucleotide encoding BTV VP2 is understood as comprising, consisting essentially of or consisting of (a) nt 20-2887 of BTV-17 (SEQ ID NO:3), (b) corresponding sequences of different BTV strains, and (c) nucleotide sequences that encode BTV VP2 but differ from (a) and (b) due to codon degeneracy.

The L2 gene of BTV that encodes the outer capsid protein, VP2, has the greatest degree of genetic variability between global strains of BTV. This is not surprising as this protein is responsible for both virus neutralization and serotype-specificity (Mecham, Dean et al. 1986; Roy 1992) and is likely to be affected by genetic drift and founder effect selection. Genetic drift and founder effect may result in variants with increased virulence (Bernard, Israel et al. 1997). A number of neutralization determinants have been identified (Ghiasi, Fukusho et al. 1987; DeMaula, Heidner et al. 1993; Jewell and Mecham 1994). VP2 has been shown to be the protein primarily responsible for attachment and entry into mammalian host cells (Hassan and Roy 1999). The variation between serotypes generally results in segregation of viruses based on serotype regardless of geographic origin of isolation when phylogenetic analysis is used (Pritchard and Gould 1995; Bonneau, Zhang et al. 1999). The M5 gene of BTV encodes the inner outer capsid protein, VP5, and has the second greatest degree of genetic variability amongst BTV genes, showing 51-71% identity within a given serogroup. VP5 can cause conformational alterations of the outer capsid structure, and changes in neutralization characteristics (Cowley and Gorman 1989; DeMaula, Bonneau et al. 2000). VP5 may also contribute to host cell recognition (Roy 1992).

Due to the inherent genetic variability within and without serotypes, the invention covers polynucleotides encoding proteins having amino acid sequences, whose sequence identity or homology with the consensus BTV amino acid sequence for the protein exhibits functional equivalency. For instance, an expressed VP2 capsid protein can have greater than 20% identity with the corresponding capsid sequence of the polypeptide expressed from (a) comprising nucleotides 20-2887 of BTV-17 segment 2 (SEQ ID NO:3), (b) corresponding sequences of different BTV strains, and/or (c) nucleotide sequences that encode BTV VP2 but differ from (a) and (b) due to codon degeneracy, and from (a) and (b) due to strain, serotype and serogroup genetic variability. Despite this variability, functionally the polynucleotides encode the VP2 capsid polypeptide.

Therefore, the invention comprehends polynucleotides that express such functionally homologous polypeptides; and the corresponding degrees of homology or identity of those polynucleotides to polynucleotides encoding polypeptides to which homologous polypeptides have homology or identity. Homologous polypeptides advantageously contain one or more epitopes of the polypeptide to which there is identity or homology, such that homologous polypeptides exhibit immunological similarity or identity to the polypeptide to which there is identity or homology, e.g., the homologous polypeptide elicits similar or better immune response (to the skilled immunologist) than polypeptide to which there is identity or homology and/or the homologous polypeptide binds to antibodies elicited by and/or to which the polypeptide to which there is identity or homology binds, advantageously and not to other antibodies.

Accordingly, fragments of homologous polypeptides and of polypeptides to which there is identity or homology, advantageously those fragments which exhibit immunological similarity or identity to homologous polypeptides or polypeptides to which there is identity or homology, are envisioned as being expressed, and therefore, polynucleotides therefore which may represent fragments of polynucleotides of homologous polypeptides and of polypeptides to which there is identity or homology, are also envisioned by and useful in the instant invention.

The term "sequence identity" indicates a quantitative measure of the degree of homology between two amino acid sequences of equal length or between two nucleotide sequences of equal length. If the two sequences to be compared are not of equal length, they must be aligned to best possible fit possible with the insertion of gaps or alternatively, truncation at the ends of the protein sequences. The sequence identity can be calculated as $((N_{ref}-N_{dif})/N_{ref}) \times 100$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{dif}=2$ and $N_{ref}=8$). A gap is counted as non-identity of the specific residue(s), i.e. the DNA sequence AGTGTC will have a sequence identity of 75% with the DNA sequence AGTCAGTC ($N_{dif}=2$ and $N_{ref}=8$). Sequence identity can alternatively be calculated by the BLAST program e.g. the BLASTP program (Pearson and Lipman 1988)(www.ncbi.nlm.nih.gov/cgi-bin/BLAST). In one aspect of the invention, alignment is performed with the sequence alignment method ClustalW with default parameters as described by (Thompson, Higgins et al. 1994), available at http://www2.ebi.ac.uk/clustalw/. Thus, a polynucleotide can be any nucleic acid molecule including DNA, RNA, LNA (locked nucleic acids), PNA, RNA, dsRNA, RNA-DNA-hybrid, and non-naturally occurring nucleosides.

And from the herein disclosure, advantageously, proteins or polypeptides expressed by vectors of the invention are immunologically active peptides and polypeptides, e.g., with respect to polypeptides or proteins of BTV-17, proteins or polypeptides expressed by vectors of the invention can be:

a) corresponding proteins or polypeptides of one or more different BTV serotypes, strains or isolates, b) proteins differing therefrom (from BTV-17 and/or a), but maintaining with a native BTV protein an identity equal to or greater than 20%. Thus, a reference to a BTV protein may involve additional proteins as herein discussed.

Different BTV serotypes and strains are accessible in collections, especially in the American Type Culture Collection (ATCC), e.g. under access numbers VR-875, VR-1231, VR-187, VR-873, VR-983, VR-1231AF, or VR-1231CAF, and as otherwise herein discussed, the full gene can also be chemically synthesized.

In the invention, preferably the polynucleotide also comprises a nucleotide sequence encoding a signal peptide, located upstream of the coding region of the expressed protein to facilitate the secretion thereof; and accordingly, the invention comprehends the expression of a BTV polypeptide, such as a BTV antigen, immunogen, or fragment thereof, e.g., epitope, with a leader or signal sequence. The leader or signal sequence can be an endogenous sequence, e.g. the natural signal sequence of a BTV polypeptide. The leader or signal sequence can also be a heterologous sequence, and thus encoded by a nucleotide sequence that is heterologous to BTV. For example, the leader or signal sequence can be endogenous to the vector, or a leader or signal sequence that is heterologous to both the vector and BTV, such as a signal peptide of tissue plasminogen activator (tPA), e.g., human tPA, and thus, the vector or the polynucleotide therein can include a sequence encoding the leader or signal peptide, e.g., the leader or signal peptide of human tissue plasminogen activator (tPA) (Hartikka, Sawdey et al. 1996). The nucleotide sequence encoding the signal peptide is advantageously inserted in frame and upstream of the sequence encoding the BTV polypeptide, e.g., VP2, VP5 or combinations, e.g. VP2 and VP5.

According to an embodiment of the invention, the vectors, e.g., in vivo expression vectors are viral vectors.

Viral vectors, e.g., viral expression vectors are advantageously: poxviruses, e.g. vaccinia virus or an attenuated vaccinia virus, (for instance, MVA, a modified Ankara strain obtained after more than 570 passages of the Ankara vaccine strain on chicken embryo fibroblasts; see (Stickl and Hochstein-Mintzel 1971; Sutter and Moss 1992); available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), avipox virus or an attenuated avipox virus (e.g., canarypox, fowlpox, dovepox, pigeonpox, quailpox, ALVAC or TROVAC; see, e.g. U.S. Pat. No. 5,505,941, 5,494,807), swinepox, raccoonpox, camelpox, or myxomatosis virus; adenoviruses, such as avian, canine, porcine, bovine, human adenoviruses; or herpes viruses, such as ovine herpes virus (OHV 1 and 2), equine herpes virus (EHV serotypes 1 and 4), canine herpes virus (CHV), feline herpes virus (FHV), bovine herpes viruses (BHV serotypes 1 and 4), porcine herpes virus (PRV), Marek's disease virus (MDV serotypes 1 and 2), turkey herpes virus (HVT or MDV serotype 3), or duck herpes virus. When a herpes virus is used, the vector HVT is preferred for the vaccination of the avian species, the bovine vector for the vaccination of cattle, the ovine vector for the vaccination of sheep, and the vector EHV for the vaccination of horses.

More generally in certain embodiments, it may be advantageous to match a vector to a host, such as an equine virus, e.g., EHV to use in equines, or a vector that is an avian pathogen, such as fowlpox, HVT, MDV or duck herpes to use in avians such as poultry or chickens, or a vector that is an ovine pathogen such as OHV, a bovine pathogen such as BHV to use in bovines such as cows, or a vector that is a porcine pathogen such a porcine herpes virus to use in porcines, or a vector that is a canine pathogen such as canine adenovirus or canine herpes virus to use in canines such as dogs, a vector that is a feline pathogen such as FHV to use in felines, as this may allow for an immune response against the vector and thus provide an immune response against a pathogen of the host or target species in addition to an immune response against an orbivirus.

However, it is also noted that it can be advantageous that the vector not be a natural pathogen of the host; for instance, so that the vector can have expression of the exogenous, e.g., BTV coding sequences, but with limited or no replication; for example, the use of an avipox vector in a mammalian host, as in U.S. Pat. No. 5,174,993. It is also noted that the invention comprehends vaccines, immunological and immunogenic compositions, with those terms being used in the sense attributed to them in the art; see, e.g., documents cited herein, such as U.S. Pat. No. 6,497,883.

According to another embodiment of the invention, the poxvirus vector, e.g., expression vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by Intervet; and, reference is also made to U.S. Pat. No. 5,766,599 which pertains to the attenuated fowlpox strain TROVAC.

For information on poxviruses and how to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter a/ia; as to canarypox mention is made of U.S. Pat. No. 5,756,103 inter alia; as to swinepox mention is made of U.S. Pat. No. 5,382,425 inter alia; and, as to raccoonpox, mention is made of WO0/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including (Carroll, Overwijk et al. 1997); (Stittelaar, Wyatt et al. 2000); (Sutter, Wyatt et al. 1994); and, in this regard it is also noted that the complete MVA genome is described in (Antoine, Scheiflinger et al. 1998), which enables the skilled artisan to use other insertion sites or other promoters.

Preferably, when the expression vector is a poxvirus, the polynucleotide to be expressed is inserted under the control of a specific poxvirus promoter, e.g., the vaccinia promoter 7.5 kDa (Cochran, Puckett et al. 1985), the vaccinia promoter I3L (Riviere, Tartaglia et al. 1992), the vaccinia promoter HA (Shida 1986), the cowpox promoter ATI (Funahashi, Sato et al. 1988), the vaccinia promoter H6 (Taylor, Weinberg et al. 1988); (Guo, Goebel et al. 1989); (Perkus, Limbach et al. 1989)), inter alia.

Preferably, for the vaccination of mammals the expression vector is a canarypox or a fowlpox. In this way, there can be expression of the heterologous proteins, e.g., BTV proteins, with limited or no productive replication. Preferably, for the vaccination of avians, e.g., chickens, ducks, turkeys and geese, the expression vector is a canarypox or a fowlpox.

When the expression vector is a herpes virus of turkeys or HVT, advantageous insertion site or sites are located in the BamHI I fragment or in the BamHI M fragment of HVT. The HVT BamHI I restriction fragment comprises several open reading frames (ORFs) and three intergenic regions and comprises several preferred insertion zones, such as the three intergenic regions 1, 2 and 3, which are preferred regions, and ORF UL55 (see, e.g., FR-A-2 728 795, U.S. Pat. No. 5,980, 906). The HVT BamHI M restriction fragment comprises ORF UL43, which is also a preferred insertion site (see, e.g., FR-A-2 728 794, U.S. Pat. No. 5,733,554).

When the expression vector is an EHV-1 or EHV-4 herpes virus, advantageous insertion site or sites include TK, UL43 and UL45 (see, e.g., EP-A-668355).

Preferably, when the expression vector is a herpes virus, the polynucleotide to be expressed is inserted under the control of a eukaryotic promoter, such as a strong eukaryote promoter, preferably a CMV-IE (murine or human) promoter; that is, in embodiments herein, the polynucleotide to be expressed is operably linked to a promoter, and in herpes virus embodiments, advantageously the polynucleotide to be expressed is operably linked to a strong eukaryotic promoter such as a mCMV-IE or hCMV-IE promoter. Strong promoters are also discussed herein in relation to plasmids as vectors.

According to a yet further embodiment of the invention, the vector, e.g., in vivo expression vector, is a plasmid vector or a DNA plasmid vector, e.g., the type of plasmid vector employed in that which is known as a DNA vaccine (in contrast with a transfection plasmid used in homologous recombination to generate a recombinant virus, which is not used in a DNA vaccine).

The term plasmid covers any DNA transcription unit in the form of a polynucleotide sequence comprising a polynucleotide according to the invention and the elements necessary for in vivo expression of that which is encoded by the polynucleotide in a cell or cells of the desired host or target; and, in this regard, it is noted that there are supercoiled and non-supercoiled circular plasmid, as well as linear and multimeric forms, all of which are intended to be within the scope of the invention.

Each plasmid comprises or contains or consists essentially of, in addition to the polynucleotide encoding the antigen(s) or epitope(s) of the pathogen or pathogens, e.g., BTV (or BTV and another pathogen), a promoter for expression, in the host cells of the polynucleotide; and, the polynucleotide may be said to be operably linked to the promoter or under the control of the promoter or dependent upon the promoter. In general, it is advantageous to employ a eukaryotic promoter, e.g., a strong eukaryotic promoter. The preferred strong eukaryote promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT WO87/03905. The CMV-IE promoter is preferably a human CMV-IE (Boshart, Weber et al. 1985) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa, van Kampen et al. 2000), or the actin promoter (Miyazaki, Takaki et al. 1989).

Functional subfragments of these promoters, i.e., portions of these promoters that maintain an adequate promoting activity, are included within the present invention, e.g. truncated CMV-IE promoters according to WO98/00166 or U.S. Pat. No. 6,156,567 can be used in the practice of the invention. A promoter in the practice of the invention consequently includes derivatives and subfragments of a full-length promoter that maintain an adequate promoting activity and hence function as a promoter, preferably promoting activity substantially similar to that of the actual or full-length promoter from which the derivative or subfragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and subfragments.

Preferably, the plasmids comprise or consist essentially of other expression control elements. It is particularly advantageous to incorporate stabilizing sequence(s), e.g., intron sequence(s), preferably intron II of the rabbit β-globin gene (van Ooyen, van den Berg et al. 1979).

As to the polyadenylation signal (polyA) for the plasmids and viral vectors other than poxviruses, use can more be made of the polyA signal of the bovine growth hormone (bGH) gene (see U.S. Pat. No. 5,122,458), or the poly(A) signal of the rabbit β-globin gene or the poly(A) signal of the SV40 virus.

As to other expression control elements usable in plasmids, attention is directed to expression control elements that are useful in herpes virus expression vectors.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

Protein production can take place by the transfection of mammalian cells by plasmids, by replication or expression without productive replication of viral vectors in mammalian cells or avian cells, or by Baculovirus replication (see, e.g., U.S. Pat. No. 4,745,051; (Vialard, Lalumiere et al. 1990); Luckow (Luckow and Summers 1988), e.g. *Autographa californica* Nuclear Polyhedrosis Virus AcNPV, on insect cells (e.g. Sf9 Spodoptera frugiperda cells, ATCC CRL 1711; see also U.S. Pat. Nos. 6,228,846, 6,103,526). Mammalian cells which can be used are advantageously hamster cells (e.g. CHO or BHK-21) or monkey cells (e.g. COS or VERO). Thus, the invention accordingly comprehends expression vectors incorporating a polynucleotide according to the invention, as well as the thus produced or expressed BTV proteins or fragments thereof from in vitro expression, and the preparations containing the same.

Accordingly, the present invention also relates to BTV protein-concentrated and/or purified preparations. When the polynucleotide encodes several proteins, they are cleaved, and the aforementioned preparations then contain cleaved proteins.

The present invention also relates to immunogenic compositions and vaccines against BTV comprising at least one in vivo expression vector according to the invention and a pharmaceutically or veterinarily acceptable excipient or carrier or vehicle, and optionally an adjuvant.

An immunogenic composition covers any composition which, once administered to the target species, induces an immune response against BTV. The term vaccine is understood to mean a composition able to induce an effective protection. The target species include mammals, e.g., equines, canines, felines, bovines, ovines, porcines and humans; reptiles, and birds or avians. This list is meant to include reproducing animals, egg-laying animals, production animals, and companion animals.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl saline solution or a phosphate buffer. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description of immunization and vaccination methods, and can also be determined by the skilled artisan from this disclosure read in conjunction with the knowledge in the art, without any undue experimentation.

The immunogenic compositions and vaccines according to the invention preferably comprise or consist essentially of one or more adjuvants. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one ore more non-methylated CpG units (Klinman, Yi et al. 1996); WO98/16247), (3) an oil in water emulsion, such as the SPT emulsion described on p 147 of "Vaccine Design, The Subunit and Adjuvant Approach" published by M. Powell, M. Newman, (Powell and Newman 1995), and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3), which is especially appropriate for viral vectors, can be based on:
  light liquid paraffin oil (European pharmacopoeia type),
  isoprenoid oil such as squalane, squalene,
  oil resulting from the oligomerization of alkenes, e.g. isobutene or decene,
  esters of acids or alcohols having a straight-chain alkyl group, such as vegetable oils, ethyl oleate, propylene glycol, di(caprylate/caprate), glycerol tri(caprylate/caprate) and propylene glycol dioleate, or
  esters of branched, fatty alcohols or acids, especially isostearic acid esters.

The oil is used in combination with emulsifiers to form an emulsion. The emulsifiers may be nonionic surfactants, such as:
  esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated,
  polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to (Regelson, Kuhar et al. 1960).

With regard to structure, the acrylic or methacrylic acid polymers and EMA are preferably formed by basic units having the following formula:

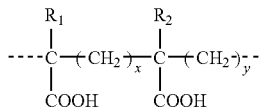

in which:
$R_1$ and $R_2$, which can be the same or different, represent H or $CH_3$
$x=0$ or 1, preferably $x=1$
$y=1$ or 2, with $x+y=2$.
For EMA, $x=0$ and $y=2$ and for carbomers $x=y=1$.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cationic lipids (4) containing a quaternary ammonium salt which are advantageously but not exclusively suitable for plasmids, are preferably those having the following formula:

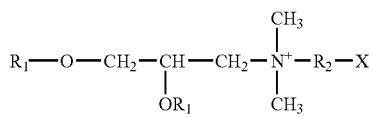

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group.

Among these cationic lipids, preference is given to DMRIE (N-(2-hydroxyethyl)-N, N-dimethyl-2,3-bis(tetradecyloxy)-1-propane ammonium; WO96/34109), preferably associated with a neutral lipid, preferably DOPE (dioleoyl-phosphatidyl-ethanol amine; Behr J. P., 1994, Bioconjugate Chemistry, 5, 382-389), to form DMRIE-DOPE.

Preferably, the plasmid mixture with the adjuvant is formed extemporaneously and preferably contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is preferably about 95: about 5 to about 5:about 95, more preferably about 1: about 1, e.g., 1:1.

The DMRIE or DMRIE-DOPE adjuvant:plasmid weight ratio can be between about 50:about 1 and about 1:about 10, such as about 10:about 1 and about 1:about 5, and preferably about 1:about 1 and about 1:about 2, e.g., 1:1 and 1:2.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefore.

The cytokine(s) can be chosen from: interleukin 18 (IL-18), interleukin 12 (IL-12), interleukin 15 (IL-15), MIP-1α (macrophage inflammatory protein 1α; (Marshall, Woolford et al. 1997), GM-CSF (Granulocyte-Macrophage Colony-Stimulating Factor). Particular reference is made to avian cytokines, for instance, those of the chicken, such as cIL-18 (Schneider, Puehler et al. 2000), cIL-15 (Xin, Hamajima et al. 1999), and equine cytokines, for instance equine GM-CSF (WO00/77210). Preferably, use is made of cytokines of the species to be vaccinated; that is, advantageously, the cytokine is matched to the target or host species, and, note for example, canine GM-CSF (example 8 of WO00/77043), feline GM-CSF (example 9 of WO00/77043).

WO00/77210 provides the nucleotide sequence and the amino acid sequence corresponding to equine GM-CSF, the in vitro GM-CSF production and the construction of vectors (e.g., plasmids and viral vectors) permitting in vivo equine GM-CSF expression. These proteins, plasmids and viral vectors can be used in immunogenic compositions and equine vaccines according to the invention. For example, use can be made of the plasmid pJP097 described in example 3 of WO00/77210 or use can be made of the teaching of the latter in order to produce other vectors or for the in vitro production of equine GM-CSF and the incorporation of the vectors or the equine GM-CSF into immunogenic compositions or equine vaccines according to the invention.

The present invention also relates to immunogenic compositions and so-called subunit vaccines, incorporating or comprising or consisting essentially of the protein VP2 and optionally one or more other herein mentioned proteins of BTV, e.g., VP5 or VP7 and advantageously produced by in vitro expression in the manner described herein, as well as a pharmaceutically or veterinarily acceptable carrier or vehicle or excipient.

The pharmaceutically or veterinarily acceptable carrier or vehicle or excipient can be determined by the skilled artisan without undue experimentation from the disclosure herein and the knowledge in the art, e.g., by reference to documents cited and incorporated herein or documents referenced in herein cited documents and incorporated herein by reference; and, can for example, be 0.9% NaCl saline solution or phosphate buffer.

The immunogenic compositions and subunit vaccines according to the invention preferably comprise or consist essentially of one or more adjuvants. Especially suitable for use in the present invention are (1) an acrylic or methacrylic acid polymer, or a maleic anhydride and alkenyl derivative polymer, (2) an immunostimulating sequence (ISS), such as an oligodeoxyribonucleotide sequence having one or more non-methylated CpG units (Klinman, Yi et al. 1996), (3) an oil in water emulsion, such as the emulsion SPT described on p 147 of "Vaccine Design, The Subunit and Adjuvant Approach", published by M. Powell, M. Newmann, (Powell and Newman 1995), and the emulsion MF59 described on p 183 of the same work, (4) a water in oil emulsion (EP-A-639 071), (5) saponin, such as Quil-A, or (6) alumina hydroxide or an equivalent. The different types of adjuvants defined under 1), 2) and 3) have been described in greater detail herein in connection with the expression vector-based vaccines and immunogenic compositions.

The doses and dose volumes are discussed herein in connection with the general description of immunization and vaccination methods.

Animals immunized with immunogenic compositions or vaccines according to the invention develop a specific immunity against BTV, which during a BTV infection involves a decrease of the viremia, and indeed can totally block the virus, as compared with unvaccinated control animals. This advantageous aspect of the invention may be used to stop the transmission of BTV to limit the existence of mammalian viral reservoirs, and to prevent outbreaks of bluetongue disease.

Another advantageous aspect of the invention is that protective immunity can be transmitted from vaccinated subjects to the offspring.

According to the invention, the vaccination against BTV can be combined with other vaccinations within the framework of vaccination programs, in the form of immunization or vaccination kits or methods, or in the form of multivalent immunogenic compositions and multivalent vaccines, i.e. comprising or consisting essentially of at least one vaccine component against BTV and at least one vaccine component against at least one other pathogenic agent. This also includes the expression by the same expression vector of genes of at least two pathogenic agents, including BTV.

The invention thus also relates to a multivalent or "cocktail" immunogenic composition or a multivalent or "cocktail" vaccine against BTV against at least one other pathogen of the target species, using the same in vivo expression vector containing and expressing at least one polynucleotide of BTV according to the invention and at least one polynucleotide expressing an immunogen of another pathogen. As to combination or multivalent or "cocktail" immunogenic compositions or vaccines, as well as to immunogens or antigens or epitopes thereof to be in or expressed by such compositions or vaccines, attention is directed to herein cited and incorporated by reference documents, as well as to U.S. Pat. Nos. 5,843,456 and 6,368,603.

The "immunogen" expressed by a vector of the invention or used in multivalent or "cocktail" compositions or vaccines is understood to mean a protein, glycoprotein, polypeptide, peptide, epitope or derivative, e.g. fusion protein, inducing an immune response, preferably of a protective nature.

As discussed herein, these multivalent compositions or vaccines can also comprise or consist essentially of a pharmaceutically or veterinarily acceptable carrier or vehicle or excipient, and optionally an adjuvant.

The invention also relates to a multivalent immunogenic composition or a multivalent vaccine comprising at least one in vivo expression vector in which at least one polynucleotide of the Bluetongue virus is inserted (and expressed in vivo) and at least a second expression vector in which a polynucleotide encoding an immunogen of another pathogenic agent is inserted (and expressed in vivo). Such multivalent compositions or vaccines also comprise or consist essentially of a pharmaceutically or veterinarily acceptable carrier or vehicle or excipient, and optionally an adjuvant.

For antigen(s) or immunogen(s) or epitope(s) to be included in or expressed by a multivalent immunogenic composition or vaccine (in addition to BTV antigen(s), immunogen(s) or epitope(s)), including as to determining or ascertaining epitope(s), the skilled artisan may consult herein cited documents and documents cited in herein cited documents, all of which are incorporated by reference into the instant application.

For ovine multivalent immunogenic compositions and multivalent vaccines, the additional ovine pathogen(s), as to which additional ovine antigen(s) or immunogen(s) or epitope(s) thereof are included in and/or expressed by the multivalent immunogenic compositions and multivalent vaccines, are advantageously chosen from among the group including viruses of the ovine herpesvirus type 1 (OHV-1), ovine herpesvirus type 2 (OHV-2), Border Disease Virus (BDV), Boma disease virus, Pestes des petit ruminants, Nairobi sheep disease virus (NSDV), Ecthyrna virus (sheep parapox virus), rabies virus (rhabdovirus), feline parvovirus (FPV), ovine rotavirus, ovine pestivirus, ovine adenovirus, Foot and Mouth Disease Virus (FMDV), Rift Valley Fever virus, and mixtures thereof. Additional antigens suitable for use in the compositions of the present invention include antigens derived from bacterial and viral pathogens of sheep. Preferred bacterial and parasitic antigens include *Cryptosporidium parvum, Chlamydia, Coxiella bumetti, Clostridium* sp., *Pasteurella multocida, Pasteurella haemolytica, Salmonella typhimurium, Brucella, Erysipelothrix rhusiopathiae, Haemonchus contortis, Ostertagia, Coccidia* and *Escherichia coli.*

For bovine multivalent immunogenic compositions and multivalent vaccines, the additional equine pathogen(s), as to which additional equine antigen(s) or immunogen(s) or epitope(s) thereof are included in and/or expressed by the multivalent immunogenic compositions and multivalent vaccines, are advantageously chosen from among the group including: bovine herpesvirus type 1 (BHV-1) also called infectious bovine rhinotrachitis (IBR), bovine respiratory syncytial virus (BRSV), mucosal disease virus also called bovine pestivirus type 1 or type 2 (bovine viral diarrhea virus or BVDV-1 and BVDV-2), and type 3 parainfluenza virus, for each valency, one or more of the genes selected from the group consisting of gB and gD for the bovine herpesvirus, F and G for the bovine respiratory syncytial virus, E2, C+E1+E2 and E1+E2 for the mucosal disease virus, and HN and F for the type 3 parainfluenza virus. Additional antigens suitable for use in the compositions of the present invention include antigens derived from bacterial and viral pathogens of cattle. Preferred bacterial antigens include Clostridial antigens such as *Clostridium botulinum* C and D, *Clostridium perfringens* type A, B, C and D, *Clostridium septicum, Clostridium tetani, Clostridium chauvoei, Clostridium novyi* type B, *Clostridium sordellii, Clostridium haemolyticum;* Leptospira antigens, for example, *Leptospira interrogans* such as *Leptospira hardjo, Leptospira Pomona, Leptospira copenhageni, Leptospira zanoni, Leptospira tarassovi;* Pasteurella antigens such as *Pasteurella multocida* and *Pasteurella haemolytica; Corynebacterium* antigens such as *Corynebacterium pseudotuberculosis, Corynebacterium renale, Corynebacterium cystitis, Corynebacterium pilosum* and *Corynebacterium bovis;* and *Haemophilus* antigens such as *Haemophilus somnus* and *Haemophilus pleuropneumoniae; Dichelobacter nodosus* pilus; *Mycoplasma* antigens such as *Mycoplasma agalactiae, Mycoplasma bovis* and *Mycoplasma ovipneumoniae.* Preferred viral antigens include Bovine Viral Diarrhea (BVD) antigens, *Bovine Rhinotracheitus* Virus (IBR) antigens, Parainfluenza-3 antigens, Respiratory Syncytial Virus (RSV) antigens and Bovine Ephemeral Fever (BEF) antigens. Thus, the invention comprehends the use of polynucleotide(s) encoding (an) immunologically active fragment(s) or (an) epitope(s) of such immunogen(s).

For equine multivalent immunogenic compositions and multivalent vaccines, the additional equine pathogen(s), as to which additional equine antigen(s) or immunogen(s) or epitope(s) thereof are included in and/or expressed by the multivalent immunogenic compositions and multivalent vaccines, are advantageously chosen from among the group including viruses of equine influenza (EI), African Horse Sickness ([AHSV]preferably with a combination of immunogens VP2 and VP5), equine encephalosis virus ([EEV] also with a combination of VP2 and VP5), Western Equine Encephalitis Virus (WEEV), Venezuelan Equine Encephalitis Virus (VEEV) Eastern Equine Encephalitis Virus (EEEV), West Nile Virus (WNV), *Clostridium tetani* (tetanus), and mixtures thereof. Preferably, for AHSV the immunogens are VP2 and/or VP5, for EIV the immunogen is advantageously HA, NP and/or N; for viruses of encephalitis, the immunogen is advantageously C and/or E2; and for *Clostridium tetani* the immunogen is all or part of the subunit C of the tetanic toxin. Thus, the invention comprehends the use of polynucleotide(s) encoding (an) immunologically active fragment(s) or (an) epitope(s) of such immunogen(s).

For canine multivalent immunogenic compositions and multivalent vaccines, the additional canine pathogen(s), as to which additional canine antigen(s) or immunogen(s) or epitope(s) thereof are included in and/or expressed by the multivalent immunogenic compositions and multivalent vaccines, are advantageously chosen from among the group including viruses of measles disease virus, canine adenovirus 1 (CAV-1), canine adenovirus 2 (CAV-2), canine distemper virus (CDV), canine parainfluenza type 2 virus (CPI-2), canine herpesvirus type 1 (CHV-1), rabies virus (rhabdovirus), canine parvovirus (CPV), canine coronavirus (CCV), canine adenovirus, *Borrelia burgdorferi, Leptospira* and mixtures thereof. Preferably, for CDV the immunogen is advantageously F and/or HA (see also U.S. Pat. Nos. 6,309,647, 5,756,102 regarding CDV immunogens and constructs); for CPV the immunogen is advantageously VP2; for CCV the immunogen is advantageously S and/or M; for CHV-1 the immunogen is advantageously gB and/or gC and/or gD (see also U.S. Pat. No. 5,688,920, 5,529,780, regarding CHV immunogens and constructs); for rabies virus the immunogen is advantageously G (see also U.S. Pat. No. 5,843,456 regarding rabies combination compositions); for *Borrelia burgdorferi* the immunogen is advantageously OspA (see also U.S. Pat. No. 6,368,603 regarding OspA combination compositions). The invention thus comprehends the use of polynucleotide(s) encoding (an) immunologically active fragment(s) or an epitope(s) of such immunogen(s).

For feline multivalent immunogenic compositions and multivalent vaccines, the additional feline pathogen(s), as to which additional feline antigen(s) or immunogen(s) or epitope(s) thereof are included in and/or expressed by the multivalent immunogenic compositions and multivalent vaccines, are advantageously chosen from among the group including viruses of the feline herpesvirus type 1 (FHV-1), feline calicivirus (FCV), rabies virus (rhabdovirus), feline parvovirus (FPV), feline infectious peritonitis virus (FIPV), feline leukemia virus (FeLV), feline immunodeficiency virus (FIV), Chlamydia and mixtures thereof. Preferably, for FeLV the immunogen is advantageously A and/or B and/or gag and/or pol, e.g., gag/pol; for FPV the immunogen is advantageously VP2; for FIPV the immunogen is advantageously S and/or M and/or N, e.g., S and M and/or N (see also U.S. Pat. Nos. 6,348,196 and 5,858,373 and immunogens and constructs thereof); for FHV the immunogen is advantageously gB and/or gC and/or gD, e.g., gB and gC and/or gD (see also U.S. Pat. Nos. 5,338,683, 6,183,750; for herpesvirus immunogens and constructs expressing the same); for FCV the immunogen is advantageously C; for FIV the immunogen is advantageously env and/or gag and/or pro, e.g., gag/pro, env, or env and gag/pro (see also immunogens and constructs discussed in Tartaglia et al., U.S. application Ser. No. 08/746, 668, filed Nov. 14, 1996); for rabies virus the immunogen is advantageously G. The invention thus comprehends the use of polynucleotide(s) encoding (an) immunologically active fragment(s) or (an) epitope(s) of said immunogen(s).

For avian multivalent immunogenic compositions and multivalent vaccines, the additional avian pathogen(s), as to which additional avian antigen(s) or immunogen(s) or epitope(s) thereof are included in and/or expressed by the multivalent immunogenic compositions and multivalent vaccines, are advantageously chosen from among the group including viruses of the Marek's disease virus (MDV) (e.g., serotypes 1 and 2, preferably 1), Newcastle disease virus (NDV), Gumboro disease virus or infectious bursal disease virus (IBDV), infectious bronchitis virus (IBV), infectious anemia virus or chicken anemia virus (CAV), infectious laryngotracheitis virus (ILTV), encephalomyelitis virus or avian encephalomyelitis virus (AEV or avian leukosis virus ALV), virus of hemorrhagic enteritis of turkeys (HEV), pneumovirosis virus (TRTV), fowl plague virus (avian influenza), chicken hydropericarditis virus, avian reoviruses, *Escherichia coli, Mycoplasma gallinarum, Mycoplasma gallisepticum, Haemophilus avium, Pasteurella gallinarum, Pasteurella multocida gallicida*, and mixtures thereof. Preferably, for MDV the immunogen is advantageously gB and/or gD, e.g., gB and gD, for NDV the immunogen is advantageously HN and/or F, e.g., HN and F; for IBDV the immunogen advantageously is VP2; for IBV the immunogen is advantageously S (more advantageously S1) and/or M and/or N, e.g., S (or S1) and M and/or N; for CAV the immunogen is advantageously VP1 and/or VP2; for ILTV the immunogen is advantageously gB and/or gD; for AEV the immunogen advantageously is env and/or gag/pro, e.g., env and gag/pro or gag/pro; for HEV the immunogen is advantageously the 100K protein and/or hexon; for TRTV the immunogen is advantageously F and/or G, and for fowl plague the immunogen is advantageously HA and/or N and/or NP, e.g., HA and N and/or NP. The invention thus comprehends the use of polynucleotide(s) encoding (an) immunologically active fragment(s) or (an) epitope(s) of said immunogen(s).

By way of example, in a multivalent immunogenic composition or a multivalent vaccine according to the invention, to which one or more adjuvants has optionally been added (and hence the composition contains or consists essentially of or consists of one or more adjuvants) as discussed herein, and which is intended for equine species, it is possible to incorporate (and hence for the composition or vaccine to comprise, consist essentially of or consist of) one or more of the plasmids described in WO98/03198, advantageously as discussed in examples 8 to 25 thereof, and/or those described in WO00/ 77043 and which relate to the equine species, advantageously those described in examples 6 and 7 thereof. For the canine species, a multivalent composition or vaccine may contain or consist essentially of or consist of one or more of the plasmids described in WO98/03199, advantageously as discussed in examples 8 to 16 thereof, and/or those described in WO00/

77043 and which relate to the canine species, advantageously those described in examples 2, 3 and 4 thereof; and, such compositions or vaccines can contain, consist essentially of or consist of one or more adjuvants. For the feline species, a multivalent composition or vaccine may contain or consist essentially of or consist of one or more of the plasmids described in WO98/03660, advantageously in examples 8 to 19 thereof, and/or those described in WO00/77043 and which relate to the feline species, advantageously those described in example 5 thereof; and, such compositions or vaccines can contain, consist essentially of or consist of one or more adjuvants. And for the avian species, a multivalent composition or vaccine may contain or consist essentially of or consist of one or more of the plasmids described in WO98/03659, advantageously in examples 7 to 27 thereof; and, such compositions or vaccines can contain, consist essentially of or consist of one or more adjuvants.

The immunogenic compositions or vaccines as discussed herein can also be combined with at least one conventional vaccine (e.g., inactivated, live attenuated, or subunit) directed against the same pathogen or at least one other pathogen of the species to which the composition or vaccine is directed. The immunogenic compositions or vaccines discussed herein can be administered prior to or after the conventional vaccine, e.g., in a "prime-boost" regimen.

The invention further comprehends combined vaccination employing immunogenic composition(s) and subunit vaccine(s) according to the invention. Thus, the invention also relates to multivalent immunogenic compositions and multivalent vaccines comprising one or more proteins according to the invention and one or more immunogens (as the term immunogen is discussed herein) of at least one other pathogenic agent (advantageously from among those herein and in documents cited and incorporated herein by reference) and/or another pathogenic agent in inactivated or attenuated form or as a subunit. In the manner described, these multivalent vaccines or compositions also contain, consist essentially of or consist of a pharmaceutically or veterinarily acceptable vehicle or excipient and optionally one or more adjuvants.

The present invention also relates to methods for the immunization and vaccination of a target species, e.g., as discussed herein.

The present invention also relates to methods for the immunization and/or vaccination of a target species, using a prime-boost regimen. The term of "prime-boost" refers to the successive administrations of two different vaccine types or immunogenic or immunological composition types having at least one immunogen in common. The priming administration (priming) is the administration of a first vaccine or immunogenic or immunological composition type and may comprise one, two or more administrations. The boost administration is the administration of a second vaccine or immunogenic or immunological composition type and may comprise one, two or more administrations, and, for instance, may comprise or consist essentially of annual administrations.

An embodiment of a prime-boost immunization or vaccination against BTV according to the invention is a prime-boost immunization or vaccination wherein the animal is first administered a (priming) DNA vaccine or immunological or immunogenic composition comprising or consisting essentially of and expressing in vivo at least one immunogen, antigen or epitope of BTV, and thereafter is administered (boosted with) a second type of vaccine or immunogenic or immunological composition containing or consisting essentially of or expressing at least one immunogen, antigen or epitope that is common to the priming vaccine or immunogenic or immunological composition. This second type of vaccine can be an inactivated or attenuated or subunit vaccine or immunogenic or immunological composition or a vector, e.g., recombinant or modified virus vaccine or immunogenic or immunological composition that has in vivo expression (e.g. poxvirus, herpesvirus, adenovirus). Poxviruses may be advantageously employed, e.g., attenuated vaccinia viruses, like MVA or NYVAC, and avipox viruses, like canarypox viruses and fowlpox viruses.

Advantageously, the DNA vaccine is intended to induce a priming immune response specific for the expressed immunogen, antigen or epitope or "DNA induced immune response" (such as a gamma-interferon+(IFN$_\gamma$+) T cell memory response specific for the expressed immunogen, antigen or epitope) which is boostable (can be boosted) by a subsequent administration (boost) of an inactivated vaccine or immunological composition or a live recombinant vaccine comprising or consisting essentially of a viral vector, such as a live recombinant poxvirus, containing or consisting essentially of and expressing in vivo at least the same immunogen(s) or antigen(s) or epitope(s) expressed by the DNA vaccine. The IFN$_\gamma$+T cell memory response specific for the expressed BTV immunogen can be shown in a quantitative enzyme-linked immune spot (ELISPOT) assay using peripheral blood mononuclear cells (PBMCs) (Laval, Paillot et al. 2002).

The "boost" may be administered from about 2 weeks to about 6 months after the "priming", such as from about 3 to about 8 weeks after the priming, and advantageously from about 3 to about 6 weeks after the priming, and more advantageously, about 4 weeks after the priming.

For ovine, bovine, or equine, the priming can be done with a DNA vaccine or immunogenic or immunological composition comprising or consisting essentially of and expressing in vivo nucleic acid molecule(s) encoding a BTV immunogen, antigen or epitope according to the invention and the boost is advantageously done with a vaccine or immunogenic or immunological composition comprising a recombinant live viral vector (e.g. poxvirus, herpesvirus, adenovirus), such as a recombinant fowlpox virus or recombinant canarypox virus, recombinant, OHV-1 or OHV-2, BHV-1 or BHV-2, EHV-1 or EHV-4, comprising or consisting essentially of nucleic acid molecule(s) encoding and expressing in vivo at least one of the same BTV immunogen(s), antigen(s) or epitope(s) as the DNA vaccine or immunogenic or immunological composition expresses. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young sheep, calf, or foal that can have maternal antibodies against BTV (against which immunization or vaccination is directed). Advantageously, the DNA vaccine or immunological or immunogenic composition is administered to the young animal from birth up to and including about 16 weeks of age, such as from birth up to and including about 8 weeks of age, for instance, from birth up to and including about 6 weeks of age, e.g., from birth up to and including about 4 weeks of age.

For felines, the priming can be done with a DNA vaccine or immunogenic or immunological composition according to the invention comprising or consisting essentially of and expressing in vivo, nucleic acid molecule(s) encoding a BTV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant FHV, recombinant canine adenovirus), comprising or consisting essentially of nucleic acid molecule(s) encoding and expressing in vivo at least one BTV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopole for the boost recombinant vaccine or immunological or immunogenic composition.

The priming may be performed on a young kitten that can have maternal antibodies against BTV (against which immunization or vaccination is directed). The DNA vaccine or immunological or immunogenic composition can be administered to the young kitten from birth up to and including about 12 weeks of age, for instance, from birth up to and including about 8 weeks of age, advantageously from birth up to and including about 6 weeks of age, e.g., from birth up to and including about 4 weeks of age.

For canines, the priming can be done with a DNA vaccine or immunogenic or immunological composition according to the invention comprising or consisting essentially of and expressing in vivo nucleic acid molecule(s) encoding a BTV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant CHV, recombinant canine adenovirus), comprising or consisting essentially of nucleic acid molecule(s) encoding and expressing in vivo at least one BTV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

The priming may be performed on a young puppy that can have maternal antibodies against BTV (against which immunization or vaccination is directed).The DNA vaccine or immunological or immunogenic composition can be administered to the young puppy from birth up to and including about 12 weeks of age, for instance, from birth up to and including about 8 weeks of age, advantageously from birth up to and including about 6 weeks of age, e.g., from birth up to and including about 4 weeks of age.

For avians, the priming can be done with a DNA vaccine or immunogenic or immunological composition according to the invention comprising or consisting essentially of and expressing in vivo nucleic acid molecule(s) encoding a BTV immunogen, antigen or epitope and the boost is advantageously done with a vaccine or immunogenic or immunological composition comprising or consisting essentially a recombinant live viral vector (e.g. poxvirus, herpesvirus, adenovirus, advantageously recombinant fowlpox virus or recombinant canarypox virus, recombinant HVT, recombinant MDV, recombinant avian adenovirus), comprising or consisting essentially of nucleic acid molecule(s) encoding and expressing in vivo at least one BTV immunogen, antigen or epitope that is the same as that expressed by the DNA vaccine do. In another embodiment these priming and boost vaccines or immunological or immunogenic compositions can be adjuvanted, for instance, by DMRIE-DOPE for the priming DNA vaccine or immunological or immunogenic composition and by Carbopol® for the boost recombinant vaccine or immunological or immunogenic composition.

Figure 10:
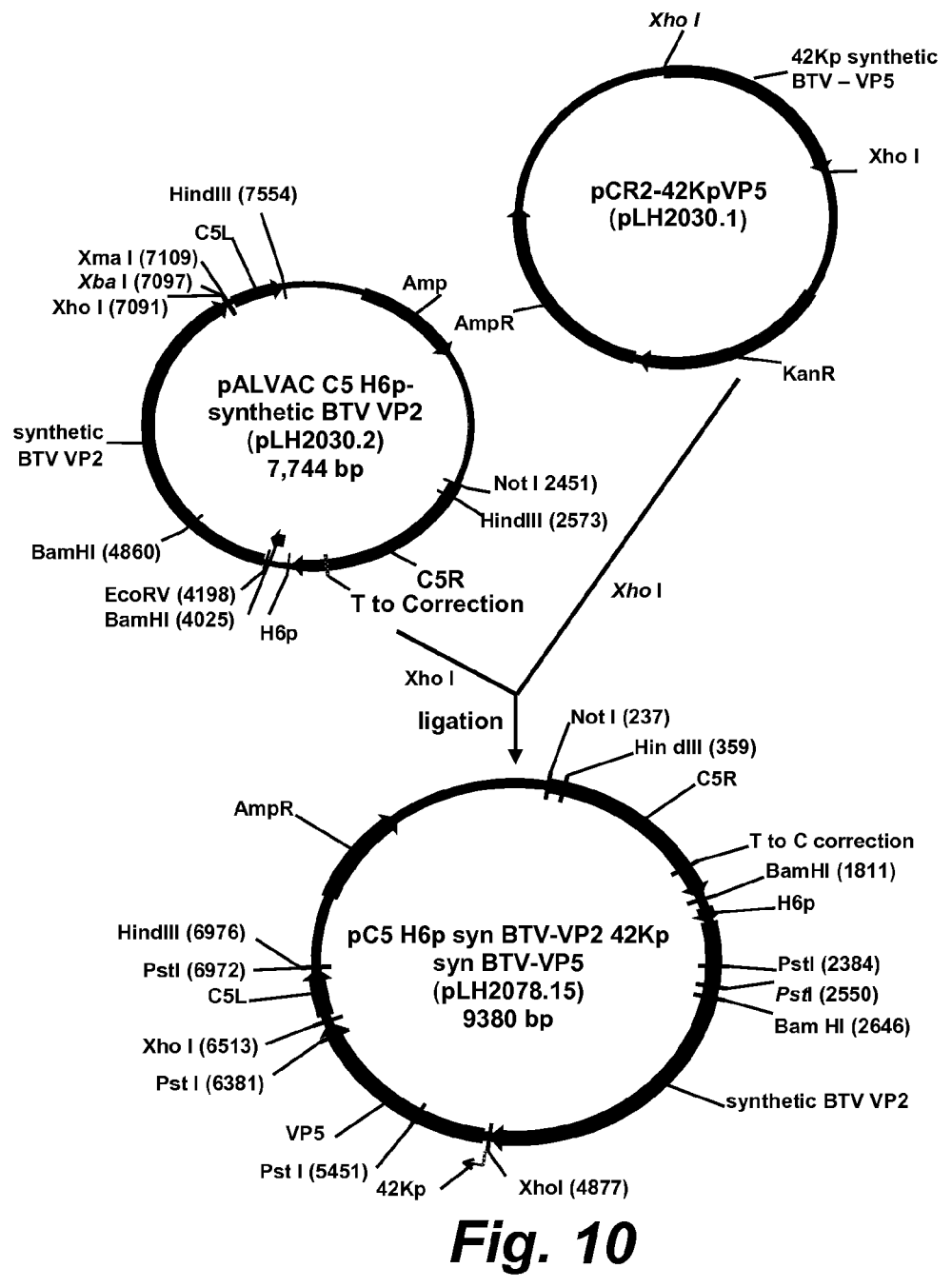

In an embodiment, the priming DNA vaccine or immunological or immunogenic composition comprises or consists essentially of a plasmid encoding and expressing VP2, VP5, or VP2 and VP5 polypeptides, such as the plasmid pLH2078.15 (FIG. 10) to which has been incorporated a ubiquitous eukaryotic promoter, i.e., the Human Cytomegalovirus Immediate Early (CMV-IE) so as to obtain efficient expression of the VP2 and VP5 proteins, and the boost of the recombinant vaccine or immunological or immunogenic composition comprises or consists essentially of a poxvirus such as a canarypox virus, for instance, the recombinant canarypox virus vCP2289 (Example 9). In another embodiment these priming and boost vaccines or immunological or immunogenic compositions can be adjuvanted: the DNA vaccine or immunological or immunogenic composition containing the plasmid pLH2078.15 (FIG. 10), comprising, but not limited to, the CMV-IE promoter can be adjuvanted by DMRIE-DOPE, such as described US patent application 20050255127; and the recombinant vaccine or immunological or immunogenic composition containing vCP2289 can be adjuvanted by Carbopol®, such as described in US patent application 20050255127.

The invention also relates to kits for performing prime-boost methods comprising or consisting essentially of a priming vaccine or immunological or immunogenic composition and a boost vaccine or immunological or immunogenic compositions in separate containers, optionally with instructions for admixture and/or administration.

The amounts (doses) administered in the priming and the boost and the route of administration for the priming and boost can be as herein discussed, such that from this disclosure and the knowledge in the art, the prime-boost regimen can be practiced without undue experimentation. Furthermore, from the disclosure herein and the knowledge in the art, the skilled artisan can practice the methods, kits, etc. herein with respect to any of the herein-mentioned target species.

These methods can comprise, consist essentially of or consist of the administration of an effective quantity of an immunogenic composition or vaccine according to the invention. This administration can be by the parenteral route, e.g. by subcutaneous, intradermic or intramuscular administration, and/or by oral and/or nasal routes. Advantageously, this administration is intramuscularly or subcutaneously. One or more administrations can take place, such as two administrations.

Vaccines or immunogenic compositions can be injected by a needleless, liquid jet injector or powder jet injector. For plasmids it is also possible to use gold particles coated with plasmid and ejected in such a way as to penetrate the cells of the skin of the subject to be immunized (Tang, DeVit et al. 1992). Other documents cited and incorporated herein may be consulted for administration methods and apparatus of vaccines or immunogenic compositions of the invention. The needleless injector can also be for example Biojector 2000 (Bioject Inc., Portland Oreg., USA).

Advantageously, the immunogenic compositions and vaccines according to the invention comprise or consist essentially of or consist of an effective quantity to elicit an immunological response such as, but not limited to, neutralizing antibodies and/or a protective immunological response of one or more expression vectors and/or polypeptides as discussed herein; and, an effective quantity can be determined from this disclosure, including the documents incorporated herein, and the knowledge in the art, without undue experimentation. Advantageously, the immunogenic compositions and vaccines according to the invention comprise or consist essentially of or consist of an effective quantity of one or more expression vectors and/or polypeptides as discussed herein a protective response such as, but not limited to, a reduction or extinction of the clinical symptoms such as, but not limited to, hyperthermia, leucopenia, lymphopenia, thrombocytopenia and/or a reduction or extinction of the viremia.

In the case of immunogenic compositions or vaccines based on a plasmid vector, a dose can comprise, consist essentially of or consist of, in general terms, about in 10 μg to about 2000 μg, advantageously about 50 μg to about 1000 μg. The dose volumes can be between about 0.1 and about 2 ml, preferably between about 0.2 and about 1 ml.

These doses and dose volumes are suitable for the vaccination of equines and other target species that are mammals such as ovines, bovines, canines, felines.

For the vaccination or immunization of an avian, a dose is advantageously between about 10 μg and about 500 μg and preferably between about 50 μg and about 200 μg. The dose volumes can be between about 0.1 and about 1 ml, preferably between about 0.2 and about 0.5 ml.

One skilled in the art can determine the effective plasmid dose to be used for each immunization or vaccination protocol and species from this disclosure and the knowledge in the art.

In the case of immunogenic compositions or vaccines based on a poxvirus, a dose can be between about $10^2$ pfu and about $10^9$ pfu.

For ovines, bovines, equines and other target species that are mammals such as felines and canines, when the vector is a vaccinia virus, the dose is more advantageously between about $10^4$ pfu and about $10^9$ pfu, preferably between about $10^6$ pfu and about $10^8$ pfu and when the vector is a canarypox virus, the dose is more advantageously between about $10^5$ pfu and about $10^9$ pfu and preferably between about $10^{5.5}$ pfu or about $10^6$ pfu and about $10^8$ pfu.

For an avian, when the vector is a poxvirus such as a canarypox virus, the dose is more advantageously between about $10^3$ pfu, and about $10^7$ pfu, preferably between about $10^4$ pfu and about $10^6$ pfu; and, when the vector is a poxvirus such as a fowlpox virus, the dose is more advantageously between about $10^2$ pfu and about $10^5$ pfu, preferably between about $10^3$ pfu and about $10^5$ pfu. From this disclosure and the knowledge in the art, the skilled artisan can determine the suitable dose when the vector is another avipox virus, such as a dovepox, pigeonpox, etc.

In the case of immunogenic compositions or vaccines for a mammalian target species, based on a viral vector other than a poxvirus, such as a herpes viruses or adenovirus, a dose is generally between about $10^3$ pfu and about $10^8$ pfu; and, in the case of such non-poxvirus-viral-vector-based immunogenic compositions for avian species or avian vaccines, a dose is generally between about $10^3$ pfu and about $10^6$ pfu. For such non-poxvirus-viral-vector-based immunogenic or vaccine compositions for larger target mammal species, e.g., larger cats (e.g., kept in a zoo) or equines, e.g., in the case of equine immunogenic or vaccine compositions, a dose is advantageously between about $10^6$ pfu and about $10^8$ pfu.

The dose volume of immunogenic and vaccine compositions for target species that are mammals, e.g., the dose volume of equine immunogenic or vaccine compositions, based on viral vectors, e.g., non-poxvirus-viral-vector-based immunogenic or vaccine compositions, is generally between about 0.5 and about 2.5 ml, such as between about 0.5 and about 2.0 ml, preferably between about 1.0 and about 2.0 ml, preferably about 1.0 ml. The dose volume of immunogenic or vaccine compositions for avians based on viral vectors, e.g., the dose volume of non-poxvirus-viral-vector-based avian immunogenic or vaccine compositions, is generally between about 0.1 and about 1.0 ml, preferably between about 0.1 and about 0.5 ml and more advantageously between about 0.2 and about 0.3 ml. Also in connection with such a vaccine or immunogenic composition, from the disclosure herein and the knowledge in the art, the skilled artisan can determine the number of administrations, the administration route, and the doses to be used for each immunization or vaccination protocol, without any undue experimentation. For instance, there can be two administrations to a sheep, cow or horse, e.g. at 35 day intervals.

In the case of subunit immunogenic compositions or subunit vaccines, with reference to the amount of active ingredient, e.g., subunit (antigen, immunogen, epitope) a dose comprises or consists essentially of or consists of, in general terms, about 10 μg to about 2000 μg, advantageously about 50 μg to approximately 1000 μg. The dose volume of such immunogenic or vaccine compositions for target species that are mammals, e.g., for equines, is generally between about 1.0 and about 2.0 ml, preferably between about 0.5 and about 2.0 ml and more advantageously about 1.0 ml. The dose volumes of such immunogenic or vaccine compositions avians is generally between about 0.1 and about 1.0 ml, preferably between about 0.1 and about 0.5 ml, and more advantageously between 0.2 and 0.3 ml. Also for such a vaccine or immunogenic composition, the skilled artisan, from this disclosure and the knowledge in the art, can, without any undue experimentation, determine the number of administrations, the administration route and the doses to be used for each immunization or vaccination protocol.

The invention also relates to the use of an in vivo expression vector or a preparation of vectors and/or polypeptides according to the invention, for the formulation of an immunogenic composition or a vaccine intended to protect a target species, or elicit in the target species an immunological response, against BTV, and in certain embodiments, against at least one other pathogenic agent.

A vaccine based on plasmid or a viral vaccine expressing one or more proteins of BTV or a BTV subunit vaccine according to the present invention will not induce in the immunized or vaccinated animal antibodies against other proteins of the virus, which are not presented in or by the immunogenic composition or vaccine (e.g., not present in the immunogenic composition or vaccine and/or not expressed by the immunogenic composition or vaccine). By this feature, the instant invention provides differential diagnostic methods. The present invention makes it possible to make a distinction between animals infected by the pathogenic field strains of BTV and animals vaccinated or immunized with vaccines or compositions according to the invention. In the former, proteins and/or antibodies directed against them are present and can be detected by an antigen-antibody reaction. In the latter (the animals vaccinated or immunized according to the invention), this is not the case as such animals remain negative in such an antigen-antibody reaction as to proteins not presented in or by the immunogenic or vaccine composition or antibodies thereto. In order to bring about this discrimination, the diagnostic method employs a protein which is not represented in or by the vaccine or immunogenic composition (not present and/or not expressed), e.g. protein VP7, NS1, NS2, or NS3 when it is not represented in the vaccine or immunogenic composition.

Accordingly, the instant invention comprehends diagnostic assays or kits that employ a protein or antibody thereto that is not presented in or by a vaccine or immunogenic composition of the invention; and, kits that contain such a diagnostic assay or kit and such a vaccine or immunogenic composition, whereby the user can inoculate and/or vaccinate animals and thereafter test the animals, to determine those animals that have been exposed to BTV versus those animals that have only been immunized and/or vaccinated against BTV.

Thus, the present invention relates to the use of vectors, preparations and polypeptides according to the invention for the preparation of immunogenic compositions and vaccines making it possible to discriminate between vaccinated or immunized animals and infected animals.

The instant invention also relates to an immunization and vaccination method associated with a diagnostic method permitting such discrimination.

The protein selected for the diagnosis or one of its fragments or epitopes is used as the antigen in the diagnostic test and/or is used for producing polyclonal or monoclonal antibodies.

The one skilled in the art has sufficient practical knowledge to produce these antibodies and to implement antigens and/or antibodies in conventional diagnostic methods, e.g. ELISA tests, and thereby perform differential diagnostic tests according to the instant invention.

The invention will now be further described and illustrated by way of the following, non-limiting examples.

EXAMPLES

All the constructions are implemented using standard molecular biology methods (cloning, digestion by restriction enzymes, synthesis of a complementary single-strand DNA, polymerase chain reaction, elongation of an oligonucleotide by DNA polymerase, etc.) described by Sambrook J. et al. (Sambrook and Russell 2001). All the restriction fragments used for these examples of the present invention, as well as the various polymerase chain reaction (PCR) products are isolated and purified using the Qiagen gel extraction or PCR purification kits Example 1

Culture of the Bluetongue (BTV) Challenge Virus

BTV serotype 17, a strain that was originally isolated from the blood of sheep from Tulare County, Calif. (USA) that died of bluetongue disease was used throughout. The virus was passaged twice in seronegative cattle prior to isolation in primary bovine lung microvacular endothelial cells. For amplification, this strain of BTV serotype 17 (Bonneau, DeMaula et al. 2002; DeMaula, Leutenegger et al. 2002) was cultured in BHK-21 cells (baby hamster kidney cells), obtainable from the American Type Culture Collection (ATCC) under no. CCL-10.

The BHK-21 cells were cultured in Eagle's medium (EMEM) supplemented with 10% fetal bovine serum (Hyclone Laboratories), 10% tryptose phosphate broth, and 1% penicillin and streptomycin. The cells were cultured at +37° C. under a 5% $CO_2$ atmosphere.

The cellular monolayer is confluent within 3 days. The culture medium is then replaced with fresh EMEM medium supplemented with 10% FBS, and the BTV added at a rate of 5 approximately pfu/cell. When the cytopathogenic effect (CPE) was complete (generally 48 to 72 hours after the start of culturing), the viral suspensions were harvested and then clarified by centrifugation and frozen at −70° C. One or two successive passages were necessary for producing a viral batch, which is stored at −70° C.

Example 2

Synthesis of Optimized BTV VP2 and VP5

Codon preference among different species can be dramatically different. To enhance the expression level of a foreign protein, i.e. BTV VP2 & VP5 using a canarypox expression system (ALVAC) in an ovine/bovine/equine mammalian cell, it is very important to adjust the codon frequency of the foreign protein to match that of the host expression system (Kim, Oh et al. 1997). For codon optimization, bioinformaticians take many other factors into consideration, e.g. secondary structure, GC content, repetitive codons, restriction endonuclease sites, etc., and develop proprietary algorithms. Geneart GmbH (Regensburg, Germany) has developed the proprietary GeneOptimizer™ software (patent pending) that implements multi-parameter optimization in one single operation. Taking into account the most important parameters in parallel, the software generates a total of up to 500,000 optimized variants of the target sequence in an evolutionary approach and selects the one that is best suited. It has been reported that such optimized genes have up to a 100-fold increase in expression yields compared to the original gene sequence (Bradel-Tretheway, Zhen et al. 2003; Disbrow, Sunitha et al. 2003).

The nucleic acid sequence information for BTV-17 VP2 (SEQ ID NO:3) (de Mattos, de Mattos et al. 1994) and for BTV-17 VP5 (SEQ ID NO:4) were submitted to Geneart for use as the "native" BTV-17 sequences. This sequence information was applied to the GeneOptimizer™ software by Geneart, and optimized synthetic sequences for VP2 and VP5 were derived.

FIG. 1 provides a comparison/alignment of nucleotide sequences between VP2 native (SEQ ID NO:3) and the optimized (by Geneart) VP2 synthetic (SEQ ID NO:1). FIG. 2 provides a comparison/alignment of nucleotide sequences between VP5 native (SEQ ID NO:4) and the optimized VP5 synthetic (SEQ ID NO:2) The optimized sequence for VP2 and VP5 was used by Geneart as a basis for chemical synthesis of an array of highly accurate oligonucleotides that taken together encompass the entire synthetic coding sequence for each of the genes. The oligonucleotides for each gene are then assembled using a PCR (polymerase chain reaction) based strategy to yield the complete synthetic VP2 and VP5 coding sequence.

Example 3 pPCR-Script Cloning of Optimized BTV-17 Synthetic VP2 and Synthetic VP5

Figure 3:
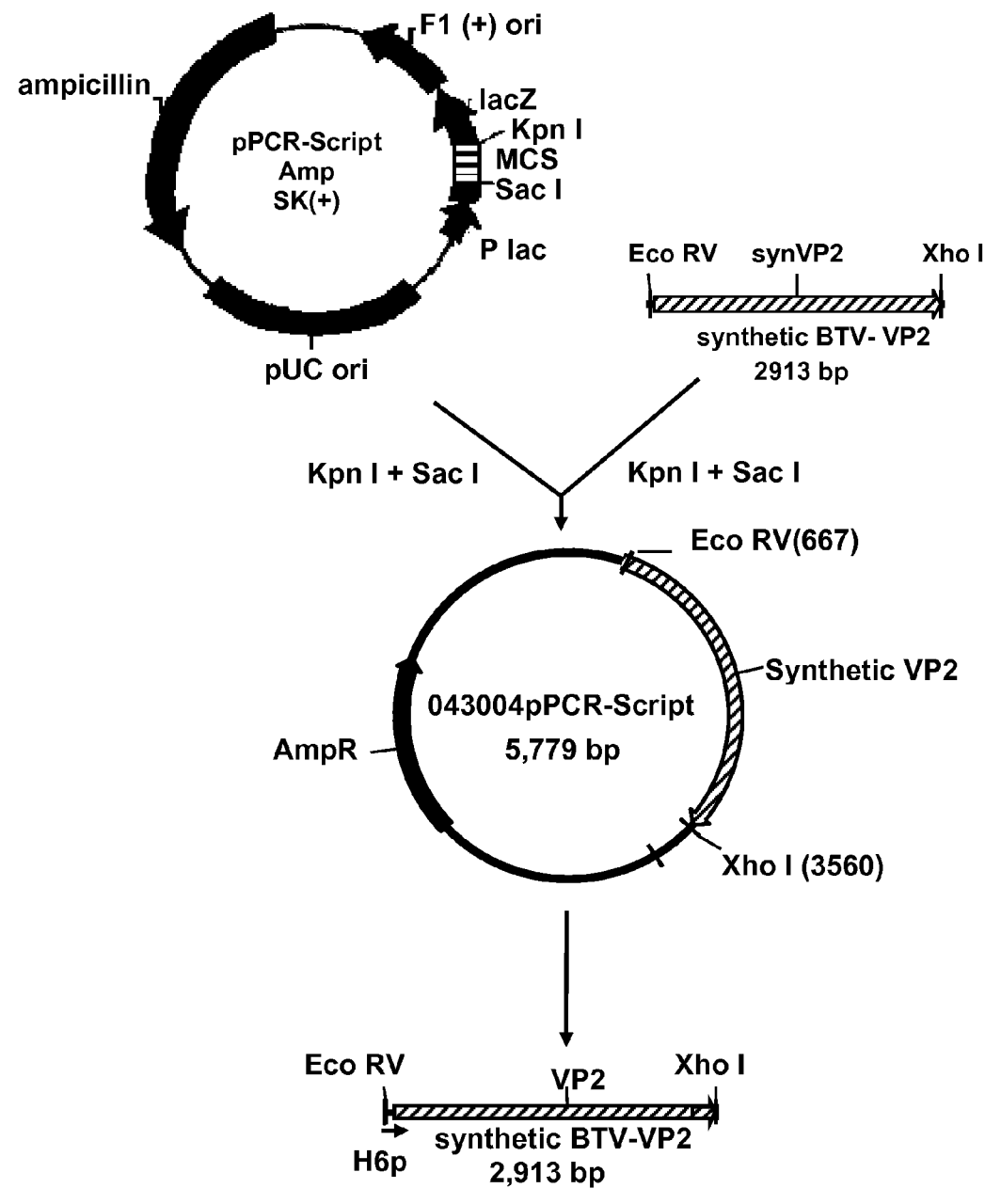

Synthetic VP2. The cloning vector pPCR-Script® Amp SK(+) available from Stratagene (San Diego, Calif., USA) was linearized at its Multiple Cloning Site (MCS) region by cleavage with Restriction Endonucleases (RE) Sac I and Kpn I. The 2,913 nucleotide linear fully assembled synthetic VP2 coding sequence containing the 3'end of the H6 promoter immediately upstream of the ATG start codon was then ligated into the plasmid vector with T4 DNA ligase. The ligated DNA was used to transform competent *E. coli* cells. Positive transformants that were Ampicillin resistant (carry plasmid vector) and that harbored the VP2 synthetic gene sequence by virtue of their 'white' phenotype on XGal indicator plates (β-galatosidase gene disrupted by insertion of VP2 in MCS of pPCR-Script®) were selected for further characterization. One clone, 043004 pPCR-Script (5,779 bp) was isolated and determined to be correct by DNA sequence analysis. FIG. 3 illustrates the preceding cloning strategy. The 043004 clone was used for subsequent cloning operations.

Figure 8:
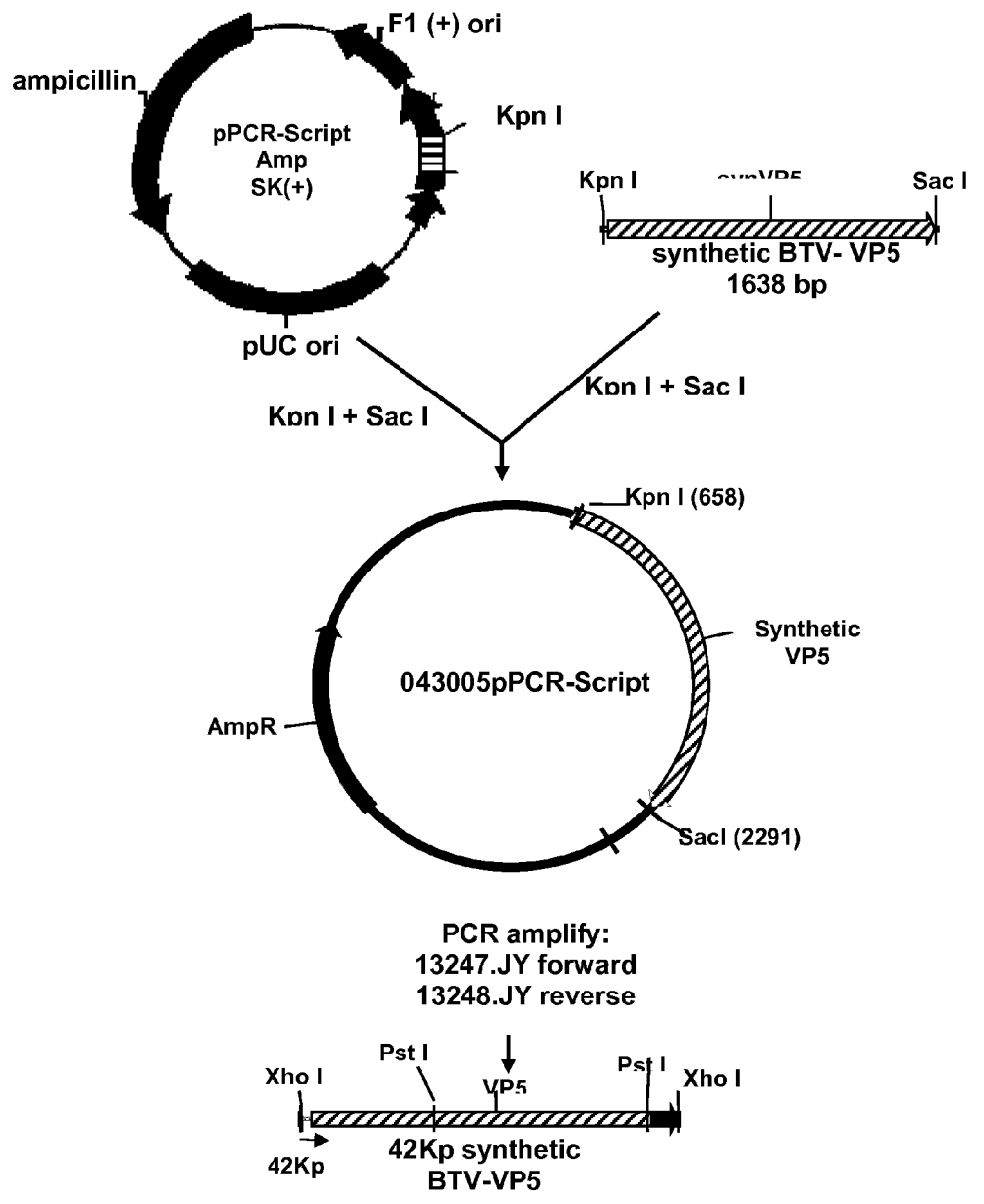

Synthetic VP5. The cloning vector pPCR-Script® Amp SK(+) available from Stratagene (San Diego, Calif., USA) was linearized in its MCS region by cleavage with REs Sac I and Kpn I The 1,638 nucleotide linear fully assembled synthetic VP5 coding sequence was then ligated to the plasmid vector with T4 DNA ligase. The ligated DNA was used to transform ultracompetent *E. coli* cells. Positive transformants that were Ampicillin resistant (carry plasmid vector) and that harbored the VP5 synthetic gene sequence by virtue of their 'white' phenotype on XGal indicator plates (β-galatosidase gene disrupted by insertion of VP2 in MCS of pPCR-Script®) were selected for further characterization. One clone, 043005 pPCR-Script (4,492 bp) was isolated and determined to be correct by DNA sequence analysis. FIG. 8 illustrates the preceding cloning strategy. This clone was used in subsequent cloning strategies.

Example 4 pNVQH6C5LSP-18 ALVAC Donor Plasmid

Construction of the ALVAC donor plasmid pNVQH6C5LSP-18 is described (US patent application 20050255127). A 5 kb locus of canarypox DNA, encoding an ORF designated C5 initiating at position 1864 and terminating at position 2187 of the viral genome was identified. The following describes a C5 insertion plasmid constructed by deleting the majority of the C5 ORF and replacing it with, the H6 promoter, a multiple cloning site (MCS) and transcriptional and translational termination sequences in all reading frames. A 1590 bp PCR fragment, containing the upstream C5R arm is amplified from genomic canarypox DNA using primers C5A1 and C5B1

(SEQ ID NO: 5) C5A:
5' GGCCGAATTCTGAATGTTAAATGTTATACTTT 3'

(SEQ ID NO: 6): C5B1:
5' CCCGGGATCGATGGATCCTTTTTATAGCTAATTAGTCACGTACCTTT

GAGAGTACCACTTCAGCTA 3'

The amplified fragment includes an EcoR I site at the 5'-end, termination sequences and an MCS containing BamH I, Cla I and Xma I sites at the 3'-end.

A 458 bp PCR fragment, containing the downstream C5L arm is amplified from genomic canarypox DNA using primers C5C1 and C5D1:

(SEQ ID NO: 7) C5C1:
5' GGATCCATCGATCCCGGGTTTTTATGACTAGTTAATCACGGCCGCTT

ATAAAGATCTAAAATGCAT 3'

(SEQ ID NO: 8) C5D1
5' GGCTGCAGGTATTCTAAACTAGGAATAGAT 3'

The amplified fragment includes 5' BamH I, Cla I and Xma I restriction endonuclease sites, termination sequences and a Pst I site at the 3'-end.

The foregoing PCR fragments were fused together by re-amplifying with primers C5A and C5D (above), generating a 2,030 bp EcoR I-Pst I fragment that is cloned into the pUC 8 plasmid vector, generating pUC/C5L/B Cia Xm/C5R. The following oligonucleotides were used to introduce a unique Not I sequence at the 5'-end of the C5R arm, by oligoinsertion into the EcoR I site, generating pUC/Not I/C5R/MCS/C5L:

Oligonucleotide for introduction of Not I 5' AATTGCG-GCCGC 3' (SEQ ID NO: 18)

The vaccinia H6 promoter is contained on plasmid pBSH6-1

A 176 bp fragment (H6 fragment) containing the H6 promoter and recognition sequences for a multiple cloning site containing Asp718 I, Xho I, Xba I, Cla I and Sma I, was amplified using primers H6A1 and H6B1:

(SEQ ID NO: 9) H6A1:
5' TCGTTAATTAATTAGAGCTTCTTTAT-TCTATACTTAAAAAG 3'

(SEQ ID NO: 10) H6B1:
5' AAAACCCGGGATCGATTCTAGACTCGAGGGTACCTACGATACAAACT

TAACGGATA 3'

The fragments encoding H6 (above) were pooled and re-amplified using and H6B1 to generate a 232 bp H6p/MCS fragment that was inserted into pUC/C5L/B Cla Xm/C5R between the BamH I and Xma I sites. FIG. 4 shows the resultant plasmid, pNH6C5LSP-18, a C5 insertion plasmid containing the H6 promoter, transcription and translation terminators functional in all reading frames, and a MCS.

Example 5 pCXL148.2 ALVAC Donor Plasmid Construction

Figure 5:
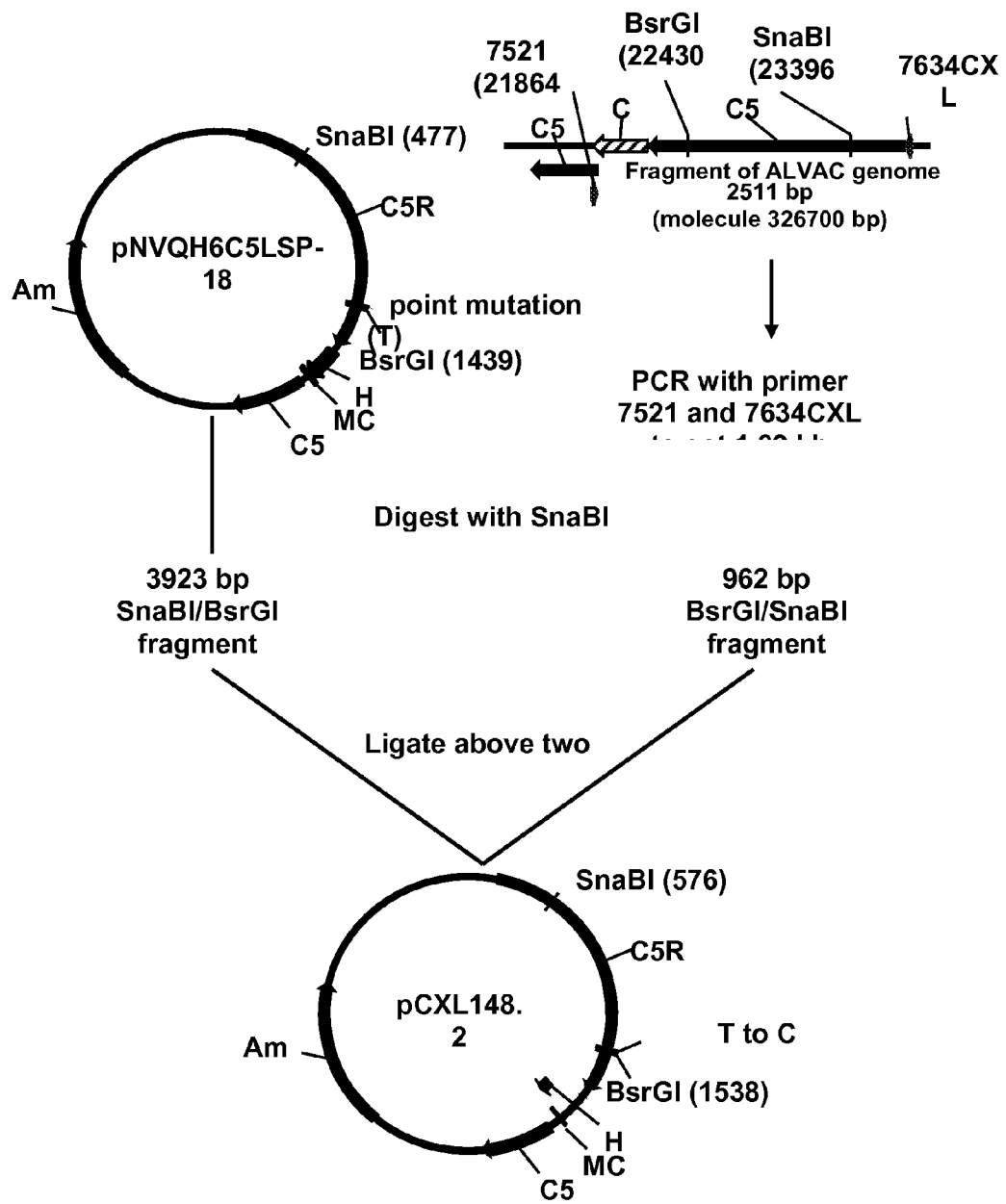
FIG. 5 is a schematic showing construction of pCXL148.2, an ALVAC donor plasmid.

Nucleotide sequence analysis of the pNVQH6C5LSP-18 donor plasmid indicated that there is a single base mutation in the C5R region of the ALVAC donor plasmid pNVQH6C5LSP-18 (described in US application 20050255127) relative to that of the ALVAC viral vector (sequence not provided). Consequently, pCXL 148 was created as follows to modify the donor plasmid sequence in order to obtain an exact match to that of the cloned (plaque purified) ALVAC, so that any sequence discrepancies that might arise during creation of recombinant-derived Bluetongue ALVAC virus constructs are minimized. FIG. 5 illustrates the construction strategy.

The plasmid pNVQH6C5LSP-18 (US application 20050255127) was digested with restriction endonucleases SnaBI+BsrGI to generate a 3,923 bp fragment and a 962 bp fragment. The RE digests were resolved by agarose gel electrophoresis, and the 3,923 bp fragment was excised from the gel. The fragment DNA was purified using the QIAquick gel extraction kit (Qiagen Inc., USA; Cat. #28704) as described by the manufacturer.

Next, ALVAC genomic DNA was used as the template for PCR reaction with primer set 7634CXL and 7521CXL (see below) to generate a 1.89 kb PCR fragment that spans the C5R region of the virus.

```
(SEQ ID NO: 11) 7521CXL (forward):
5' TTATTTAGAAATTATGCATTTTAGA (SEQ ID NO: 12) 7634CXL (reverse):
5' GTTCTCGTAGGAGAGAACTATTGAC
```

The 1.89 kb PCR amplified fragment was digested with SnaBI+BsrGI to generate three fragments: 361 bp, 569 bp and 962 bp. This RE digest was displayed by agarose gel electrophoresis, and the 962 bp fragment was excised from the gel and the DNA was purified using the QIAquick gel extraction kit (Qiagen Inc., USA; Cat. #28704) as described by the manufacturer.

Reconstruction of the ALVAC donor plasmid pNVQH6C5LSP-18 in which the mutated "T" nucleotide in the C5R encoding region of the donor plasmid is replaced with the corresponding ALVAC wild-type nucleotide "C" is accomplished by combining RE fragments to create pCXL148.2 as follows:
  a. The purified 3,923 bp fragment from RE (SnaBI+BsrGI) digestion of pNVQH6C5LSP-18 is directionally ligated with T4 DNA ligase to the 962 bp SnaBI+BsrGI fragment derived from the PCR amplified C5R region of ALVAC.
  b. Ligation reactions were used to transform competent *E. coli* cells, and the transformation reactions were grown under Ampicillin selection.

Transformants were selected, and their plasmid DNA was characterized by RE digests. The nucleotide sequence of one candidate clone pCXL148.2 was found to have the correct "C" nucleotide in the C5R region. The new C5 donor plasmid pCXL148.2 has an exact homology with the corresponding sequences in the ALVAC viral vector. Nucleic acid sequence of the pCXL148.2 donor plasmid in provided in FIG. 6 (SEQ ID NO:13)

Example 6

Construction of pC5 H6pVP2

The plasmid VP2 BTV 17 (043004, FIG. 3) was RE digested with EcoR V+Xho I to generate a unique 2,913 bp fragment comprising: a 5' EcoR V site followed by the full-length synthetic codon optimized BTV-VP2 followed by a 3' Xho I site. This RE digest was displayed by agarose gel electrophoresis, and the 2,913 bp fragment was excised from the gel and the DNA was purified using the QIAquick gel extraction kit (Qiagen Inc., USA; Cat. #28704) as described by the manufacturer.

pCXL148.2 (pC5 donor plasmid, see FIG. 5) was digested with EcoR V and Xho I to generate a linearized 4879 bp homology vector containing the C5 right arm, H6 promoter and C5 left arm.

Figure 7:
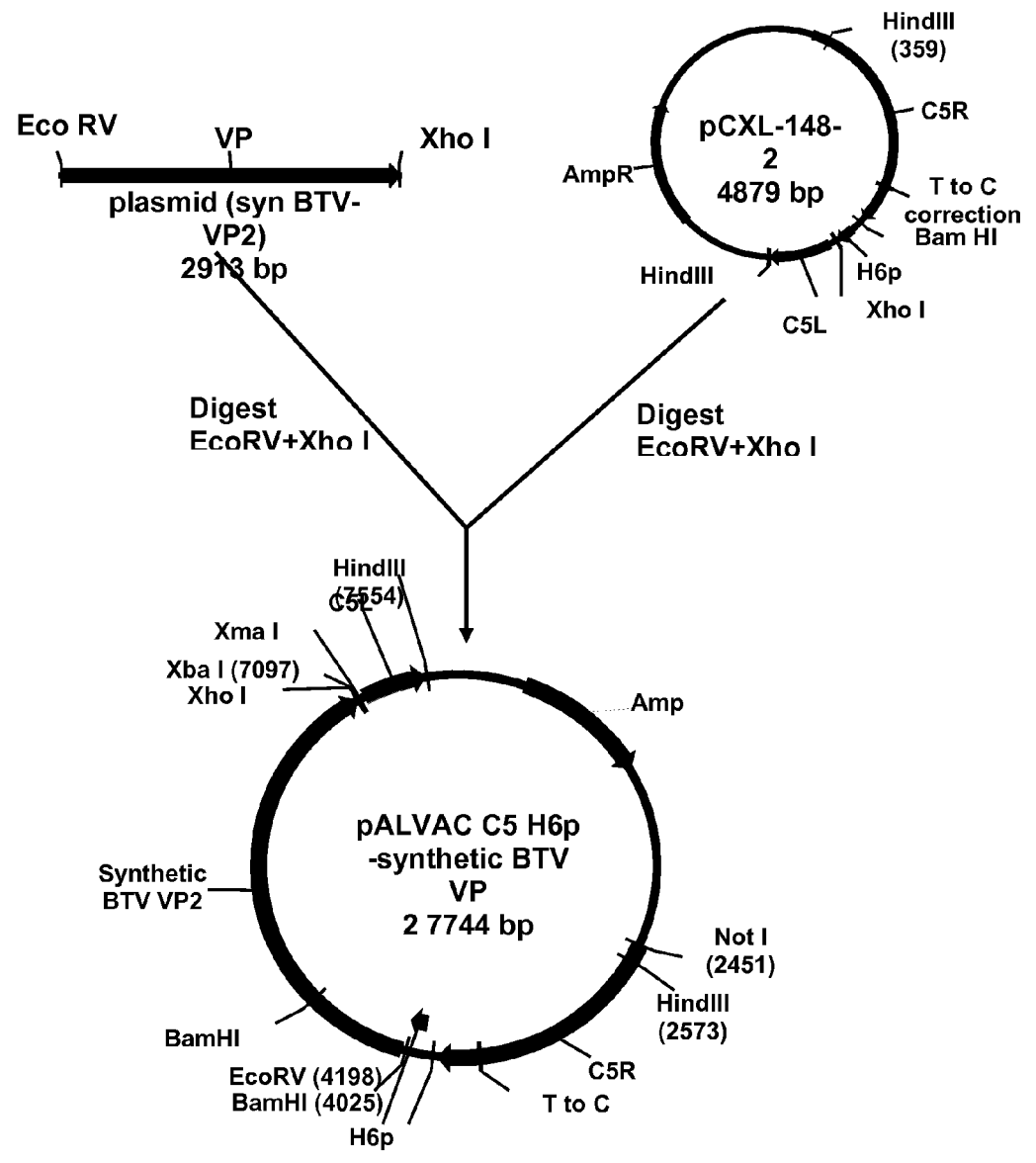

The purified 2,913 bp fragment from RE (Eco RV+Xho I) digestion of 043004p VP2 BTV 17 is directionally ligated with T4 DNA ligase to the 4879 bp Eco RV+Xho I digested and linearized pCXL-148.2 donor ALVAC plasmid. The ligation reactions were used to transform competent *E. coli* cells, and the transformation reactions were grown under Ampicillin selection. Transformants were selected, grown, and their plasmid DNA was characterized by RE digests. Clones with the correct RE maps were probed on Southern blots with VP2-specific nucleic acid oligonucleotides. One positive clone, pALVAC C5H6p-syntheticBTV VP2, was selected for subsequent cloning manipulation. The foregoing cloning strategy is provided in FIG. 7.

Example 7

PCR Amplification of VP5 Incorporating the 42K Promoter

Figures 20, 21:
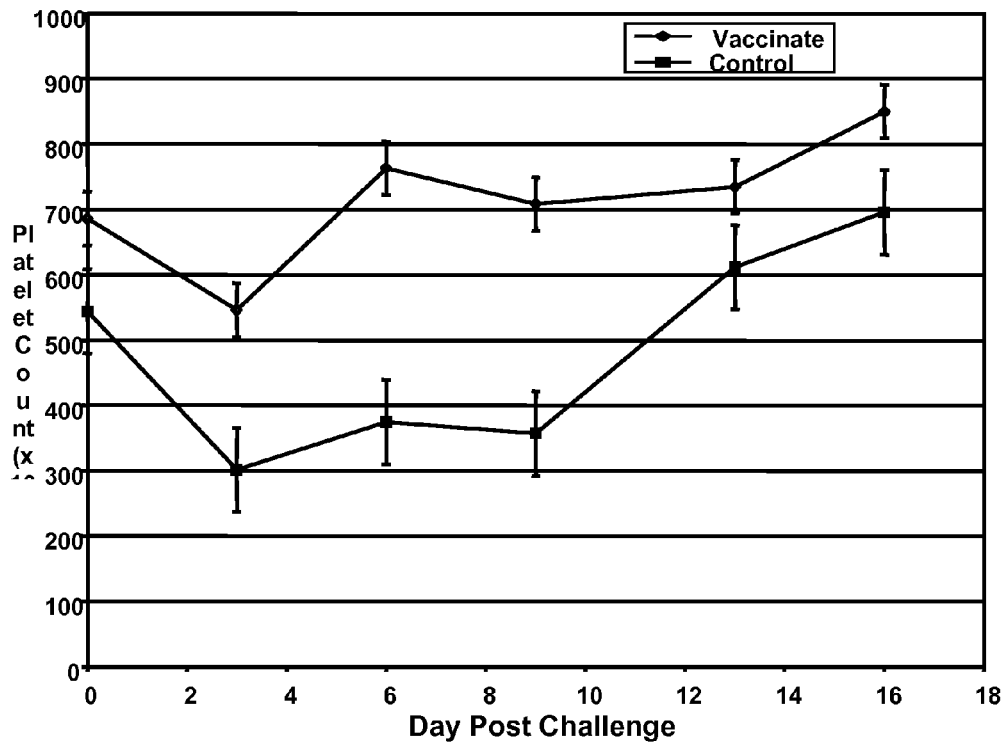
FIG. 20 is a chart showing the mean platelet count of sheep immunized with vCP2289 compared to a WNV-CP control vaccine after challenge with virulent wild-type BTV-17.

The Entomopoxvirus Amsacta moorei 42K promoter (Barcena, Lorenzo et al. 2000) was selected to regulate expression of the optimized synthetic VP5 gene. The nucleic acid sequence of the 42K promoter (see below: promoter sequence is Italicized and Underlined) was placed adjacent to the 5' ATG start codon of the synthetic VP5 gene using a PCR-based strategy in which the 42K promoter was embedded in the 5' end of a forward synthetic primer. Using this primer in conjunction with a reverse primer allows amplification directly from the plasmid VP5 BTV 17 (043005), which serves as the template (see FIG. 8). The pair of primers 13247.JY/13248.JY (below, and FIG. 21) were used in a PCR reaction to amplify a DNA fragment comprising 42Kp -VP5 expression cassette flanked by Xho I sites.

Primers for amplification of 42Kp-BTV VP5 expressing cassette:

```
(SEQ ID NO: 14) 13247.JY forward:
5'
GCGCTCGAGTTTTTATTCAAAATTGAAAATATATAATTACAATATAAAA

TGGGCAAGATCATCAAGAGCCTG (SEQ ID NO: 15) 13247.JY reverse:
5'
ATCTCGAGATAAAAATCATCAGGCGTTCCTCAGGAACAGGGGCACGTC
```

Figure 9:
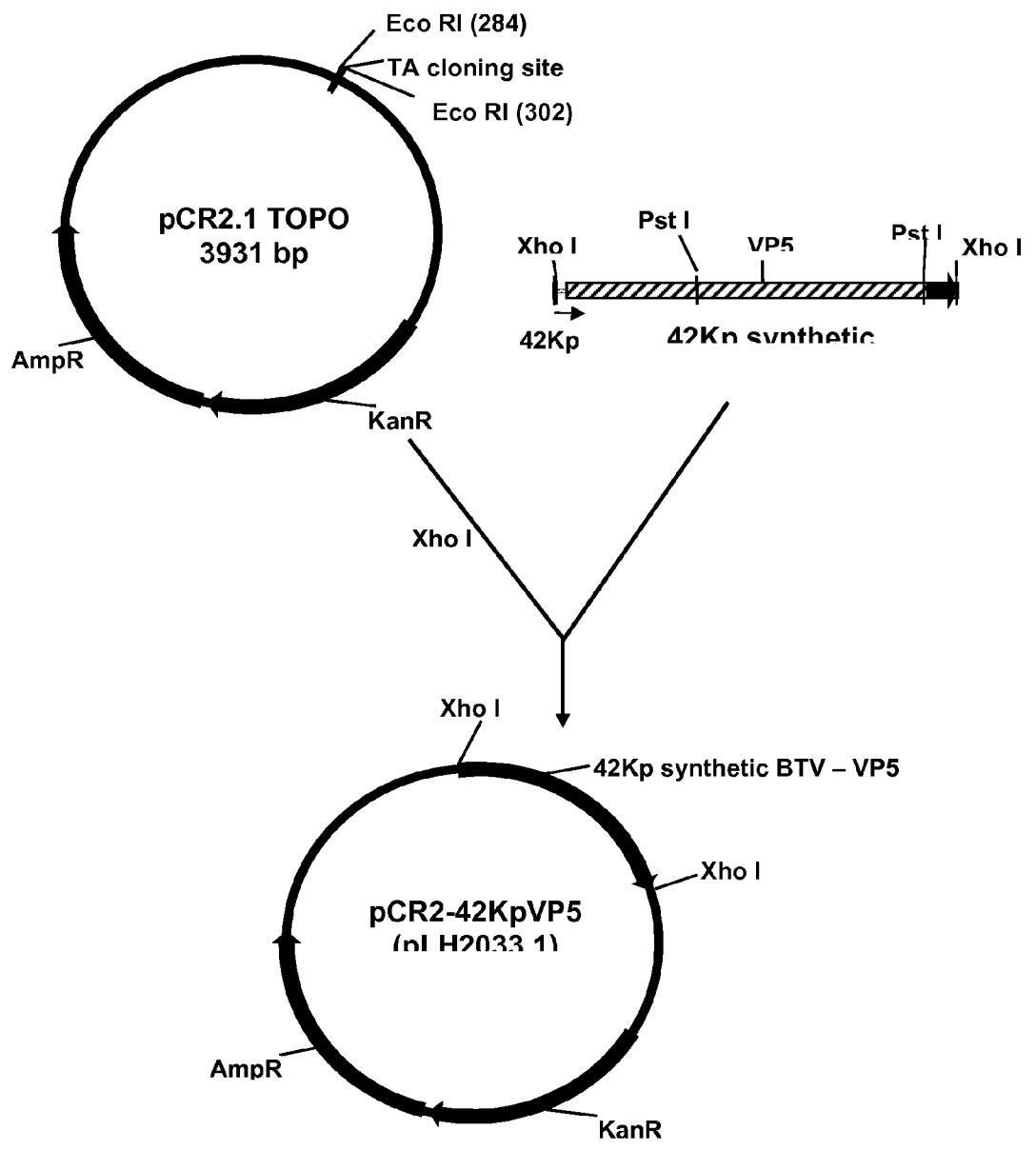

A reverse transcriptase polymerase chain reaction (PCR reaction) was carried out with the forgoing primers, and the resulting PCR product was cloned into the XhoI site of the pCR® 2.1-TOPO cloning vector according to the manufacturers' instructions (Invitrogen Corp., Carlsbad, Calif., USA) to create pLH2033.1 (pCR2.1 42Kp synthetic BTV-VP5). This construct was confirmed to contain the correct sequence. This cloning strategy is illustrated in FIG. 9. The pLH2033.1 clone was expanded to amplify plasmid yields as needed in subsequent cloning activities.

Example 8

Construction Donor Homology Vector pLH2078.15 (pC5H6VP242KpVP5)

pLH2033.1 harboring the 42Kp-synthetic BTV VP5 sequence was cleaved with Xho I which releases a 1,647 bp fragment that encodes BTV VP5. This Xho I digest was displayed by agarose gel electrophoresis, and the 1,647 bp VP2 fragment was excised from the gel and the DNA was purified using the QIAquick gel extraction kit (Qiagen Inc., USA; Cat. #28704) as described by the manufacturer.

pLH2030.2 (pALVAC C5H6p-syntheticBTV VP2 the pC5 donor plasmid, see FIG. 7) was digested with Xho I to generate a linearized 7,744 bp homology vector containing the C5 right arm, H6 promoter, synthetic BTV VP2, and the C5 left arm.

The purified 1,647 bp fragment from Xho I digestion of pLH2033.1 is ligated with T4 DNA ligase to the 7,744 bp Xho I linearized pLH2030.2 donor ALVAC plasmid. The ligation reactions were used to transform competent *E. coli* cells, and the transformation reactions were grown under Ampicillin selection. Transformants were selected, grown, and their plasmid DNA was characterized by RE digests. Because the ligation described is non-directional, an elemental component of clone selection entails proper orientation of the 42Kp-synthetic VP5 insert relative to that of H6pVP2 in the donor plasmid, in this embodiment the preferred orientation is head-to-tail, e.g. VP2 and VP5 are transcribed and translated in the same 5' to 3' direction on the plasmid. Clones with the correct RE pattern were selected for further characterization. One positive clone, pLH2978.15 was selected and sequenced. The described cloning strategy for construction of the final ALVAC-BTV donor plasmid is provided in FIG. 10. The annotated nucleotide sequence of pLH2978.15 is provided in FIG. 11.

Example 9

Generation and Characterization of ALVAC BTV (vCP2289)

To generate ALVAC-based BTV recombinants, primary chick embryo fibroblast cells (CEFs) were transfected with 15 μg of Not I-linearized pLH2078.15 donor plasmid DNA (pC5 H6p-BTV VP2-42Kp-BTV VP5) mixed with FuGENE-6 transfection reagent (Roche). The transfected cells were subsequently infected with ALVAC ($6.3 \times 10^9$ pfu/ml HM1372) as the rescue virus at a MOI of 10. After 24 hours, the transfected-infected cells were harvested, sonicated and used for plaque purification and recombinant virus screening. 24-48 hours after plating on fresh CEFs, recombinant plaques were transferred onto nylon membrane and hybridized with a BTV-specific DNA probe that was labelled with horseradish peroxidase according to the manufacturer's protocol (Amersham Cat# RPM3001). Following 4 sequential rounds of plaque purification, single plaques were amplified to produce stocks designated as vCP2289.1.2.1.1 and vCP2289.1.1.1. Recombinant viruses were confirmed by hybridization as 100% positive for the BTV insert and 100% negative for the empty C5 site.

Figure 12:
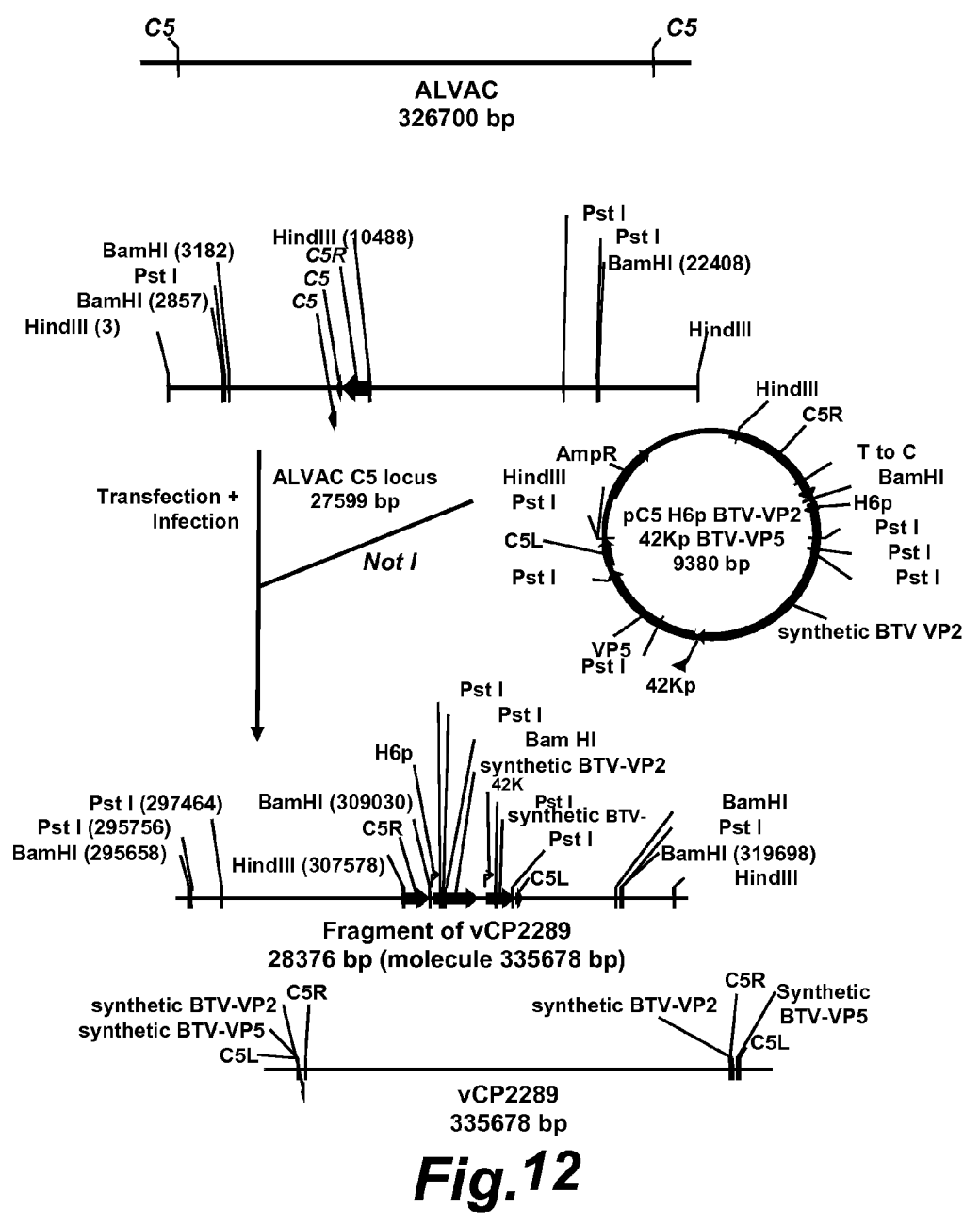

Single plaques were selected from the final round of plaque purification, and expanded to obtain P1 (T-25 flask), P2 (T-75 flask) and P3 (roller bottle) stocks to amplify vCP2289.1.2.1.1 and vCP2289.2.1.1.1. The recombinants were re-confirmed at the P2 level by hybridization and found to be 100% positive for the insert and 100% negative for the empty C5 site. The infected cell culture fluid from the roller bottles was harvested and concentrated to produce the virus stocks (1.8 ml of vCP2289.1.2.1.1 at $1.25 \times 10^{10}$ pfu/ml, and 1.9 ml of vCP2289.2.1.1.1 at $10 \times 10^{10}$ pfu/ml. FIG. 12 presents a flow diagram for the construction of the recombinant ALVAC+BTV VP2 and VP5 (vCP2289).

Example 10

Characterization of ALVAC BTV (vCP2289)

Figure 13:
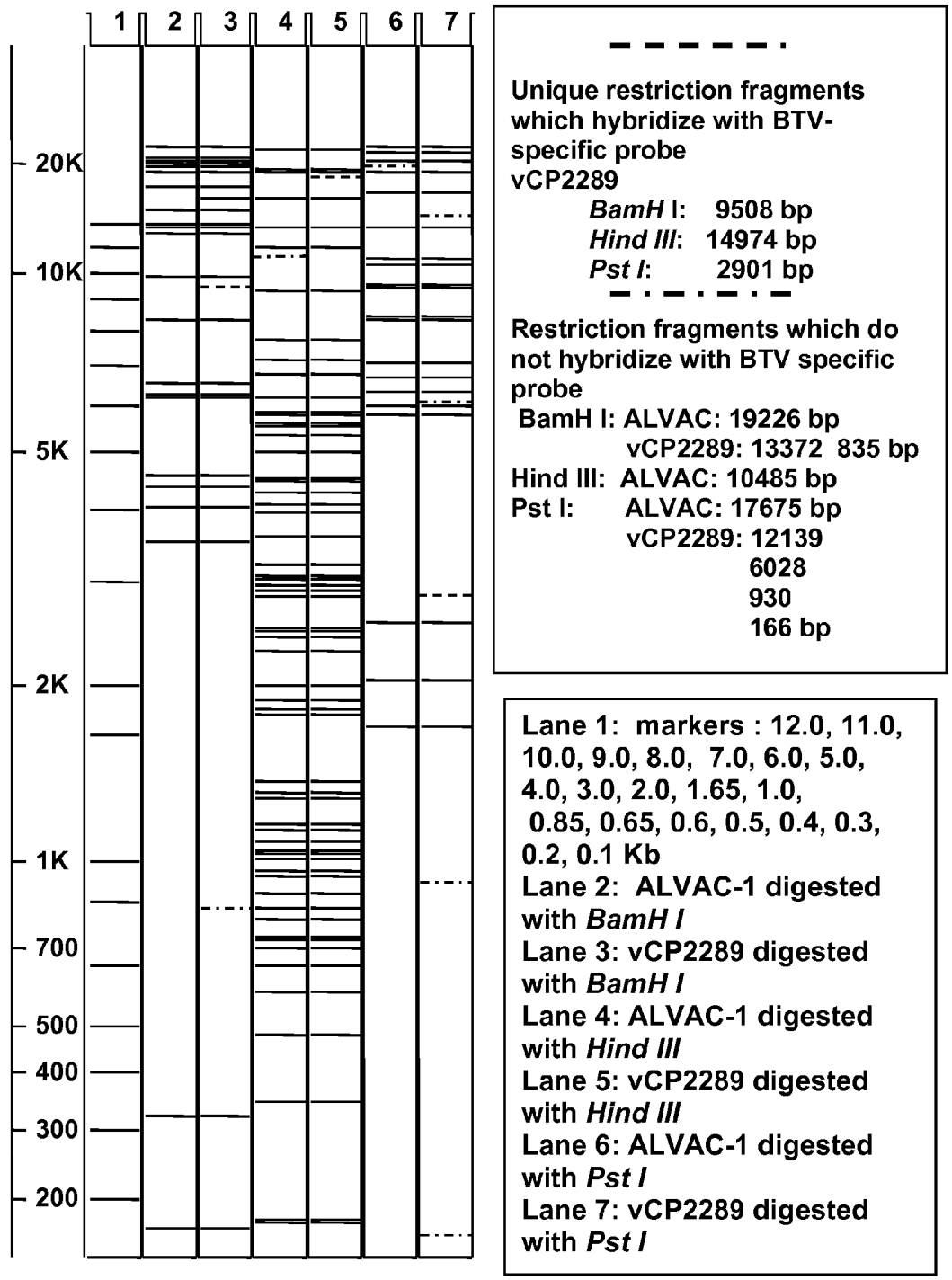
FIG. 13 is a theoretical RE digest map for recombinant ALVAC-BTV vCP2289 generated from plasmid and ALVAC nucleic acid sequences made by Vector NTI (Invitrogen, Carlsbad, Calif.
Figure 14:
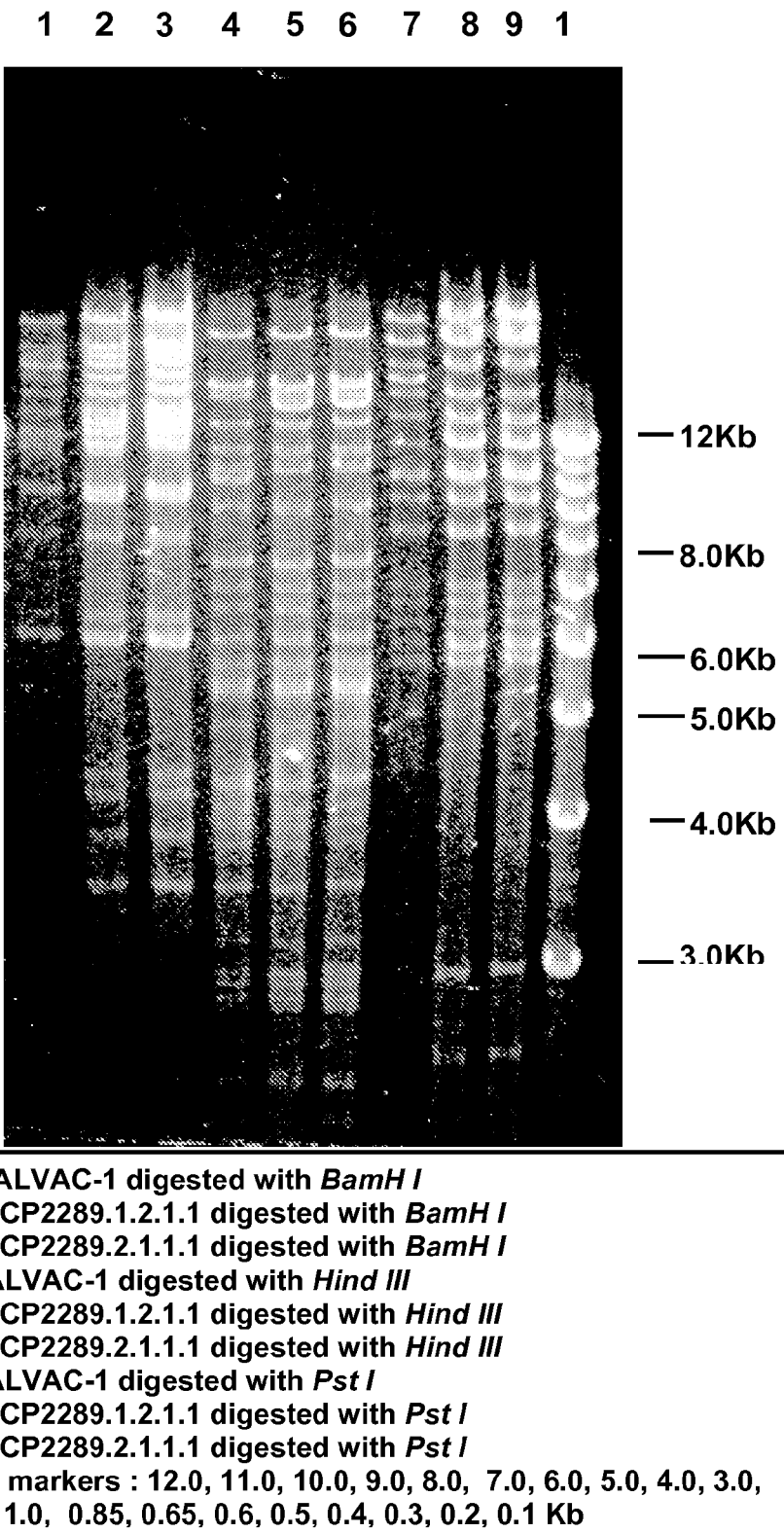
FIG. 14 is a stained agarose gel showing restriction endonuclease digestion of genomic. DNA prepared from ALVAC+BTV recombinant virus vCP2289 (compare with theoretical expected banding pattern as illustrated in FIG. 13, above).
Figure 16:
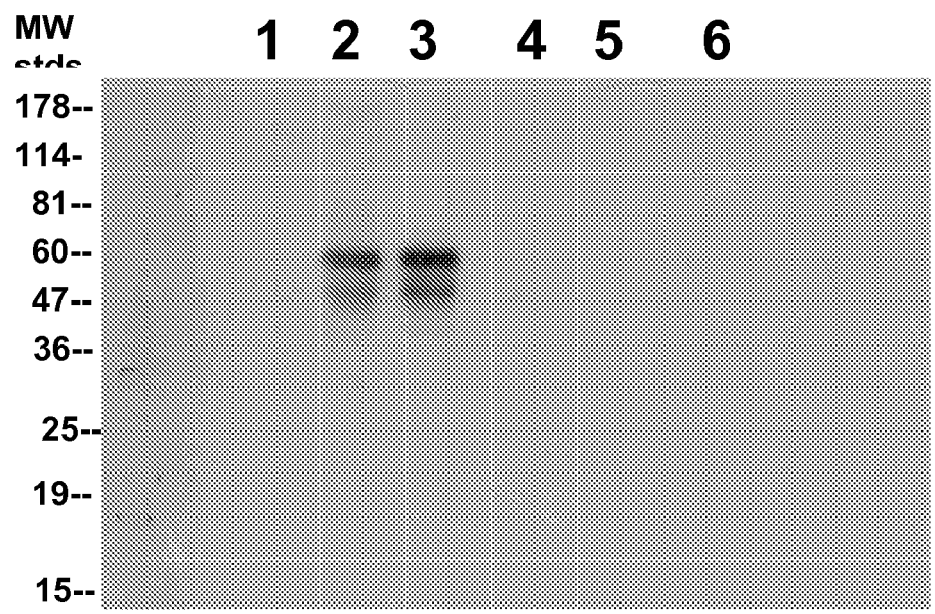
FIG. 16 presents a Western Blot of CEF lysate and supernatant fractions prepared after infection with two different isolates of vCP2289 probing for expression of VP5 from the ALVAC recombinant virus. Primary antibody probe was rabbit anti-BTV-17 VP5 specific polyclonal sera used at a 1:2000 dilution.
Figure 17:
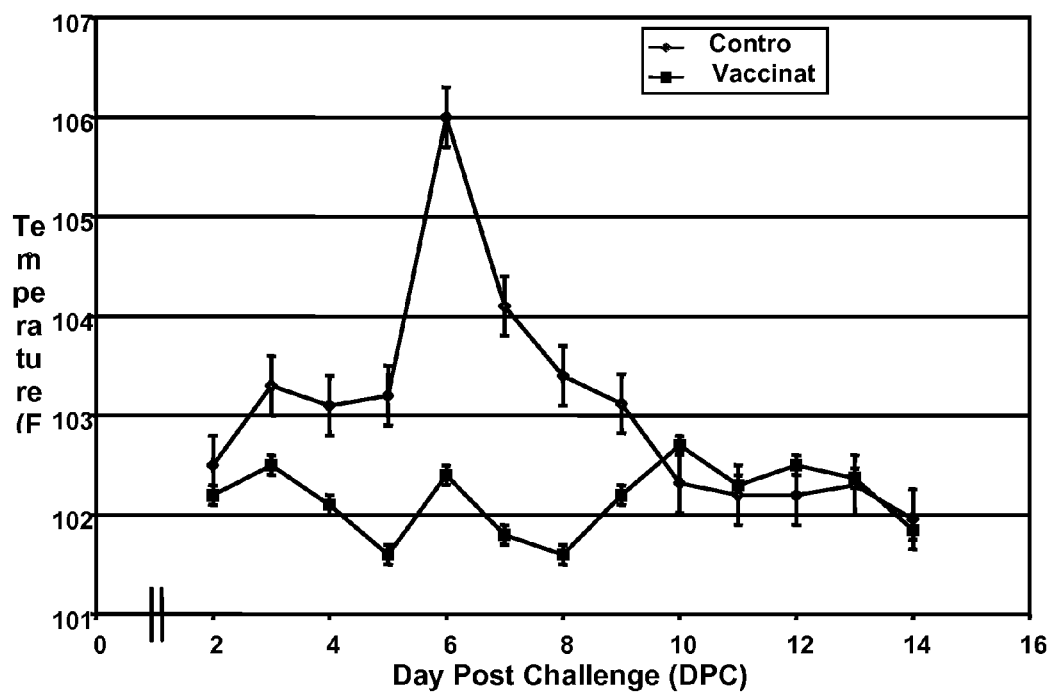
FIG. 17 is a chart of the mean body temperatures of sheep immunized with vCP2289 compared to the WNV-CP control vaccine after challenge with virulent wild-type BTV-17.
Figure 18:
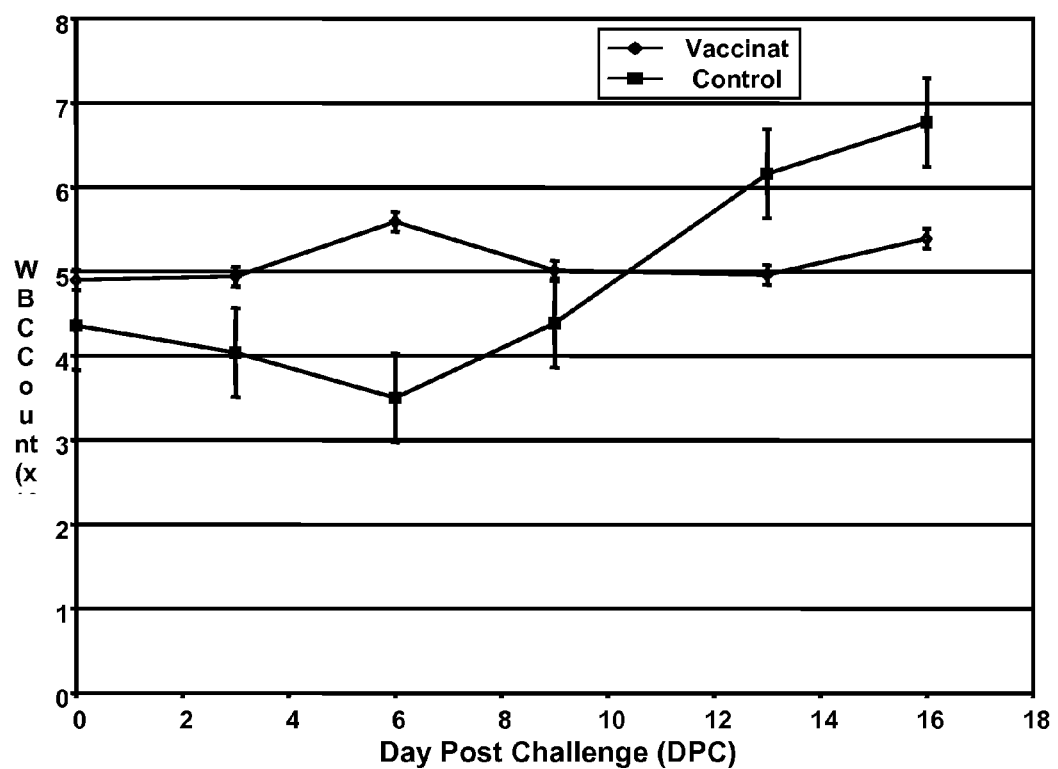
FIG. 18 is a chart showing the mean white blood cell count (WBC) of sheep immunized with vCP2289 compared to a WNV-CP control vaccine after challenge with virulent wild-type BTV-17.
Figure 19:
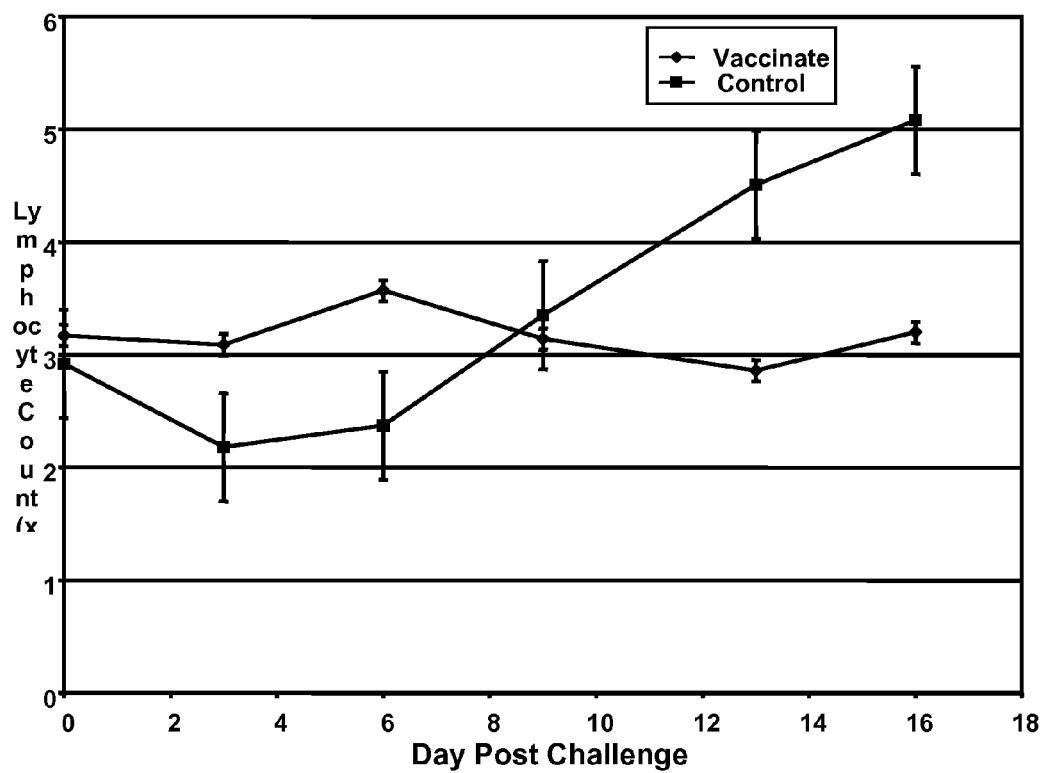
FIG. 19 is a chart showing the mean lymphocyte count of sheep immunized with vCP2289 compared to a WNV-CP control vaccine after challenge with virulent wild-type BTV-17.

1. Confirmation of Genetic Purity. P3 stocks were re-confirmed by hybridization, as 100% positive for the BTV insert and 100% negative for the empty C5 site.
2. Genomic Analysis.
   a. Restriction map:
      i. A theoretical restriction endonuclease (RE) gel electrophoresis fragment analysis for the genomic DNA was created in Vector NTI (Invitrogen, USA) and is shown in FIG. 13.
      ii. The genomic DNA was extracted from vCP2289.1.2.1.1 and vCP2289.2.1.1.1, digested with BamH I, Hind III or Pst I, and separated by 0.8% agarose gel electrophoresis. The results revealed the correct insertion of the foreign gene sequence (see FIG. 14).
   b. Southern Blot: The genomic DNA digested with BamH I, Hind III, or Pst I was transferred to nylon membrane and Southern blot analysis was performed by probing with the BTV probe. BTV-specific 9508 bp BamH I, 14974 bp Hind III and 2901 bp Pst I bands were observed at the expected sizes. The results indicated the correct insertion of the BTV insert into the C5 locus. FIG. 15 provides the results of the Southern Blot.
3. Expression Analysis:
   a. Western blot. 1° CEF cells were infected with the P3 stocks of vCP2289.1.2.1.1 and vCP2289.2.1.1.1 at an MOI of 10 and incubated at 37° C. for 24 hrs. The cells and culture supernatant were then harvested. Sample proteins were separated on a 10% SDS-PAGE gel, electroblot transferred to Immobilon nylon membrane, and probed with the rabbit anti-BTV 17 VP5 affinity purified IgG (University of California, Davis, USA) at a dilution of 1:2000. Peroxidase conjugated goat anti-rabbit antiserum was used as a secondary antibody and the bands were visualized using Amersham detection reagents. Two protein bands between 47 KDa and 60 KDa were detected in the cell pellets of vCP2289.1.2.1.1 and vCP2289.2.1.1.1, indicating expression of the BTV-17 VP5 protein (see FIG. 16). The expressed BTV-17 VP5 protein was not secreted into the cell culture media.
   b. Immunofluorescence. Using a mixture of four mouse anti-BTV-17 VP2 antibodies (ABX IgG 17.81 α-BTV 17; PA IgG17.815 α-BTV 17; PA IgG 17.85 α-BTV 17; PA IgG 17.813 α-BTV-17, from University of California, Davis, USA), western blots and immunoplaque assays for VP2 expression were negative probably due to conformational sensitivities of the reagents and the 'denaturing-like' environments imposed by transfer and hybridization. Consequently, 1° CEF cells were infected with P3 stocks of vCP2289.1.2.1.1 and vCP2289.2.1.1.1 at a MOI of 0.1 and incubated at 37° C. for 24 hrs. The cells were then fixed with 3% paraformaldehyde and permeabilized with 0.5% Triton X-100. The mixture of four mouse anti-BTV 17 VP2 antibodies (ABX IgG 17.81 anti-BTV 17, PA IgG17.815 anti-BTV 17, PA IgG 17.85 anti-BTV 17, PA IgG 17.813 anti-BTV-17, from University of California, USA) was used as the primary antibody at 1:100 dilution and a FITC conjugated goat anti-mouse antibody was used as a secondary antibody. Strong green fluorescent cells were visualized under the Nikon Eclipse TE300 fluorescence microscope, indicating the expression of BTV VP2 protein (data not shown).
4. Sequence Analysis: A more detailed analysis of the P3 stock genomic DNA was performed by PCR amplification and sequence analysis of the flanking arms of the C5 locus and the BTV insert. Primers 7931.DC and 7932.DC located beyond the arms of the C5 locus, were used to amplify the entire C5R-BTV insert-C5L fragment.

Primers for PCR amplification of the vCP2289 C5 arms plus insert:

```
(SEQ ID NO: 16) 7931.DC:
5' GAATCTGTTAGTTAGTTACTTGGAT (SEQ ID NO: 17) 7932.DC:
5' TGATTATAGCTATTATCACAGACTC
```

The results showed that the sequences of the BTV insert and the C5 left and right arms around the BTV insert in vCP2289.1.2.1.1 and vCP2289.2.1.1.1 were correct.

Example 11

Production of Recombinant Vaccines

For the preparation of ovine, bovine or equine vaccines, the recombinant canarypox vCP2289 virus (Example 9) will be adjuvanted with carbomer solutions, namely Carbopol™ 974P manufactured by BF Goodrich, Ohio, USA (molecular weight about 3,000,000).

A 1.5% Carbopol™ 974P stock solution was initially prepared in distilled water containing 1 g/l of sodium chloride. This stock solution was then used for the preparation of a 4 mg/ml Carbopol™ 974P solution in physiological salt solution. The stock solution was mixed with the adequate volume of the physiological salt solution, either in a single stage or in several successive stages, the pH value being adjusted in each stage with a 1N sodium hydroxide solution (or even more concentrated) in order to obtain a final pH value of 7.3 to 7.4.

The ready-to-use Carbopol™ 974P solution obtained in this way was used for taking up recombinant, lyophilized viruses or for diluting concentrated, recombinant virus stock solutions. For example, to obtain a viral suspension containing $10^8$ pfu/1 ml dose, a viral stock solution was diluted so as to obtain a titer of $10^{8.3}$ pfu/ml, followed by dilution in equal parts with said ready-to-use 4 mg/ml Carbopol™ 974P solution.

Example 12

Production of DNA Vaccines for Ovines, Bovines, or Equines

For DNA immunization, plasmids will be constructed in which the codon optimized BTV VP2 nucleotide sequence (Drawing 1, SEQ ID: 1) is located on one plasmid, and BTV VP5 (SEQ ID: 2) nucleotide sequences are on a separate plasmid. Expression of the BTV sequences from each plasmid can be driven by, but is not limited to, CMV-IE promoter (human CMV or murine CMV)). Poly Adenine (polyA) sequence signal (either from the bovine growth hormone gene or rabbit beta globin gene, but not limited to) will be incorporated at the 3' end of the BTV coding sequence in each plasmid.

It may be desirable to express BTV VP2 and VP5 from the same plasmid to ensure co-expression of BTV proteins in the same cell. In this case, a plasmid similar to pLH2078.15 (Example 8, Drawing 10) will be constructed in which the poxvirus promoters have been replaced with, but not limited to, ubiquitous eukaryotic promoters such as the human CMV-IE promoter. Expression of BTV VP2 and VP5 will necessarily be controlled by different promoters. PolyA signal sequences will be included at the 3' end of each BTV nucleotide sequence.

A DNA solution containing the plasmid(s) described above will be concentrated by ethanol precipitation in the manner described by Sambrook et al (1989). The DNA pellet will be taken up by a 0.9% NaCl solution so as to obtain a concentration of 1 mg/ml. A 0.75 mM DMRIE-DOPE solution will be prepared by taking up a DMRIE-DOPE lyophilizate by a suitable sterile $H_2O$ volume.

The formation of plasmid-lipid DNA complexes will be accomplished by diluting in equal parts the 0.75 mM DMRIE-DOPE solution (1:1) with the 1 mg/ml DNA solution in 0.9% NaCl. The DNA solution will be progressively introduced with the aid of a 26G crimped needle along the wall of the flask containing the cationic lipid solution so as to prevent the formation of foam. Gentle stirring will take place as soon as the two solutions are mixed. Finally a composition comprising 0.375 mM of DMRIE-DOPE and 500 μg/ml plasmid will be obtained.

It is desirable for all the solutions used to be at ambient temperature for all the operations described herein. DNA/DMRIE-DOPE complexing will take place at ambient temperature for 30 minutes before immunizing the animals.

Example 13

Vaccination of Sheep with Recombinant Canarypox Viruses

Eleven polled Dorset lambs (9 males, 2 females) were purchased from a supplier in northwestern CA, a region free of BTV infection. The animals were housed in insect secure isolation facilities throughout the described studies, and prior to vaccination they were all confirmed to be free of antibodies to BTV by competitive ELISA. At approximately 13 months of age (Nov. 22, 2005), 6 lambs were each inoculated SQ/IM with approximately 1 ml of BTV-CP diluted in PBS (0.2 ml undiluted [$10^{9.5}$ $TCID_{50}$/ml] vCP2289/sheep=~$6.3 \times 10^8$ viral particles) and 5 were vaccinated with recombinant canary pox expressing the preM and E proteins of West Nile virus vCP/WNV; Recombitek) that was reconstituted and administered according to the manufacturer's instructions. All sheep were revaccinated 22 days later (Dec. 14, 2005) with the respective vaccine construct at the same dose as the primary immunization. The animals were co-housed regardless of vaccine type.

Example 14

Titrating Anti-BTV Neutralizing Antibodies

Dilution series were produced for each serum at a rate of 3 in DMEM medium to which was added 10% fetal calf serum in 96 well plates of the cellular culture type. To 0.05 ml of diluted serum was added 0.05 ml of culture medium containing approximately 100 $CCIP_{50}$/ml of BTV. This mixture was incubated for 2 hours at 37° C. in an oven in an atmosphere containing 5% CO2.

0.15 ml of a suspension of BHK-21 cells containing approximately 100,000 cells/ml was then added to each mixture. The cytopathic effect (CPE) was observed by phase contrast microscopy after 4 to 5 days culturing at 37° C. in an atmosphere containing 5% $CO_2$. The neutralizing titers of each serum were calculated using the Kärber method. The titers were given in the form of the largest dilution inhibiting the cytopathic effect for 50% of the wells. The titers were expressed in log10 $VN_{50}$. Each serum was titrated at least twice and preferably four times.

Example 15

BTV Infection of Sheep and Sample Collection

All 11 lambs were challenged by subcutaneous inoculation of $10^{5.5}$ $TCID_{50}$ of BTV-17 at 34 days after the second vaccination. The animals were evaluated daily for 3 weeks after inoculation for manifestations of bluetongue. Blood for hematology (collected in EDTA) was collected prior to inoculation and at 3, 6, 9, 13 and 16 days post-inoculation (DPI) for complete blood counts (CBC). Blood samples (acid citrate dextrose) were collected at 0, 1, 3, 5, 7, 9, 11, 14 and 21 DPI for virus isolation. Serum was collected ("Tiger Top", serum separator) from all sheep at weekly intervals immediately prior to vaccination. The sheep were all humanely euthanized at 25 days after challenge exposure to BTV.

Example 16

BTV Virus Isolation

Virus isolation was from whole sheep blood as previously described (Bonneau, Mullens et al. 2001; Bonneau, DeMaula et al. 2002; DeMaula, Leutenegger et al. 2002). Briefly, Vacutainer tubes were centrifuged at 2,500 G for 10 minutes at 4 degrees C. Serum was decanted and discarded. Red/white blood cells were washed 1× with 5 ml of sterile PBS (1×), re-centrifuged and the cell pellet was resuspended in an equal volume of sterile double-distilled water (ddH$_2$O). The washed/lysed blood cells were sonicated for 1-2 min. prior to dilution ($10^{-1}$ through $10^{-4}$) in EMEM and inoculation (0.25 ml/well) onto confluent BHK-21 monolayers in 24 well plates. The cultures were incubated for 1 hr. at 37 C, when maintenance media was added. The cultures were examined daily for 10 days and virus titers determined by the method of Reed and Münch.

Example 17

Immunogenicity of the BTV-vCP2289 Recombinant ALVAC in Sheep

All sheep were seronegative to BTV by both competitive ELISA and BTV-17 microneutralization assays prior to vaccination (data not shown). The sheep vaccinated with the vCP/BTV expression vector developed neutralizing antibodies to BTV-17, whereas those immunized with the vCP/WNV did not (see table 3, below). All sheep remained healthy and showed no adverse effects after vaccination.

TABLE 3

Titers of BTV 17 neutralizing antibodies

| | Weeks Post Vaccination | | | |
|---|---|---|---|---|
| | −1 | 2 | 4 | 6 |
| Vaccinate: | | | | |
| 353 | ≦10 | ≦10 | 80 | 40 |
| 355 | ≦10 | ≦10 | 80 | 40 |
| 359 | ≦10 | 10 | 160 | 80 |
| 361 | ≦10 | ≦10 | 160 | 80 |
| 363 | ≦10 | 10 | 80 | 160 |
| 364 | ≦10 | 10 | 80 | 160 |
| Controls: | | | | |
| 354 | ≦10 | ≦10 | ≦10 | ≦10 |
| 356 | ≦10 | ≦10 | ≦10 | ≦10 |
| 357 | ≦10 | ≦10 | ≦10 | ≦10 |
| 358 | ≦10 | ≦10 | ≦10 | ≦10 |
| 362 | ≦10 | ≦10 | ≦10 | ≦10 |

Example 18

Protection of Sheep Immunized with BTV-CP After Challenge

The ability of vCP/BTV to protectively immunize sheep was evaluated by comparing titers of BTV-17 in the blood of vCP/BTV vCP2289 and vCP/WNV immunized sheep after challenge exposure to BTV-17.

Table 4. Titers of bluetongue virus in the blood of sheep challenged with the virus following immunization with recombinant canary pox viruses expressing coat proteins of either bluetongue virus (vCP/BTV) or West Nile virus (vCPI-WNV)

TABLE 4 titers of bluetongue virus in the blood of sheep challenged with BTV-17 after immunization with recombinant canarypox viruses expressing coat proteins of either bluetongue virus (BTV-CP) or West Nile Virus (WNV-CP)

| Treatment/ | Virus Titer $\log^{10}$ TCID$_{50}$ per ml of blood (days post inoculation) | | | | | | | |
|---|---|---|---|---|---|---|---|---|
| Sheep ID | 1 | 3 | 5 | 7 | 9 | 11 | 14 | 21 |
| Vaccinated: | | | | | | | | |
| 353 | —* | — | — | — | — | — | — | — |
| 355 | — | — | — | — | — | — | — | — |
| 359 | — | — | — | — | — | — | — | — |
| 361 | — | — | — | — | — | — | — | — |
| 363 | — | — | — | — | — | — | — | — |
| 364 | — | — | — | — | — | — | — | — |
| Controls: | | | | | | | | |
| 354 | — | $10^{4.1}$ | $10^{4.1}$ | $10^{3.6}$ | $10^{3.1}$ | $10^{3.1}$ | $10^{2.1}$ | $10^{1.6}$ |
| 356 | — | $10^{2.1}$ | $10^{3.1}$ | $10^{3.1}$ | $10^{3.1}$ | $10^{1.6}$ | — | — |
| 357 | — | — | $10^{3.6}$ | $10^{3.1}$ | $10^{2.1}$ | $10^{2.1}$ | — | — |
| 358 | — | $10^{2.1}$ | $10^{2.6}$ | $10^{3.6}$ | $10^{3.1}$ | $10^{1.6}$ | — | $10^{2.1}$ |
| 362 | — | $10^{3.6}$ | $10^{4.1}$ | $10^{3.1}$ | — | — | — | — |

*indicates virus was not isolated from 50 ul of washed and lysed blood cells

Results (Table 4, above) show that control sheep (WNV-CP) are actively infected with the BTV challenge virus at 3 days post challenge. The controls continue to exhibit viremia as long as 21 days post challenge at which point the experiment was terminated.

Sheep that were immunized with the BTV-CP vaccine exhibited exquisite protection from viremia after experimental challenge infection as no BTV was detectable in the blood in the blood of vaccinated sheep for the 21 day duration of the study. All six BTV-CP immunized sheep were completely resistant to virulent challenge indicating the effectiveness of the vaccine.

Example 19

Clinical Responses of BTV Infected Sheep

Comparison of the clinical response of sheep vaccinated with BTV-CP (vaccinates) and WNV-CP (controls) after challenge with BTV-17 is provided in the following:

1. Body temperature (BT). For 14 days post challenge, body temperature was monitored on a daily basis for all 6 BTC-CP vaccinates and for all 5 control (WNV-CP immunized) sheep. The temperature data from the challenged sheep are shown below in Table 3 and in Drawing 17. The data show an −1° C. rise in mean BT day 3 post challenge in the controls, with no change in the mean BT in the BTV-CP vaccinates. At day 6, a 4° C. temperature spike (105° C.) in the control animals was observed. This is a typical response for a viremic BTV-infected animal. The BTV-CP immunized animals exhibit normal temperatures that do not significantly deviate from pre-challenge animals. These results confirm vaccine (BTV-CP) efficacy.

TABLE 5

BTV 17 Challenge Temperature Data

BTV Vaccinated

| Sheep # | Day 2 | Day 3 | Day 4 | Day 5 | Day 6 | Day 7 | Day 8 | Day 9 | Day 10 | Day 11 | Day 12 | Day 13 | Day 14 |
|---|---|---|---|---|---|---|---|---|---|---|---|---|---|
| 353 | 102.6 | 102.2 | 102.6 | 101.8 | 102.6 | 102.6 | 100.8 | 101.1 | 102 | 102 | 102.2 | 101.6 | 101.6 |
| 355 | 102.2 | 102 | 102.1 | 101.6 | 102.4 | 102.2 | 101.4 | 102.2 | 102.4 | 102.2 | 102.8 | 102.8 | 102.2 |
| 359 | 102.4 | 102.7 | 101.8 | 101.8 | 102 | 101.8 | 101.2 | 103 | 101.6 | 102.4 | 102.4 | 102 | 101.8 |
| 361 | 101.2 | 102.8 | 101.8 | 101.2 | 102.6 | 100.6 | 102 | 102 | 102.4 | 102.4 | 102.4 | 102 | 101.8 |
| 363 | 102.6 | 102.9 | 102 | 101.2 | 102.2 | 102 | 102 | 102.8 | 102.6 | 102.4 | 102.6 | 101.8 | 101.8 |
| 364 | 102 | 102.6 | 102.4 | 101.8 | 102.8 | 101.6 | 102 | 102 | 102.6 | 102.4 | 102.6 | 104 | 101.9 |
| Mean: | 102.1667 | 102.5333 | 102.1167 | 101.5667 | 102.4333 | 101.8 | 101.5667 | 102.1833 | 102.2667 | 102.3 | 102.5 | 102.3667 | 101.85 |

WNV Controls

| Sheep # | Day 2 | Day 3 | Day 4 | Day 5 | Day 6 | Day 7 | Day 8 | Day 9 | Day 10 | Day 11 | Day 12 | Day 13 | Day 14 |
|---|---|---|---|---|---|---|---|---|---|---|---|---|---|
| 354 | 101.4 | 103.6 | 103.2 | 103.6 | 104.6 | 104.6 | 104 | 100.8 | 101 | 101.2 | 101.6 | 102 | 101.8 |
| 356 | 102.2 | 103.5 | 103.2 | 101.6 | 106.6 | 102.4 | 103 | 103.8 | 102 | 101.8 | 102 | 102.4 | 101.6 |
| 357 | 102.2 | 103 | 102.5 | 101.6 | 106.6 | 104.4 | 104.4 | 105.8 | 103 | 102 | 102.2 | 101.9 | 101.6 |
| 358 | 103.9 | 103.3 | 103.4 | 105.1 | 106.2 | 104.2 | 102.2 | 103.4 | 103.2 | 103 | 102.6 | 102.4 | 102.6 |
| 362 | 102.8 | 103 | 103.4 | 104 | 106.2 | 105 | 103.6 | 101.8 | 102.4 | 102.8 | 102.4 | 103 | 102.2 |
| Mean: | 102.5 | 103.28 | 103.14 | 103.18 | 106.04 | 104.12 | 103.44 | 103.12 | 102.32 | 102.16 | 102.16 | 102.34 | 101.96 |

2. White blood cell count. For 16 days post challenge, white blood cell (WBC) counts were monitored on day 0 and at approximately 3 day intervals through day 16 for all 6 BTC-CP vaccinates and for all 5 control (WNV-CP immunized) sheep. The WBC data from the challenged sheep are shown below in Table 6 and in Drawing 18. The data show an initial slight decrease in meanWBC through day 8 post-challenge with a continual rise in meanWBC at day 9-16 post challenge in the controls, with no change in the meanWBC in the BTV-CP vaccinates. The delayed increase in WBC after challenge is a typical response for a viremic BTV infected animal. The BTV-CP immunized animals exhibit normal WBC's that do not significantly deviate from pre-challenge animals. These results confirm vaccine (BTV-CP) efficacy.

3. Lymphocyte count. For 16 days post challenge, Lymphocyte counts were monitored on day 0 and at approximately 3 day intervals through day 16 for all 6 BTC-CP vaccinates and for all 5 control (WNV-CP immunized) sheep The lymphocyte data from the challenged sheep are shown below in Table 7 and in Drawing 19. The data show an initial slight decrease in meanWBC through day 8 post challenge with a continual rise in the mean lymphocyte count at day 9-16 post challenge in the controls, with no change in the mean lymphocyte number in the BTV-CP vaccinates The delayed increase in lymphocyte counts after challenge is a typical response for a viremic BTV infected animal. The BTV-CP immunized animals exhibit normal lymphocyte counts that do not significantly deviate from pre-challenge animals. These results confirm vaccine (BTV-CP) efficacy.

TABLE 6

BTV 17 Challenge Study-WBC Data

| Sheep # | Day 0 | Day 3 | Day 6 | Day 9 | Day 13 | Day 16 | Day | Mean |
|---|---|---|---|---|---|---|---|---|
| BTV Vaccinated | | | | | | | | |
| 353 | 3.73 | 4.16 | 4.68 | 3.91 | 3.84 | 4.79 | 0 | 4.9 |
| 355 | 5.13 | 4.77 | 5.51 | 4.36 | 4.51 | 3.6 | 3 | 4.94 |
| 359 | 6.11 | 6.46 | 7.47 | 6 | 6.07 | 6.86 | 6 | 5.59 |
| 361 | 3.69 | 4.25 | 4.62 | 4.44 | 4.32 | 4.46 | 9 | 5.01 |
| 363 | 5.86 | 4.61 | 5.69 | 5.66 | 5.68 | 6.7 | 13 | 4.96 |
| 364 | 4.9 | 5.36 | 5.59 | 5.7 | 5.32 | 5.91 | 16 | 5.39 |
| Mean: | 4.903333 | 4.935 | 5.593333 | 5.011667 | 4.956667 | 5.386667 | | |
| WNV Controls | | | | | | | | |
| 354 | 3.46 | 2.43 | 3.46 | 3.82 | 4.71 | 5.1 | 0 | 4.36 |
| 356 | 3.39 | 3.61 | 3.12 | 3.16 | 4.63 | 5.4 | 3 | 4.04 |
| 357 | 4.94 | 6.73 | 2.97 | 5.28 | 7.74 | 7.73 | 6 | 3.5 |
| 358 | 4.15 | 4.01 | 3.85 | 4.31 | 6.36 | 8.24 | 9 | 4.39 |
| 362 | 5.86 | 3.41 | 4.08 | 5.38 | 7.37 | 7.4 | 13 | 6.16 |
| | | | | | | | 16 | 6.77 |

TABLE 7

BTV 17 Challenge Study-Lymphocyte Data

| Sheep # | Day 0 | Day 3 | Day 6 | Day 9 | Day 13 | Day 16 | Day | Mean |
|---|---|---|---|---|---|---|---|---|
| BTV Vaccinated | | | | | | | | |
| 353 | 2.5 | 2.09 | 2.65 | 1.92 | 1.84 | 2.48 | 0 | 3.17 |
| 355 | 3.3 | 3.04 | 3.79 | 3.11 | 3 | 2.43 | 3 | 3.09 |
| 359 | 4.33 | 3.88 | 4.73 | 4.03 | 3.62 | 4.33 | 6 | 3.57 |
| 361 | 1.84 | 2.9 | 3.2 | 2.85 | 2.64 | 2.67 | 9 | 3.14 |
| 363 | 3.51 | 2.9 | 3.6 | 3.25 | 3.42 | 3.93 | 13 | 2.86 |
| 364 | 3.56 | 3.74 | 3.44 | 3.69 | 2.66 | 3.34 | 16 | 3.2 |
| Mean: | 3.173333 | 3.091667 | 3.568333 | 3.141667 | 2.863333 | 3.196667 | | |
| WNV Controls | | | | | | | | |
| 354 | 2.19 | 1.05 | 2.16 | 2.6 | 2.87 | 3.73 | 0 | 2.92 |
| 356 | 1.85 | 1.58 | 1.98 | 2.11 | 2.7 | 2.72 | 3 | 2.18 |
| 357 | 3.14 | 3.93 | 1.82 | 3.8 | 5.4 | 6.16 | 6 | 2.37 |
| 358 | 2.74 | 2.49 | 3.06 | 3.37 | 5.71 | 6.47 | 9 | 3.35 |
| 362 | 4.69 | 1.84 | 2.82 | 4.85 | 5.89 | 6.3 | 13 | 4.51 |
| | | | | | | | 16 | 5.08 |
| Mean: | 2.922 | 2.178 | 2.368 | 3.346 | 4.514 | 5.076 | | |

4. Platelet count. For 16 days post challenge, platelet counts were monitored on day 0 and at approximately 3 day intervals through day 16 for all 6 BTC-CP vaccinates and for all 5 control (WNV-CP immunized) sheep The platelet data from the challenged sheep are shown below in Table 8 and in Drawing 20. The data show an initial decrease in platelet counts through day 8 post challenge with a continual rise in the mean platelet count at day 9-16 post challenge in the controls. In the BTV-CP vaccinates there is a gradual increase in platelets over the course of the study. In the BTV-CP vaccinate, the platelet counts are elevated above the controls throughout the course of the study. The decrease in platelet count after challenge in is a typical response for a viremic BTV infected animal. The BTV-CP immunized animals exhibit normal platelet counts. These results confirm vaccine (BTV-CP) efficacy.

REFERENCES

Anderson, G. A., J. L. Stott, et al. (1985). "Subclinical and clinical bluetongue disease in cattle: clinical, pathological and pathogenic considerations." *Prog Clin Biol Res* 178: 103-7.

Andreansky, S. S., B. He, et al. (1996). "The application of genetically engineered herpes simplex viruses to the treatment of experimental brain tumors." *Proc Natl Acad Sci U S A* 93(21): 11313-8.

Andrew, M., P. Whiteley, et al. (1995). "Antigen specificity of the ovine cytotoxic T lymphocyte response to bluetongue virus." *Vet Immunol Immunopathol* 47(3-4): 311-22.

Antoine, G., F. Scheiflinger, et al. (1998). "The complete genomic sequence of the modified vaccinia A Pakara strain: comparison with other orthopoxviruses." *Virolog* 244(2): 365-96.

TABLE 8

BTV Platelet counts.

| Sheep # | Day 0 | Day 3 | Day 6 | Day 9 | Day 13 | Day 16 | Day | Mean |
|---|---|---|---|---|---|---|---|---|
| BTV Vaccinated | | | | | | | | |
| 353 | 822 | 566 | 863 | 945 | 909 | 936 | 0 | 686.3 |
| 355 | 1076 | 935 | 941 | 905 | 956 | 1056 | 3 | 546.3 |
| 359 | 602 | 528 | 692 | 607 | 739 | 854 | 6 | 763.3 |
| 361 | 510 | 405 | 580 | 553 | 442 | 680 | 9 | 708.5 |
| 363 | 565 | 327 | 828 | 865 | 705 | 775 | 13 | 734.8 |
| 364 | 543 | 517 | 676 | 376 | 658 | 799 | 16 | 850 |
| Mean: | 686.3333 | 546.3333 | 763.3333 | 708.5 | 734.8333 | 850 | | |
| WNV Controls | | | | | | | | |
| 354 | 792 | 7.2 | 479 | 439 | 550 | 800 | 0 | 544 |
| 356 | 495 | 423 | 373 | 308 | 594 | 621 | 3 | 301.6 |
| 357 | 625 | 548 | 435 | 418 | 760 | 873 | 6 | 374.6 |
| 358 | 627 | 144 | 371 | 366 | 489 | 579 | 9 | 357 |
| 362 | 181 | 386 | 215 | 254 | 665 | 605 | 13 | 611.6 |
| | | | | | | | 16 | 695.6 |
| Mean: | 544 | 301.64 | 374.6 | 357 | 611.6 | 695.6 | | |

Ballay, A., M. Levrero, et al. (1985). "In vitro and in vivo synthesis of the hepatitis B virus surface antigen and of the receptor for polymerized human serum albumin from recombinant human adenoviruses." *Embo J* 4(13B): 3861-5.

Barcena, J., M. M. Lorenzo, et al. (2000). "Sequence and analysis of a swinepox virus homologue of the vaccinia virus major envelope protein P37 (F13L)." *J Gen Virol* 81(Pt 4): 1073-85.

Bernard, K. A., B. A. Israel, et al. (1997). "Sequence and cognitive analyses of two virulence-associated markers of bluetongue virus serotype 17." *Intervirology* 40(4): 226-31.

Bonneau, K. R., C. D. DeMaula, et al. (2002). "Duration of viraemia infectious to Culicoides sonorensis in bluetongue virus-infected cattle and sheep." *Vet Microbiol* 88(2): 115-25.

Bonneau, K. R., B. A. Mullens, et al. (2001). "Occurrence of genetic drift and founder effect during quasispecies evolution of the VP2 and NS3/NS3A genes of bluetongue virus upon passage between sheep, cattle, and Culicoides sonorensis." *J Virol* 75(17): 8298-305.

Bonneau, K. R., N. Zhang, et al. (1999). "Sequence comparison of the L2 and S10 genes of bluetongue viruses from the United States and the People's Republic of China." *Virus Res* 61(2): 153-60.

Boshart, M., F. Weber, et al. (1985). "A very strong enhancer is located upstream of an immediate early gene of human cytomegalovirus." *Cell* 41(2): 521-30.

Bradel-Tretheway, B. G., Z. Zhen, et al. (2003). "Effects of codon-optimization on protein expression by the human herpesvirus 6 and 7 U51 open reading frame." *J Virol Methods* 111(2): 145-56.

Carroll, M. W., W. W. Overwijk, et al. (1997). "Highly attenuated modified vaccinia virus Ankara (MVA) as an effective recombinant vector: a murine tumor model." *Vaccine* 15(4): 387-94.

Cochran, M. A., C. Puckett, et al. (1985). "In vitro mutagenesis of the promoter region for a vaccinia virus gene: evidence for tandem early and late regulatory signals." *J Virol* 54(1): 30-7.

Cowley, J. A. and B. M. Gorman (1989). "Cross-neutralization of genetic reassortants of bluetongue virus serotypes 20 and 21." *Vet Microbiol* 19(1): 37-51.

De Groot, A. S. and F. G. Rothman (1999). "In silico predictions; in vivo veritas." *Nat Biotechnol* 17(6): 533-4.

de Mattos, C. A., C. C. de Mattos, et al. (1994). "Heterogeneity of the L2 gene of field isolates of bluetongue virus serotype 17 from the San Joaquin Valley of California." *Virus Res* 31(1): 67-87.

DeMaula, C. D., K. R. Bonneau, et al. (2000). "Changes in the outer capsid proteins of bluetongue virus serotype ten that abrogate neutralization by monoclonal antibodies." *Virus Res* 67(1): 59-66.

DeMaula, C. D., H. W. Heidner, et al. (1993). "Neutralization determinants of United States bluetongue virus serotype ten." *Virology* 195(1): 292-6.

DeMaula, C. D., C. M. Leutenegger, et al. (2002). "The role of endothelial cell-derived inflammatory and vasoactive mediators in the pathogenesis of bluetongue." *Virology* 296(2): 330-7.

Disbrow, G. L., I. Sunitha, et al. (2003). "Codon optimization of the HPV-16 E5 gene enhances protei expression." *Virology* 311(1): 105-14.

Felgner, J. H., R. Kumar, et al. (1994). "Enhanced gene delivery and mechanism studies with a novel series of cationic lipid formulations." *J Biol Chem* 269(4): 2550-61.

Frolov, I., T. A. Hoffman, et al. (1996). "Alphavirus-based expression vectors: strategies and applications." *Proc Natl Acad Sci U S A* 93(21): 11371-7.

Funahashi, S., T. Sato, et al. (1988). "Cloning and characterization of the gene encoding the major protein of the A-type inclusion body of cowpox virus." *J Gen Virol* 69(Pt 1): 35-47.

Geysen, H. M. (1990). "Molecular technology: peptide epitope mapping and the pin technology." *Southeast Asian J Trov Med Public Health* 21(4): 523-33.

Geysen, H. M., S. J. Barteling, et al. (1985). "Small peptides induce antibodies with a sequence and structural requirement for binding antigen comparable to antibodies raised against the native protein." *Proc Natl Acad Sci U S A* 82(1): 178-82.

Geysen, H. M., R. H. Meloen, et al. (1984). "Use of peptide synthesis to probe viral antigens for epitopes to a resolution of a single amino acid." *Proc Natl Acad Sci U S A* 81(13): 3998-4002.

Ghiasi, H., A. Fukusho, et al. (1987). "Identification and characterization of conserved and variable regions in the neutralization VP2 gene of bluetongue virus." *Virology* 160(1): 100-9.

Graham, F. L. (1990). "Adenoviruses as expression vectors and recombinant vaccines." *Trends Biotechnol* 8(4): 85-7.

Guo, P. X., S. Goebel, et al. (1989). "Expression in recombinant vaccinia virus of the equine herpesvirus 1 gene encoding glycoprotein gp13 and protection of immunized animals." *J Virol* 63(10): 4189-98.

Hartikka, J., M. Sawdey, et al. (1996). "An improved plasmid DNA expression vector for direct injection into skeletal muscle." *Hum Gene Ther* 7(10): 1205-17.

Hassan, S. S. and P. Roy (1999). "Expression and functional characterization of bluetongue virus VP2 protein: role in cell entry." *J Virol* 73(12): 9832-42.

Heidner, H. W., P. V. Rossitto, et al. (1990). "Identification of four distinct neutralizing epitopes on bluetongue virus serotype 10 using neutralizing monoclonal antibodies and neutralization-escape variants." *Virology* 176(2): 658-61.

Hemmer, B., C. Pinilla, et al. (1998). "The use of soluble synthetic peptide combinatorial libraries to determine antigen recognition of T cells." *J Pept Res* 52(5): 338-45.

Huang, I. J., G. Y. Hwang, et al. (1995). "Sequence analyses and antigenic epitope mapping of the putative RNA-directed RNA polymerase of five U.S. bluetongue viruses." *Virology* 214(1): 280-8.

Huismans, H. and B. J. Erasmus (1981). "Identification of the serotype-specific and group-specific antigens of bluetongue virus." *Onderstepoort J Vet Res* 48(2): 51-8.

Huismans, H., N. T. van der Walt, et al. (1987). "Isolation of a capsid protein of bluetongue virus that induces a protective immune response in sheep." *Virology* 157(1): 172-9.

Jewell, J. E. and J. O. Mecham (1994). "Identification of an amino acid on VP2 that affects neutralization of bluetongue virus serotype 10." *Virus Res* 33(2): 139-44.

Ju, Q., D. Edelstein, et al. (1998). "Transduction of non-dividing adult human pancreatic beta cells by an integrating lentiviral vector." *Diabetoloaia* 41(6): 736-9.

Kim, C. H., Y. Oh, et al. (1997). "Codon optimization for high-level expression of human erythropoietin (EPO) in mammalian cells." *Gene* 199(1-2): 293-301.

Kitsonl, J. D., K. L. Burke, et al. (1991) "Chimeric polioviruses that include sequences derived from two independent antigenic sites of foot-and-mouth disease virus (FMDV) induce neutralizing antibodies against FMDV in guinea pigs." *J Virol* 65(6): 3068-75.

Klinman, D. M., A. K. Yi, et al. (1996). "CpG motifs present in bacteria DNA rapidly induce lymphocytes to secrete interleukin 6, interleukin 12, and interferon gamma." *Proc Natl Acad Sci U S A* 93(7): 2879-83.

Kwissa, M., K. van Kampen, et al. (2000). "Efficient vaccination by intradermal or intramuscular inoculation of plasmid DNA expressing hepatitis B surface antigen under desmin promoter/enhancer control." *Vaccine* 18(22): 2337-44.

Laval, F., R. Paillot, et al. (2002). "Quantitative analysis of the antigen-specific IFNgamma+T cell-mediated immune response in conventional outbred pigs: kinetics and duration of the DNA-induced IFNgamma+CD8+T cell response." *Vet Immunol Immunopathol* 90(3-4): 191-201.

Lobato, Z. I., B. E. Coupar, et al. (1997). "Antibody responses and protective immunity to recombinant vaccinia virus-expressed bluetongue virus antigens." *Vet Immunol Immunopathol* 59(3-4): 293-309.

Luckow, V. A. and M. D. Summers (1988). "Signals important for high-level expression of foreign genes in Autographa californica nuclear polyhedrosis virus expression vectors." *Virology* 167(1): 56-71.

MacLachlan, N. J. (1994). "The pathogenesis and immunology of bluetongue virus infection of ruminants." *Comp Immunol Microbiol Infect Dis* 17(3-4): 197-206.

MacLachlan, N. J. and J. E. Pearson (2004). Bluetongue: Proceedings of the Third International Symposium. *Bluetongue: Prodeedings of the Third International Symposium*. N. J. MacLachlan and J. E. Pearson, Vet Italiana. 40: 1-730.

Marshall, E., L. B. Woolford, et al. (1997). "Continuous infusion of macrophage inflammatory protein MIP-l alpha enhances leucocyte recovery and haemopoietic progenitor cell mobilization after cyclophosphamide." *Br J Cancer* 75(12): 1715-20.

Martinez-Torrecuadrada, J. L., J. P. Langeveld, et al. (1999). "Antigenic profile of African horse sickness virus serotype 4 VP5 and identification of a neutralizing epitope shared with bluetongue virus and epizootic hemorrhagic disease virus." *Virology* 257(2): 449-59.

McClements, W. L., M. E. Armstrong, et al. (1996). "Immunization with DNA vaccines encoding glycoprotein D or glycoprotein B, alone or in combination, induces protective immunity in animal models of herpes simplex virus-2 disease." *Proc Natl Acad Sci U S A* 93(21): 11414-20.

Mecham, J. O., V. C. Dean, et al. (1986). "Correlation of serotype specificity and protein structure of the five U.S. serotypes of bluetongue virus." *J Gen Virol* 67 (Pt 12): 2617-24.

Mecham, J. O. and D. J. Johnson (2005). "Persistence of bluetongue virus serotype 2 (BTV-2) in the southeast United States." *Virus Res* 113(2): 116-22.

Miyazaki, J., S. Takaki, et al. (1989). "Expression vector system based on the chicken beta-actin promoter directs efficient production of interleukin-5." *Gene* 79(2): 269-77.

Moss, B. (1996). "Genetically engineered poxviruses for recombinant gene expression, vaccination, and safety." *Proc Natl Acad Sci U S A* 93(21): 11341-8.

Mullens, B. A., W. J. Tabachnick, et al. (1995). "Effects of temperature on virogenesis of bluetongue virus serotype 11 in Culicoides variipennis sonorensis." *Med Vet Entomol* 9(1): 71-6.

Paoletti, E. (1996). "Applications of pox virus vectors to vaccination: an update." *Proc Natl Acad Sci U S A* 93(21): 11349-53.

Pearson, W. R. and D. J. Lipman (1988). "Improved tools for biological sequence comparison." *Proc Natl Acad Sci U S A* 85(8): 2444-8.

Pennock, G. D., C. Shoemaker, et al. (1984). "Strong and regulated expression of *Escherichia coli* beta-galactosidase in insect cells with a baculovirus vector." *Mol Cell Biol* 4(3): 399-406.

Perkus, M. E., K. Limbach, et al. (1989). "Cloning and expression of foreign genes in vaccinia virus, using a host range selection system." *J Virol* 63(9): 3829-36.

Powell, M. F. and M. J. Newman (1995). Vaccine Design, The Subunit and Adjuvant Approach. *A Compendium of Vaccine Adiuvants and Excipients*. F. Vogel and M. Powell. New York, Plenum Press. 6: 147, 183.

Prevec, L., M. Schneider, et al. (1989). "Use of human adenovirus-based vectors for antigen expression in animals." *J Gen Virol* 70 (Pt 2): 429-34.

Pritchard, L. I. and A. R. Gould (1995). "Phylogenetic comparison of the serotype-specific VP2 protein of bluetongue and related orbiviruses." *Virus Res* 39(2-3): 207-20.

Regelson, W., S. Kuhar, et al. (1960). "Synthetic polyelectrolytes as tumour inhibitors." *Nature* 186: 778-80.

Riviere, M., J. Tartaglia, et al. (1992). "Protection of mice and swine from pseudorabies virus conferred by vaccinia virus-based recombinants." *J Virol* 66(6): 3424-34.

Robertson, E. S., T. Ooka, et al. (1996). "Epstein-Barr virus vectors for gene delivery to B lymphocytes." *Proc Natl Acad Sci U S A* 93(21): 11334-40.

Robinson, H. L. and C. A. Torres (1997). "DNA vaccines." *Semin Immunol* 9(5): 271-83.

Roizman, B. (1996). "The function of herpes simplex virus genes: a primer for genetic engineering of novel vectors." *Proc Natl Acad Sci U S A* 93(21): 11307-12.

Rossitto, P. V. and N. J. MacLachlan (1992). "Neutralizing epitopes of the serotypes of bluetongue virus present in the United States." *J Gen Virol* 73 (Pt 8): 1947-52.

Roy, P. (1992). "Bluetongue virus proteins." *J Gen Virol* 73 (Pt 12): 3051-64.

Roy, P. (1996). "Orbivirus structure and assembly." *Virology* 216(1): 1-11.

Roy, P. (1996). Orbiviruses and their replication. *Fields Virology*. B. N. Fields, D. M. Knipe, P. M. Howley. Philadelphia, Pa., Lippincott-Raven: 1709-1734.

Roy, P., T. Urakawa, et al. (1990). "Recombinant virus vaccine for bluetongue disease in sheep." *J Virol* 64(5): 1998-2003.

Sambrook, J. and D. W. Russell (2001). *Molecular Cloning: a laboratory manual*/Joseph Sambrook. David W. Russell. Cold Spring Harbor, N.Y., Cold Spring Harbor Laboratory Press.

Schneider, K., F. Puehler, et al. (2000). "cDNA cloning of biologically active chicken interleukin-18." *J Interferon Cytokine Res* 20(10): 879-83.

Shida, H. (1986). "Nucleotide sequence of the vaccinia virus hemagglutinin gene." *Virology* 150(2): 451-62.

Smith, G. E., M. D. Summers, et al. (1983). "Production of human beta interferon in insect cells infected with a baculovirus expression vector." *Mol Cell Biol* 3(12): 2156-65.

Spreull, J. (1905). "Malarial catarrhal fever (bluetongue) of sheep in South Africa." *J. Comp. Path. Ther.* 18: 321-337.

Stickl, H. and V. Hochstein-Mintzel (1971). "[Intracutaneous smallpox vaccination with a weak pathogenic vaccinia virus ("MVA virus")]." *Munch Med Wochenschr* 113(35): 1149-53.

Stittelaar, K. J., L. S. Wyatt, et al. (2000). "Protective immunity in macaques vaccinated with a modified vaccinia virus Ankara-based measles virus vaccine in the presence of passively acquired antibodies." *J Virol* 74(9): 4236-43.

Sutter, G. and B. Moss (1992). "Nonreplicating vaccinia vector efficiently expresses recombinant genes." *Proc Natl Acad Sci U S A* 89(22): 10847-51.

Sutter, G., L. S. Wyatt, et al. (1994). "A recombinant vector derived from the host range-restricted and highly attenuated MVA strain of vaccinia virus stimulates protective immunity in mice to influenza virus." *Vaccine* 12(11): 1032-40.

Tang, D. C., M. DeVit, et al. (1992). "Genetic immunization is a simple method for eliciting an immune response." *Nature* 356(6365): 152-4.

Taylor, J., R. Weinberg, et al. (1988). "Protective immunity against avian influenza induced by a fowlpox virus recombinant." *Vaccine* 6(6): 504-8.

Thompson, J. D., D. G. Higgins, et al. (1994). "CLUSTAL W: improving the sensitivity of progressive multiple sequence alignment through sequence weighting, position-specific gap penalties and weight matrix choice." *Nucleic Acids Res* 22(22): 4673-80.

Ulmer, J. B., J. J. Donnelly, et al. (1993). "Heterologous protection against influenza by injection of DNA encoding a viral protein." *Science* 259(5102): 1745-9.

Van der Zee, R., W. Van Eden, et al. (1989). "Efficient mapping and characterization of a T cell epitope by the simultaneous synthesis of multiple peptides." *Eur J Immunol* 19(1): 43-7.

van Ooyen, A., J. van den Berg, et al. (1979). "Comparison of total sequence of a cloned rabbit beta-globin gene and its flanking regions with a homologous mouse sequence." *Science* 206(4416): 337-44.

Verwoerd, D. W., H. J. Els, et al. (1972). "Structure of the bluetongue virus capsid." *J Virol* 10(4): 783-94.

Vialard, J., M. Lalumiere, et al. (1990). "Synthesis of the membrane fusion and hemagglutinin proteins of measles virus, using a novel baculovirus vector containing the beta-galactosidase gene." *J Virol* 64(1): 37-50.

Wang, L. F., D. H. Du Plessis, et al. (1995). "Use of a gene-targeted phage display random epitope library to map an antigenic determinant on the bluetongue virus outer capsid protein VP5." *J Immunol Methods* 178(1): 1-12.

White, D. M., W. C. Wilson, et al. (2005). "Studies on overwintering of bluetongue viruses in insects." *J Gen Virol* 86(Pt 2): 453-62.

Wilson, W. C. and J. O. Mecham (2000). "Molecular Evolution of Orbiviruses." *Proc USAHA* 104: 169-180.

Xin, K. Q., K. Hamajima, et al. (1999). "IL-15 expression plasmid enhances cell-mediated immunity induced by an HIV-1 DNA vaccine." *Vaccine* 17(7-8): 858-66.

Having thus described in detail preferred embodiments of the present invention, it is to be understood that the invention defined by the appended claims is not to be limited to particular details set forth in the above description as many apparent variations thereof are possible without departing from the spirit or scope of the present invention.

What is claimed is:

1. An immunogenic composition comprising a recombinant poxvirus, wherein the recombinant poxvirus comprises nucleic acid molecules encoding Bluetongue Virus (BTV) VP2 having the sequence as set forth in SEQ ID NO:20 and BTV VP5 having the sequence as set forth in SEQ ID NO:21.

2. An immunogenic composition comprising a recombinant poxvirus comprising one or more nucleic acid molecules, wherein the one or more nucleic acid molecules comprise the sequence as set forth in SEQ ID NO:1, or the sequence as set forth in SEQ ID NO:2, or combinations thereof.

3. The immunogenic composition of claim 1 or 2, wherein the recombinant poxvirus is a recombinant avipox virus.

4. The immunogenic composition of claim 3 wherein the recombinant avipox virus is a canarypox virus.

5. The immunogenic composition of claim 4 wherein the canarypoxvirus is ALVAC.

6. The immunogenic composition of claim 1 or 2, further comprising an adjuvant.

7. The immunogenic composition according to claim 6, wherein the adjuvant is a carbomer.

8. The immunogenic composition of claim 1 or 2 further comprising an antigen or immunogen or epitope thereof of a pathogen other than BTV of the animal, or a vector that contains and expresses in vivo in the animal a nucleic acid molecule encoding the antigen, immunogen or epitope thereof, or an inactivated or attenuated pathogen other than BTV of the animal.

9. The immunogenic composition of claim 1 or 2, wherein the animal is ovine, bovine, feline or eqauine.

10. The immunogenic composition of claim 1 or 2, wherein the one or more nucleic acid molecules are operably linked to one or more promoters.

11. The immunogenic composition of claim 10, wherein the one or more nucleic acid molecules have the sequence as set forth in SEQ ID NO:1 operably linked to the promoter H6, and/or wherein the nucleic acid molecules have the sequence as set forth in SEQ ID NO:2 operably linked to the promoter 42K.

12. A kit for performing a method of administering to an animal (a) an immunogenic composition of claim 1 or 2, and/or (b) a BTV antigen, immunogen or epitope, and testing the animals for presence or absence of a BTV protein or antibody, the kit comprising (a) and (b) in separate containers, optionally with instructions for admixture and/or administration.

13. The kit of claim 12, wherein the animal is ovine, bovine, feline or equine.

14. A kit comprising (a) the immunogenic composition according to claim 1 or 2, and (b) an antigen or immunogen, or epitope thereof of a pathogen other than BTV of the animal, or a vector that contains and expresses in vivo in the animal a nucleic acid molecule encoding the antigen, immunogen, or epitope thereof, or the inactivated or attenuated pathogen other than BTV of the animal, the kit comprising (a) and (b) in separate containers, and the kit optionally contains instructions for admixture and/or administration of (a) and (b).

15. The kit of claim 14, wherein the animal is a feline, an ovine, a bovine or an equine.

16. A method for inducing an immunological or protective response against BTV in an animal comprising administering to the animal the immunogenic composition of claim 1 or 2.

17. A method for inducing an immunological response against BTV in an animal comprising administering to the animal the immunogenic composition of claim 1 or 2.

18. The method according to claim 17 further comprising a carbomer adjuvant.

19. A method for inducing an immunological response against BTV in an animal comprising administering to the animal (a) the immunogenic composition according to claim 1 or 2, and (b) a BTV isolated antigen, immunogen or epitope thereof, wherein (a) is administered prior to (b) in a prime-boost regimen, or (b) is administered prior to (a) in a prime-boost regimen, or (a) and (b) are administered together, either sequentially or in admixture.

20. The method of claim 16, wherein the animal is an ovine, a bovine, a feline, or an equine.

21. A differential diagnosis method comprising administering to animals an immunogenic composition of claim 1 or 2, and testing the animals for the presence or absence of a BTV protein or antibody thereto not expressed by the administered poxvirus.

22. The method of claim 21, wherein the animal is an ovine, a bovine, a feline, or an equine.

* * * * *